US010238821B2

(12) United States Patent
Akouka et al.

(10) Patent No.: US 10,238,821 B2
(45) Date of Patent: Mar. 26, 2019

(54) INHALER AND METHODS OF USE THEREOF

(71) Applicant: MicroDose Therapeutx, Inc., Ewing, NJ (US)

(72) Inventors: Henri Akouka, Mount Laurel, NJ (US); Daniel Becker, Washington Crossing, PA (US); Renee Hyer, Troy, NY (US); Craig Oakum, Moorestown, NJ (US)

(73) Assignee: MicroDose Therapeutx, Inc., Ewing, NJ (US)

( * ) Notice: Subject to any disclaimer, the term of this patent is extended or adjusted under 35 U.S.C. 154(b) by 0 days.

(21) Appl. No.: 15/729,526

(22) Filed: Oct. 10, 2017

(65) Prior Publication Data

US 2018/0104424 A1 Apr. 19, 2018

Related U.S. Application Data

(60) Provisional application No. 62/406,854, filed on Oct. 11, 2016, provisional application No. 62/406,844, (Continued)

(51) Int. Cl.
*A61M 15/00* (2006.01)
*A61P 11/12* (2006.01)
(Continued)

(52) U.S. Cl.
CPC ....... *A61M 15/0091* (2013.01); *A61K 9/0075* (2013.01); *A61K 31/167* (2013.01);
(Continued)

(58) Field of Classification Search
CPC .............. A61M 15/00; A61M 15/0001; A61M 15/0005; A61M 15/001; A61M 15/0021;
(Continued)

(56) References Cited

U.S. PATENT DOCUMENTS

| 2,517,482 A | 8/1950 | Hall |
| 3,507,277 A | 4/1970 | Altounyan et al. |

(Continued)

FOREIGN PATENT DOCUMENTS

| CA | 2811947 | 4/2012 |
| CN | 1215346 | 4/1999 |

(Continued)

OTHER PUBLICATIONS

Aydin M., et al. Respiratory Drug Delivery 2010. vol. 3, 2010: 675-680.
(Continued)

*Primary Examiner* — (Jackie) Tan-Uyen T Ho
*Assistant Examiner* — Joseph D Boecker
(74) *Attorney, Agent, or Firm* — Morgan, Lewis & Bockius LLP

(57) ABSTRACT

A medicament delivery device comprises a dosing chamber configured to contain dry powder medicament, a transducer and a controller electrically coupled to the transducer. The medicament delivery device is capable of delivering a therapeutically effective dose of dry powder medicament in response to between 2-20 tidal inhalations, the dose preferably having a mass median aerodynamic diameter (MMAD) of about 6 microns or less and a fine particle fraction of at least 30%.

30 Claims, 64 Drawing Sheets

Related U.S. Application Data filed on Oct. 11, 2016, provisional application No. 62/406,847, filed on Oct. 11, 2016, provisional application No. 62/406,860, filed on Oct. 11, 2016, provisional application No. 62/406,865, filed on Oct. 11, 2016, provisional application No. 62/406,848, filed on Oct. 11, 2016, provisional application No. 62/406,867, filed on Oct. 11, 2016, provisional application No. 62/406,858, filed on Oct. 11, 2016.

(51) Int. Cl.

| | |
|---|---|
| *A61P 11/06* | (2006.01) |
| *A61P 11/00* | (2006.01) |
| *A61K 9/00* | (2006.01) |
| *A61K 31/167* | (2006.01) |
| *A61K 31/40* | (2006.01) |
| *A61K 31/4418* | (2006.01) |
| *A61K 38/46* | (2006.01) |
| *A61M 16/14* | (2006.01) |
| *A61M 16/00* | (2006.01) |

(52) U.S. Cl.
CPC .......... *A61K 31/40* (2013.01); *A61K 31/4418* (2013.01); *A61K 38/465* (2013.01); *A61M 15/0021* (2014.02); *A61M 15/0051* (2014.02); *A61M 15/0085* (2013.01); *A61M 15/0086* (2013.01); *A61M 16/14* (2013.01); *A61P 11/00* (2018.01); *A61P 11/06* (2018.01); *A61P 11/12* (2018.01); *A61M 15/001* (2014.02); *A61M 2016/0021* (2013.01); *A61M 2016/0027* (2013.01); *A61M 2016/0039* (2013.01); *A61M 2202/064* (2013.01); *A61M 2205/502* (2013.01); *A61M 2205/583* (2013.01); *A61M 2205/8206* (2013.01)

(58) Field of Classification Search
CPC .......... A61M 15/0045; A61M 15/0051; A61M 15/0085; A61M 15/0086; A61M 15/0091; A61M 11/00; A61M 11/001; A61M 11/003; A61M 11/005; A61M 2202/064; A61K 9/0075
See application file for complete search history.

(56) References Cited

U.S. PATENT DOCUMENTS

| | | |
|---|---|---|
| 3,518,992 A | 7/1970 | Altounyan et al. |
| 3,635,218 A | 1/1972 | Altounyan et al. |
| 3,653,380 A | 4/1972 | Hansen |
| 3,795,244 A | 3/1974 | Lax et al. |
| 3,807,400 A | 4/1974 | Cocozza |
| 3,831,606 A | 8/1974 | Damani |
| 3,948,264 A | 4/1976 | Wilke et al. |
| 3,991,304 A | 11/1976 | Hillsman |
| 4,094,317 A | 6/1978 | Wasnich |
| 4,240,418 A | 12/1980 | Rosskamp et al. |
| 4,345,592 A | 8/1982 | Giorgini et al. |
| 4,452,239 A | 6/1984 | Malem |
| 4,733,797 A | 3/1988 | Haber |
| 4,938,209 A | 7/1990 | Fry |
| 4,986,269 A | 1/1991 | Hakkinen |
| 5,152,284 A | 10/1992 | Valentini et al. |
| 5,260,321 A | 11/1993 | Hof et al. |
| 5,344,043 A | 9/1994 | Moulding et al. |
| 5,349,947 A | 9/1994 | Newhouse et al. |
| 5,429,302 A | 7/1995 | Abbott |
| 5,458,135 A | 10/1995 | Patton et al. |
| 5,479,920 A | 1/1996 | Piper et al. |
| 5,487,378 A | 1/1996 | Robertson et al. |
| 5,497,763 A * | 3/1996 | Lloyd ................ A61K 51/1206 128/200.14 |
| 5,694,920 A | 12/1997 | Abrams et al. |
| 5,699,649 A | 12/1997 | Abrams et al. |
| 5,724,959 A | 3/1998 | McAughey et al. |
| 5,727,546 A | 3/1998 | Clarke et al. |
| 5,740,793 A | 4/1998 | Hodson et al. |
| 5,758,823 A | 6/1998 | Glezer et al. |
| 5,823,434 A | 10/1998 | Cooper |
| 5,853,002 A | 12/1998 | Kawasaki |
| 5,884,624 A | 3/1999 | Barnett et al. |
| 5,894,990 A | 4/1999 | Glezer et al. |
| 5,906,202 A | 5/1999 | Schuster et al. |
| 5,908,158 A | 6/1999 | Cheiman |
| 5,938,118 A | 8/1999 | Cooper |
| 5,954,049 A | 9/1999 | Foley et al. |
| 6,026,809 A | 2/2000 | Abrams et al. |
| 6,116,237 A | 9/2000 | Schultz et al. |
| 6,120,441 A | 9/2000 | Griebel |
| 6,142,146 A | 11/2000 | Abrams et al. |
| 6,152,130 A | 11/2000 | Abrams et al. |
| 6,196,218 B1 | 3/2001 | Voges |
| 6,205,999 B1 | 3/2001 | Ivri |
| 6,209,538 B1 | 4/2001 | Casper et al. |
| 6,294,582 B1 | 9/2001 | Jerussi |
| 6,312,909 B1 | 11/2001 | Shyjan |
| 6,328,033 B1 | 12/2001 | Avrahami |
| 6,347,629 B1 | 2/2002 | Braithwaite |
| 6,387,470 B1 | 4/2002 | Denyer et al. |
| 6,415,790 B1 | 7/2002 | Leedom et al. |
| 6,457,654 B1 | 10/2002 | Glezer et al. |
| 6,526,966 B1 | 3/2003 | Peesay |
| 6,536,427 B2 | 3/2003 | Davies et al. |
| 6,536,432 B2 | 3/2003 | Truschel |
| 6,543,442 B2 | 4/2003 | Gonda et al. |
| 6,584,971 B1 | 7/2003 | Denyer et al. |
| 6,622,720 B2 | 9/2003 | Hadimioglu |
| 6,629,646 B1 | 10/2003 | Ivri |
| 6,698,428 B2 | 3/2004 | Widerstrom |
| 6,722,581 B2 | 4/2004 | Dassoughi |
| 6,759,159 B1 | 7/2004 | Gray et al. |
| 6,792,945 B2 | 9/2004 | Davies et al. |
| 6,840,239 B2 | 1/2005 | Myrman |
| 6,871,647 B2 | 3/2005 | Allan et al. |
| 6,889,690 B2 | 5/2005 | Crowder et al. |
| 6,962,266 B2 | 11/2005 | Morgan et al. |
| 6,968,840 B2 | 11/2005 | Smith et al. |
| 6,971,383 B2 | 12/2005 | Hickey et al. |
| 7,077,126 B2 | 7/2006 | Kummer et al. |
| 7,080,644 B2 | 7/2006 | Gumaste |
| 7,100,608 B2 | 9/2006 | Brewer et al. |
| 7,231,920 B2 | 6/2007 | Harvey et al. |
| 7,233,228 B2 | 6/2007 | Lintell |
| 7,290,541 B2 | 11/2007 | Ivri et al. |
| 7,318,434 B2 | 1/2008 | Gumaste et al. |
| 7,334,577 B2 | 2/2008 | Gumaste et al. |
| 7,343,914 B2 | 3/2008 | Abrams et al. |
| 7,451,764 B2 | 11/2008 | Wang |
| 7,467,629 B2 | 12/2008 | Rand |
| 7,538,473 B2 | 5/2009 | Blandino et al. |
| 7,607,435 B2 | 10/2009 | Lipp |
| 7,748,382 B2 | 7/2010 | Denyer et al. |
| 7,793,660 B2 | 9/2010 | Kimmel et al. |
| 8,371,294 B2 | 2/2013 | Gumaste et al. |
| 8,439,033 B2 | 5/2013 | Gumaste et al. |
| 8,474,452 B2 | 7/2013 | Gumaste et al. |
| 8,763,606 B2 | 7/2014 | Mosier et al. |
| 8,985,101 B2 | 3/2015 | Mosier |
| 8,991,390 B2 | 3/2015 | Akouka et al. |
| 9,040,569 B2 | 5/2015 | Cook et al. |
| 2001/0027790 A1* | 10/2001 | Gieschen .......... A61M 15/0086 128/203.15 |
| 2002/0032409 A1 | 3/2002 | Ritsche |
| 2002/0046751 A1 | 4/2002 | MacRae |
| 2002/0078947 A1 | 6/2002 | Gumaste |
| 2002/0148462 A1* | 10/2002 | Fugelsang ......... A61M 15/0086 128/200.14 |
| 2002/0168322 A1* | 11/2002 | Clark .................... A61M 15/00 424/45 |
| 2003/0041859 A1 | 3/2003 | Abrams et al. |
| 2003/0192540 A1 | 10/2003 | Myrman et al. |

(56) References Cited

U.S. PATENT DOCUMENTS

| | | |
|---|---|---|
| 2003/0196660 A1 | 10/2003 | Haveri |
| 2003/0235538 A1* | 12/2003 | Zierenberg .......... A61K 9/0075 424/46 |
| 2004/0025871 A1 | 2/2004 | Davies |
| 2004/0050860 A1 | 3/2004 | Crowder et al. |
| 2004/0084045 A1 | 4/2004 | Ziegler et al. |
| 2004/0123864 A1 | 7/2004 | Hickey et al. |
| 2004/0250812 A1 | 12/2004 | Davies et al. |
| 2004/0263567 A1 | 12/2004 | Hess et al. |
| 2005/0026909 A1 | 2/2005 | Landau et al. |
| 2005/0087189 A1 | 4/2005 | Crockford et al. |
| 2005/0103337 A1 | 5/2005 | Hickey et al. |
| 2005/0109659 A1 | 5/2005 | Hickey et al. |
| 2005/0121027 A1 | 6/2005 | Nilsson et al. |
| 2005/0133024 A1* | 6/2005 | Coifman .......... A61B 5/087 128/200.14 |
| 2005/0154491 A1* | 7/2005 | Anderson .......... A61M 15/00 700/236 |
| 2005/0155601 A1 | 7/2005 | Steiner et al. |
| 2005/0172962 A1 | 8/2005 | Gumaste et al. |
| 2005/0174216 A1 | 8/2005 | Lintell |
| 2005/0183724 A1 | 8/2005 | Gumaste et al. |
| 2005/0183725 A1 | 8/2005 | Gumaste et al. |
| 2005/0229928 A1 | 10/2005 | Ivri et al. |
| 2005/0267628 A1 | 12/2005 | Crowder et al. |
| 2006/0078505 A1 | 4/2006 | McAffer et al. |
| 2006/0163269 A1 | 7/2006 | Anderson et al. |
| 2006/0174869 A1 | 8/2006 | Gumaste et al. |
| 2006/0213503 A1 | 11/2006 | Borgschulte et al. |
| 2006/0257327 A1 | 11/2006 | Zierenberg et al. |
| 2007/0060652 A1 | 3/2007 | Fraser et al. |
| 2007/0119969 A1 | 5/2007 | Collins et al. |
| 2007/0137645 A1 | 6/2007 | Eason et al. |
| 2007/0157931 A1 | 7/2007 | Parker et al. |
| 2007/0240712 A1 | 10/2007 | Fleming et al. |
| 2007/0267010 A1 | 11/2007 | Fink |
| 2008/0035143 A1 | 2/2008 | Sievers et al. |
| 2008/0115784 A1 | 5/2008 | Gumaste et al. |
| 2008/0173302 A1* | 7/2008 | Mecikalski .......... A61M 15/0028 128/203.21 |
| 2008/0178872 A1 | 7/2008 | Genova et al. |
| 2008/0202514 A1 | 8/2008 | Kriksunov et al. |
| 2009/0000615 A1 | 1/2009 | Pohlmann et al. |
| 2009/0007908 A1 | 1/2009 | Eason et al. |
| 2009/0020113 A1 | 1/2009 | Watanabe |
| 2009/0090361 A1 | 4/2009 | Gumaste et al. |
| 2009/0165788 A1 | 7/2009 | Warden et al. |
| 2009/0165790 A1 | 7/2009 | Crowder et al. |
| 2009/0241949 A1* | 10/2009 | Smutney .......... A61M 15/0028 128/203.15 |
| 2009/0308390 A1 | 12/2009 | Smutney et al. |
| 2010/0059051 A1* | 3/2010 | Kladders .......... A61M 15/0065 128/203.15 |
| 2010/0108058 A1* | 5/2010 | Glusker .......... A61M 15/0028 128/200.14 |
| 2010/0139654 A1 | 6/2010 | Thoemmes et al. |
| 2010/0252032 A1 | 10/2010 | Thoemmes et al. |
| 2010/0282247 A1 | 11/2010 | Kadrichu et al. |
| 2011/0000481 A1 | 1/2011 | Gumaste et al. |
| 2011/0041844 A1 | 2/2011 | Dunne |
| 2011/0162642 A1 | 7/2011 | Akouka et al. |
| 2012/0085344 A1 | 4/2012 | Luber |
| 2012/0192861 A1* | 8/2012 | Surber .......... A61K 9/0078 128/200.16 |
| 2012/0255548 A1 | 10/2012 | Denny et al. |
| 2013/0255678 A1 | 10/2013 | Gumaste et al. |
| 2014/0261414 A1 | 9/2014 | Weitzel et al. |
| 2014/0341998 A1 | 11/2014 | Onoue et al. |
| 2015/0024050 A1 | 1/2015 | Shaaltiel et al. |
| 2016/0158469 A1 | 6/2016 | Milton-Edwards et al. |
| 2016/0296717 A1 | 10/2016 | Yoch et al. |

FOREIGN PATENT DOCUMENTS

| | | |
|---|---|---|
| DE | 102005005540 | 8/2006 |
| DE | 102009005048 | 7/2010 |
| EP | 1499276 | 1/2005 |
| EP | 0799076 | 3/2005 |
| EP | 1124602 | 4/2005 |
| EP | 1534366 | 6/2005 |
| EP | 1617820 | 1/2006 |
| EP | 1691781 | 8/2006 |
| EP | 1713530 | 10/2006 |
| EP | 1986721 | 11/2008 |
| EP | 1581291 | 1/2009 |
| EP | 2054167 | 5/2009 |
| EP | 1292347 | 10/2009 |
| EP | 1691783 | 11/2009 |
| EP | 2162174 | 3/2010 |
| EP | 2016965 | 5/2010 |
| EP | 2047881 | 8/2010 |
| EP | 2234728 | 10/2010 |
| EP | 1706099 | 5/2011 |
| JP | 2002524107 | 8/2002 |
| JP | 2003516825 | 5/2003 |
| JP | 2003526480 | 9/2003 |
| JP | 4504671 | 7/2005 |
| JP | 2007523700 | 8/2007 |
| WO | 9013328 | 11/1990 |
| WO | 97/29799 | 8/1997 |
| WO | 97/26934 | 9/1997 |
| WO | 98/32479 | 7/1998 |
| WO | 9913420 | 3/1999 |
| WO | 99/65550 | 12/1999 |
| WO | 99/64095 | 3/2000 |
| WO | 9964065 | 6/2000 |
| WO | 0071108 | 11/2000 |
| WO | 0143804 | 6/2001 |
| WO | 0168169 | 9/2001 |
| WO | 0172605 | 10/2001 |
| WO | 03039464 | 5/2003 |
| WO | 03059424 | 7/2003 |
| WO | 03092576 | 3/2004 |
| WO | 2004039763 | 5/2004 |
| WO | 2005041848 | 2/2005 |
| WO | 2004002394 | 3/2005 |
| WO | 2004093848 | 4/2005 |
| WO | 2005053646 | 6/2005 |
| WO | 2006033713 A2 | 3/2006 |
| WO | 2005081833 | 4/2006 |
| WO | 2006047427 | 5/2006 |
| WO | 2005074455 | 6/2006 |
| WO | 2005081977 | 7/2006 |
| WO | 2007096111 | 11/2007 |
| WO | 2008021281 | 2/2008 |
| WO | 2008106616 | 9/2008 |
| WO | 2008106616 | 10/2008 |
| WO | 2007121097 | 11/2008 |
| WO | 2009007068 | 1/2009 |
| WO | 2009090084 | 7/2009 |
| WO | 2010138158 A1 | 2/2010 |
| WO | 2010040815 | 4/2010 |
| WO | 2011003017 | 1/2011 |
| WO | 2011085022 | 7/2011 |
| WO | 2011163272 | 12/2011 |
| WO | 20111160932 | 12/2011 |
| WO | 2015173153 A1 | 11/2015 |
| WO | 2016007356 | 1/2016 |
| WO | 2016014153 | 1/2016 |
| WO | 2016014154 | 1/2016 |
| WO | 2016014586 | 1/2016 |
| WO | 2016033418 | 3/2016 |

OTHER PUBLICATIONS

2. Dal Negro, Multidisciplinary Respiratory Medicine (2015) 10:13.
3. Tiddens et al. Journal of Aerosol Medicine, vol. 19, No. 4, 2006, pp. 456-465.

(56) References Cited

OTHER PUBLICATIONS

International Search Report and Written Opinion issued in corresponding PCT Application No. US17/55968 filed on Oct. 10, 2017.

* cited by examiner

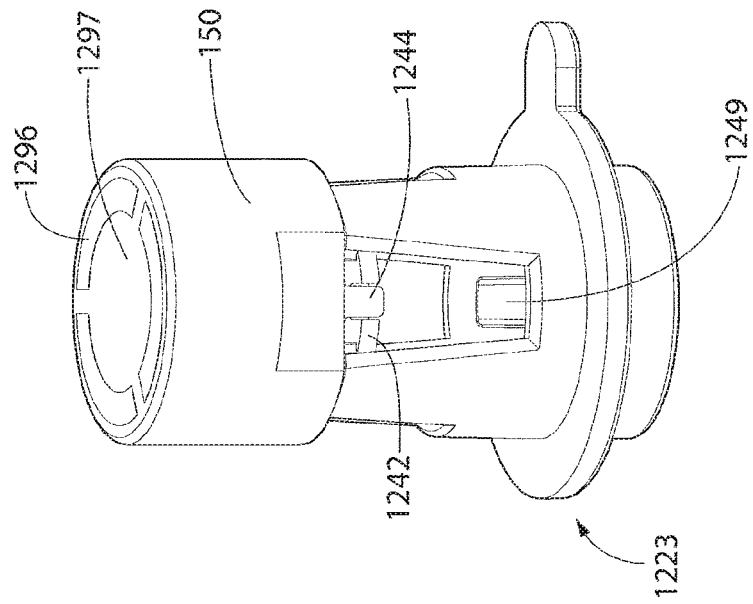
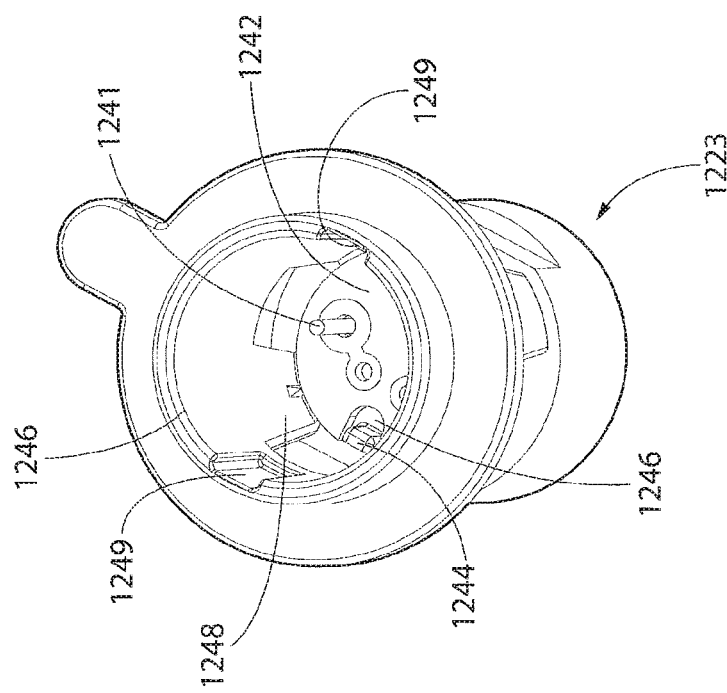
FIG. 27
FIG. 26

INHALER AND METHODS OF USE THEREOF

CROSS-REFERENCE TO RELATED APPLICATIONS

This application claims the benefit of priority of U.S. Provisional Application Nos. 62/406,844; 62/406,847; 62/406,848; 62/406,854; 62/406,858; 62/406,860; 62/406,865; and 62/406,867; each of which was filed Oct. 11, 2016. Each application is incorporated by reference herein, in its entirety and for all purposes.

FIELD OF THE INVENTION

The present invention relates to a device for administering medicament. In particular, the invention relates to a device for use in administering medicament in powder form.

BACKGROUND OF THE INVENTION

Certain diseases and disorders of the respiratory tract are known to respond to treatment by the direct application of therapeutic agents. As these agents are most readily available in dry powder form, their application is most conveniently accomplished by inhaling the powdered material through the nose or mouth. This powdered form results in better utilization of the medication, as the drug is deposited at the site where its action is needed; hence, very small doses of the drug are often as efficacious as larger doses administered orally or by injection, with a consequent marked reduction in the incidence of undesired side effects and medication cost. Alternatively, a drug in powder form may be used for the treatment of diseases and disorders other than those of the respiratory system. When the drug is deposited on the large surface areas of the lungs, it may be rapidly absorbed into the blood stream; hence, this method of application may take the place of administration by injection, tablet, or other conventional means.

Dry powder inhalers (DPI's) of the prior art have means for introducing a drug formulation into an air stream. Several inhalation devices useful for dispensing a powder form of medication are known in the prior art. For example, U.S. Pat. Nos. 2,517,482; 3,507,277; 3,518,992; 3,635,219; 3,795,244; 3,807,400; 3,831,606; 3,948,264; and 5,458,135 describe inhalation devices, many of which have means for piercing or removing the top of a capsule containing a powdered medication. Several of these patents disclose propeller means, which aid in dispensing the powder out of the capsule. Other DPI's utilize a vibratory element, such as those described in U.S. Pat. Nos. 5,694,920; 6,026,809; 6,142,146; 6,152,130; 7,080,644 and 7,318,434.

The prior art devices possess several disadvantages. For example, they often require that the user exert considerable effort in inhalation to effect withdrawal of the powder into the inhaled air stream. Thus, their performance often heavily depends on the flow rate generated by the user—a low flow rate may not result in the powder being sufficiently deaggregated, which can cause uncontrolled amounts or clumps of powder being inhaled into the user's mouth, rather than a constant inhalation of controlled amounts of finely dispersed pharmaceutical. This adversely affects the dose delivered to the patient and can lead to inconsistency in the bioavailability of the drug from dose-to-dose due to lack of consistency in the deaggregation process. Consequently, patients that cannot produce sufficiently high flow rates, such as pediatric, elderly, and patients with severely compromised lung function (e.g., COPD), may receive reduced and/or variable doses at the intended site of delivery. Moreover, suction of powder through the pierced holes of a capsule by inhalation often does not withdraw all or even most of the powder out of a capsule, thus causing a waste of the medication. The large energy requirements for driving electromechanical based inhalers typically increase the size of the devices, making them unsuitable for portable use.

Nebulizers provide an alternative mechanism for delivering medication to the respiratory system in a manner that may not require forceful inspiration. However, current nebulization systems are limited by relatively slow drug delivery; for example, some systems require a session of at least 10-20 minutes. This is especially undesirable for patients that regularly use a nebulizer several times per day. Also, nebulizers typically lack portability, are cumbersome to set up, and require a significant amount of cleaning and maintenance, among other drawbacks.

Efficient delivery of inhaled medication is desirable for the success of pulmonary-delivered therapies. One of the most desirable factors in pulmonary delivery from a DPI is a high-quality aerosol, in terms of the aerosol's aerodynamic particle size, and its potential to consistently achieve the desired lung deposition in vivo. The optimal delivery of inhaled medications is hindered in current devices by the need for patients to inhale forcefully while coordinating inspiration with the device, as well as by the physical limitations of the patient. Devices that provide means for deaggregating the powder have not been shown to provide consistent dose delivery or particle size distribution. These problems highlight the significant unmet need for simpler, portable, easier-to-use devices that do not require coordination with forceful inspiration, provide a short duration of administration, and deagglomerate the drug formulation in a manner that ensures a consistent particle size distribution of the delivered dose throughout the life of the device.

BRIEF SUMMARY OF THE INVENTION

In one embodiment, a medicament delivery device comprises a dosing chamber comprising an interior configured to contain dry powder medicament, a transducer confronting the dosing chamber, wherein the dosing chamber and the transducer are acoustically resonant such that the dosing chamber is configured to resonate in response to an activation of the transducer, and a controller electrically coupled to the transducer and configured to send an electrical signal that activates the transducer when the device senses a subject's dosing breath. The medicament delivery device may have a flow resistance in a range from about 0.040 cmH2O0.5/LPM to about 0.1 cmH2O0.5/LPM at 30 liters per minute (LPM) and may be capable of delivering a therapeutically effective dose of dry powder medicament in response to between 2-20 tidal inhalations, the dose preferably having a mass median aerodynamic diameter (MMAD) of about 6 microns or less and a fine particle fraction of at least 30%.

The controller may be configured to activate the transducer for a total on-time of 5 seconds or less over the 2-20 tidal inhalations. The controller may be configured to activate the transducer for between 50 ms and about 1000 ms during each dosing breath. The medicament delivery device may be capable of delivering the dose of dry powder medicament at flow rates at least within a range of about 15 LPM to about 30 LPM. The medicament delivery device may be capable of delivering the dose of dry powder medicament at flow rates at least within a range of about 15

LPM to about 90 LPM. The medicament delivery device may be configured to administer at least 10% of the dry powder medicament dose in response to a first dosing breath. The medicament delivery device may include a base and a removable cartridge, and one or more doses of dry powder medicament may be contained in the removable cartridge. The amount of each of the one or more doses of dry powder medicament may be from about 1 mg to about 10 mg. One or more lights may be configured to illuminate when a dose has been administered.

In another embodiment, a method of treating a respiratory disease or condition, or one or more symptoms thereof, comprises inhaling a therapeutically effective dose of dry powder medicament through a medicament delivery device using between 2-20 tidal inhalations over the course of an inhalation cycle, the inhalation cycle comprising dosing breaths. The medicament delivery device may comprise a vibratory element that may be activated upon each dosing breath and causes dry powder medicament to be aerosolized within a dosing chamber and expelled from one or more openings in the dosing chamber into an air flow conduit. Pressure oscillations in the dosing chamber may be preferably sufficiently high at the one or more openings to aerosolize and expel the dry powder medicament via synthetic jetting. The medicament delivery device may have a flow resistance in a range from about 0.040 cmH2O0.5/LPM to about 0.1 cmH2O0.5/LPM at 30 liters per minute (LPM) and may be capable of delivering the dose of dry powder medicament at flow rates at least within a range of about 15 LPM to about 30 LPM, wherein the dose of dry powder medicament delivered by the medicament delivery device preferably has a mass median aerodynamic diameter (MMAD) of about 6 microns or less and a fine particle fraction of at least 30%.

The method may include exhaling away from the medicament delivery device after each tidal inhalation. The medicament delivery device may comprise a base and a removable cartridge, the method further comprising attaching the base and the removable cartridge together. The medicament delivery device may administer at least 10% of the dry powder medicament dose in response to the first dosing breath in the inhalation cycle. The transducer may have an on-time of about 5 seconds or less over the course of the inhalation cycle. The medicament delivery device may achieve maximum synthetic jetting within about 1000 ms or less from the start of each transducer activation. The dose of dry powder medicament may be administered within 2 minutes or less. The respiratory disease or condition may be COPD. The respiratory disease or condition may be COPD and the dry powder medicament may comprise a LAMA and a LABA. The respiratory disease or condition may be COPD and the dry powder medicament may comprise glycopyrronium bromide and formoterol fumarate. The respiratory disease or condition may be asthma. The respiratory disease or condition may be cystic fibrosis and the dry powder medicament may comprise one or more antibiotics. The respiratory disease or condition may be cystic fibrosis and the dry powder medicament may comprise DNase. The respiratory disease or condition may be idiopathic pulmonary fibrosis and the dry powder medicament may comprise pirfenidone.

A method of increasing $FEV_1$ in a subject may include inhaling a therapeutically effective dose of dry powder medicament through a medicament delivery device using between 2-20 tidal inhalations over the course of an inhalation cycle. The inhalation cycle may comprise dosing breaths. The medicament delivery device may comprise a vibratory element that is activated upon each dosing breath and causes dry powder medicament to be aerosolized within a dosing chamber and expelled from one or more openings in the dosing chamber into an air flow conduit. Pressure oscillations in the dosing chamber may be sufficiently high at the one or more openings to aerosolize and expel the dry powder medicament via synthetic jetting. The medicament delivery device may have a flow resistance in a range from about 0.040 cmH2O0.5/LPM to about 0.1 cmH2O0.5/LPM at 30 liters per minute (LPM) and capable of delivering the dose of dry powder medicament at flow rates at least within a range of about 15 LPM to about 30 LPM. The dose of dry powder medicament delivered by the medicament delivery device may have a mass median aerodynamic diameter (MMAD) of about 6 microns or less and a fine particle fraction of at least 30%.

The medicament delivery device may administer at least 10% of the dry powder medicament dose in response to the first dosing breath in the inhalation cycle. The transducer may have an on-time of about 5 seconds or less over the course of the inhalation cycle. The medicament delivery device may achieve maximum synthetic jetting within about 1000 ms or less from the start of each transducer activation. The dry powder medicament may comprise formoterol fumarate. The medicament delivery device may be capable of delivering the dose of dry powder medicament at flow rates at least within a range of about 15 LPM to about 30 LPM.

In one embodiment, a medicament delivery device comprises a dosing chamber which may comprise an interior that is configured to contain dry powder medicament and a transducer confronting the dosing chamber. The dosing chamber and the transducer may be acoustically resonant such that the dosing chamber is configured to resonate in response to an activation of the transducer. The delivery device may include a controller electrically coupled to the transducer and configured to send an electrical signal that activates the transducer when the device senses a subject's dosing breath, and an air flow conduit extending from an air inlet to an outlet. The air flow conduit may comprise (i) an upstream area disposed upstream from the area of the air flow conduit into which the dry powder medicament is expelled from the dosing chamber, and (ii) a downstream area disposed downstream from the area of the air flow conduit into which the dry powder medicament may be expelled from the dosing chamber. The downstream area may comprise the outlet and an exit channel disposed about an exit channel axis. The upstream area may comprise the air inlet and a first leg of an upper flow path in fluid communication with the exit channel. The first leg may be disposed about a first leg axis transverse to both the exit channel axis and the dosing chamber axis. The dosing chamber's interior shape may be at least partially defined by a lower sidewall that transitions to a shoulder, the shoulder may transitions to an apex extending away from the lower sidewall, and the apex may converge to a point. The one or more openings in the dosing chamber may be disposed in the apex. The internal height of the dosing chamber may be configured so that pressure oscillation at the one or more openings is sufficiently high to cause the dry powder medicament to become aerosolized and delivered from the one or more openings. The medicament delivery device may have a flow resistance in a range from about 0.040 cmH2O0.5/LPM to about 0.1 cmH2O0.5/LPM at 30 liters per minute (LPM) and capable of delivering a therapeutically effective dose of dry powder medicament in response to between 2-20 tidal inhalations, the dose having a mass median aerodynamic diameter (MMAD) of about 6 microns or less and a fine particle fraction of at least 30%.

BRIEF DESCRIPTION OF THE SEVERAL VIEWS OF THE DRAWINGS

The foregoing summary, as well as the following detailed description of embodiments of the device and method of use, will be better understood when read in conjunction with the appended drawings of exemplary embodiments. It should be understood, however, that the invention is not limited to the precise arrangements and instrumentalities shown. It will also be appreciated that the drawings show merely schematic representation of possible embodiments of a device in accordance with the invention; for example, the shape of the device illustrated is not essential to the present invention, and alternative embodiments of the device could look different from the exterior views shown in the drawings.

In the drawings:

FIG. 26 is a bottom perspective view of the assembled transducer and holder of FIG. 25;

FIG. 27 is a side perspective view of the assembled transducer and holder of FIG. 25;

DETAILED DESCRIPTION OF THE INVENTION

Figure 1A:
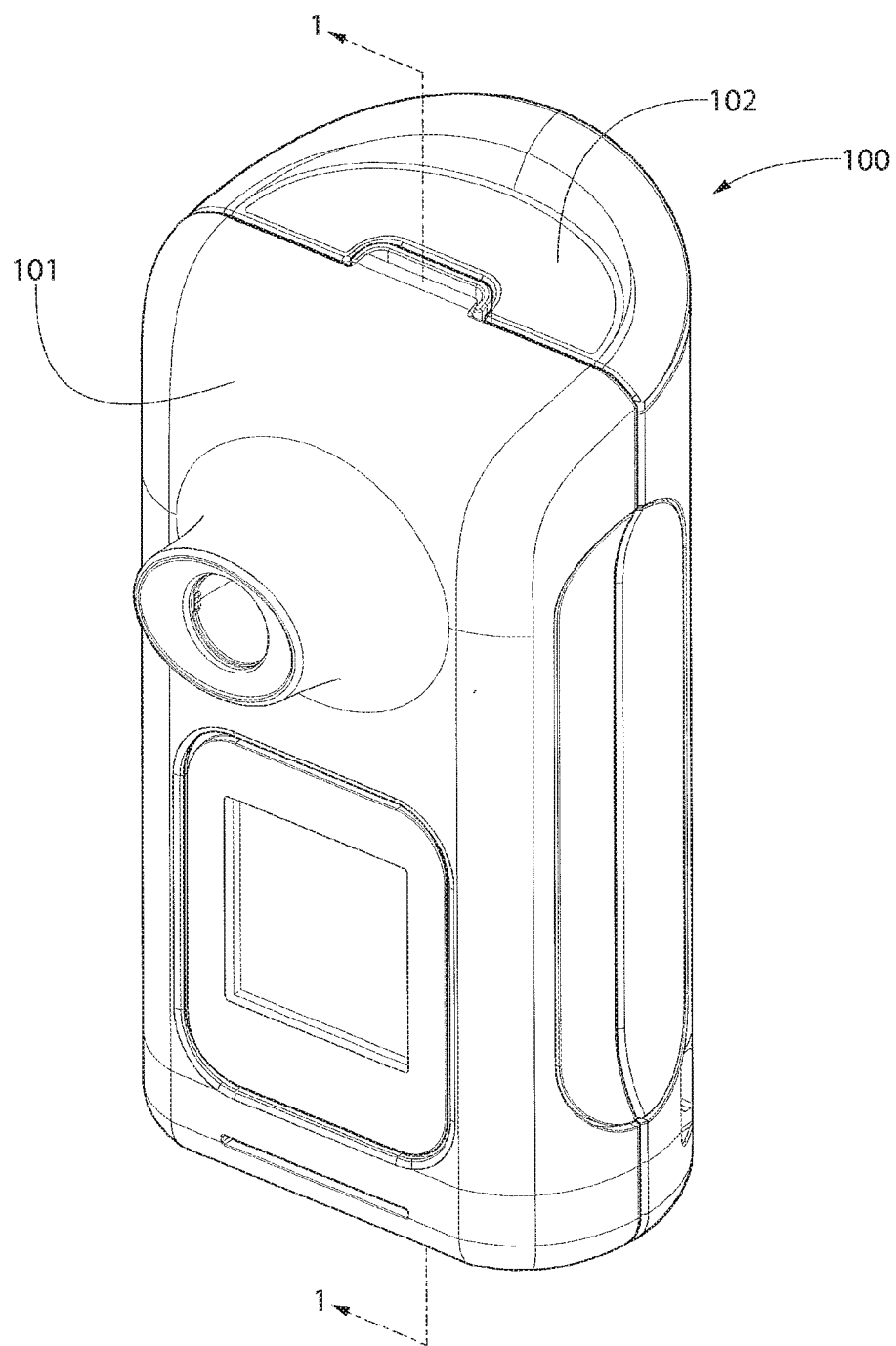
FIG. 1A illustrates an inhaler in accordance with one embodiment of the present invention.

The present invention relates to a device for administering medicament as a dry powder for inhalation by a subject. Some embodiments of the device may be classified as a dry powder inhaler (DPI). Some embodiments of the device may also be classified as a dry powder nebulizer (as opposed to a liquid nebulizer), particularly when tidal breathing (e.g., tidal inhalation) is used to deliver dry powder medicament over multiple inhalations. The device may be referred to herein interchangeably as a "medicament delivery device" or an "inhaler," both of which refer to a device for administering medicament as a dry powder for inhalation by a subject, preferably over multiple inhalations, and most preferably when tidal inhalation is used. "Tidal breathing" preferably refers to inhalation and exhalation during normal breathing at rest, as opposed to forceful breathing. Similarly, "tidal inhalation" refers to normal inhalation at rest, as opposed to inhalation that requires extra effort on the part of the user, such as forceful inhalation at a high inspiratory flow, or slow, deep inhalation. Stated another way, inhalation that requires extra effort may include inhalation that is slower, deeper, faster or stronger than normal inhalation at rest, whereas tidal inhalation refers to normal inhalation at rest which requires no extra effort.

As used herein, the term therapeutically effective amount may refer to an amount that, when administered to a particular subject, achieves a therapeutic effect by inhibiting, alleviating or curing a disease, disorder or symptom(s) in the subject or by prophylactically inhibiting, preventing or delaying the onset of a disease, disorder or symptom(s). A therapeutically effective amount may be an amount which relieves to some extent one or more symptoms of a disease or disorder in a subject; and/or returns to normal either partially or completely one or more physiological or biochemical parameters associated with or causative of the disease or disorder; and/or reduces the likelihood of the onset of the disease, disorder or symptom(s).

The terms medicament, pharmaceutical, active agent, active pharmaceutical ingredient, API, drug, medication, and active are used herein interchangeably to refer to the pharmaceutically active compound(s) in the drug composition. Other ingredients in a drug composition, such as carriers or excipients, may be substantially or completely pharmaceutically inert. A drug composition (also referred to herein as a composition, formulation, drug formulation, pharmaceutical composition, medicament formulation or API formulation) may comprise the medicament in combination with one or more carriers and/or one or more excipients. Some examples of suitable medicaments in accordance with the present invention include those that treat respiratory diseases or disorders. Non-limiting examples of respiratory diseases and disorders include chronic obstructive pulmonary disease (COPD) (including chronic bronchitis and/or emphysema), asthma, bronchitis, cystic fibrosis, idiopathic pulmonary fibrosis and chest infections such as pneumonia.

The term "pharmaceutically acceptable," as used herein, means permitted by a regulatory agency, e.g. of a European or U.S. Federal or state government, or listed in the U.S. Pharmacopeia or other generally recognized pharmacopeia for use in animals, and more particularly in humans.

The terms user, subject and patient are used interchangeably herein and may refer to a mammalian individual, preferably a human being.

The terms micrometers, microns and μm may be used interchangeably. The terms micrograms, mcg and μg may be used interchangeably.

As used herein, the terms respiratory diseases and disorders may be used interchangeably with pulmonary diseases and disorders, respectively.

Each compound used herein may be discussed interchangeably with respect to its chemical formula, chemical name, abbreviation, etc. For example, glycopyrronium bromide may be used interchangeably with glycopyrrolate.

Embodiments of the medicament delivery device of the present invention (also referred to herein as an inhaler) are capable of delivering doses of dry powder medicament in consistent amounts with consistent particle size distributions over a wide range of breathing patterns and flow rates. For example, embodiments of the inhaler can deliver consistent doses to patients that use regular breathing patterns (e.g., tidal breathing or tidal inhalation) to trigger the delivery of medication, and forceful inspiration is not needed. According to a preferred embodiment, the medicament delivery device of the present invention delivers substantially uniform doses and particle size distributions over a wide range of flow rates. Preferably, the device also delivers an effective amount of medicament from smaller doses of medicament in comparison to conventional inhalers and nebulizers. In other words, the device's aerosol engine achieves uniform dose delivery and particle size distributions with efficiency and precision.

According to preferred embodiments, the inhaler detects inhalation and administers medicament in response to the detected inhalation, whereby aerosolized medicament is released into the air flow conduit and becomes entrained into the subject's inhaled air. As described in more detail below, this is preferably achieved through the use of a vibration means (or "vibrating element") for aerosolizing and releasing material into an air flow conduit, wherein the vibrating element preferably creates mechanical vibrations and acoustic vibrations that aerosolize the medicament via synthetic jetting.

According to an embodiment, a user inhales through the mouthpiece of the device, preferably via tidal inhalation, and the dose is delivered over a plurality of consecutive inhalations. Thus, in one embodiment illustrated in FIGS. 1A-1I, the inhaler 100 is configured to activate the transducer 150 more than once to deliver a complete pharmaceutical dose from a single blister 130 to a user. When the user inhales through the mouthpiece, air is drawn into the device's air inlet, through an air flow conduit in the device, and out of the mouthpiece into the user's lungs. As air is being inhaled through the air flow conduit, dry powder medicament is expelled into the airflow pathway and becomes entrained in the user's inhaled air. Thus, the air flow conduit preferably defines an air path from the air inlet to the outlet (i.e., the opening that is formed by the mouthpiece). Each breath cycle includes an inhalation and an exhalation, i.e., each inhalation is followed by an exhalation, so consecutive inhalations preferably refer to the inhalations in consecutive breath cycles. After each inhalation, the user may either exhale back into the mouthpiece of the inhaler, or exhale outside of the inhaler (e.g., by removing his or her mouth from the mouthpiece and expelling the inhaled air off to the side). Preferably, the user exhales outside the inhaler.

According to an embodiment, the inhaler of the present invention contains a plurality of pre-metered doses of a dry powder drug composition comprising at least one medicament, wherein each individual dose of the plurality of pre-metered doses is inside a container, such as a blister. As used herein, a blister is preferably a container that is suitable for containing a dose of dry powder medicament. Preferably, a plurality of blisters is arranged as pockets on a strip, i.e., a blister strip. Access to the medicament doses contained within the pockets of the blister strip is by any suitable access means including tearing, piercing or peeling apart the relevant pockets. According to a preferred embodiment, the individual blisters are arranged on a peelable blister strip, which comprises a base sheet in which blisters are formed to define pockets therein for containing distinct medicament doses and a lid sheet which is sealed to the base sheet in such a manner that the lid sheet and the base sheet can be peeled apart; thus, the respective base and lid sheets are peelably separable from each other to release the dose contained inside each blister. The blisters are preferably arranged in a spaced fashion, more preferably in progressive arrangement (e.g. series progression) on the strip such that each dose is separately accessible. A blister strip and its dose advance mechanism are not required in accordance with all embodiments of the present invention, as one or more doses of dry powder medicament may be contained in an alternative type of container or compartment within the device prior to being aerosolized and expelled to the user.

Figure 33:
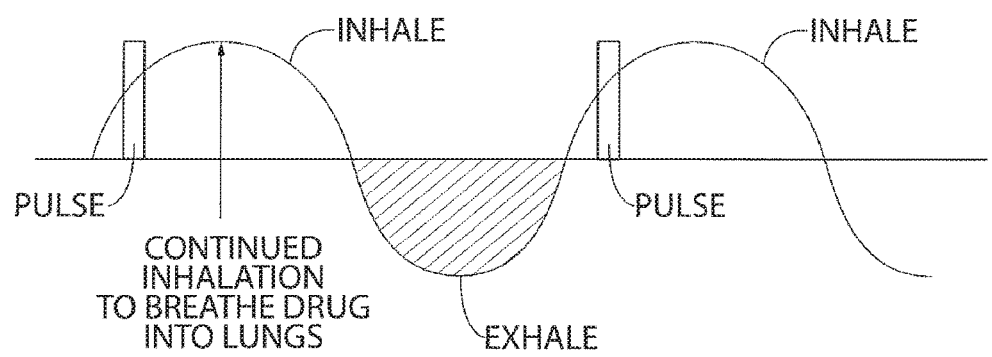
FIG. 33 is a graph showing pulse duration in relation to a breathing cycle.

According to exemplary embodiments, the inhaler comprises an inhalation sensor (also referred to herein as a flow sensor or breath sensor) that senses when a patient inhales through the device; for example, the inhalation sensor may be in the form of a pressure sensor, air stream velocity sensor or temperature sensor. Thus, according to one embodiment, the transducer 150 is activated each time a sensor 1278 (FIG. 11) detects an inhalation by a user such that the dose is delivered over several inhalations by the user. The relatively short time period of transducer 150 activation at the beginning of a user's inhalation and the delivery over several inhalations may allow a user to utilize their natural, tidal breathing pattern to receive the pharmaceutical dose as best seen in FIG. 33.

Figure 34:
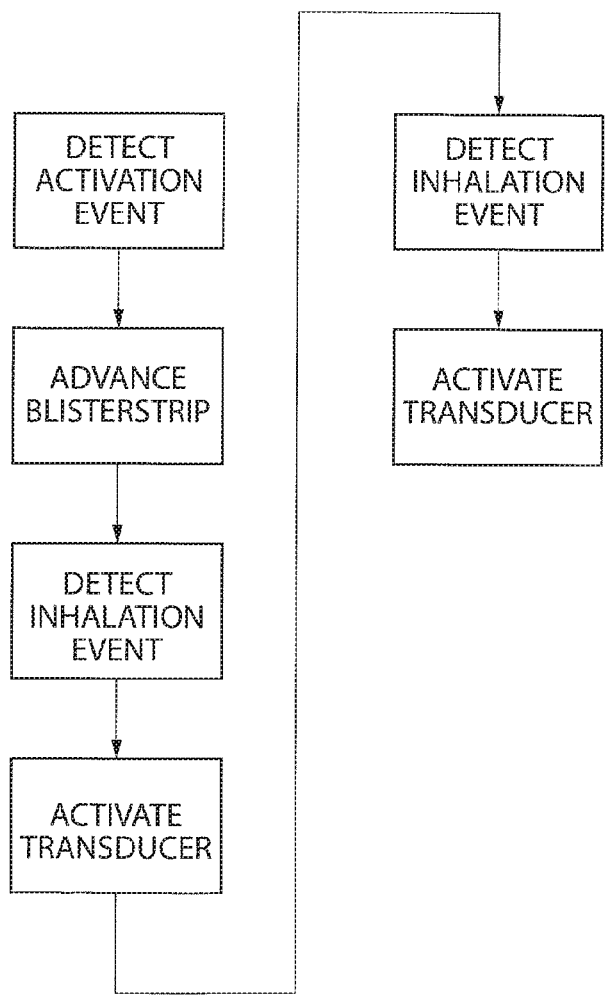
FIG. 34 is a flowchart depicting operation of the inhaler of FIG. 1 according to an embodiment of the invention.

Preferably, the breath sensor is a pressure sensor. Non-limiting examples of pressure sensors that may be used in accordance with embodiments of the present invention include a microelectromechanical system (MEMS) pressure sensor or a nanoelectromechanical system (NEMS) pressure sensor, as described in WO 2016/033418, which is incorporated by reference herein. The inhalation sensor may be located in or near an air flow conduit to detect when a user is inhaling through the mouthpiece in order to trigger the motor to advance a dose. According to a preferred embodiment, the inhaler comprises a pressure sensor pneumatically coupled to an air flow conduit through which the user can inhale; a processor configured to process data received from the sensor to make a determination that inhalation of a breath through the air flow conduit is in progress (or when exhalation is occurring); a controller configured to, responsive to said determination, issue a start dosing signal; and an aerosol engine configured to release dry powder medicament into the air flow conduit during inhalation in response to receiving the start dosing signal. An aerosol engine preferably refers to an assembly that causes a powder formulation to be aerosolized as it is transferred from a container and entrained in a subject's inhaled air flow. Aerosolizing preferably comprises converting a mass of powder inside a container into particles that are sufficiently deagglomerated (i.e., small and light enough) to be carried in the air.

According to an embodiment, the device is configured to administer dry powder medicament during a dosing breath of an inhalation cycle, preferably over the course of multiple dosing breaths. In one embodiment, during each dosing breath, when the patient inhales through the device and the inhalation sensor detects the inhalation, the aerosol engine is triggered to deliver dry powder medicament to the patient by causing medicament in the drug container (e.g., blister) to become aerosolized and entrained in the patient's inhaled air. Preferably, the aerosol engine comprises a vibratory element that vibrates upon activation. According to exemplary embodiments, the aerosol engine comprises a vibrating means such as a transducer (e.g., piezoelectric transducer) that confronts a dosing chamber, as described in more detail below. In some embodiments, the inhalation sensor is configured to signal the detection of a dosing breath only after an activation event has occurred. That activation event may include a selected number of breaths (e.g., 1, 2, 3, 4 or 5 preliminary breaths), a fixed quantity of breaths (e.g., a total volume or mass of air is breathed) or a selected threshold is met. An embodiment of the inhaler's operation is illustrated in FIG. 34, in which an "inhalation event" is a dosing breath.

According to an exemplary embodiment, when the inhalation sensor detects a dosing breath, an electrical signal is supplied to a vibratory element that converts the electrical signal into mechanical vibrations and acoustic energy. The vibratory element is preferably a transducer, more preferably a piezoelectric transducer or "piezo." When the transducer is activated to vibrate, the vibration and resulting acoustic waves causes the dry powder medicament in the container to become aerosolized so that it can be entrained in the patient's inhaled air. According to an embodiment, upon activation of the transducer, at least a portion of the dry powder medicament dose aerosolizes and transfers from a blister into a dosing chamber. In response to the same activation or a subsequent activation of the transducer, mechanical vibration and/or acoustic waves cause at least a portion of the medicament in the dosing chamber to be ejected from one or more openings in the dosing chamber into the air flow conduit so that it becomes entrained in the inhaled breath of the patient. According to an embodiment, at least a portion of the dry powder medicament transfers from a blister into a dosing chamber when the transducer is activated and the same or a subsequent activation of the transducer transfers at least a portion of the medicament from the dosing chamber into the air flow conduit so that it becomes entrained in the inhaled breath of the patient. Preferably, the transducer is triggered by each sensed dosing breath in an inhalation cycle to administer at least a portion of the dry powder medicament dose, whereby the dose is administered over a plurality of dosing breaths.

According to a preferred embodiment, a method of using the inhaler comprises completing an inhalation cycle of consecutive inhalations from the inhaler (e.g., from a mouthpiece of the inhaler). As used herein, an inhalation cycle preferably refers to a user's consecutive inhalations through the inhaler in order to receive a dose of medicament. Consecutive inhalations refer to a series of inhalations over which a dose of dry powder medicament is administered by the inhaler, including whether the subject inhales through the inhaler on every inhalation in the series, or whether the subject periodically inhales air that does not contain medicament over the course of the series. Preferably, the subject inhales through the inhaler on every inhalation over the course of the series. Consecutive inhalations may include dosing breaths, which trigger drug delivery, in addition to breaths that do not trigger drug delivery, such as verifying breaths and dose advance breaths.

The inhaler of embodiments of the present invention is capable of administering a dose of medicament in accordance with several possible dosing schemes (i.e., variations of an inhalation cycle), as described below. A dosing scheme may vary according to the number of consecutive inhalations in an inhalation cycle, the number of dosing breaths in an inhalation cycle, the number of times a transducer is activated in an inhalation cycle (which preferably equals the number of dosing breaths in an inhalation cycle), the total amount of on-time that the transducer is activated over an inhalation cycle, and the amount of time that a transducer is activated in response to each dosing breath. The inhaler (e.g., controller) may be programmed with different drive schemes as described herein; for example, the controller may be configured (programmed) to activate the transducer for a total on-time of 5 seconds or less over 2-20 tidal inhalations and/or the controller may be configured (programmed) to activate the transducer for between about 50-1000 milliseconds (ms) during a dosing breath.

Preferably, an inhalation cycle comprises from 2 to 30 consecutive inhalations, or from 2 to 20 consecutive inhalations, or from 3 to 30 consecutive inhalations, or from 3 to 20 consecutive inhalations, or from 2 to 15 consecutive inhalations, or from 3 to 15 consecutive inhalations, or from 2 to 12 consecutive inhalations, or from 3 to 12 consecutive inhalations, or from 2 to 10 consecutive inhalations, or from 3 to 10 consecutive inhalations, or from 2 to 8 consecutive inhalations, or from 3 to 8 consecutive inhalations, or from 4 to 30 consecutive inhalations, or from 4 to 20 consecutive inhalations, or from 4 to 15 consecutive inhalations, or from 4 to 12 consecutive inhalations, or from 4 to 10 consecutive inhalations, or from 4 to 8 consecutive inhalations, or from 5 to 30 consecutive inhalations, or from 5 to 20 consecutive inhalations, or from 5 to 10 consecutive inhalations, or 30 consecutive inhalations or fewer, or 20 consecutive inhalations or fewer, or 15 consecutive inhalations or fewer, or 12 consecutive inhalations or fewer, or 10 consecutive inhalations or fewer, or 8 consecutive inhalations or fewer, or 6 consecutive inhalations or fewer, or 5 consecutive inhalations or fewer. As described in more detail below, the inhalations in an inhalation cycle may include one or more activation events which do not cause the device to administer medicament (e.g., one or more verifying breaths and/or one or more dose advance breaths as described in more detail below) in addition to a plurality of the dosing breaths, which cause the device to administer medicament.

Exemplary embodiments of the inhaler provide a short duration of administration because so few inhalations are necessary to deliver a dose, especially when fewer than 30 breaths, fewer than 20 breaths, fewer than 15 breaths, fewer than 12 breaths, fewer than 10 breaths, fewer than 8 breaths, or fewer than 6 breaths are needed; for example, the inhaler is capable of delivering a dose of medicament within 5 minutes or less, or within 4 minutes or less, or within 3 minutes or less, or within 2 minutes or less, or preferably within 90 seconds or less, or within 60 seconds or less, or within 45 seconds or less, or within 30 seconds or less.

According to one embodiment, during the first inhalation in an inhalation cycle, the device verifies that it is an actual breath and not a false trigger, and looks for a second inhalation to validate the inhalation; for example, a processor configured to process data received from the sensor makes a determination that inhalation of a breath through the air flow conduit is in progress. Thus, according to one embodiment, the first breath is a verifying breath. Verifying breaths are optional, and not required in every dosing scheme embodiment.

According to another embodiment, at least one inhalation in an inhalation cycle causes the device to advance a dose of medicament into dosing position (referred to as a dose advance breath); for example, by advancing a blister so that the dose of medicament contained inside the blister becomes accessible for administration by the device to the patient. Preferably, an inhalation cycle includes only one dose advance breath. As described herein, any suitable access means may be used to access a dose inside a blister pocket, including tearing, piercing or peeling apart the relevant pockets. According to one embodiment, when an inhalation is detected by the inhalation sensor, voltage is supplied to a motor which causes a blister strip to advance (e.g., by engaging a gear train). The dose advancement mechanism may comprise a cog wheel that cradles the used, empty blisters and moves the blister strip around a track, and a spool sub-assembly that peels lidding from the strip to uncover the next dose.

Thus, according to one embodiment, the first breath of an inhalation cycle is a dose advance breath. According to an alternative embodiment, the first breath of an inhalation cycle is a verifying breath and the second breath is a dose advance breath. According to yet another embodiment, the last breath of an inhalation cycle is a dose advance breath, instead of the first breath. According to still yet another embodiment, the dose is advanced after the last breath of an inhalation cycle and a dose advance breath is not necessary. Preferably, medicament is not administered during a verifying breath or dose advance breath. Verifying breaths and dose advance breaths are also referred to herein as activation events because they may activate the device so that it is ready to administer medicament, but preferably do not cause the device to administer medicament. According to an additional embodiment, the dosing scheme does not include any verifying breaths or dose advance breaths because the dose is advanced by other means, e.g., by pressing a button on the device.

The inhaler is preferably configured to trigger a vibratory element during each dosing breath of an inhalation cycle in order to administer a dose of dry powder medicament over the course of the inhalation cycle. A portion of a dose of dry powder medicament is preferably administered during each dosing breath, although it is possible that a subject may continue taking one or more dosing breaths after the full dose is delivered, in which case medicament may not be administered, or only a negligible amount may be administered, during the last dosing breath(s) in an inhalation cycle. Consecutive dosing breaths preferably refer to a series of inhalations over which a dose of dry powder medicament is administered by the inhaler, including whether the subject inhales through the inhaler on his or her every inhalation over the course of the series, or whether the subject periodically inhales air that does not contain medicament over the course of the series. Preferably, the subject inhales through the inhaler on his or her every dosing breath over the course of the series.

Preferably, an inhalation cycle comprises from 2 to 30 consecutive dosing breaths, or from 2 to 20 consecutive dosing breaths, or from 2 to 15 consecutive dosing breaths, or from 2 to 12 consecutive dosing breaths, or from 2 to 10 consecutive dosing breaths, or from 2 to 8 consecutive dosing breaths, or from 3 to 30 consecutive dosing breaths, or from 3 to 20 consecutive dosing breaths, or from 3 to 15 consecutive dosing breaths. Most preferably, the inhalation cycle comprises from 3 to 12 consecutive dosing breaths, or from 3 to 10 consecutive dosing breaths, or from 3 to 8 consecutive dosing breaths, or from 4 to 12 consecutive dosing breaths, from 4 to 10 consecutive dosing breaths, or from 4 to 8 consecutive dosing breaths, or from 4 to 6 consecutive dosing breaths, or 30 consecutive dosing breaths or fewer, or 20 consecutive dosing breaths or fewer, or 15 consecutive dosing breaths or fewer, or 12 consecutive dosing breaths or fewer, or 10 consecutive dosing breaths or fewer, or 8 consecutive dosing breaths or fewer, or 6 consecutive dosing breaths or fewer, or 5 consecutive dosing breaths or fewer, or 4 consecutive dosing breaths or fewer, or 3 consecutive dosing breaths or fewer. As described above, the consecutive inhalations in each inhalation cycle may comprise one or more verifying breaths and/or one or more dose advance breaths (i.e., activation events) in addition to the dosing breaths.

According to particular embodiments, feedback may be provided to the patient via one or more indicators, e.g., lights that illuminate during an inhalation cycle (e.g., light-emitting diodes, LEDs) and/or a screen on the device that communicates the status of drug delivery. For example, when inhalation is in progress, a light on the device illuminates a first color (e.g., blue) with each inhalation, confirming that the inhalation sequence progressed correctly, and illuminates a second color that is the same or different from the first color (e.g., green) at the completion of the dose.

According to a preferred embodiment, the inhaler comprises a reusable component (also referred to herein as a base or back portion) that attaches to a replaceable component (also referred to herein as a cartridge or front portion), wherein the replaceable component comprises the one or more doses of medicament, such as pre-metered doses of medicament (e.g., a blister strip). According to one embodiment, the reusable component comprises one or more of a power source (e.g., battery), breath sensor, controller, and transducer; and the replaceable cartridge comprises one or more of pre-metered dose(s) of medicament, dose advance mechanism, dosing chamber, air flow conduit, and mouthpiece. For example, the reusable component may comprise the power source and controller; and the disposable cartridge may comprise the one or more pre-metered doses of medicament and dose advance mechanism. Alternative embodiments are also contemplated in which any of the power source, breath sensor, controller, transducer or mouthpiece could form part of the replaceable component instead of the reusable component; and/or any of the dose advance mechanism, dosing chamber or air flow conduit could form part of the reusable component instead of the replaceable component. The reusable component preferably comprises a user interface (e.g., screen display); however, the user interface may alternatively be part of the replaceable component. Also, the replaceable component preferably comprises the air flow conduit; however, the air flow conduit may alternatively be part of the reusable component, or one portion of the air flow conduit may be part of the replaceable component and another portion of the air flow conduit may be part of the reusable component.

According to a preferred method of using the inhaler, the user attaches the cartridge to the base prior to using the device to administer medicament. Thus, the method of using the inhaler may include a first step of attaching the base to the cartridge, prior to using the inhaler to administer medicament. For example, the method may comprise steps of attaching the base to the cartridge, turning on the device (e.g., by pressing a button or touch screen on the inhaler, or by another activation event) and inhaling through the device to initiate dosing. It may not be necessary to attach the cartridge to the base prior to administering each dose, e.g., the method may comprise attaching the cartridge to the base prior to delivery of the first dose of medicament in the cartridge, and the cartridge may remain attached to the base until the last dose of medicament in the cartridge has been delivered; alternatively, a user may remove the cartridge in between doses (e.g., in between each dose, or in between every 2 or 3 doses, etc.) and reattach the cartridge to the base prior to administering a dose. According to one embodiment, the device is configured such that when the cartridge is removed between doses, the device ensures that the next available dose (e.g., in the blister strip) is made available to the patient upon reattachment so doses are not skipped or wasted.

According to a preferred embodiment, the inhaler of the present invention is a handheld device, i.e., it is small enough to be held in a human's hand. This is contrary to conventional nebulizers, which are typically large and bulky, and enable a user to hold only the mouthpiece in his or her hand. For example, the inhaler of the present invention preferably has a width of about 50 mm to about 100 mm, or about 50 mm to about 90 mm, or about 60 mm to about 100 mm, or about 60 mm to about 90 mm, or about 60 mm to about 80 mm; and a height of about 100 mm to about 140 mm, or about 100 mm to about 130 mm, or about 100 mm to about 120 mm, or about 110 mm to about 140 mm, or about 110 mm to about 130 mm, or about 120 mm to about 130 mm; and a depth (excluding the mouthpiece that extends from the surface of the device) of about 50 mm to about 80 mm, or about 50 mm to about 70 mm, or about 50 mm to about 60 mm, or about 60 mm to about 80 mm, or about 60 mm to about 70 mm. For example, the inhaler may have dimensions of about 100-140 mm (height) by about 55-95 mm (width) by about 45-75 mm (depth, excluding the mouthpiece). The mouthpiece may be any size; preferably, the mouthpiece extends about 15 mm to about 70 mm, or about 20 mm to about 70 mm, or about 30 mm to about 70 mm, or about 15 mm to about 60 mm, or about 15 mm to about 50 mm, or about 15 mm to about 40 mm, or about 15 mm to about 30 mm from the surface of the device.

According to a preferred embodiment, the inhaler comprises a controller, i.e., one or more components and associated circuitry integrated into one or more circuit boards for control of the inhaler, data storage and programming interface. Preferably, the inhaler comprises a power source (e.g., a battery, solar cell, etc.) that interfaces with the controller, so that power is provided to the inhaler by the battery. The battery is preferably rechargeable, whereby it can be charged via an external power adapter and allows multiple doses to be administered before requiring recharge. Preferably, the battery is a lithium ion rechargeable battery that provides power for the electronics, dose advance, and excitation of the vibratory element (e.g., piezoelectric transducer). Preferably, the battery meets the following specifications: 0.1-450 mA and voltage 3000-5000 mV, or 3500-4500 mV, or 3700-4300 mV.

According to a preferred embodiment, the inhaler has a flow resistance from about 0.040 $cmH_2O^{0.5}$/LPM to about 0.1 $cmH_2O^{0.5}$/LPM, or from about 0.040 $cmH_2O^{0.5}$/LPM to about 0.090 $cmH_2O^{0.5}$/LPM, or from about 0.050 $cmH_2O^{0.5}$/LPM to about 0.1 $cmH_2O^{0.5}$/LPM, or from about 0.050 $cmH_2O^{0.5}$/LPM to about 0.090 $cmH_2O^{0.5}$/LPM, or from about 0.040 $cmH_2O^{0.5}$/LPM to about 0.085 $cmH_2O^{0.5}$/LPM, or from about 0.050 $cmH_2O^{0.5}$/LPM to about 0.085 $cmH_2O^{0.5}$/LPM, or from about 0.060 $cmH_2O^{0.5}$/LPM to about 0.085 $cmH_2O^{0.5}$/LPM at a flow rate of about 30 liters per minute (LPM). Flow resistance may be determined by known methods, such as, the method described in Example 2. Many commercially available inhalers have a flow resistance that is higher than that of the present invention. For most commercially available inhalers with flow resistance similar to the present invention, their optimal performance is typically at a flow rate of 60 L/min or higher, but many children and adult patients with compromised lung function are unable to generate a flow rate of 60 L/min at that level of resistance, and such sub-optimal flow rates may result in incomplete dispersion of the dry powder, an increase of particle size and ultimately lower dosing to the lower airway. As described below, the inhaler of the present invention is capable of delivering therapeutically effective doses of dry powder medicament at flow rates as low as 15 Liters per minute (L/min or LPM), or as low as 20 LPM, or as low as 25 LPM, or as low as 30 LPM while still achieving the preferred APSD profiles described herein (e.g., MMAD, FPF, etc.).

As discussed herein, the inhaler contains one or more doses of dry powder medicament. According to one embodiment, the inhaler contains a plurality of pre-metered individual doses of dry powder medicament. Each individual dose may be contained inside a container, such as a blister, with the plurality of blister pockets arranged along one or more blister strips (preferably one blister strip). According to one embodiment, the inhaler contains from 1 to 70 doses, or from 1 to 60 doses, or from 1 to 50 doses, or from 1 to 40 doses, or from 1 to 30 doses, or from 10 to 70 doses, or from 10 to 60 doses, or from 10 to 50 doses, or from 15 to 50 doses, or from 20 to 50 doses, or from 25 to 50 doses, or from 35 to 50 doses, or from 10 to 50 doses, or from 15 to 40 doses, or from 20 to 40 doses; preferably from 25 to 40 doses, or from 35 to 40 doses, or from 28 to 35 doses, or from 35 to 35 doses, optionally in pre-metered doses contained in blister strip. For example, the inhaler may be configured to administer any of those dose amounts from a single cartridge that is attachable to a base. According to certain embodiments shown in the figures, a blister strip is arranged around a track (see, e.g., FIG. 2B). Embodiments are also contemplated in which the blister strip is arranged around a double track, whereby the inhaler accommodates more doses (e.g., the track is made longer by extending around the outside or inside of the first track), or the blister may be stored as a coil inside the inhaler instead of being arranged around a track.

According to an embodiment, an individual dose inside the inhaler (e.g., the amount of dry powder drug formulation in a blister) is about 10 mg or less, more preferably about 8 mg or less, about 7 mg or less, about 6 mg or less, about 5 mg or less, about 4 mg or less, about 3 mg or less, about 2.5 mg or less, or about 2 mg or less. For example, the amount of drug formulation in each blister may be from about 0.1 mg to about 10 mg, or from about 0.1 mg to about 5 mg, or from about 0.1 mg to about 4 mg, or from about 0.1 mg to about 3 mg, or from about 0.1 mg to about 2.5 mg, or from about 0.1 mg to about 2 mg, or from about 0.5 mg to about 10 mg, or from about 0.5 mg to about 5 mg, or from about 0.5 mg to about 4 mg, or from about 0.5 mg to about 3 mg, or from about 0.5 mg to about 2.5 mg, or from about 0.5 mg to about 2 mg, or from about 1 mg to about 10 mg, or from about 1 mg to about 5 mg, or from about 1 mg to about 4 mg, or from about 1 mg to about 3 mg, or from about 1 mg to about 2.5 mg, or from about 1 mg to about 2 mg.

Particular embodiments of the device are capable of administering doses of dry powder medicament that are much smaller than those administered by conventional DPI's, particularly in comparison to DPI's that administer a formulation comprising a carrier, such as lactose. For example, Advair® Diskus contains about 12.5 mg of formulation per blister (comprising lactose monohydrate as a carrier); Breo® Ellipta contains about 12.5 mg formulation per blister (comprising lactose monohydrate as a carrier); and Foradil® Aerolizer administers about 25 mg of formulation (comprising lactose as a carrier). In contrast, particular embodiments of the device administer 10 mg or less formulation per dose, or 8 mg or less formulation per dose, or 6 mg or less formulation per dose, or 5 mg or less formulation per dose, or 4 mg or less formulation per dose, or 3 mg or less formulation per dose, or 2.75 mg or less formulation per dose, or 2.5 mg or less formulation per dose, or from about 0.5 mg to about 2.5 mg per dose. For example, particular embodiments of the device administer less than about 10 mg formulation per blister, or less than about 8 mg formulation per blister, or less than about 6 mg formulation per blister, or less than about 5 mg formulation per blister, or less than about 4 mg formulation per blister, or less than about 3 mg formulation per blister, or less than about 2.75 mg formulation per blister, or less than about 2.5 mg formulation per blister, or from about 0.5 mg to about 2.5 mg per blister. Moreover, the device is capable of delivering each dose via normal tidal breathing, instead of via deep or forceful inhalation.

According to a particular embodiment, the dry powder drug formulation in each dose (e.g., in each blister) of the present invention comprises at least one medicament and at least one carrier, such as lactose (e.g., lactose monohydrate). For example, the dry powder drug formulation in each dose (e.g., blister) may comprise at least one medicament in combination with at least 70 wt % carrier (e.g., lactose), or at least 75 wt % carrier, or at least 80 wt % carrier, or at least 85 wt % carrier, or at least 90 wt % carrier, or at least 92 wt % carrier, or at least 95 wt % carrier, or at least 96 wt % carrier, or at least 97 wt % carrier, or at least 97.5 wt % carrier, or at least 98 wt % carrier, or at least 98.5 wt % carrier, or at least 99 wt % carrier, or at least 99.5 wt % carrier, or from 85 wt % to 99.9 wt %, or from 90 wt % to 99.9 wt %, or from 92 wt % to 99.9 wt %, or from 95 wt % to 99.9 wt %, or from 97 wt % to 99.9 wt %, or from 97.5 wt % to 99.9 wt % carrier.

According to one embodiment, the carrier and medicament(s) are blended together by a conventional mixing process, such as high shear mixing; for example, they are not blended by co-spray drying the carrier and medicament(s) together. According to one embodiment, the lactose has a particle size distribution of approximately the following: $D_{10}$: 10 micrometers or less; $D_{50}$: 70 micrometers or less; $D_{90}$: 200 micrometers or less. According to one embodiment, the lactose has a particle size distribution of approximately the following: $D_{10}$: 2 micrometers or more; $D_{50}$: 30 micrometers or more; $D_{90}$: 120 micrometers or more. According to one embodiment, the lactose has a particle size distribution of approximately the following: $D_{10}$: 2-10 micrometers; $D_{50}$: 30-70 micrometers; $D_{90}$: 120-200 micrometers. According to one embodiment, the lactose has a particle size distribution of approximately the following: $D_{10}$: 3-7 micrometers; $D_{50}$: 37-61 micrometers; $D_{90}$: 124-194 micrometers. According to one embodiment, lactose monohydrate used in the formulation is Respitose® ML001.

According to an alternative embodiment, the carrier(s) and/or excipient(s) are blended with the medicament(s) by co-spraying them together, such as by spray drying.

According to particular embodiments, the total amount of the at least one medicament in the drug formulation (e.g., one, two, or three medicaments) is from 0.1 wt % to 80 wt %, or from 0.1 wt % to 70 wt %, or from 0.1 wt % to 60 wt %, or from 0.1 wt % to 50 wt %, or from 0.1 wt % to 40 wt %, or from 0.1 wt % to 35 wt %, or from 0.1 wt % to 30 wt %, or from 0.1 wt % to 25 wt %, or from 0.1 wt % to 20 wt %, or from 0.1 wt % to 15 wt %, or from 0.1 wt % to 12 wt %, or from 0.1 wt % to 10 wt %, or from 0.1 wt % to 8 wt %, or from 0.1 wt % to 6 wt %, or from 0.1 wt % to 5 wt %, or from 0.1 wt % to 4 wt %, or from 0.1 wt % to 3 wt %, or from 0.1 wt % to 2.5 wt %, or from 0.1 wt % to 2 wt %, or from 0.1 wt % to 1.5 wt %, or from 0.1 wt % to 1 wt %. The formulation may optionally comprise one or more excipients, such as magnesium stearate. Examples of API's that may be included in the formulations are described below and in the Examples. According to one embodiment, each drug formulation comprises a LAMA (e.g., glycopyrronium bromide or tiotropium bromide) and/or a LABA (e.g., formoterol fumarate). According to another embodiment, each drug formulation comprises albuterol sulfate.

According to certain embodiments in which the device contains a blister strip, each blister contains the same drug formulation in the same amount (with the understanding that there may be slight differences across blisters due to normal manufacture variability). According to alternative embodiments, different blisters in a device may contain different types and/or amounts of drug formulation in order to provide alternative therapeutic regimens; for example, a series of blisters on a blister strip may contain two different drug formulations in alternating blisters, or a first series of blisters may contain a first formulation and a second series of blisters may contain a second formulation, etc.

According to one embodiment, a method of using the inhaler to administer a dose of medicament (i.e., a therapeutically effective amount of medicament) comprises completing an inhalation cycle of from 2 to 30 consecutive inhalations, or from 2 to 20 consecutive inhalations, or from 3 to 30 consecutive inhalations, or from 3 to 20 consecutive inhalations, or from 2 to 15 consecutive inhalations, or from 3 to 15 consecutive inhalations, or from 2 to 12 consecutive inhalations, or from 3 to 12 consecutive inhalations, or from 2 to 10 consecutive inhalations, or from 3 to 10 consecutive inhalations, or from 2 to 8 consecutive inhalations, or from 3 to 8 consecutive inhalations, or from 4 to 30 consecutive inhalations, or from 4 to 20 consecutive inhalations, or from 4 to 15 consecutive inhalations, or from 4 to 12 consecutive inhalations, or from 4 to 10 consecutive inhalations, or from 4 to 8 consecutive inhalations, or from 5 to 30 consecutive inhalations, or from 5 to 20 consecutive inhalations, or from 5 to 10 consecutive inhalations (preferably 30 consecutive inhalations or fewer, or 20 consecutive inhalations or fewer, or 15 consecutive inhalations or fewer, or 12 consecutive inhalations or fewer, or 10 consecutive inhalations or fewer, or 8 consecutive inhalations or fewer, or 6 consecutive inhalations or fewer, or 5 consecutive inhalations or fewer) from the mouthpiece of the inhaler by tidal inhalation, wherein the inhaler comprises one or more doses of dry powder medicament. Each individual dose may be about 10 mg or less, about 8 mg or less, about 7 mg or less, about 6 mg or less, about 5 mg or less, about 4 mg or less, about 3 mg or less, about 2.5 mg or less, or about 2 mg or less, and an aerosol engine comprising a vibratory element for aerosolizing a dose, wherein the dose is administered by the inhaler over the course of the inhalation cycle.

According to one embodiment in which the device contains a blister strip, a method of using the inhaler to administer a dose of medicament from a blister (i.e., a therapeutically effective amount of medicament) comprises completing an inhalation cycle of from 2 to 30 consecutive inhalations, or from 2 to 20 consecutive inhalations, or from 3 to 30 consecutive inhalations, or from 3 to 20 consecutive inhalations, or from 2 to 15 consecutive inhalations, or from 3 to 15 consecutive inhalations, or from 2 to 12 consecutive inhalations, or from 3 to 12 consecutive inhalations, or from 2 to 10 consecutive inhalations, or from 3 to 10 consecutive inhalations, or from 2 to 8 consecutive inhalations, or from 3 to 8 consecutive inhalations, or from 4 to 30 consecutive inhalations, or from 4 to 20 consecutive inhalations, or from 4 to 15 consecutive inhalations, or from 4 to 12 consecutive inhalations, or from 4 to 10 consecutive inhalations, or from 4 to 8 consecutive inhalations, or from 5 to 30 consecutive inhalations, or from 5 to 20 consecutive inhalations, or from 5 to 10 consecutive inhalations (preferably 30 consecutive inhalations or fewer, or 20 consecutive inhalations or fewer, or 15 consecutive inhalations or fewer, or 12 consecutive inhalations or fewer, or 10 consecutive inhalations or fewer, or 8 consecutive inhalations or fewer, or 6 consecutive inhalations or fewer, or 5 consecutive inhalations or fewer) from the mouthpiece of the inhaler by tidal inhalation, wherein the inhaler comprises a plurality of pre-metered doses of dry powder medicament, wherein each individual dose is about 10 mg or less, about 8 mg or less, about 7 mg or less, about 6 mg or less, about 5 mg or less, about 4 mg or less, about 3 mg or less, about 2.5 mg or less, or about 2 mg or less contained inside a blister, and an aerosol engine comprising a vibratory element for aerosolizing each dose, wherein the dose is administered by the inhaler over the course of the inhalation cycle.

According to an embodiment, energy transfer (e.g., in the form of mechanical vibrations and/or acoustic energy) from the vibratory element to the container (e.g., blister on a blister strip) causes the device to administer the therapeutically effective dose of medicament over the course of the inhalation cycle. According to an embodiment, energy transfer (e.g., in the form of mechanical vibrations and/or acoustic energy) from the vibratory element to a container (e.g., blister) causes the device to administer at least 75%, or at least 80%, or at least 85%, or at least 90%, or at least 95%, or at least 96%, or at least 97%, or at least 98%, or at least 99%, or 100% of the drug formulation in the dose (e.g., contained inside a blister) over the course of the inhalation cycle. The percentage of powder left in the dose may be determined, for example, by weighing the container before and after an inhalation cycle and determining the % difference. Preferably, all the dry powder inside the container is administered over the course of an inhalation cycle (with the understanding that a small but consistent amount of powder may still be left in the container after the entire dose is administered; for example, a slight film, or negligible amount, of powder may remain on the surface of the container), or substantially all the contents are administered from the container.

According to preferred embodiments, the inhaler is capable of achieving these levels of blister clearance over a wide range of user flow rates, for example, at flow rates as low as 15 L/min (LPM), or ranging from about 15 L/min to about 90 L/min, or from about 15 L/min to about 60 L/min, or about 15 L/min to about 30 L/min, or about 22 L/min to about 32 L/min, or about 30 L/min to about 60 L/min, or about 30 L/min to about 90 L/min. Thus, according to preferred embodiments, the entire dose contained inside a blister, or nearly the entire dose, can be administered over the course of an inhalation cycle (e.g., over 5-10 consecutive inhalations, or over 4-8 dosing breaths, etc.) regardless of whether a user that inhales through the device via tidal inhalation or via a strong inhalation, and also regardless of whether the user has compromised lung function. Preferably, the device also achieves these levels of blister clearance for all of the doses contained inside the device, e.g., for all the doses contained in a blister strip, or for at least 90% of the doses contained inside the device. This ability to deliver consistent doses across a wide range of flow rates is contrary to conventional DPI's.

According to preferred embodiments, the inhaler of the present invention administers from 65% to 135%, or from 75% to 125%, or from 80% to 120% of a targeted delivered dose of a medicament for each dose contained in a device and/or the device administers a mean of from 65% to 135%, or from 75% to 125%, or from 80% to 120% of a targeted delivered dose of a medicament for all of the doses contained in a device or for 90% of the doses contained in a device. For example, the device maintains a delivered dose uniformity of ±20% or ±25% or ±35% for all of the doses contained in a device or for 90% of the doses contained in a device. Preferably, this delivered dose uniformity is achieved at flow rates as low as 15 L/min (LPM), or ranging from about 15 L/min to about 90 L/min, or from about 15 L/min to about 60 L/min, or from about 15 L/min to about 30 L/min, or about 22 L/min to about 32 L/min, or from about 30 L/min to about 60 L/min, or from about 30 L/min to about 90 L/min or at flow rates of 15 L/min and/or 30 L/min and/or 60 L/min and/or 90 L/min. As used herein, a targeted delivered dose preferably refers to the nominal dose of medicament that is prescribed by a physician to be delivered by the inhaler. The targeted delivered dose of medicament is not necessarily the same as the amount of loaded dose that is contained inside each blister; for example, a blister may contain 5 mcg loaded dose of medicament with a targeted delivered dose or nominal dose of 4 mcg. The amount of a dose that is administered or delivered by the inhaler preferably refers to an amount that exits the inhaler and that can be measured by in vitro test methods. The actual amount of drug delivered to a subject's lungs will depend on patient factors, such as anatomical attributes and inspiratory flow profile.

According to preferred embodiments, the inhaler delivers a fine particle fraction (FPF) of at least 30%, or at least 35%, or at least 40%, or at least 45%, or at least 50%, or from about 30% to about 90%, or from about 30% to about 80%, or from about 30% to about 70%, or from about 30% to about 60%, or from about 30% to about 50%, or from about 40% to about 90%, or from about 40% to about 80%, or from about 40% to about 70%, or from about 40% to about 60%. As used herein, FPF refers to the percentage of the delivered dose that has an aerodynamic diameter less than or equal to 5 micrometers (μm). Preferably, this FPF is achieved at flow rates as low as 15 L/min, or ranging from about 15 L/min to about 90 L/min, or from about 15 L/min to about 60 L/min, or from about 15 L/min to about 30 L/min, or from about 22 L/min to about 32 L/min, or from about 30 L/min to about 60 L/min, or from about 30 L/min to about 90 L/min or at flow rates of 15 L/min and/or 30 L/min and/or 60 L/min and/or 90 L/min. Preferably, the device achieves this FPF for a single dose or for all of the doses contained inside the inhaler, e.g., for all the doses contained on a blister strip, or for at least 90% of the doses contained inside the inhaler. Preferably, this FPF is the mean for all of the doses contained inside the inhaler.

According to preferred embodiments, the inhaler of the present invention delivers dry powder medicament comprising particles having a size sufficiently small so as to be delivered to the lungs. For optimal delivery to the lungs, the dry powder preferably should be micronized or spray dried to a mass median aerodynamic diameter powder size of from about 0.1 microns to about 10 microns, preferably from about 0.5 microns to about 6 microns. However, other methods for producing controlled size particles, e.g. supercritical fluid processes, controlled precipitation, etc., also advantageously may be employed. "Mass median aerodynamic diameter" or "MMAD" as used herein preferably refer to the median aerodynamic size of a plurality of particles, typically in a polydisperse population. The "aerodynamic diameter" is preferably the diameter of a unit density sphere having the same settling velocity, generally in air, as a powder and is therefore a useful way to characterize an aerosolized powder or other dispersed particle or particle formulation in terms of its settling behavior. MMAD is determined herein by cascade impaction.

According to preferred embodiments, the inhaler delivers dry powder formulations having an MMAD of about 10 μm (microns) or less, or about 8 microns or less, or about 6 microns or less, or about 5 microns or less, or about 4 μm or less, or about 3.75 microns or less, or about 3.5 microns or less, or about 3.0 microns or less, or from about 0.1 μm to about 10 μm, or from about 0.1 μm to about 8 μm, or from about 0.1 μm to about 6 μm, or from about 0.1 μm to about 5 μm, or from about 0.1 μm to about 4 μm, or from about 1 μm to about 10 μm, or from about 1 μm to about 8 μm, or from about 1 μm to about 6 μm, or from about 1 μm to about 5 μm, or from about 1 μm to about 4 μm. Preferably, this MMAD is achieved at flow rates as low as 15 L/min, ranging from about 15 L/min to about 90 L/min, or from about 15 L/min to about 60 L/min, or from about 15 L/min to about 30 L/min, or from about 22 L/min to about 32 L/min, or from about 30 L/min to about 60 L/min, or from about 30 L/min to about 90 L/min or at flow rates of 15 L/min and/or 30 L/min and/or 60 L/min and/or 90 L/min. Preferably, the device achieves this MMAD for all of the doses contained inside the device, e.g., for all the doses contained in a blister strip, or for at least 90% of the doses contained inside the device. Preferably, this MMAD is the mean for all of the doses contained inside the device.

According to a preferred embodiment, the inhaler's vibratory element is a piezoelectric transducer, embodiments of which are described in more detail below. According to one embodiment, the amount of voltage supplied to the vibratory element (e.g., piezoelectric transducer) when it is activated to vibrate is from about 180-260 V p-p, or about 190-250 V p-p, or preferably about 200-240 V p-p. According to one embodiment, the piezoelectric transducer is vibrated at a frequency from about 36 kHz to about 43 kHz, or about 37 kHz to about 43 kHz, or about 38 kHz to about 43 kHz, or about 36 kHz to about 42 kHz, or about 36 kHz to about 41 kHz, or about 36 kHz to about 40 kHz, or about 36 kHz to about 39 kHz, or about 37 kHz to about 42 kHz, or about 37 kHz to about 41 kHz, or about 37 kHz to about 40 kHz, or about 38 kHz to about 42 kHz, or about 38 kHz to about 41 kHz, or about 38 kHz to about 40 kHz, or about 38 kHz to about 39 kHz.

According to one embodiment, upon activation by a dosing breath, the piezoelectric transducer (piezo) is activated to vibrate for between about 50 ms to about 1000 ms upon each inhalation. Each activation of the piezo in response to a dosing breath may be referred to as a burst or pulse. Preferably, this activation or burst is effective to aerosolize at least a portion of a dose toward the beginning of a user's inhalation so that the remainder of the inhalation is chase air that draws the aerosolized dose (or portion thereof) into the user's lungs. According to additional embodiments, the piezoelectric transducer is activated to vibrate for from about 50 ms to about 1000 ms, or from about 50 ms to about 900 ms, or about 50 ms to about 800 ms, about 50 ms to about 700 ms, or about 50 ms to about 600 ms, or about 50 ms to about 500 ms, or about 50 ms to about 400 ms, or about 50 ms to about 300 ms, or about 50 ms to about 200 ms, or about 50 ms to about 100 ms, or about 100 ms to about 900 ms, or about 100 ms to about 800 ms, or about 100 ms to about 700 ms, or about 100 ms to about 600 ms, or about 100 ms to about 500 ms, or about 100 ms to about 400 ms, or about 100 ms to about 300 ms, or about 100 ms to about 200 ms upon each dosing breath.

In accordance with different dosing scheme embodiments, the piezo may be activated for different amounts of time over the course of an inhalation cycle, or may be activated for the same amount of time over the course of an inhalation cycle. For example, the piezo may be activated for 100 ms for each of the first four dosing breaths, and 300 ms for each of the subsequent four dosing breaths over the course of eight total dosing breaths in an inhalation cycle (for a total of 1.6 seconds of "on-time"). According to another example, the piezo may be activated for 500 ms for each of four total dosing breaths in an inhalation cycle (for a total "on-time" of 2 seconds). In one embodiment, the transducer 150 is activated for between about 100 milliseconds to about 500 milliseconds during the first burst of a series of bursts (e.g., from 3 bursts to 12 bursts, or from 3 bursts to 10 bursts, or from 3 bursts to 8 bursts, or from 3 bursts to 6 bursts) to deliver the contents of a container, such as a single blister 130, over the course of the series.

The "on-time" preferably refers to the total amount of time the transducer is activated at its resonant frequency, sufficient to cause synthetic jetting in the dosing chamber, over the course of an inhalation cycle, i.e., the number of bursts that occur at a resonant frequency of the transducer sufficient to cause synthetic jetting (e.g., 4 bursts), multiplied by the amount of time per burst (e.g., 500 ms), over the inhalation cycle (4×500 ms=2 seconds on-time). For example, if a transducer having a resonant frequency between 38-42 kHz is activated a total of 4 times at that frequency for 500 ms each time because the inhalation cycle includes 4 dosing breaths, and each of those activations occurs at a resonant frequency of the transducer sufficient to generate synthetic jetting, the total on-time for that inhalation cycle is 2 seconds (with brief interruptions by hop frequencies included in the on-time, as described herein). An "off-time" is not part of the on-time and preferably includes those periods of time during an inhalation cycle when the transducer is not being activated, or the transducer is activated at one or more frequencies that do not cause the dosing chamber to resonate sufficient to cause synthetic jetting (e.g., the transducer that is resonant at 38-42 kHz runs at a frequency of 10 kHz in between dosing breaths, for a total of 20-30 seconds of off-time over the course of the inhalation cycle), and those "off-time" periods of activation are not considered to be part of the on-time.

According to an embodiment, the transducer is activated to vibrate for a total of 5 seconds or less "on-time" over the course of an inhalation cycle (according to any dosing scheme, e.g., 10 bursts at 500 ms each, etc.), or for a total of 4 seconds or less, or for a total of 3 seconds or less, or for a total of 2 seconds or less, or for a total of from about 1 second to about 5 seconds, or about 1 second to about 4 seconds, or about 1 second to about 3 seconds, or about 1 second to about 2 seconds, or about 1 second to about 1.8 seconds, or about 1 second to about 1.6 seconds, or about 1 second to about 1.4 seconds, or about 1.2 seconds to about 3 seconds, or about 1.2 seconds to about 2 seconds.

According to one embodiment, the aerosol engine is capable of delivering the therapeutically effective dose (e.g., from a blister 130) over the course of an inhalation cycle comprising at least three piezo bursts at its resonant frequency, or over at least four piezo bursts, or over at least five piezo bursts, or over at least six piezo bursts, or over at least seven piezo bursts, or over at least eight piezo bursts, or over at least nine piezo bursts, or over at least ten piezo bursts, when the piezo is activated to vibrate for a total on-time of 5 seconds or less over the course of an inhalation cycle, as set forth above. For example, an inhalation cycle may comprise from 3 to 12 piezo bursts at its resonant frequency, or from 3 to 10 piezo bursts, or from 3 to 8 piezo bursts, or from 4 to 12 piezo bursts, from 4 to 10 piezo bursts, or from 4 to 8 piezo bursts, or from 4 to 6 piezo bursts, or 30 piezo bursts or fewer, or 20 piezo bursts or fewer, or 15 piezo bursts or fewer, or 12 piezo bursts or fewer, or 10 piezo bursts or fewer, or 8 piezo bursts or fewer, or 6 piezo bursts or fewer, or 5 piezo bursts or fewer, or 4 piezo bursts or fewer, or 3 piezo bursts or fewer.

According to an embodiment, the medicament delivery device delivers at least 0.1 micrograms (µg) of API per piezo activation (burst), or at least 0.5 µg API per burst, or at least 1 µg API per burst, or at least 2 µg API per burst, or at least 3 µg API per burst, or at least 4 µg API per burst, or at least 5 µg API per burst, or at least 6 µg API per burst, or at least 7 µg API per burst, or at least 8 µg API per burst. The amount of API delivered per burst may vary depending on the amount or wt % of API in the dose. The medicament delivery device may deliver different amounts of API per burst over the course of an inhalation cycle; for example, the amount of API delivered by the first burst, or the first two bursts, may be higher than the amount of API delivered by the last burst, or the last two bursts, respectively. In one embodiment, a burst (e.g., the first burst in response to a first dosing breath) delivers at least about 20%, or at least about 30%, or at least about 40%, or at least about 50%, or at least about 60% of the dose.

Examples of different drive schemes are provided in Example 4. In the example of a dry powder drug formulation comprising at least one API in combination with at least 90 wt % carrier (e.g., lactose), or at least 92 wt % carrier, or at least 95 wt % carrier, or at least 96 wt % carrier, or at least 97 wt % carrier, or at least 97.5 wt % carrier, or at least 98 wt % carrier, or at least 98.5 wt % carrier, or at least 99 wt % carrier, or at least 99.5 wt % carrier, or from 85 wt % to 99.9 wt %, or from 90 wt % to 99.9 wt %, or from 92 wt % to 99.9 wt %, or from 95 wt % to 99.9 wt %, or from 97 wt % to 99.9 wt %, or from 97.5 wt % to 99.9 wt % carrier, in one embodiment, the first burst delivers at least 0.5 micrograms of the API, or at least 1 micrograms of the API, or at least 1.5 micrograms of the API, or at least 2 micrograms of the API, or at least 3 micrograms of the API, or at least 4 micrograms of the API, or at least 5 micrograms of the API, or at least 6 micrograms of the API, or at least 7 micrograms of the API, or at least 8 micrograms of the API, or from about 0.5 micrograms to about 8 micrograms, or from about 0.5 micrograms to about 6 micrograms, or from about 0.5 micrograms to about 4 micrograms of API.

According to one embodiment, the medicament delivery device administers at least about 10%, or at least about 15%, or at least about 20%, or at least about 25%, or at least about 30%, or at least about 40%, or at least about 50%, or at least about 60% of the dose of medicament in response to the first dosing breath (i.e., on the first burst), and the remainder of the dose is administered over the remaining dosing breaths in the inhalation cycle. Stated another way, the medicament delivery device may be configured to administer at least about 10%, or at least about 15%, or at least about 20%, or at least about 25%, or at least about 30%, or at least about 40%, or at least about 50%, or at least about 60% of the dry powder medicament dose in response to a first dosing breath in an inhalation cycle.

In the example of a dry powder drug formulation comprising at least one API in combination with at least 90 wt % carrier (e.g., lactose), or at least 92 wt % carrier, or at least 95 wt % carrier, or at least 96 wt % carrier, or at least 97 wt % carrier, or at least 97.5 wt % carrier, or at least 98 wt % carrier, or at least 98.5 wt % carrier, or at least 99 wt % carrier, or at least 99.5 wt % carrier, or from 85 wt % to 99.9 wt %, or from 90 wt % to 99.9 wt %, or from 92 wt % to 99.9 wt %, or from 95 wt % to 99.9 wt %, or from 97 wt % to 99.9 wt %, or from 97.5 wt % to 99.9 wt % carrier, in one embodiment (e.g., Example 4), the transducer is activated four times from about 400 milliseconds to about 600 milliseconds each time to deliver the complete pharmaceutical dose. The first burst may be configured to deliver about 70% to about 80% of the dose originally in the blister 130. The second, third, and fourth burst may each be configured to deliver about 5% to about 15% of the dose originally in the blister 130.

In one embodiment (e.g., Example 4), the first burst delivers at least about 20%, or at least about 30%, or at least about 40%, or at least about 50%, or at least about 60% of the targeted delivered dose of medicament; or from about 40% to about 85% of the targeted delivered dose. According to another embodiment, the first burst delivers at least about 20%, or at least about 30%, or at least about 40%, or at least about 50%, or at least about 60% of the medicament in the dose (e.g., in a blister 130). In one embodiment, the second burst delivers at least about 5%, or at least about 10%, or at least about 20% of the original medicament amount in the blister 130. In one embodiment, the third and fourth bursts each deliver at least about 1%, or at least about 5%, or at least about 10% of the original medicament dose in the blister. In one embodiment, the remaining bursts deliver the remainder of the original medicament dose in the blister.

According to an embodiment, as described in more detail below, upon each activation of the piezoelectric transducer, at least a portion of the dry powder medicament dose aerosolizes and transfers from a blister into a dosing chamber, whereby the acoustic waves cause the medicament to be ejected from one or more openings in the dosing chamber into the air flow conduit so that it becomes entrained in the inhaled breath of the patient. Preferably, the inhaler of the present invention employs synthetic jetting to help aerosolize the drug powder. Synthetic jetting has been described in U.S. Pat. Nos. 7,318,434; 7,779,837; 7,334,577; and 8,322,338, which are incorporated by reference herein. As described in the aforesaid patents, if a chamber is bound on one end by an acoustic wave generating device and on the other end by a rigid wall with a small orifice, when acoustic waves are emitted at high enough frequency and amplitude from the generator, a jet of air that emanates from the orifice outward from the chamber can be produced. The jet, or so-called synthetic jet, is comprised of a train of vortical air puffs that are formed at the orifice.

According to particular embodiments, the piezo confronts a dosing chamber, and is capable of achieving maximum synthetic jetting out of the opening(s) in the dosing chamber when the piezo is activated for as few as 50 ms, or as few as 100 ms in a single burst, or as few as 200 ms in a single burst, or as few as 300 ms in a single burst. Preferably, the synthetic jetting achieves at least 0.5 V, or at least 0.6 V, or at least 0.7 V, or at least 0.8 V, or at least 0.9 V, or at least 1.0 V, or at least 1.1 V, or at least 1.2 V, or at least 1.3 V, or at least 1.4 V, or at least 1.5 V, or at least 1.6 V, or at least 1.7 V; for example, from 0.5 V to 1.7 V, or 0.5 V to 1.6 V, or 0.5 V to 1.5 V, or 0.5 V to 1.4 V, or 0.5 V to 1.3 V, or 0.5 V to 1.2 V, or 0.5 V to 1.0 V, e.g., as quantified by an oscilloscope which converts pressure signals into voltages. Synthetic jetting may be observed and quantified in accordance with the procedure described in Example 1. As described in Example 1, the aerosol engine is connected to a Pneumotach Amplifier 1 (PA-1), which measures gas flow coming out of the dosing chamber opening(s). A differential pressure signal is measured and amplified to provide an analog output proportional to the flow rate. The PA-1 is connected to an oscilloscope, which converts the signal to voltages.

As demonstrated by the in vitro and in vivo studies described herein, the inhaler is capable of delivering therapeutically effective amounts of dry powder medicament(s) to a subject's lungs, preferably for the treatment of a respiratory disease or disorder, or one more symptoms thereof (e.g., selected from the group comprising or consisting of COPD, asthma, cystic fibrosis, IPF, etc.), preferably when the subject inhales through the inhaler using tidal inhalation. The inhaler is capable of delivering such therapeutically effective amounts within 80% to 120% of a mean delivered dose across a wide range of flow rates (e.g., 15-90 LPM or 15-60 LPM or 30-90 LPM or 30-60 LPM), and preferably across a wide range of transducer drive schemes, wherein the drive schemes vary by the number of bursts (e.g., 4-8 bursts) and the amount of "on-time" per burst (e.g., 100 ms/burst to 500 ms/burst), e.g., for a total "on-time" ranging from about 1 second to about 5 seconds over all the bursts.

The device preferably maintains a consistent aerodynamic particle size distribution (APSD) across different flow rates and preferably across different drive schemes, wherein the mass median aerodynamic diameter (MMAD) is consistently about 10 μm (microns) or less, or about 8 microns or less, or more preferably about 6 microns or less, or about 5 microns or less, or about 4 μm or less, or about 3.75 microns or less, or about 3.5 microns or less, or about 3.0 microns or less, or from about 0.1 μm to about 10 μm, or from about 0.1 μm to about 8 μm, or from about 0.1 μm to about 6 μm, or from about 0.1 μm to about 5 μm, or from about 0.1 μm to about 4 μm, or from about 1 μm to about 10 μm, or from about 1 μm to about 8 μm, or from about 1 μm to about 6 μm, or from about 1 μm to about 5 μm, or from about 1 μm to about 4 μm. Preferably, the FPF is also consistent across different flow rates and drive schemes, e.g., at least 30%, or at least 35%, or at least 40%, or at least 45%, or at least 50%, or from about 30% to about 90%, or from about 30% to about 80%, or from about 30% to about 70%, or from about 30% to about 60%, or from about 30% to about 50%, or from about 40% to about 90%, or from about 40% to about 80%, or from about 40% to about 70%, or from about 40% to about 60%.

According to one embodiment, the medicament delivery device comprises a dosing chamber comprising an interior that is configured to contain dry powder medicament, a transducer confronting the dosing chamber, wherein the dosing chamber and the transducer are acoustically resonant such that the dosing chamber is configured to resonate in response to an activation of the transducer, and a controller electrically coupled to the transducer and configured to send an electrical signal that activates the transducer when the device senses a subject's tidal inhalation (e.g., the device contains a program code capable of generating said electric signal). The medicament delivery device preferably has a flow resistance in a range from about 0.040 cmH2O0.5/LPM to about 0.1 cmH2O0.5/LPM at 30 liters per minute (LPM) and is capable of delivering a therapeutically effective dose of dry powder medicament in response to between 2-20 tidal inhalations, the dose having a mass median aerodynamic diameter (MMAD) of about 6 microns or less and a fine particle fraction of at least 30%.

According to another embodiment, a method of treating a respiratory disease or condition (e.g., COPD, asthma, CF, IPF, etc.), or one or more symptoms thereof (e.g., a method of increasing a subject's $FEV_1$) comprises inhaling a therapeutically effective dose of dry powder medicament through a medicament delivery device using between 2-20 tidal inhalations over the course of an inhalation cycle, the inhalation cycle comprising dosing breaths, wherein the medicament delivery device comprises a vibratory element that is activated upon each dosing breath and causes dry powder medicament to be aerosolized within a dosing chamber and expelled from one or more openings in the dosing chamber into an air flow conduit, wherein pressure oscillations in the dosing chamber are sufficiently high at the one or more openings to aerosolize and expel the dry powder medicament via synthetic jetting. The medicament delivery device preferably has a flow resistance in a range from about 0.040 cmH2O0.5/LPM to about 0.1 cmH2O0.5/LPM at 30 liters per minute (LPM) and is capable of delivering the dose of dry powder medicament in response to tidal inhalation (e.g., in response to flow rates at least within a range of about 15 LPM to about 30 LPM), wherein the dose of dry powder medicament delivered by the medicament delivery device has a mass median aerodynamic diameter (MMAD) of about 6 microns or less and a fine particle fraction of at least 30%. Preferably, the dose of medicament is delivered within 5 minutes or less, or within 4 minutes or less, or within 3 minutes or less, or within 2 minutes or less, or preferably within 90 seconds or less, or within 60 seconds or less, or within 45 seconds or less, or within 30 seconds or less. Preferably, the medicament delivery device is configured to administer at least about 10%, or at least about 15%, or at least about 20%, or at least about 25%, or at least about 30%, or at least about 40%, or at least about 50%, or at least about 60% of the dry powder medicament dose in response to a first dosing breath in an inhalation cycle.

According to another embodiment, a method of treating COPD, or one or more symptoms thereof (e.g. for the long-term, maintenance bronchodilator treatment of airflow obstruction in patients with chronic obstructive pulmonary disease (COPD), including chronic bronchitis and/or emphysema) comprises completing an inhalation cycle of from 2 to 20 consecutive inhalations from the inhaler by tidal breathing. Preferably, the inhaler comprises pre-metered dry powder doses and an aerosol engine comprising a vibratory element for aerosolizing each dose. The dose contained inside the blister may be about 5 mg or less, wherein the dose of medicament is administered by the inhaler over the course of the inhalation cycle. Preferably, the inhaler administers approximately the same or greater amount of API per dose compared to a passive device that is configured to deliver the same amount of API per dose (e.g., wherein the passive device has no vibratory element and delivers a greater amount of dry powder per dose). The medicament delivery device preferably has a flow resistance in a range from about 0.040 cmH2O0.5/LPM to about 0.1 cmH2O0.5/LPM at 30 liters per minute (LPM) and is capable of delivering the dose of dry powder medicament in response to tidal inhalation (e.g., in response to flow rates at least within a range of about 15 LPM to about 30 LPM), wherein the dose of dry powder medicament delivered by the medicament delivery device has a mass median aerodynamic diameter (MMAD) of about 6 microns or less and a fine particle fraction of at least 30%. Preferably, the dose of medicament is delivered within 5 minutes or less, or within 4 minutes or less, or within 3 minutes or less, or within 2 minutes or less, or preferably within 90 seconds or less, or within 60 seconds or less, or within 45 seconds or less, or within 30 seconds or less.

Preferably, the time to maximum $FEV_1$ after using the inhaler of the present invention to administer a dose is less than the time to maximum $FEV_1$ after using a passive inhaler to administer a dose containing the same amount of API. Preferably, the inhaler of the present invention exhibits a higher $C_{max}$ following administration of a dose compared to the $C_{max}$ exhibited by a passive inhaler used to administer a dose containing the same amount of API. Preferably, use of the inhaler of the present invention to administer a dose results in a faster appearance of API in plasma than a passive inhaler used to administer a dose containing the same amount of API, as demonstrated by $t_{max}$.

Embodiments of the present invention relate to a blister strip adapted for use in an inhaler. According to particular embodiments, the dimensions of the blister strip, the volume of the blister pockets, and the volume of the drug pellets dispensed into the blister strip, are smaller than competitive products. The smaller pellets and blister pockets may require precise manufacturing methods to ensure that correct pellet sizes are dispensed. The strip is preferably stored in a track instead of a coil, as compared to competitive products; however, embodiments are contemplated in which the strip is stored as a coil inside the inhaler. The following objectives were achieved in accordance with embodiments of the blister strip: minimizing the cavity size to minimize strip length while providing enough room for drug load when filled with automated equipment; maximizing number of doses per inhaler; providing sufficient space to store both unused and used blisters; minimizing peel force to reduce motor torque requirements without compromising seal integrity and stability; and overcoming seal integrity issues related to the small seal area. Despite the small volume of the blister cavities relative to the larger volume of the dosing chamber, the device is precisely adapted to transfer dry powder medicament from the blister cavity into the dosing chamber, and aerosolize and expel the medicament from one or more openings in the dosing chamber.

According to an embodiment, the inhaler comprises a blister strip, the blister strip comprising: (i) a base sheet in which blisters are formed to define pockets therein, the pockets containing dry powder medicament, and (ii) a lid sheet which is mechanically peelable from the base sheet; and the inhaler comprising: (i) a dosing chamber as described herein configured to receive medicament from the blister, (ii) a transducer confronting the dosing chamber, the transducer being configured to aerosolize the medicament when the transducer is activated, and (iii) indexing means configured to peel a bottom surface of the lid sheet from a top surface of the base sheet, preferably at an angle of from about 110° to about 160° between the bottom surface of the lid sheet and the top surface of the base sheet. Preferably, the ratio of an internal volume of the dosing chamber to an internal volume of each blister is from about 20:1 to about 80:1. As described herein, the dosing chamber preferably comprises a tunnel configured to receive the medicament from each blister. As described herein, the dosing chamber comprises one or more openings out of which aerosolized medicament is expelled, the one or more openings having a diameter of, e.g., from about 0.01 inches (0.25 mm) to about 0.05 inches (1.3 mm).

According to one embodiment, a blister strip adapted for use in an inhaler comprises: a base sheet in which blisters are formed to define pockets therein, the pockets containing inhalable medicament in dry powder form; and a lid sheet which is mechanically peelable from the base sheet to enable release of said inhalable medicament, wherein each blister has a cavity volume from about 6 mm³ to about 15 mm³, or from about 6 mm³ to about 12 mm³, or from about 6 mm³ to about 10 mm³, or from about 7 mm³ to about 15 mm³, or from about 7 mm³ to about 12 mm³, or from about 7 mm³ to about 10 mm³, or from about 8 mm³ to about 14 mm³, or from about 8 mm³ to about 13 mm³, or from about 8 mm³ to about 12 mm³, or from about 8 mm³ to about 10 mm³, or from about 9 mm³ to about 14 mm³, or from about 9 mm³ to about 13 mm³, or from about 9 mm³ to about 12 mm³, or from about 9 mm³ to about 11 mm³, or from about 9 mm³ to about 10 mm³. According to one embodiment, each blister has a volume of about from about 9 mm³ to about 14 mm³, or from about 9 mm³ to about 13 mm³, or about 10 mm³ to about 13 mm³. These blister strip cavity volumes are preferably smaller than prior art cavity volumes for inhalers; for example, the Advair blister has a cavity volume of about 18 mm³ and the Forspiro blister has a cavity volume of about 115 mm³.

According to an embodiment, the depths of the blister cavities are from about 1 mm to about 3 mm, more preferably from about 1 mm to about 2.5 mm, or from about 1 mm to about 2 mm, or from about 1 mm to about 1.5 mm, or from about 1.25 mm to about 1.75 mm. The volume of the drug pellet dispensed into the blister cavity may be from about 1 mm³ to about 5 mm³, or from about 1.5 mm³ to about 4 mm³, from about 1.5 mm³ to about 3 mm³, or from about 2 mm³ to about 4 mm³, or from about 2 mm³ to about 3 mm³, or about 2.4 mm³, as opposed to the approximately 18 mm³ volume of powder that is dispensed into Advair blister cavities.

Figure 38A:
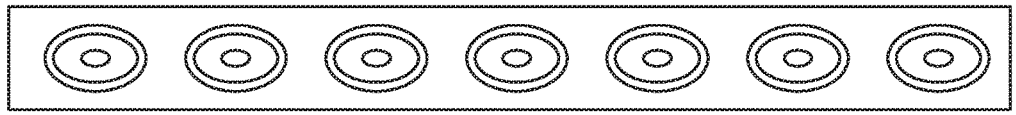
FIG. 38A and FIG. 38B illustrate embodiments of the blister strip.
Figure 38B:
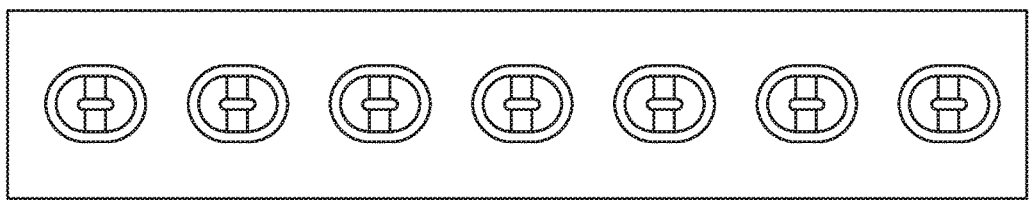

According to one embodiment, the base sheet (and preferably the lid sheet) has a width of from about 4 mm to about 10 mm, or from about 4 mm to about 8 mm, or from about 4 mm to about 6 mm, or from about 5 mm to about 10 mm, or from about 5 mm to about 8 mm, or from about 5 mm to about 7 mm, or from about 5 mm to about 6 mm. Preferably, the lid sheet has approximately the same width as the base sheet. According to an alternative embodiment, the width of the base sheet (and preferably the lid sheet) is from about 5 mm to about 12 mm, more preferably from about 5 mm to about 11 mm, or from about 5 mm to about 10 mm, or from about 7 mm to about 12 mm, or from about 7 mm to about 11 mm, or from about 7 mm to about 10 mm, or from about 8 mm to about 12 mm, or from about 8 mm to about 11 mm, or from about 8 mm to about 10 mm. The shape of the blister cavity is preferably circular, oval or oblong, more preferably oblong, which tends to reduce forming stress. Embodiments of the blister strip are shown in FIGS. 38A and 38B, with FIG. 38A illustrating oval cavities and FIG. 38B illustrating oblong cavities.

According to one embodiment, the blister strip comprises from 10 to 50 blisters, or from 15 to 50 blisters, or from 20 to 50 blisters, or from 25 to 50 blisters, or from 35 to 50 blisters, or from 10 to 50 blisters, or from 15 to 40 blisters, or from 20 to 40 blisters; preferably from 25 to 40 blisters, or from 35 to 40 blisters, or from 28 to 35 blisters, or from 30 to 35 blisters.

According to one embodiment, the base sheet has a laminate structure comprising a layer of aluminum foil and a layer of polymeric material; for example, the base sheet may comprise at least the following successive layers: oriented polyamide (OPA); adhesively bonded to aluminum foil; adhesively bonded to a layer of polymeric material (e.g., PVC). According to an embodiment, the lid sheet has a laminate structure comprising at least the following successive layers: paper; bonded to plastic film; bonded to aluminum foil. Preferably, a coating layer bonds the lid sheet to the base sheet; for example, the coating layer may be selected from the group comprising or consisting of heat seal lacquer, film and extrusion coating.

Figure 38C:
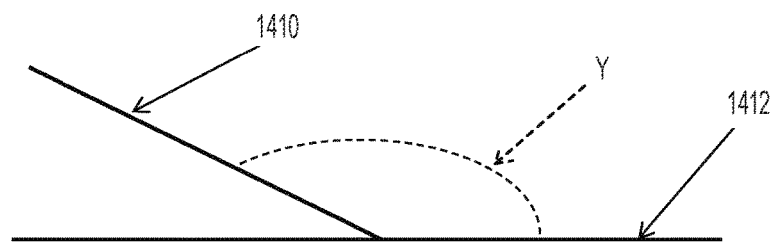
FIG. 38C is a schematic diagram of an embodiment of a blister strip lid sheet and base sheet.

According to an embodiment, the lid sheet has a top surface and a bottom surface, wherein the bottom surface 1410 of the lid sheet is peelably adhered to the top surface 1412 of the base sheet, e.g., as shown in FIG. 38C. When the lid sheet is being peeled off the base sheet by a blister strip advance mechanism, the bottom surface of the lid sheet 1410 is preferably peeled at an angle Y with respect to the top surface of the base sheet 1412 that is from about 110° to about 160°, or from about 110° to about 150°, or from about 110° to about 140°, or from about 120° to about 160°, from about 120° to about 150°, or from about 120° to about 140°.

Figure 43A:
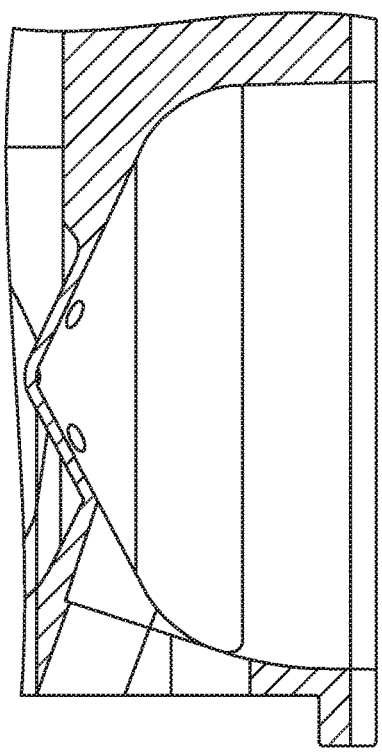
FIG. 43A illustrates an embodiment of a dosing chamber having a shorter internal height compared to the embodiment of the dosing chamber shown in FIG. 43B.
Figure 43B:
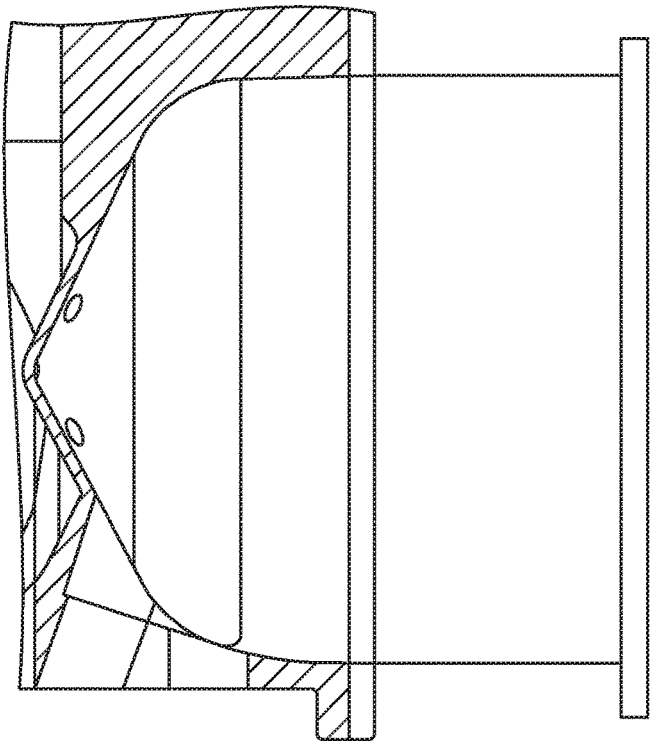

According to one embodiment, an inhaler comprises a dosing chamber configured to receive medicament from the blister in combination with a transducer confronting the dosing chamber, the transducer and dosing chamber being configured to aerosolize the medicament when the transducer is activated, and the ratio of the volume of the dosing chamber to the volume of the blister is from about 5:1 to about 50:1, or from about 10:1 to about 50:1, or from about 20:1 to about 50:1, or from about 30:1 to about 50:1, or from about 10:1 to about 40:1, or from about 10:1 to about 30:1, or from about 20:1 to about 30:1. According to an alternative embodiment in which the dosing chamber has a larger volume (e.g., as shown in FIG. 43B, from about 550 mm$^3$ to about 700 mm$^3$), the ratio of the volume of the dosing chamber to the volume of the blister may be from about 40:1 to about 70:1, or from about 30:1 to about 80:1, or from about 45:1 to about 70:1, or from about 50:1 to about 70:1, or from about 50:1 to about 65:1, or from about 60:1 to about 60:1. In general, the ratio of the volume of the dosing chamber to the volume of the blister may be from about 20:1 to about 80:1 or from about 20:1 to about 70:1.

An embodiment of a blister advance mechanism is configured to move the blister into position such that components of the inhaler 100 can aerosolize the pharmaceutical from each blister 130 and deliver it to the user, as explained in greater detail below. The embodiments of the blister strip advance mechanism described below are exemplary, but other mechanisms for advancing each dose may be used in accordance with the present invention.

Elements shown in the FIGS. are not necessarily drawn to scale, but only to illustrate operation. One way of preventing over-advancement of a blister strip is to employ mechanical indexing means, such as the indexing gear train proposed herein and described in US2016/0296717, which is incorporated by reference herein.

Such an indexing gear train is driven by drive means such as an electric motor e.g. a stepper or DC (direct current) motor. The drive means may be under electronic control to switch it on and off in order to advance the blister strip by one blister. This electronic control may be responsive to user input or to sensing means (such as a mechanical switch) configured to sense when a blister has been successfully located in a dosing position at which it can be emptied. For example, the dosing position may correspond to the entrance to a dosing chamber into which medicament (such as a dry powder pharmaceutical) contained in the blister must be released so that it can be entrained in a user's inhalation and delivered into their airway. For example, a dry powder medicament may be expelled from the inhaler in artificial jets by excitation of a piezoelectric element during inhalation.

At the other end of the gear train to the drive means a hub is provided with at least one recess, each configured to engage a single (first) blister of a blister strip so that another (second) blister of the strip can be moved into a dosing position and optionally held against the dose tunnel wall with biasing means. Thus, the hub holds the blister strip in place with a (second) blister in the dosing position and an empty (first) blister in the hub, while the (second) blister in the dosing position is emptied. Thus, in this example arrangement, the hub and dosing chamber opening are arranged one blister spacing apart. The (second) blister in the dosing position is arranged such that there is a tight seal between the blister cup walls and the dosing chamber walls so that medicament from the blister preferably exits into the dosing chamber. This prevents wastage of medicament and clogging of the mechanism with medicament. Optional biasing means (spring finger 172 in FIG. 1I) can be incorporated to improve the seal by urging the blister strip towards (or into contact with) the dosing chamber.

The drive train is arranged such that, once a second blister arrives at the dosing position, the drive means is temporarily disengaged from the hub. This means that, provided the indexing gear train is configured to make this temporary disengagement last as long or longer than the time taken for the electronic control system to receive and respond to a signal indicating that the second blister is in the dosing position, over-advancement of the blister strip is avoided. This reduces the need for high motor speed and control accuracy, since there is a large window within which to stop the motor in order to not over- or under-advance the blister. This also prevents inadvertent movement of the blister strip if the cartridge is removed in between dose events.

The mechanism for temporarily disengaging the hub from the drive means may comprise one or more spur gears and one or more sector gears. A spur gear comprises radially extending teeth substantially evenly spaced all the way around its circumference. A sector gear is effectively a spur gear with the teeth missing from one or more portions of the circumference. When a rotating sector gear drives a spur gear, the spur gear is only driven while the toothed portion(s) of the sector gear engage it. When a toothless portion of the sector gear aligns with the teeth of the spur gear, the spur gear stops rotating. The sector gear continues to rotate until a toothed portion contacts and engages with the teeth of the spur gear. The spur and sector gears then rotate together until a toothless portion of the sector gear contacts the spur gear again. Therefore, if rotation of the hub is driven by a spur gear, temporary disengagement of the hub from the drive means can be provided if the drive means drives a sector gear which in turn drives the spur gear which in turn drives the hub.

Figure 1B:
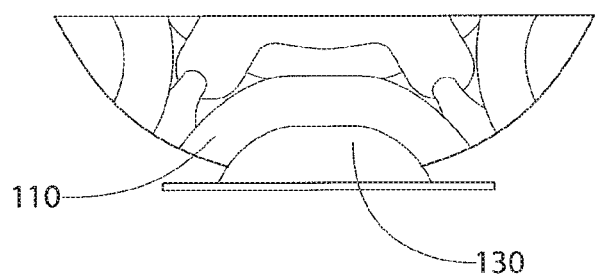
FIG. 1B illustrates a blister and a cog in accordance with one embodiment of the present invention.
Figure 1C:
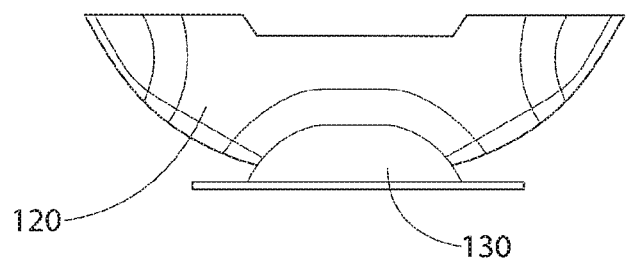
FIG. 1C illustrates a blister and a cog in accordance with one embodiment of the present invention.
Figure 1D:
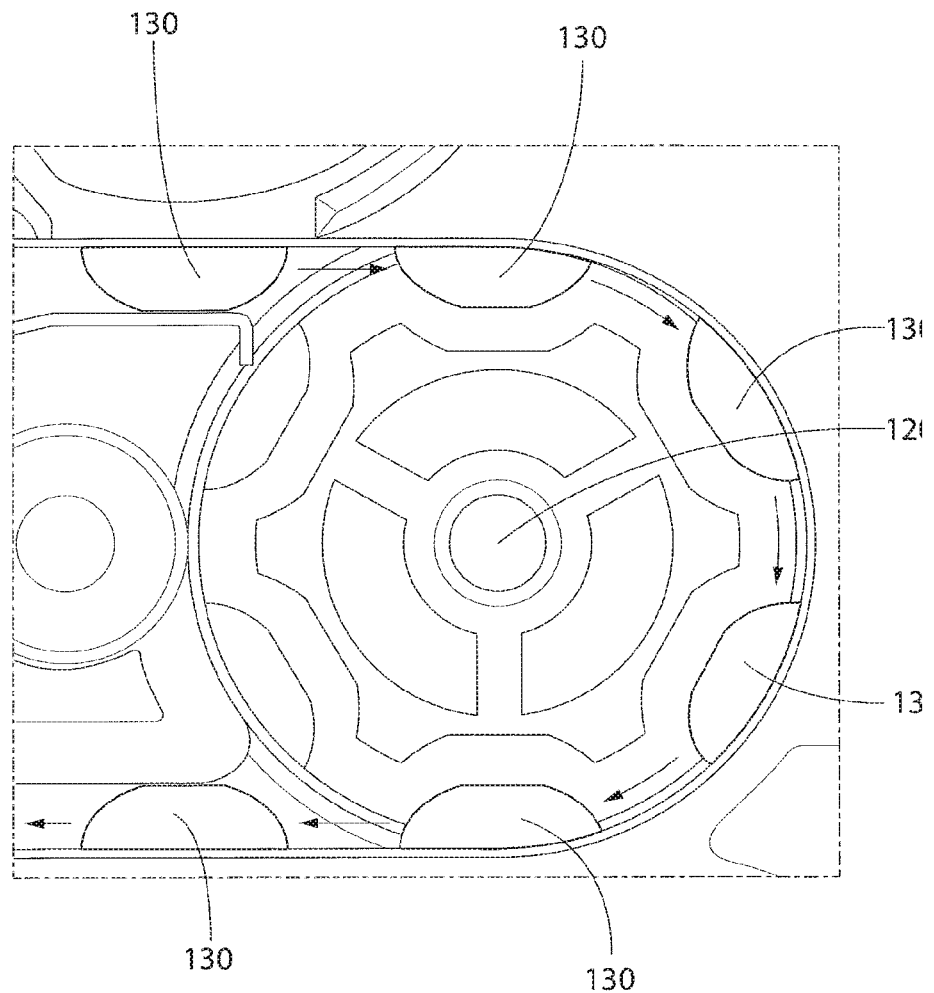
FIG. 1D illustrates a blister strip and including the blister and offset cog of FIG. 1C.
Figure 1E:
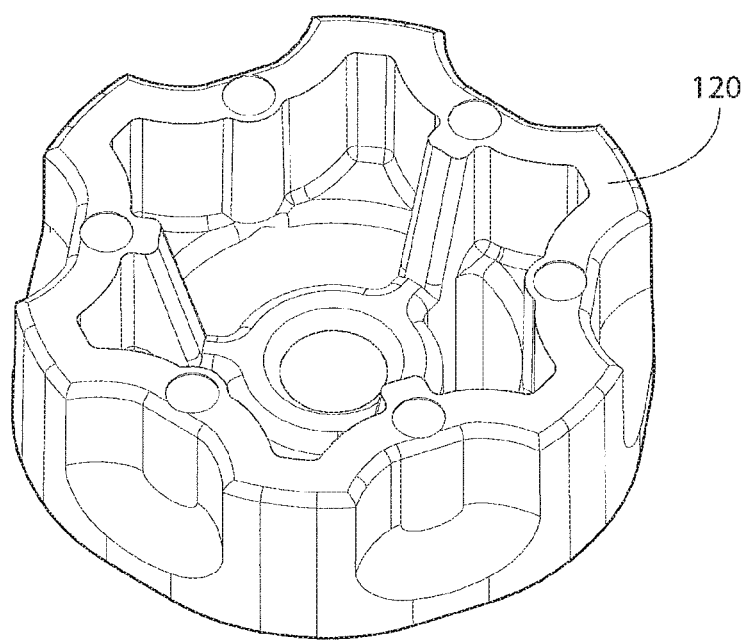
FIG. 1E illustrates an isolated, top perspective view of the offset cog of FIG. 1C.
Figure 1F:
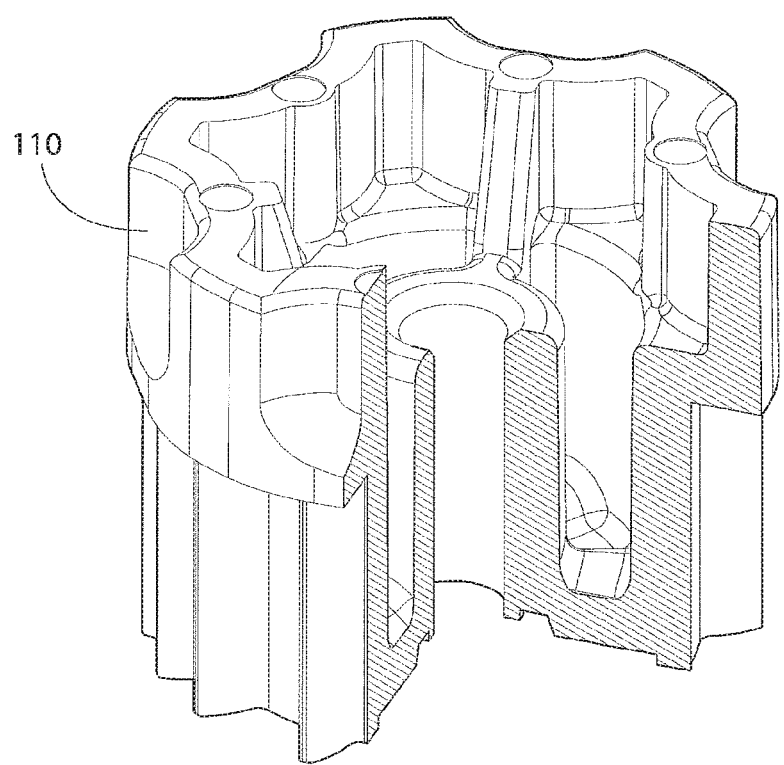
FIG. 1F illustrates a sectional view of the involute cog of FIG. 1B.

The hub may, for example, be in the form of an involute cog 110 as shown in FIG. 1B or an offset cog 120 as shown in FIG. 1C. By involute cog is intended an open type of blister seat in the hub such that the blister strip will twist in to the seat of the cog, and then twist out (much like the fashion in which involute gear teeth engage as they come together to a point of tangency and then pivot away from one another). An offset cog in one embodiment is a cut out arrangement where the blister strip wraps around the hub with the empty blisters engaging with the recesses on the hub without twisting of the strip; this is the arrangement illustrated in FIG. 4A. The recesses formed around the circumference of either shape cog can be sized to receive a single blister 130 of the blister strip to be advanced. Advantageously, the offset cog profile does not tend to misalign or crush blisters or cause the blister strip to buckle. FIG. 1D illustrates an example hub 120 in use. In this example, the track through which the blister strip moves passes around about half the circumference of the hub so that multiple blisters 130 are engaged by the hub at once. FIGS. 1E and 1F illustrate alternative example designs for hub 110.

Figure 1G:
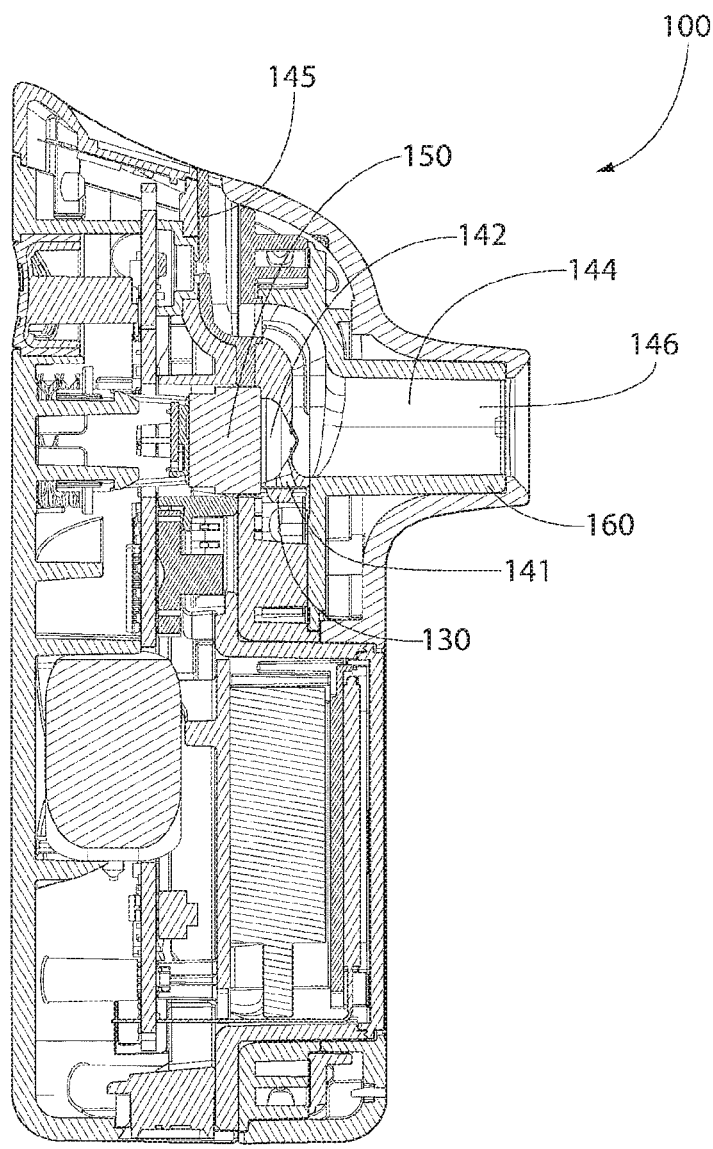
FIG. 1G illustrates a sectional view of the inhaler of FIG. 1A along a plane defined by line 1-1.
Figure 1H:
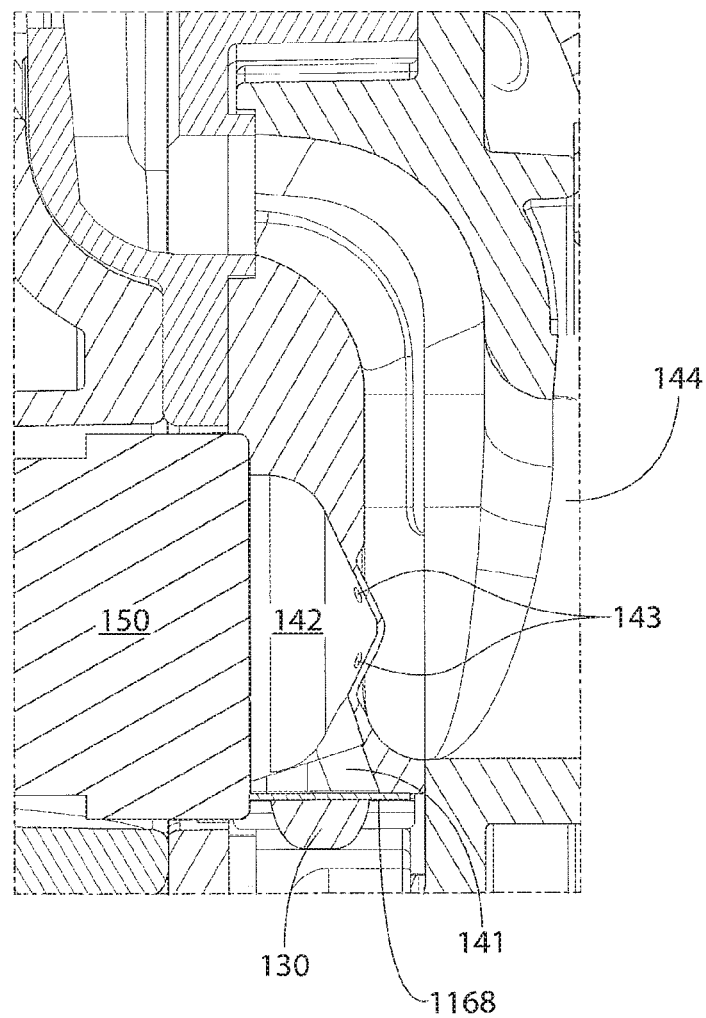
FIG. 1H illustrates a close up view of a portion of FIG. 1G.

FIGS. 1G and 1H (which shows detail on FIG. 1G) illustrate an example of how the blister dosing position could be arranged with respect to other elements of an inhaler 100. Blister 130 is shown in the dosing position, with its open (peeled) side facing on to blister dose tunnel 141 which pneumatically connects the dosing position to dose chamber 142. Piezoelectric vibrator 150, in one embodiment, is arranged to vibrate a film, that is in contact with the edge of the dose chamber 142 bottom, which is in contact with the Piezoelectric vibrator 150 head, such that dry powder medicament contained in the blister 130 and dosing chamber 142 is expelled from the dosing chamber 142 through openings (holes) 143 into air tunnel 144. Thus, the vibration from the piezoelectric vibrator 150 acts on the film. The medicament is thus entrained in airflow from inlet 145 through air tunnel 144 and out of outlet 146 in mouthpiece 160.

Figure 1I:
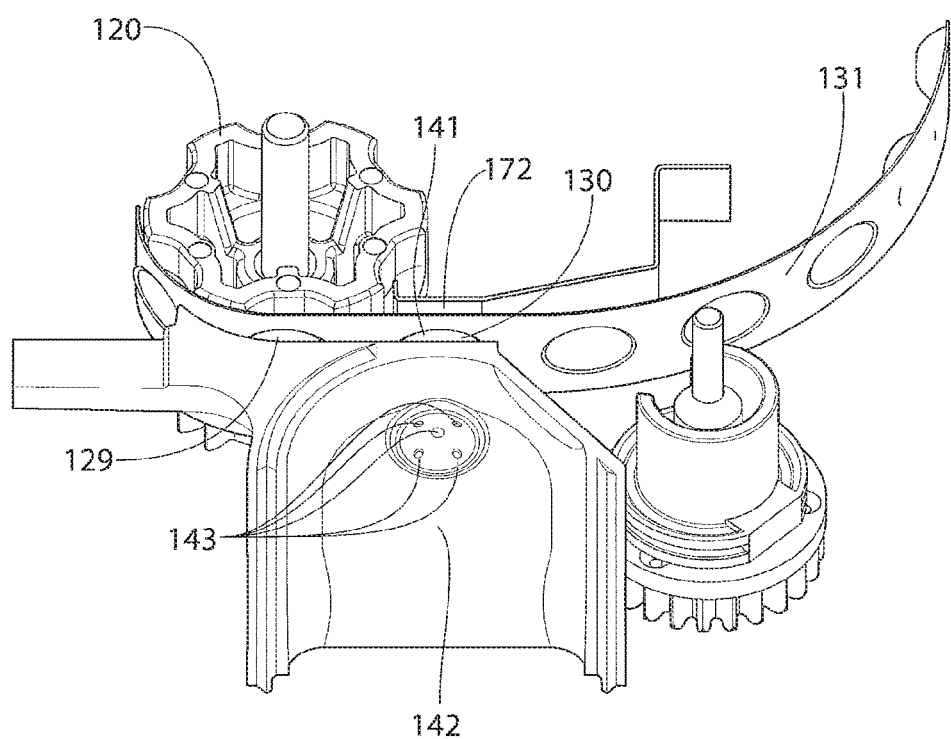
FIG. 1I illustrates a blister strip advance mechanism in accordance with one embodiment of the present invention that includes the involute cog of FIG. 1B.

FIG. 1I shows a different view on FIGS. 1G and 1H, with the dosing position shown relative to hub 120. First blister 129 is held in the hub 120. Also shown is spring finger 172 which biases the second blister 130 towards tunnel 141. This, in combination with the fact that the dosing position holds the open face of second blister 130 approximately horizontal in use, with the hollow part extending downwards, minimizes spillage of medicament from the blister other than into the tunnel 141.

The blister strip advance mechanism may be configured to incrementally move successive blisters of a blister strip through the dosing position. That is, once the second blister has been moved into the dosing position and emptied, the hub can be rotated such that the empty second blister is engaged by the hub and a third (full) blister is moved into the dosing position and so on until every blister on the strip has been emptied, empty blisters being released from the hub at a suitable point before they have completed a full hub rotation.

Once the second blister has been emptied, the leading end of the strip (comprising the first, empty, blister) may be fed out of the inhaler where it could for example be cut off with scissors, or torn off (e.g., using a tearing notch or a score line or perforation in the strip between blisters) and disposed of (If individual blisters are only held together as a strip by the backing tape then no cutting or tearing would be necessary.) Alternatively, the inhaler could comprise a waste chamber into which used blisters are fed. The used blister strip sections could, for example, accordion-fold into such a chamber, or be wound onto a spool.

As another option, if the blister strip is short enough relative to the inhaler geometry, a single loop track could be provided with the hub positioned anywhere inside it, the hub's teeth extending into the track. This would allow used blisters to be stored within the inhaler and disposed of with the inhaler when all of the blisters are used (or with the cartridge if a replaceable blister cartridge is provided for attachment to a reusable inhaler body). In such an arrangement the leading end of the strip could be fed into a refuse track within the inhaler. This track could be an extension of a holding track in which the blister strip is stored prior to use and in which the trailing end of the strip (comprising one or more full blisters) reside during advancement of the strip. The refuse track could loop around into the holding track, the dual track being formed thereby being sized and arranged such that the leading end of the blister strip is fed into a portion of the dual track vacated by the trailing end.

Figure 2A:
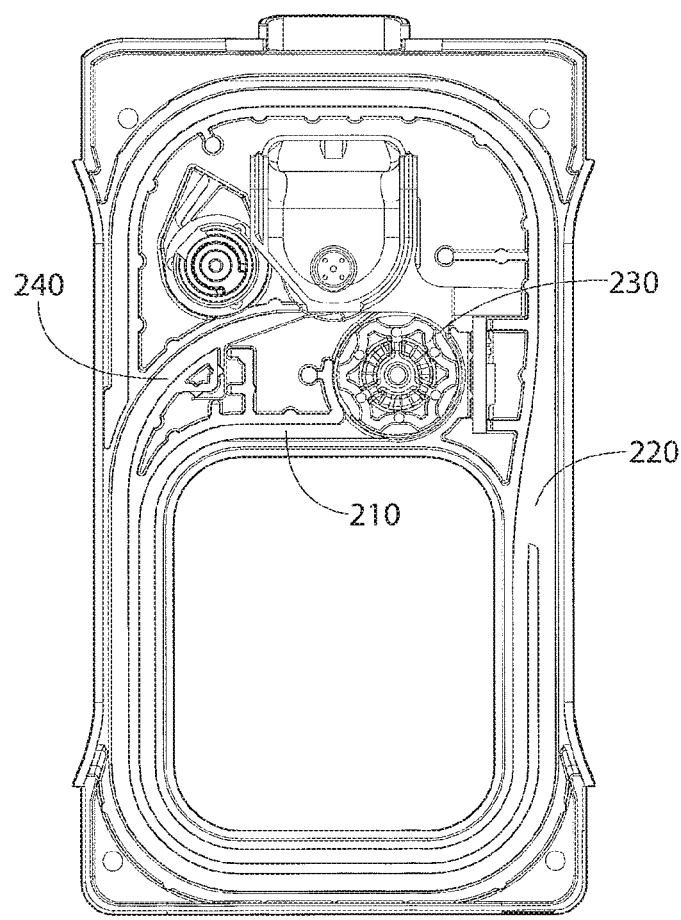
FIG. 2A illustrates a front elevational view of the front portion of the inhaler of FIG. 1A with a cover removed to show the internal components.
Figure 2B:
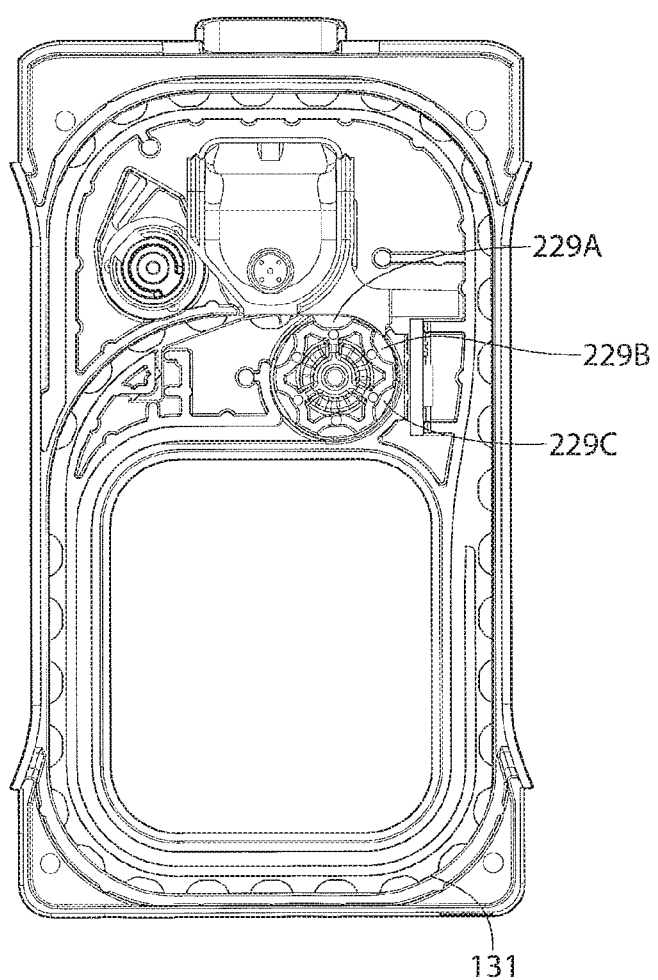
FIG. 2B illustrates the front elevational view of the front portion of the inhaler of FIG. 2A and includes a blister strip in accordance with one embodiment of the present invention.
Figure 2C:
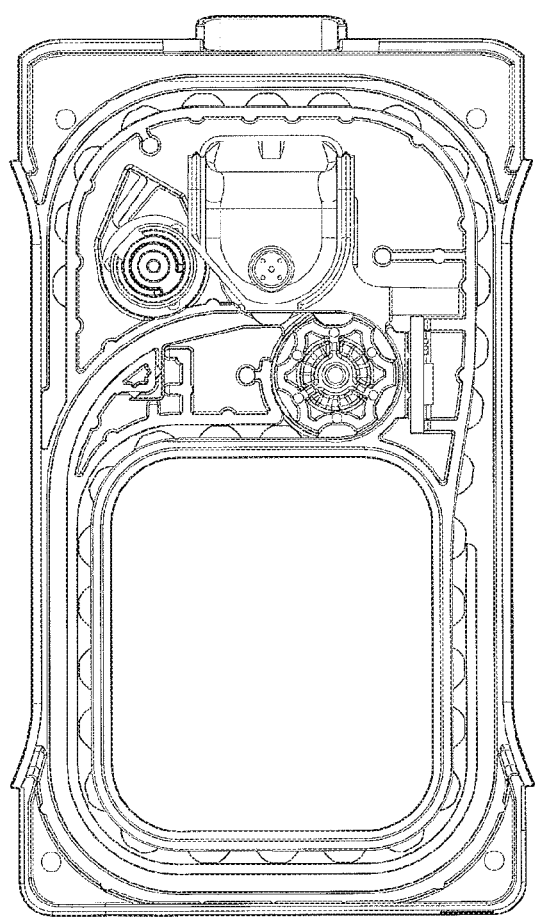
FIG. 2C illustrates the front elevational view of the inhaler of FIG. 2A with the blister strip in an advanced position.

A variant of the dual track arrangement is illustrated in FIGS. 2A-2C. This variant reduces the required footprint of the track for the same length of blister strip relative to the single loop variant and thus potentially reduces the size of the inhaler/cartridge and/or increases its blister capacity. Since some inhalers (e.g., rescue inhalers and frequent use inhalers) must be carried at all times this is advantageous since it improves the inhaler's portability. Shown in FIG. 2A is a holding track 240 fed by a dual track 220. The holding track 240 approaches and follows a portion of the circumference of hub 230 and then becomes refuse track 210. Refuse track 210 then leads back into dual track 220.

FIGS. 2B and 2C illustrate one embodiment of a blister strip track. The initial position of the blister strip is shown in FIG. 2B and the final position of the blister strip (when all blisters have been emptied) in FIG. 2C.

As shown in FIG. 2B, in addition to first blister 229A, the hub also engages blisters 229B and 229C in the starting position to improve engagement of the blister strip as a whole. Any blisters engaged by the hub in the starting position may suitably be provided empty to avoid medicament spilling around the hub or into the refuse track.

Alternatively to a dual track arrangement, the blister strip may be stored on a spool from which it is incrementally unwound.

The blister strip may be formed of a plurality of relatively rigid (e.g., plastic or aluminum) domes or cups connected and enclosed by a strip of backing tape (sometimes known as lidding material). Medicament (e.g., in liquid or dry powder form) may be enclosed in the cups. Individual blisters may be opened by piercing the backing tape, the dome or both. Alternatively, blisters may be opened by peeling away the backing tape.

If the backing tape is peeled to open the blisters, a spool may be provided around which to wind peeled backing tape. Such a spool may be carried on a peeling/spooling gear. The leading end of the blister strip may comprise a lip of backing tape or a tab extending out past the distal end of the distal blister cup. This lip or tab can be affixed to the spool. The peeling/spooling gear can be rotated by the indexing gear train while the hub is rotated so that backing is peeled off each blister and wound around the spool as the blister cup is moved into the dosing position. The blister cup is therefore open when in the dosing position, making medicament available to the dosing chamber.

To ensure the timing of the peeling matches the timing of the blister cup being moved into the dosing position, the peeling/spooling gear can be driven by a gear (e.g., a sector gear) that also (directly or indirectly) drives the hub.

The peeling/spooling gear and the hub can be located such that backing is peeled off each blister cup at an angle close to a right angle to the backing remaining on the blister cup, for example at from 40° to 140° (e.g., 135°), for example at from 60° to 120°, for example at approximately 90°. The closer the peel angle to 90°, the lower the friction between the backing tape and the edge it is peeled off with. Reducing friction reduces motor load, thus saving power, and reduces the likelihood of the backing strip breaking.

Figure 3A:
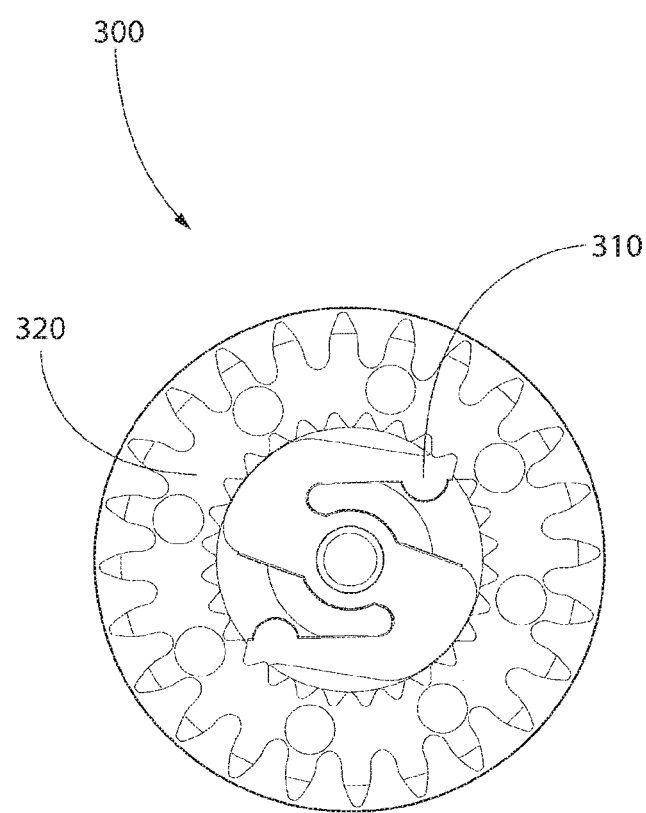
FIG. 3A illustrates a front elevational view of a detent clutch in accordance with one embodiment of the present invention.
Figure 3B:
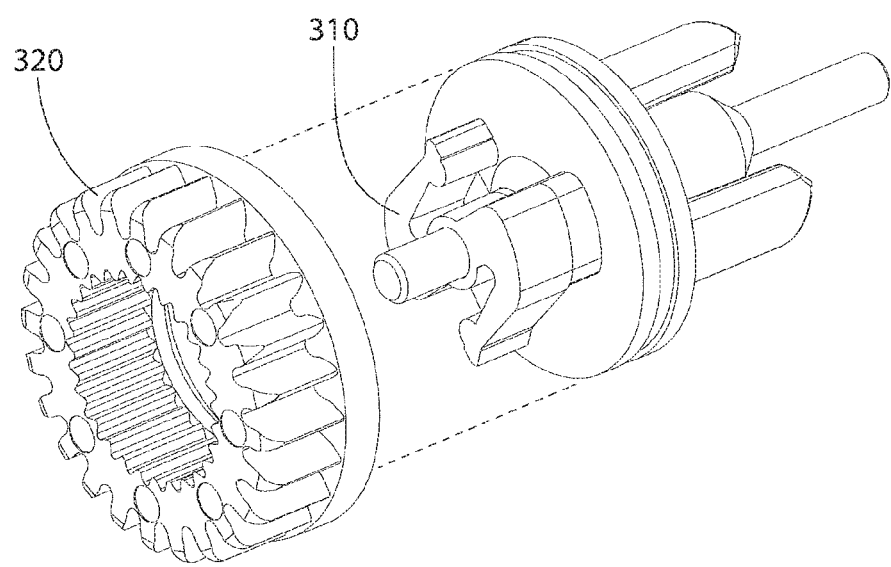
FIG. 3B illustrates an exploded, perspective view of the detent clutch of FIG. 3A.

As tape is wound around the spool, the spool's diameter grows. This increases the surface speed of the spool relative to the tape still on the blister strip, creating tension since the blister strip is held by the hub. In order to avoid snapping of the tape, there may be a slip or detent clutch 300 provided on the peeling/spooling gear as shown in FIG. 3 to periodically release the tension and re-set the arrangement. The slip of the clutch is arranged to be less than the breaking strength of the backing tape but more than the peel strength of the tape. The slip clutch 300 is formed by z-shaped part 310, which rotates with the spool, and toothed ring portion 320 as shown in exploded form in FIG. 3B. Ring portion 320 is fixed relative to the inhaler so that z-shaped part 310 rotates incrementally inside it by slipping over the inner teeth of ring portion 320 one by one. Instead of a slip clutch, a flexible diameter spool or a tensioning arm could be provided.

Figure 4A:
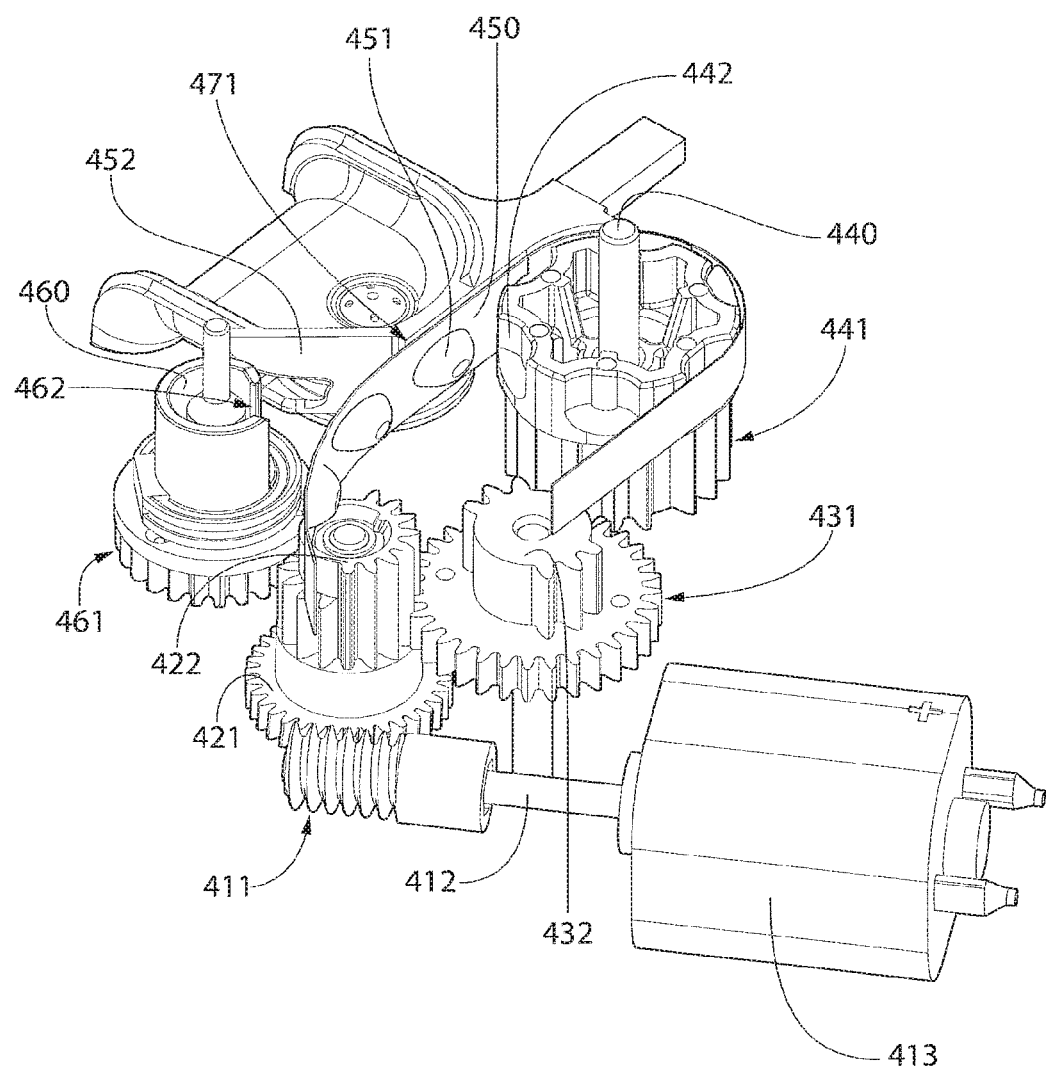
FIGS. 4A-4B illustrate an example drive train in accordance with one embodiment of the present invention.
Figure 4B:
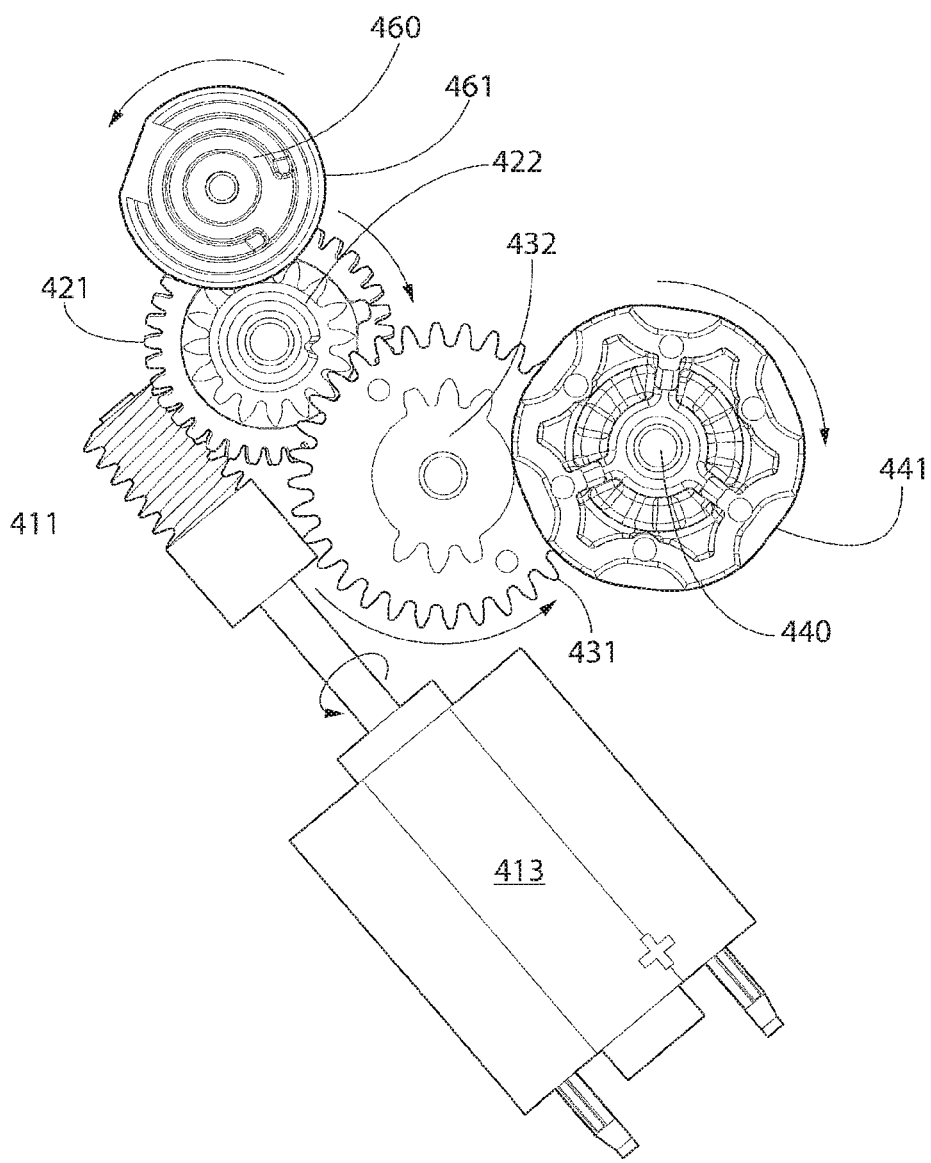

FIGS. 4A and 4B illustrate an example indexing gear train in full. A worm gear 411 is mounted on the output shaft 412 of a motor 413 such that the worm gear 411 rotates about its axis when the motor 413 is on. The worm gear 411 meshes with a first spur gear 421 such that first spur gear 421 rotates with worm gear 411. (In an alternative example a spur gear could be used in place of the worm gear 411, e.g., being a spur bevel gear with teeth angled to mesh with first spur gear 421.) A first sector gear 422 is mounted coaxially on the first spur gear 421 such that first sector gear 422 rotates with first spur gear 421. A second spur gear 431 meshes with the first sector gear 422 such that second spur gear 431 rotates with first sector gear 422 when a toothed part of the first sector gear 422 contacts the second spur gear 431. A second sector gear 432 is mounted coaxially on the second spur gear 431 such that the second sector gear 432 rotates with second spur gear 431. A third sector gear 441, having as many toothed portions as the hub 440 has blister recesses (in the example shown, six), meshes with second sector gear 432 such that third sector gear 441 rotates with second sector gear 432 when toothed parts of the second and third sector gears 432 and 441 contact one another. The hub 440 is mounted coaxially on the third sector gear 441 such that the hub 440 rotates with the third sector gear 441.

FIG. 4A shows the location of the blister strip 450 at the point blister 451 is in the dosing position. Blister 451 of blister strip 450 is then moved into recess 442 of hub 440.

A spool 460 is mounted coaxially on a peeling/spooling gear 461 (which is a spur gear) such that spool 460 rotates with peeling/spooling gear 461. Peeling/spooling gear 461 meshes with first sector gear 422 such that peeling/spooling gear 461 rotates with first sector gear 422 when a toothed part of the first sector gear 422 contacts the peeling/spooling gear 461. A lip formed by the end of blister strip backing tape 452 is fed through a slot 471 in the outer wall of the blister strip track and affixed into slot 462 of spool 460. Such a lip could be reinforced to aid in slip through the slot 471, for example by the addition of a plastic layer or by doubling over of the backing material (which could, for example, be heat-sealed to itself). As backing tape 452 is peeled off each blister by rotation of spool 460 it slides around the peel edge of the slot 471.

Note that a gear, hub or spool being mounted on, carried on or sitting on another gear such that the two rotate together may be achieved by the two being affixed together, permanently or reversibly (for example with one or more pins, nuts, bolts, screws, adhesives, clutches etc.) or by the two being integrally formed (for example as pieces of plastic or metal formed in a single mold). All of the gear pairs may be coupled in the same manner. Alternatively, one or more pairs of gears, for example first spur and sector gears 421 and 422 and third sector gear 441 and hub 440, may be integrally formed while one or more other pairs of gears, for example second spur and sector gears 431 and 432 and peeling/spooling gear 461 and spool 460, may be formed separately and subsequently coupled to rotate together.

As shown in FIG. 4B, when motor 413 is on, output shaft 412 and therefore worm gear 411 rotate clockwise when viewed from worm gear end-on. This drives first spur gear 421 and therefore first sector gear 422 to rotate clockwise. This drives peeling/spooling gear 461 and therefore spool 460 to rotate anti-clockwise. The clockwise rotation of first sector gear 422 also drives the second spur gear 431 and therefore the second sector gear 432 to rotate anti-clockwise. This drives the third sector gear 441 and therefore the hub 440 to rotate clockwise. This drives the blister strip 450 to advance clockwise around the hub portion of the blister strip track.

Figure 5A:
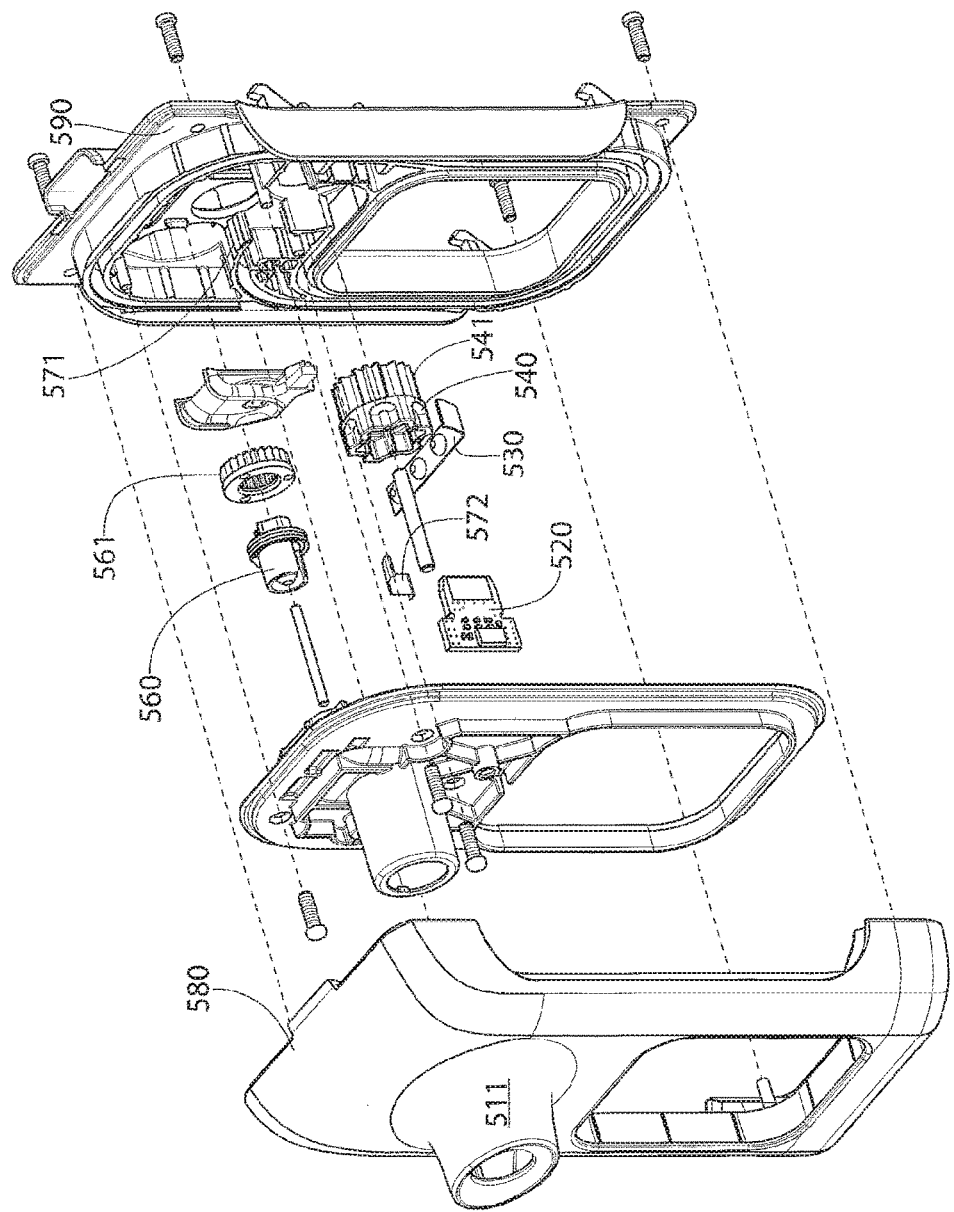
FIG. 5A illustrates an exploded view of a front portion of an inhaler in accordance with one embodiment of the present invention.

FIG. 5A is an exploded view of part of an example inhaler. A PCB (printed circuit board) 520, a third sector gear 541, a hub 540, a spool 560, a peeling/spooling gear 561, a slot 571 in the outer wall of the portion of the blister strip track curved around the hub and a spring finger 572 (for biasing the blister strip 530 such that the blister in the dosing position is pushed against the dose chamber opening) are all shown together with a cover 580, a base plate 590 and various axles for the gears and fastening means such as screws, nuts and bolts to hold the various layers of the inhaler together.

The inhaler may comprise a reusable inhaler body and a disposable blister strip cartridge. The inhaler body could for example comprise the dosing chamber, mouthpiece, motor, worm gear, indexing gear train (e.g., including the first and second spur gears, the first to third sector gears and the peeling/spooling gear), hub and spool while the cartridge could comprise the blister strip located in a track. This arrangement would minimize the cost of the cartridge.

Alternatively, one or more gears of the indexing drive train and/or the hub (or one or more gears of the indexing drive train and/or the motor) could be located in the cartridge. The drive means would then be disengaged from the hub whenever the cartridge is removed. This would prevent rotation of the hub by the motor when the cartridge is not in place.

As another option, the dosing chamber (together with a piezoelectric vibrator for pushing dry powder medicament into the mouthpiece) and mouthpiece could be included in the disposable part of the inhaler. This arrangement could be advantageous for reasons of hygiene, reducing the need to clean the mouthpiece and air flow conduit parts of the inhaler. It could also allow the inhaler body to be used by multiple patients, each attaching their own cartridge with their own mouthpiece and the drug prescribed for them.

Figure 5B:
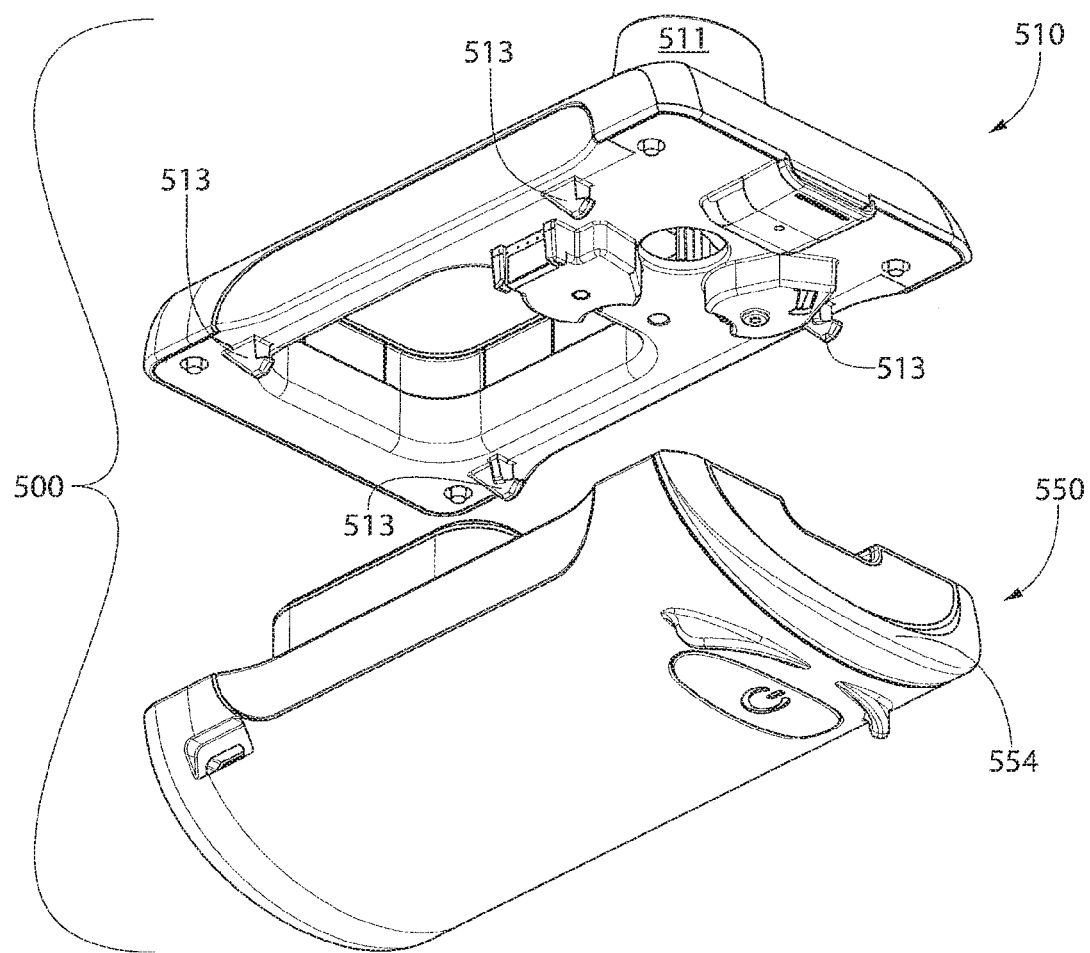
FIG. 5B illustrates a bottom exploded view of an inhaler in accordance with one embodiment of the present invention including the front portion of FIG. 5A.
Figure 5C:
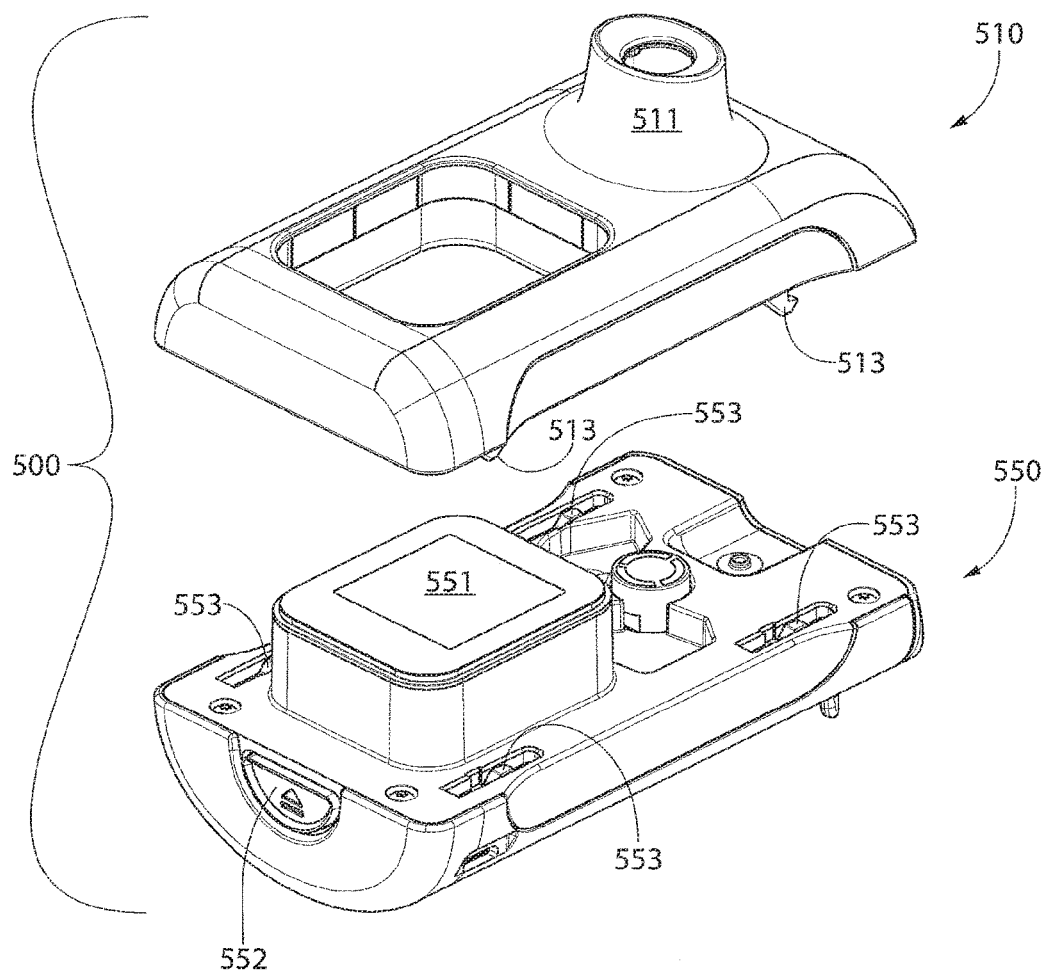
FIG. 5C illustrates a top exploded view of the inhaler of FIG. 5B.
Figure 5D:
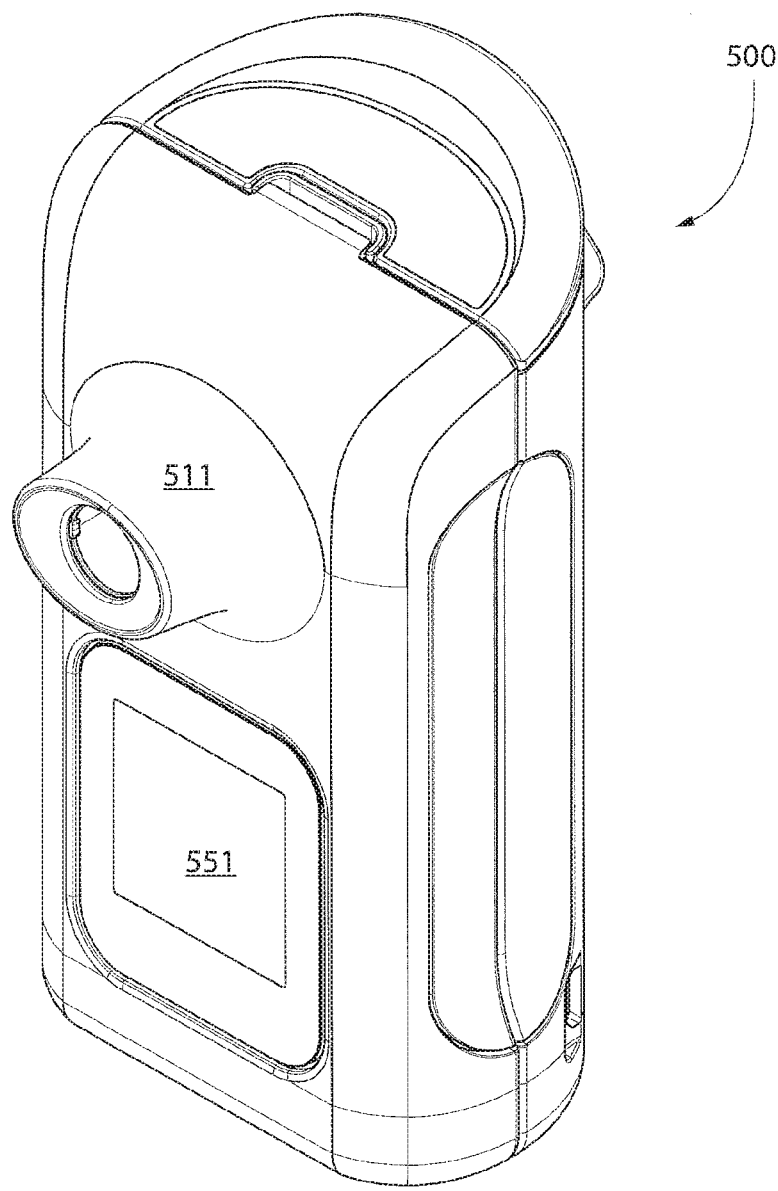
FIG. 5D illustrates a front perspective view of the inhaler of FIG. 5B

FIGS. 5B and 5C show an example replaceable cartridge inhaler 500 with a disposable cartridge 510 and a reusable part 550 separated, while FIG. 5D shows them joined together. Visible in FIGS. 5B to 5D are mouthpiece 511, display screen 551, cartridge release button 552, connector clips 513 and connector slots 553 into which connector clips 513 fit to join the cartridge to the reusable part.

Figure 6:
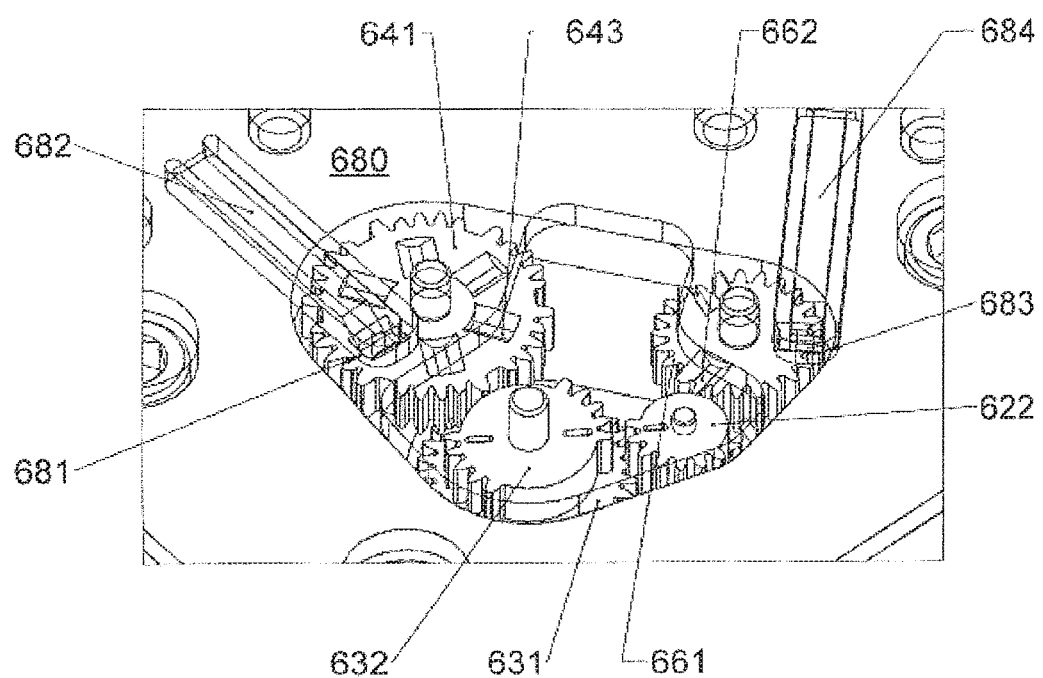
FIG. 6 illustrates an example detent arrangement in accordance with one embodiment of the present invention.

In a cartridge-based inhaler with a design similar to that shown in FIG. 5A, when the cartridge is removed then the indexing drive train is free to rotate. This may not be desirable if there is any possibility of the cartridge being removed before it is empty, for example if multiple different cartridges (e.g., holding different types of medicament) can be attached to the inhaler body. For example a user may need to administer two or three different types of medicament each day and may do so using a single inhaler body onto which are swapped multiple different cartridges. Problems could arise in these circumstances since the hub may not be located with a recess in the dosing position, aligned with the dosing chamber, when a cartridge is attached to the inhaler body. FIG. 6 illustrates a means of solving this problem.

FIG. 6 shows a cover 680 on top of a first sector gear 622 (mounted on a first spur gear, not seen), a second spur gear 631, a second sector gear 632, a third sector gear 641 and a peeling/spooling gear 661.

The upper face of the third sector gear 641 as shown (i.e. the face over which the hub will be mounted) comprises recesses 643. The cover 680, which is fitted between the third sector gear 641 and the hub (not shown) comprises detent 681 on the distal end of spring arm 682. Spring arm 682 biases detent 681 down towards the upper face of the third sector gear 641. The detent 681 is located such that it sits in one of the recesses 643 when the hub is in one of its stopped positions (e.g., with a blister in the dosing position). The number of recesses 643 corresponds to the number of blister recesses on the hub. Each time the blister strip is advanced by one blister, the detent 681 is forced upwards out of the recess 643 in which it has been residing and then snaps back down into the next recess 643 due to the biasing provided by the spring arm 682.

Similarly, the upper face of the peeling/spooling gear 661 as shown (e.g. the face over which the spool will be mounted) comprises recesses 662. The cover 680, which is fitted between the peeling/spooling gear 661 and the spool (not shown) comprises detent 683 on the distal end of spring arm 684. Spring arm 684 biases detent 683 down towards the upper face of the peeling/spooling gear 661. The detent 683 is located such that it sits in one of the recesses 662 when the spool is in one of its stopped positions (e.g. when a blister is in the dosing position). The number of recesses 662 is set according to the ratio of the sizes of the third sector gear 641 and peeling/spooling gear 661 and the number of blister recesses on the hub. Each time the blister strip is advanced by one blister, the detent 683 is forced upwards out of the recess 662 in which it has been residing and then snaps back down into the next recess 662 due to the biasing provided by the spring arm 684.

The strength of the biasing provided by the spring arms 682 and 684 and the sizes of the detents 681 and 683 and recesses 643 and 662 are arranged such that the drive means can generate sufficient force to index the gear train despite the detents, while the detents hold the drive train in place when disconnected from the drive means. This means that no complex position sensing is needed to establish the phase of the drive train on re-connection to the inhaler body since correct alignment is guaranteed. The power chosen for the motor should be balanced against the forces likely to be encountered during typical transportation and use of an inhaler. For example, drop tests could establish how strong the lock created by the spring arms and detents needs to be to prevent misalignment caused by the inhaler falling off a table or out of a pocket or handbag.

In addition, the detent arrangement on the third sector gear prevents any accidental rotation of the hub (for example as might be caused by the inhaler being dropped) while it is disengaged from the motor. Similarly, the detent arrangement on the peeling/spooling gear prevents any accidental rotation of the spool while it is disengaged from the motor (which could for example cause inadvertent unwinding of backing from the spool). These detent arrangements are therefore also useful in a non-cartridge based inhaler.

Figure 7A:
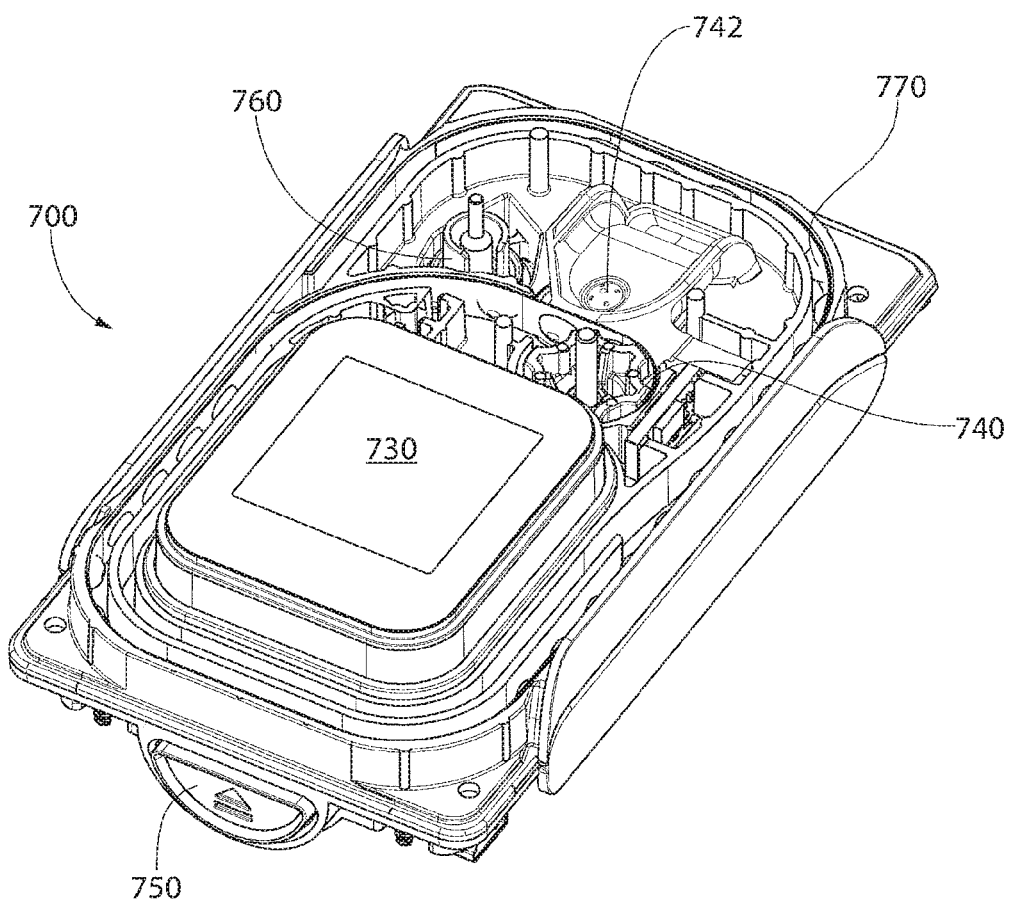
FIG. 7A illustrate a blister strip advance mechanism in an inhaler in accordance with one embodiment of the present invention.
Figure 7B:
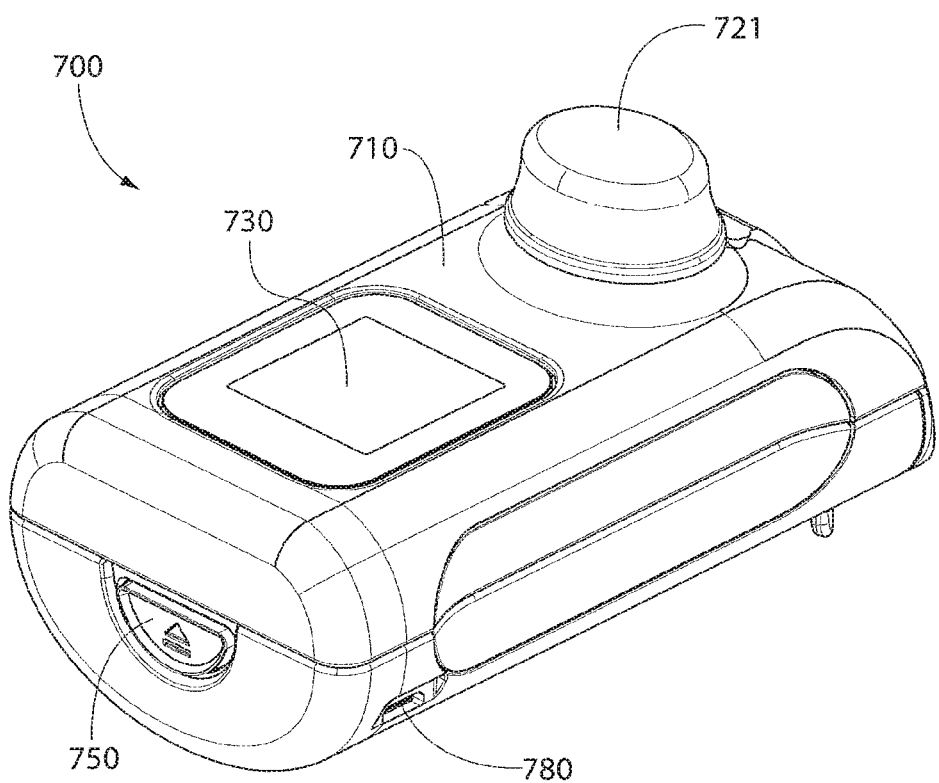
FIG. 7B illustrates an inhaler including the blister strip advance mechanism of FIG. 7A.

FIGS. 7A and 7B illustrate how the blister strip advance mechanism could fit into an inhaler according to one embodiment. Inhaler 700 is shown in FIG. 7A with outer housing 710 and mouthpiece cover 721 (both shown in FIG. 7B) removed. FIG. 7A shows a dosing chamber 742, display screen 730, hub 740, cartridge release button 750, spool 760 and blister strip track 770. Most of the blister strip track 770 is arranged close to the outer edge of the inhaler to maximize its length and therefore the number of doses per cartridge/disposable inhaler. The hub 740 and spool 760 are located in the space between the dosing chamber 742 and display screen 730.

A charging socket 780 as shown in FIG. 7B may connect to a battery within the inhaler, for example located under display screen 730. A PCB may also be located under the display screen 730 in order to connect some or all of the display screen 730, charging socket 780, battery, motor and any other electronic components. For example, a switch could be provided close to the hub which cuts off power to the motor once a blister is successfully located in the dosing position. Such a switch could for example be mechanical, optical, or comprise a Hall effect sensor. User-actuated control means could be provided to re-start the motor when dose advancement is required. For example, display screen 730 could be a touch screen, a button or slider could be located on the exterior of the inhaler or an inhalation sensor somewhere in the air flow conduit comprising the mouthpiece and dosing chamber could detect when a user is inhaling through the mouthpiece in order to trigger the motor.

Figure 8:
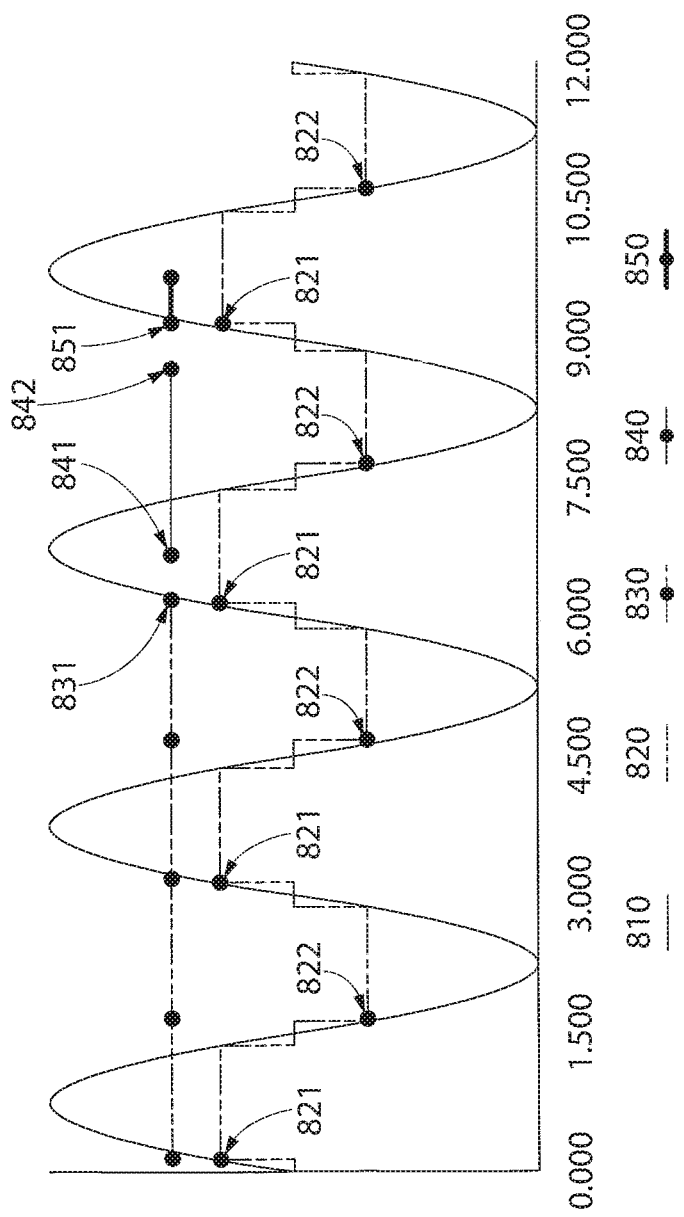
FIG. 8 illustrates an example airflow pattern with associated example sensor and control logic.

FIG. 8 illustrates the latter example used in a dry powder inhaler in which opened blisters are emptied by action of a piezoelectric vibrator. Sinusoid 810 is a trace of the airflow through the mouthpiece. Stepped square wave 820 shows the resulting airflow (e.g., digital pressure) sensor logic. Line 830 indicates the time period over which breathing pattern frequency is measured. (This may be done for example by a processor responsive to the sensor logic.) Line 840 indicates the time period over which a dose is advanced. Line 850 indicates the time period over which the piezo is vibrated. This may optionally be repeated over multiple, for example 4 to 12, e.g., 8, breath cycles. Points 821 indicate where inhalation is detected and points 822 indicate where exhalation is detected. At point 831 a processor verifies the user's breathing pattern is correct for dosing according to a comparison with some predetermined parameters and decides to deliver drug. At point 841 dose advance begins. At point 842 completion of dose advance is confirmed, for example using a photo gate. At 851 the piezo is fired. This could be timed to occur at a particular point during inhalation e.g., to maximize drug delivery to a particular section of the patient's airway.

Figure 9:
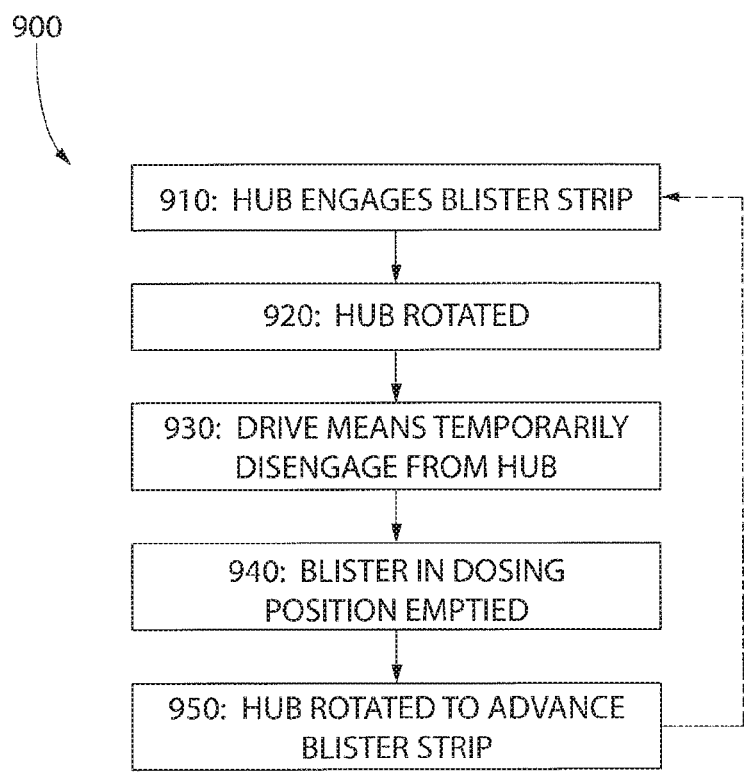
FIG. 9 is a flowchart of an example method.

FIG. 9 is a flowchart illustrating an example blister strip advance method 900. At 910 a recess of a hub engages a first, empty blister of the blister strip. At 920 the hub is rotated by means of an indexing gear train driven by drive means to move preceding second, full blister of the blister strip to a dosing position from which it can be emptied. At 930 the drive means is temporarily disengaged from the hub. At 940 the second blister in the dosing position is suitably emptied. Suitably, at 950 the hub is further rotated to advance the blister strip. The method may then suitably be repeated one or more times until every full blister of the blister strip has been emptied.

Figure 10:
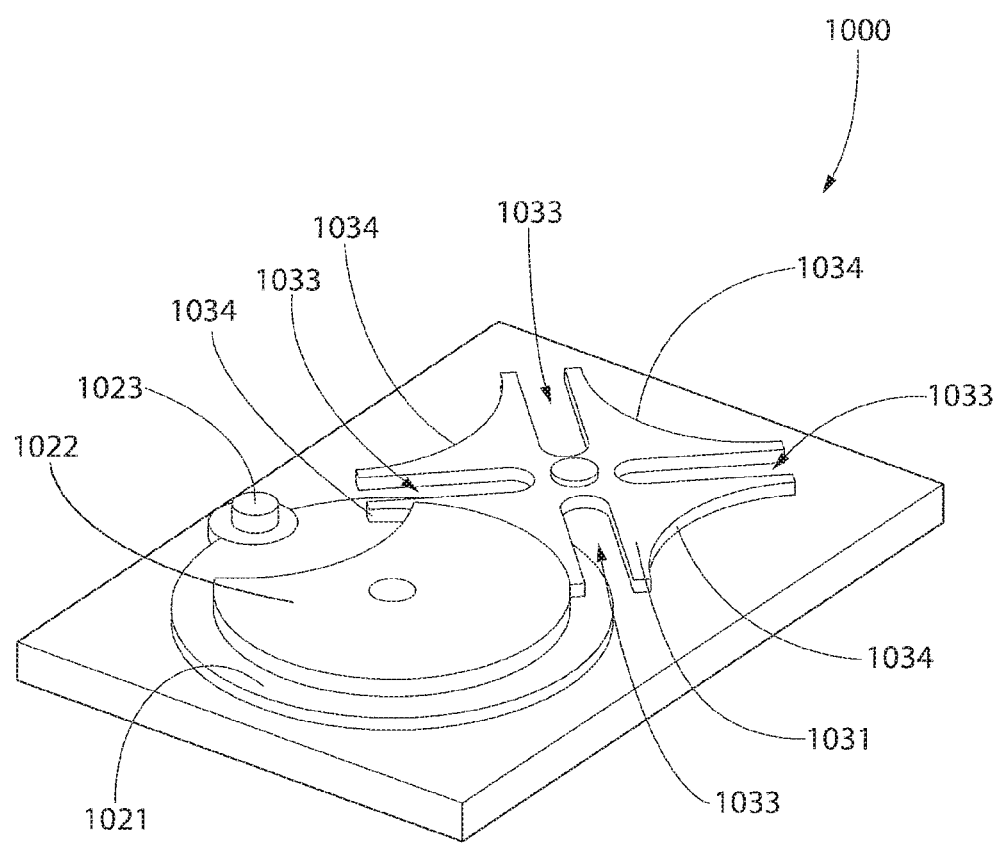
FIG. 10 illustrates an alternative example means for temporarily disengaging a hub from a drive means.

FIG. 10 illustrates a Geneva drive 1000; which could be used in place of a spur and sector gear arrangement to provide the temporary disengagement of the drive means from the hub. A sector gear 1022 is mounted on pin gear 1021, which carries pin 1023. Pin gear 1021 and sector gear 1022 are driven to rotate (directly or indirectly) by the drive means. When pin 1023 enters one of the slots 1033 in Maltese gear 1031, Maltese gear 1031 is driven to rotate. (It is free to do so since at this point it is not contacting sector gear 1022.) As pin gear 1021 rotates further, pin 1023 travels deeper into slot 1033, and then reverses direction relative to the slot until it emerges from the mouth of the slot again. By the time this occurs, sector gear 1022 is again contacting one of the recesses 1034 in the Maltese gear, blocking any further rotation. The Maltese gear 1031 thus undergoes indexed rotation. If the recesses 1034 are shaped to receive blisters, the Maltese gear 1031 could be the hub.

A blister strip for containing medicament and its dose advance mechanism are not required in accordance with all embodiments of the present invention. While certain embodiments of the inhaler comprise a detachable cartridge containing a blister strip and dose advance mechanism, alternative embodiments are contemplated in which, instead of a blister strip, one or more doses of dry powder medicament are contained in an alternative type of container or compartment within the device, preferably in the detachable cartridge. Stated another way, the inhaler may comprise one or more doses of dry powder medicament contained in the detachable cartridge, wherein the one or more doses are optionally stored in a blister strip. According to certain embodiments, when the one or more doses are stored in a container other than a blister cavity, the amount of dry powder medicament in a dose may be higher, e.g., from about 1 mg to about 70 mg, or from about 1 mg to about 60 mg, or from about 1 mg to about 50 mg, or from about 1 mg to about 40 mg, or from about 1 mg to about 30 mg, or from about 1 mg to about 20 mg, or from about 1 mg to about 10 mg, or from about 1 mg to about 5 mg, or from about 1 mg to about 4 mg, or from about 1 mg to about 3 mg, or from about 1 mg to about 2.5 mg, or from about 1 mg to about 2 mg.

Figure 11:
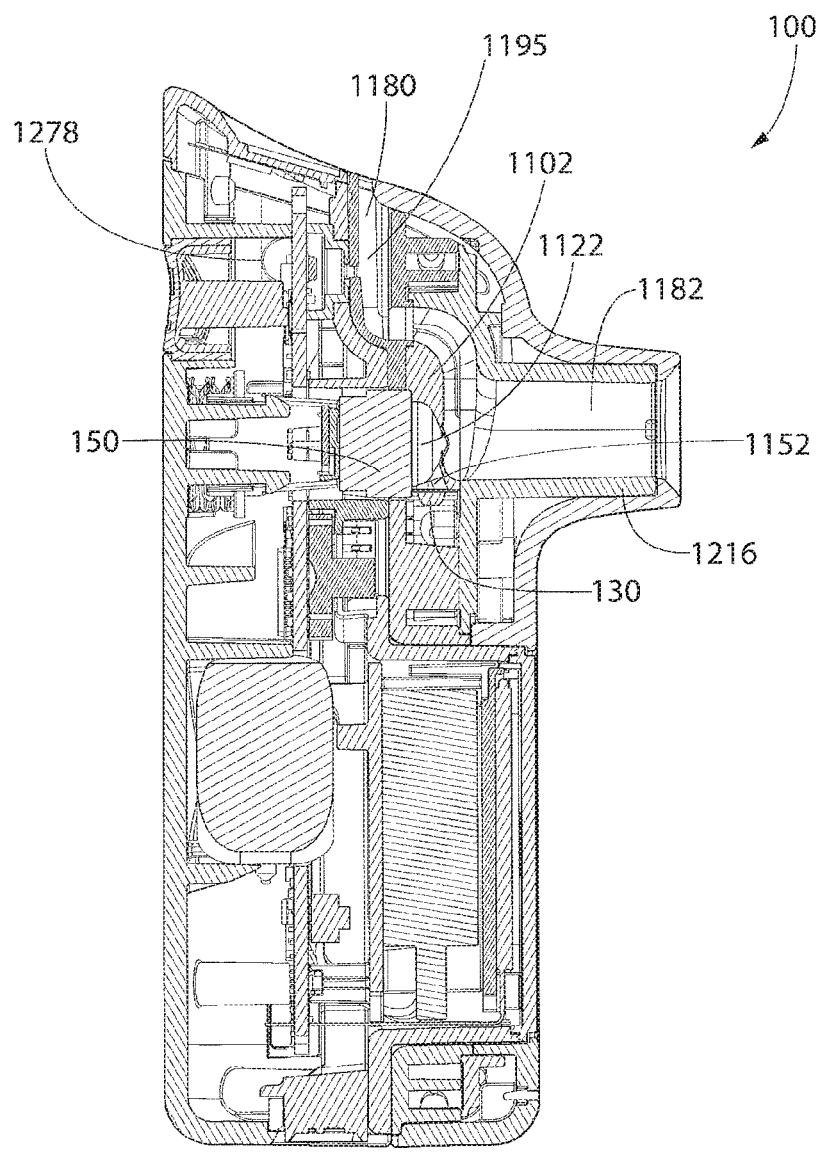
FIG. 11 is a side sectional view of the inhaler of FIG. 1 along a plane defined by line 1-1.

Turning to FIG. 11, a sectional view of the inhaler 100 of FIG. 1A is shown. In one embodiment, the inhaler 100 includes a channeling means (e.g., air flow conduit 1195) configured to allow air to travel through the inhaler 100 when a user inhales through a mouthpiece 1216. In one embodiment, the inhaler 100 includes a sensor 1278 (best seen in FIG. 31) configured to detect airflow through the air flow conduit 1195 and send a signal to a controller when airflow is detected. In one embodiment, the controller is configured to activate a blister strip advance mechanism, such as the one explained above, when a flow of air is detected by the sensor 1278 (in some cases, when a first flow of air is detected). The blister strip advance mechanism is configured to advance a blister 130 a fixed distance (e.g., the length of one blister) such that the blister 130 is in close proximity to (or in one embodiment adjacent to or substantially adjacent to) a tunnel 1152 in fluid communication with a dosing chamber 1122 as explained above, for example. In one embodiment, a housing 1102 comprises the tunnel 1152 and the tunnel is in fluid communication with a dosing chamber 1122. A membrane is configured to cover an open end of the dosing chamber 1122 in one embodiment. In one embodiment, a transducer 150 confronts the membrane 1166 (best seen in FIG. 32). In some embodiments, a separation means (e.g., spacer 1286 shown in FIG. 32) for separating a vibration means from membrane 1166 is positioned between the transducer 150 and the membrane 1166. In one embodiment, the controller is configured to activate a transducer 150 when an activation event is detected. In one embodiment, detection of multiple inhalations are required to trigger activation of transducer 150. For example, the controller may be configured to activate a transducer 150 when a flow of air is detected by the sensor 1278 (in some cases, when a subsequent flow of air is detected, e.g., second, third, or later). The transducer 150 is configured to vibrate, thereby vibrating the membrane 1166, to aerosolize and transfer pharmaceutical from the blister 130, through the tunnel 1152, and into the dosing chamber 1122. In one embodiment, the vibration of the transducer 150 also delivers the aerosolized pharmaceutical through openings 1148 in the dosing chamber 1122, through the exit channel 1182, and to a user, as explained in greater detail below. In one embodiment, the transducer 150 is configured to transfer acoustic vibration to the membrane. In some embodiments, the transducer 150 is configured to transfer vibration to the membrane 1166 via acoustic vibration and/or physical vibration. In one embodiment, one or more elements (e.g., dosing chamber, transducer, membrane, exit channel) are configured for efficient energy coupling through a common resonant frequency and/or acoustic impedance matching, as explained in greater detail below.

Embodiments of the present invention relate to a dosing chamber, which may be a molded acoustic chamber designed for ultrasonic synthetic jetting. According to preferred embodiments, the shape of the chamber has been optimized for powder delivery via synthetic jetting. Preferably, precision molding is used to provide a thin chamber top and one or more small jetting holes, i.e., openings that extend through the chamber wall.

According to preferred embodiments, the design of the dosing chamber helps to achieve the following objectives: sufficient volume to allow synthetic jet drug delivery while having a resonance frequency that matches that of a commercially available piezoelectric transducer; achievement of synthetic jetting from the acoustic chamber while providing a sufficient egress area to deliver drug quickly; and sufficient redundancy to prevent loss of delivery function due to intermittent clogging of holes.

In preferred embodiments, the geometries of the dosing chamber are configured such that the dosing chamber would resonate at the same or similar frequencies as the piezoelectric transducer (e.g., from about 37 kHz to about 42 kHz). The chamber geometry may also be configured to provide strong synthetic jetting and uniform dose delivery. As discussed in greater detail below, acoustic resonance frequency is preferably adjusted to match the mechanical resonance frequency of the piezoelectric transducer; that is, to match the frequency at which the maximum real power is consumed, and therefore the desired mechanical displacement is achieved.

Preferably, the geometry, size, and hole placement of the dosing chamber enable the chamber to resonate at a specific frequency coincident with the resonance frequency of the piezoelectric transducer in order to provide fast-onset synthetic jetting and maximal robustness against the effects of temperature, which tends to move the resonance frequencies of the piezoelectric transducer and the acoustic chamber in opposite directions.

According to preferred embodiments, the dosing position of the container (e.g., blister) relative to the dosing chamber is different from that of the prior art, i.e., the dry powder medicament may not be positioned directly adjacent to the piezoelectric transducer, but may be levitated out of the container and through a tunnel into the dosing chamber. In contrast, the prior art describes arrangements in which the powder is positioned directly adjacent to the vibrating element.

According to one embodiment, the inhaler comprises: a dosing chamber configured to receive medicament; a transducer confronting the dosing chamber, the transducer being configured to aerosolize the medicament when the transducer is activated; and a membrane between the dosing chamber and the transducer, the membrane being affixed to the dosing chamber, wherein the inhaler produces a synthetic jet to deliver the aerosolized medicament to a user when the transducer is activated.

According to one embodiment, the geometry, size and hole placement of the dosing chamber are configured such that the inhaler produces synthetic jetting to deliver the aerosolized medicament to a user when the transducer is activated, wherein the synthetic jetting causes medicament to be expelled into the exit channel in response to an activation of the transducer (i.e., a burst of the transducer) as short as 100 milliseconds (e.g., from about 100 ms to about 1000 ms, or from about 100 ms to about 800 ms, or from about 100 ms to about 500 ms).

According to an embodiment, the medicament delivery device comprises a dosing chamber comprising an interior that is configured to contain dry powder medicament (e.g., the dosing chamber may contain dry powder medicament that has been transferred from a blister), and a transducer confronting the dosing chamber. The dosing chamber and transducer are acoustically resonant such that the dosing chamber resonates in response to an activation of the transducer. The dosing chamber has an interior shape, internal height and location of one or more openings configured to cause the dry powder medicament to become aerosolized and delivered from the dosing chamber via synthetic jetting upon an activation of the transducer. Preferably, the dosing chamber's interior shape is at least partially defined by a lower sidewall that transitions to a shoulder, the shoulder transitions to an apex extending away from the lower sidewall, and the apex converges to a point, wherein the one or more openings in the dosing chamber are disposed in the apex. The internal height of the dosing chamber is configured so that pressure oscillation (e.g., at one or more anti-nodes) is sufficiently high to cause the dry powder medicament to become aerosolized and delivered from the one or more openings. Preferably the one or more openings are disposed at one or more anti-nodes of the dosing chamber when the transducer is activated.

According to this embodiment, each of the dosing chamber's (1) interior shape, (2) internal height and (3) location of one or more openings affects the deaggregation and/or delivery of powder. For example, one or more of the speed of onset of synthetic jetting, maximum synthetic jetting, delivered dose per burst, total delivered dose, and aerodynamic particle size distribution may be affected by a change in one or more of the dosing chamber's interior shape, internal height and location of one or more openings. Preferably, the dosing chamber's interior shape and height are configured such that the combined acoustic resonance of the transducer and dosing chamber is sufficient to cause aerosolization and delivery of the dry powder medicament having an MMAD within the preferred ranges described herein, e.g., about 6 µm or less, preferably with a fine particle fraction within the preferred ranges described herein, e.g., at least 30%. Maximum synthetic jetting is preferably achieved within ranges of time described herein, e.g., within about 500 ms or less from the start of a transducer activation.

Figure 40:
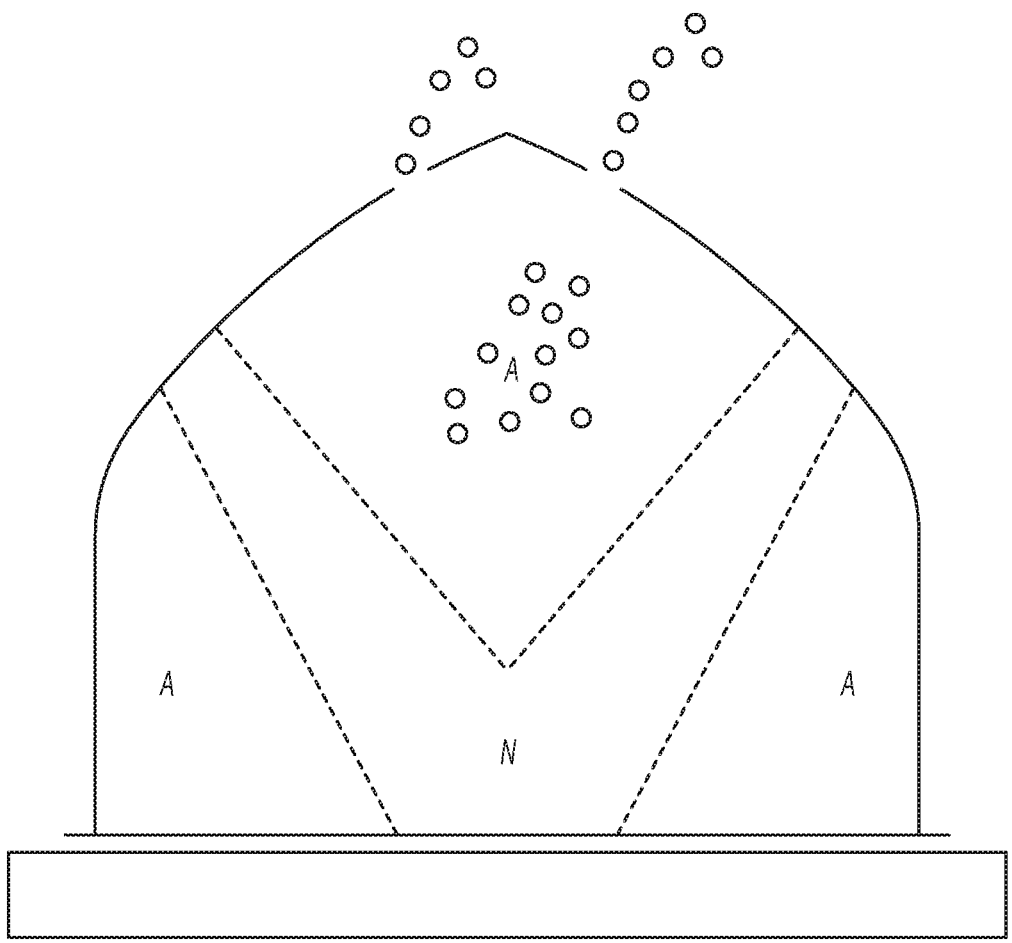
FIG. 40 illustrates an embodiment of a dosing chamber having nodes (N) and anti-nodes (A)

As illustrated in the embodiment shown in FIG. 40, certain areas inside the dosing chamber (labeled "N" for node) exhibit little or no oscillation in pressure when the transducer is activated, whereas other areas (labeled "A" for anti-node) exhibit higher oscillations in pressure when a transducer is activated. The highest amount of synthetic jetting within the dosing chamber, i.e., the occurrence of internal jets that stir the contents of the dosing chamber, occurs in those areas where there is high pressure oscillations, whereas synthetic jetting does not occur (or minimally occurs) in those areas with no oscillating pressure or very little oscillating pressure. Stated another way, the anti-nodes exhibit higher oscillations in pressure relative to the nodes. The opening(s) in the dosing chamber are preferably placed in one or more areas of high oscillating pressure ("anti-nodes"), instead of areas of little or no oscillating pressure ("nodes"), so that synthetic jetting can be maximized at the opening(s). Preferably, the dosing chamber shape, including its conical configuration near the holes, prevents powder from getting into nodes and achieves suitable intensity of oscillating pressures at the anti-nodes. According to a preferred embodiment, optimal synthetic jetting occurs when the dosing chamber's opening(s) are positioned at the conical configuration in the area of an anti-node where there are higher oscillations in pressure compared to the nodes. The location of nodes and anti-nodes inside a chamber can be determined by conventional methods of eigen frequency analysis, based on the size and shape of the chamber (e.g., using Comsol® software).

Figure 42:
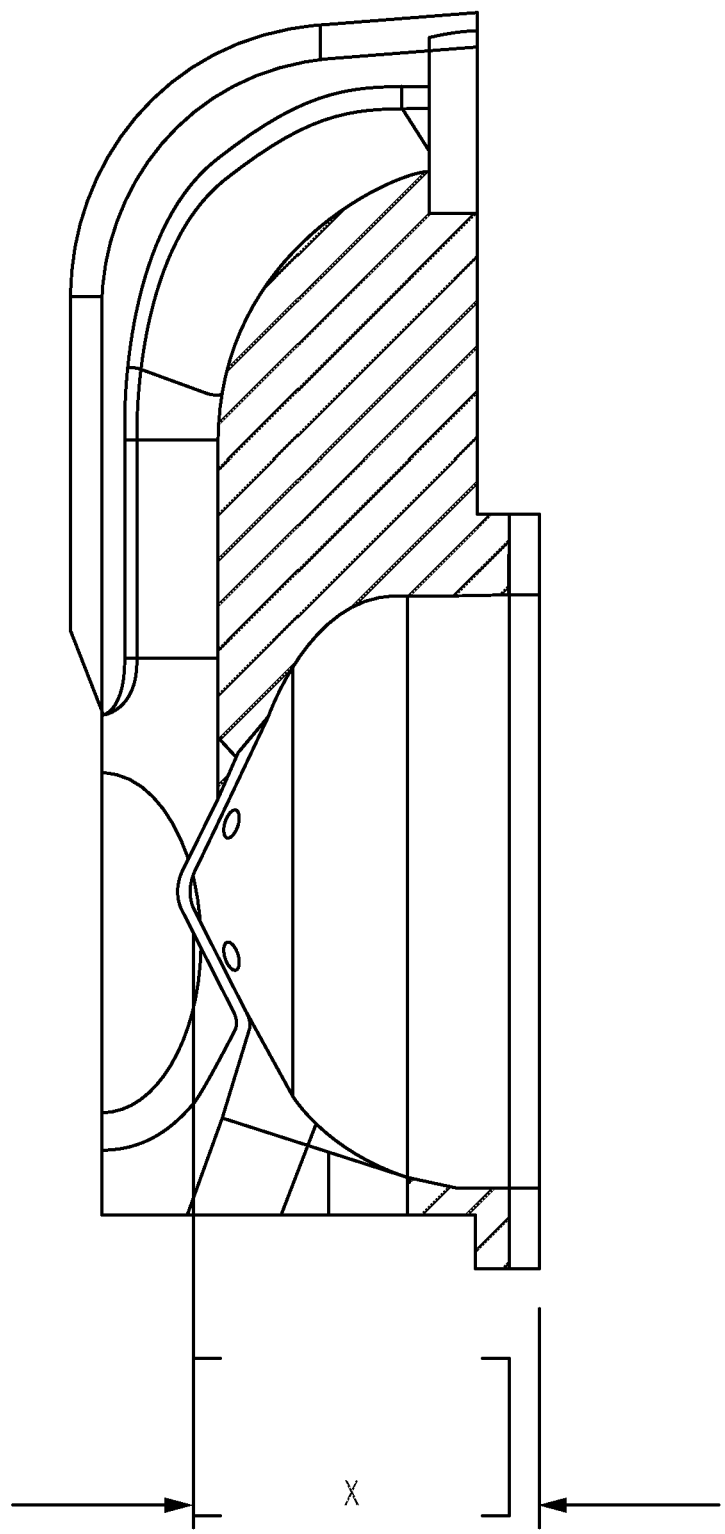
FIG. 42 illustrates an embodiment of a dosing chamber with an internal height X.

For a transducer's frequency range (e.g., 37-42 kHz), not all internal heights of a dosing chamber will provide suitable synthetic jetting, dose delivery and aerodynamic particle size distribution (APSD) because the internal height affects the acoustic resonance of the system, including the location of nodes and anti-nodes. In some cases, if the internal height of the dosing chamber is changed, the transducer's activation frequency must also be changed, in order to match the new acoustic resonance of the new dosing chamber shape. In other cases, the transducer's activation frequency may remain the same for different internal heights if those heights provide sufficiently high oscillating pressure at the opening(s). According to an embodiment, a dosing chamber having an internal height X, as shown in FIG. 42, has a resonant frequency Y that is approximately the same as that of the transducer; and a dosing chamber having an internal height that is approximately 2X, or between 1.7X and 2.3X (i.e., at the next approximate harmonic) has approximately the same resonant frequency Y because at the next approximate harmonic the anti-nodes (high oscillating pressure) are again located at the opening(s) of the dosing chamber.

According to one embodiment, the internal height of the dosing chamber may be adjusted by lengthening the lower sidewall 1126, as shown by dashed lines in FIG. 43B. For example, the internal height of the dosing chamber may be between about 8 mm and about 12 mm, or between about 9 mm and about 11 mm. According to an embodiment shown in FIG. 43A, the internal height is between about 4 mm and about 6 mm, or between about 5 mm and about 6 mm, when the dosing chamber has a resonant frequency that is approximately the same as that of the transducer (between about 37 kHz and about 42 kHz). According to an alternative embodiment shown in FIG. 43B, when the transducer is activated at the same frequency of 37-42 kHz, the internal height of the dosing chamber is about twice the internal height shown in FIG. 43A, or about 1.7-2.3 times the internal height, or about 1.7-2.1 times the internal height e.g., between about 8 mm and about 12 mm, or between about 9 mm and about 11 mm. For example, it was found that a dosing chamber with an internal height of about 5.5 mm (X) had approximately the same resonant frequency as a dosing chamber with an internal height between about 9.9 mm (about 1.8X) and about 10.5 mm (about 1.9X), due to similar locations of anti-nodes at the opening(s), as evidenced by similar performance in synthetic jetting and dose delivery.

According to one embodiment, the synthetic jetting includes a maximum velocity when the transducer is activated for an unlimited amount of time. In some embodiments, the maximum velocity may be achieved in a relatively short amount of time of operating the transducer. In one embodiment, the maximum velocity is achieved when the transducer is activated for, e.g., from about 100 ms to about 1000 ms, or from about 100 ms to about 800 ms, or from about 100 to about 500 milliseconds.

According to one embodiment, the dosing chamber includes a vertical sidewall, wherein the vertical sidewall transitions to a shoulder, the shoulder being concave relative to a dosing chamber interior. The shoulder preferably transitions to a slope extending away from the sidewall and toward a center of the dosing chamber. Stated another way, the dosing chamber 1122 preferably includes a first portion 1128 having a lower sidewall 1126 (e.g., vertical sidewall), a second portion 1130 having an intermediate sidewall 1138 (e.g., comprising the shoulder), and a third portion 1132 having an upper sidewall 1140 (e.g., a slope extending away from the sidewall, radially disposed about axis 1124 and converging at a point 1136 to form a conical section). In one embodiment, the lower sidewall 1126 defines a cylindrical portion and the upper sidewall 1140 defines a conical portion.

According to one embodiment, the slope transitions to an apex having a radius of curvature smaller than a radius of the shoulder. The dosing chamber further comprises one or more openings in the apex (e.g., between 1-10 openings, between 1-8 openings, between 1-6 openings, between 1-4 openings, between 2-10 openings, between 2-8 openings, between 2-6 openings, or between 2-4 openings). In an exemplary embodiment, the dosing chamber has 4 openings. As used herein, the term "apex" preferably refers to the conical portion of the dosing chamber defined by the upper sidewall 1140, which converges to a point 1136, i.e., the "apex" not only refers to the point 1136 but also to the conical portion defined by the upper sidewall that transitions to the point. The point of the apex is preferably rounded or pointed. The one or more openings positioned in the apex are preferably located closer to the point than to the shoulder.

Figure 41A:
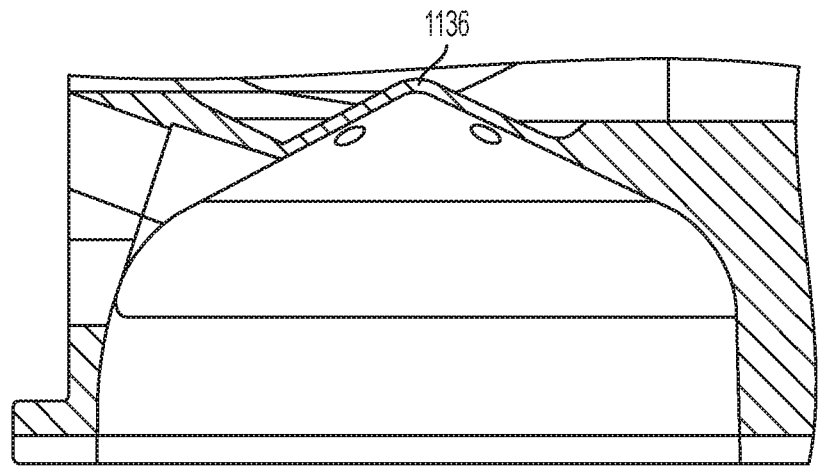
FIG. 41A illustrates an embodiment of a dosing chamber having an apex.
Figure 41B:
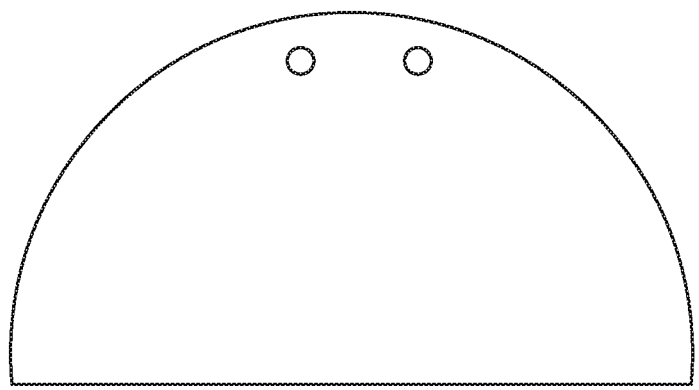
FIG. 41B illustrates an embodiment of a dosing chamber without an apex.

FIG. 41A provides an example of a dosing chamber with openings disposed in the apex 1136, contrary to FIG. 41B which shows a dosing chamber without an apex and openings instead disposed within a domed area that does not come to a point. The applicants have found according to certain embodiments that synthetic jetting is improved when the openings (holes) of the dosing chamber are disposed within an apex rather than a flat top or a domed area that does not come to a point; for example, the maximum velocity is achieved when the transducer is activated for, e.g., from about 100 ms to about 1000 ms, or from about 100 ms to about 800 ms, or from about 100 to about 500 milliseconds. Without being bound by any theory, it is believed that the shape of the conical portion contributes to the achievement of suitable oscillating pressures (one or more anti-nodes) near the opening(s). Preferably, each of the plurality of openings has a centerpoint spaced equidistantly on a circle, the circle having its centerpoint on an axis defined by the apex.

The apex preferably has an apex wall thickness that is less than the wall thickness of the remainder of the dosing chamber, i.e., the conical portion of the dosing chamber comprising the opening(s) has a wall thickness that is the thickness of the vertical sidewall (also referred to as the lower sidewall), or less than the wall thickness of the remainder of the dosing chamber (e.g., the lower sidewall and intermediate sidewall comprising the shoulder). The aspect ratio of each opening, i.e., the length to cross-section or diameter of the passageway preferably is at least 0.5 and preferably is greater than or equal to about one, helps ensure that the mass of gas that moves back and forth in the passageway is created as discrete, well-formed slugs of air. The applicants have found that the mechanical and acoustic energy of the transducer is more efficiently transferred to the dosing chamber when the walls of the dosing chamber, other than the apex, are not too thin, and have a thickness that is greater than the thickness of the portion of the apex where the opening(s) are disposed, in order to better retain vibratory energy.

According to one embodiment, the apex wall thickness is from about 0.002 inches (0.05 mm) to about 0.03 inches (0.8 mm), more preferably from about 0.004 inches (0.10 mm) to about 0.02 inches (0.5 mm), more preferably from about 0.004 inches (0.10 mm) to about 0.01 inches (0.25 mm), more preferably from about 0.006 inches (0.15 mm) to about 0.01 inches (0.25 mm). In one embodiment, the apex wall thickness is about 98% of the thickness of the largest wall thickness of the remainder of the dosing chamber. In one embodiment, the apex wall thickness is about 95% of the thickness of the largest wall thickness of the remainder of the dosing chamber. In one embodiment, the apex wall thickness is about 90% of the thickness of the largest wall thickness of the remainder of the dosing chamber. In one embodiment, the apex wall thickness is about 85% of the thickness of the largest wall thickness of the remainder of the dosing chamber. In one embodiment, the apex wall thickness is about 80% of the thickness of the largest wall thickness of the remainder of the dosing chamber. In one embodiment, the apex wall thickness is about 75% of the thickness of the largest wall thickness of the remainder of the dosing chamber. In one embodiment, the apex wall thickness is about 70% of the thickness of the largest wall thickness of the remainder of the dosing chamber. In one embodiment, the apex wall thickness is about 65% of the thickness of the largest wall thickness of the remainder of the dosing chamber. In one embodiment, the apex wall thickness is about 60% of the thickness of the largest wall thickness of the remainder of the dosing chamber. In one embodiment, the apex wall thickness is less than about 50% of the thickness of the largest wall thickness of the remainder of the dosing chamber. In one embodiment, the thickness of the remainder of the dosing chamber is substantially uniform.

According to one embodiment, the opening(s) fluidly connect the dosing chamber to the exit channel, wherein the aerosolized medicament is delivered from the dosing chamber to a user through the exit channel in response to an activation of the transducer. According to one embodiment, each opening has a diameter of from about 0.005 inches (0.13 mm) to about 0.05 inches (1.3 mm), or from about 0.008 inches (0.2 mm) to about 0.04 inches (1.0 mm), more preferably from about 0.01 inches (0.25 mm) to about 0.05 inches (1.3 mm), or from about 0.01 inches (0.25 mm) to about 0.04 inches (1.0 mm), or from about 0.01 inches (0.25 mm) to about 0.03 inches (0.76 mm); for example, about 0.019 inches (0.48 mm)±0.012 inches (0.30 mm), preferably from about 0.015 (0.38 mm) inches to about 0.03 inches (0.76 mm).

According to one embodiment, the inhaler includes at least one of: a) a ratio of a volume of the dosing chamber between the vertical sidewalls to a volume of the dosing chamber above the vertical sidewalls is about 0.9 to about 1.5, b) a ratio of a height of the vertical sidewalls to a height of the dosing chamber is about 0.25 to about 0.5, and c) a ratio of a height of the dosing chamber to a lower diameter of the dosing chamber is about 0.5 to about 0.65.

According to one embodiment, the dosing chamber comprises an entrance (preferably extending through the slope) configured to deliver the medicament into the dosing chamber from a container (e.g., blister). Preferably, the entrance has a longitudinal wall disposed about a tunnel axis, the container has an opening plane, and the tunnel axis is oblique or perpendicular to the opening plane. Preferably, the dosing chamber has a chamber axis of symmetry and the chamber axis is transverse to the tunnel axis. For example, an angle between the entrance axis and the chamber axis is from about 15° to about 25°. The term "transverse" preferably means extending across an axis.

According to one embodiment, the entrance comprises a tunnel in fluid communication with the dosing chamber, the tunnel configured to have at least one of (a) a top length to bottom length ratio of from about 4 to about 7.5, (b) a top length to median length ratio of from about 1.5 to about 3, and (c) a median length to bottom length ratio of from about 1.25 to about 3. A ratio of a tunnel diameter to a dosing chamber diameter may be from about 0.2 to about 0.4.

Embodiments of the dosing chamber are described in more detail below with reference to the Figures.

Figure 12:
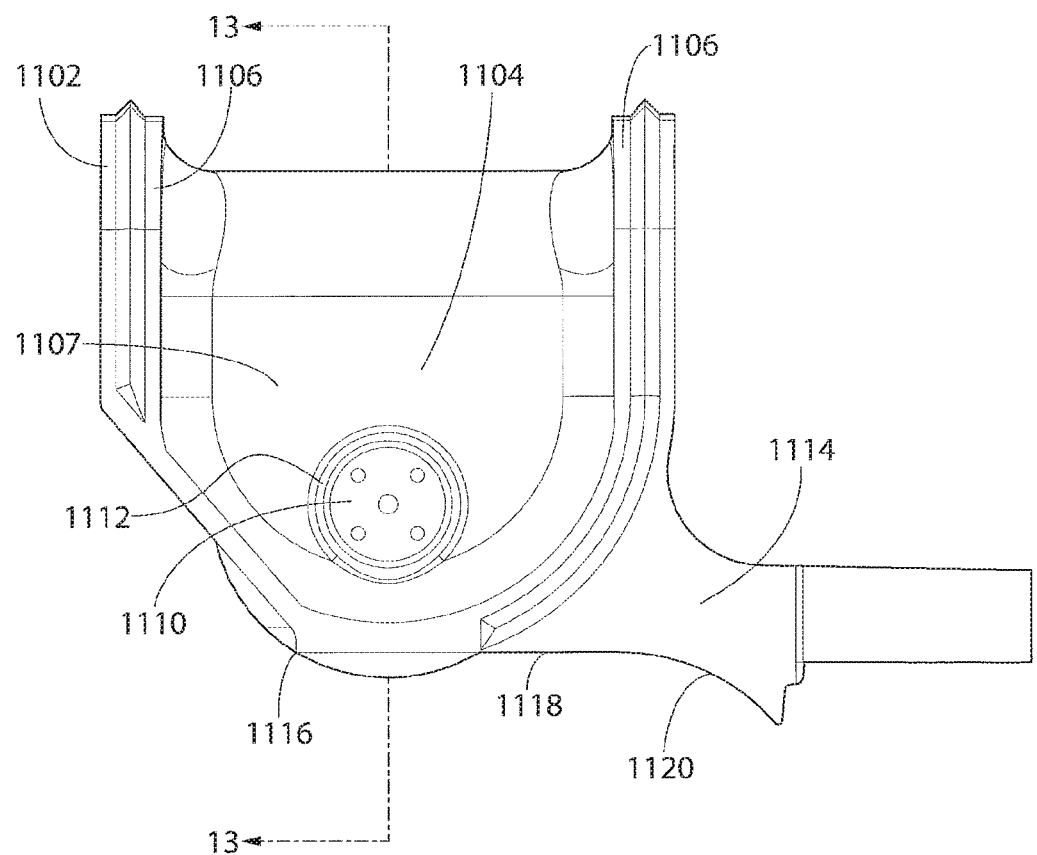
FIG. 12 is a front elevational view of a housing in accordance with an exemplary embodiment of the present invention.
Figure 13:
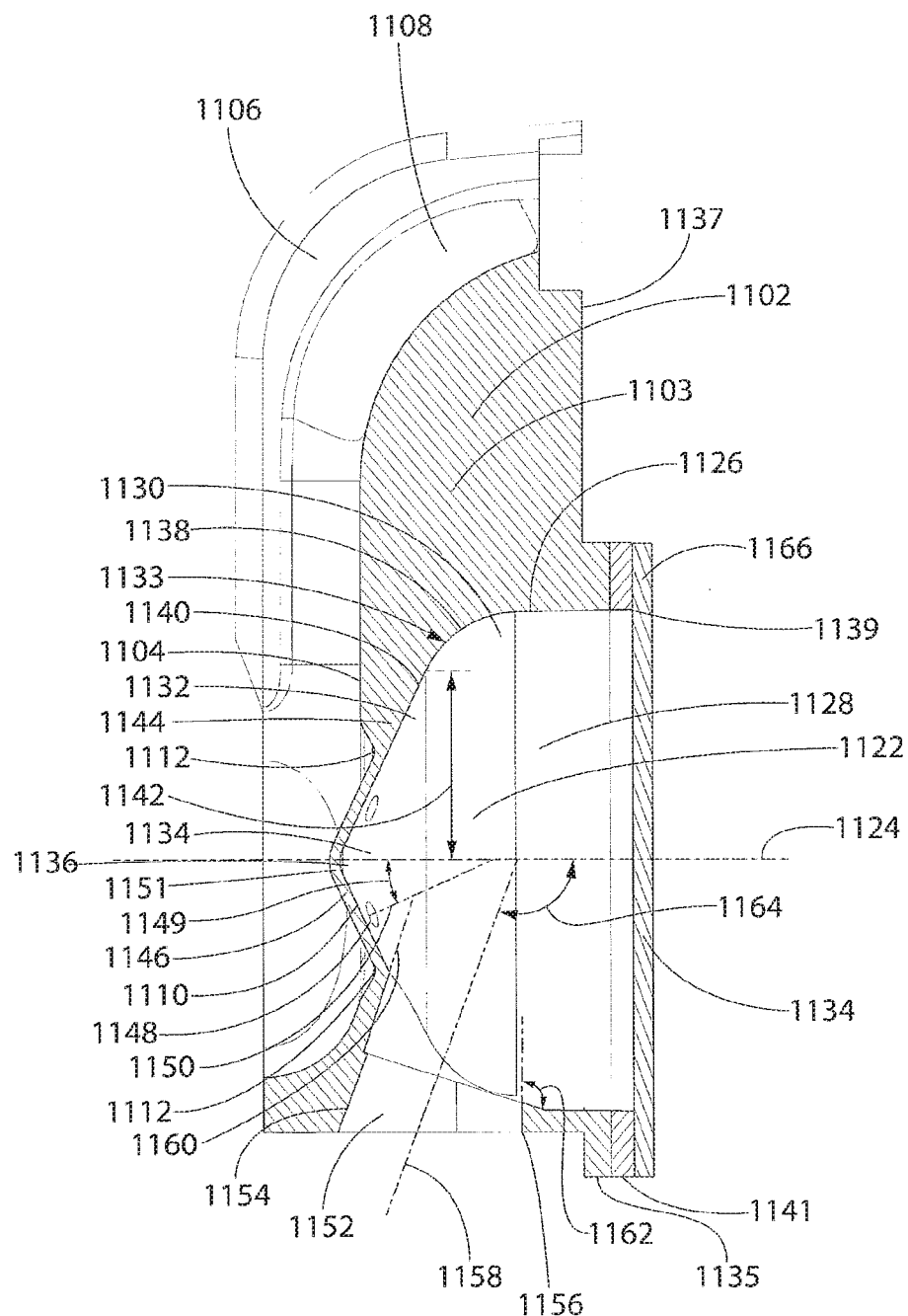
FIG. 13 is a side elevational view of the housing of FIG. 12.
Figure 14:
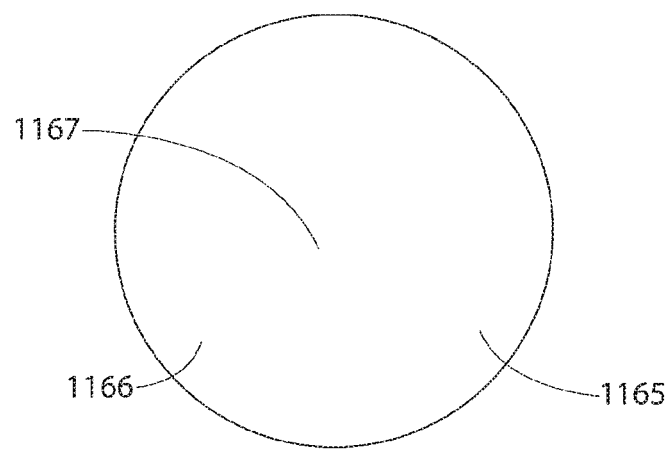
FIG. 14 is a front elevational view of a membrane in accordance with one embodiment of the present invention.
Figure 15:
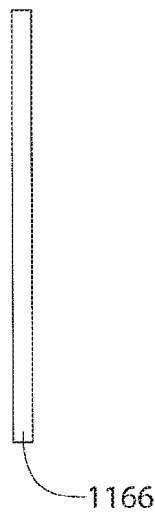
FIG. 15 is a side elevational view of the membrane of FIG. 14.
Figure 18:
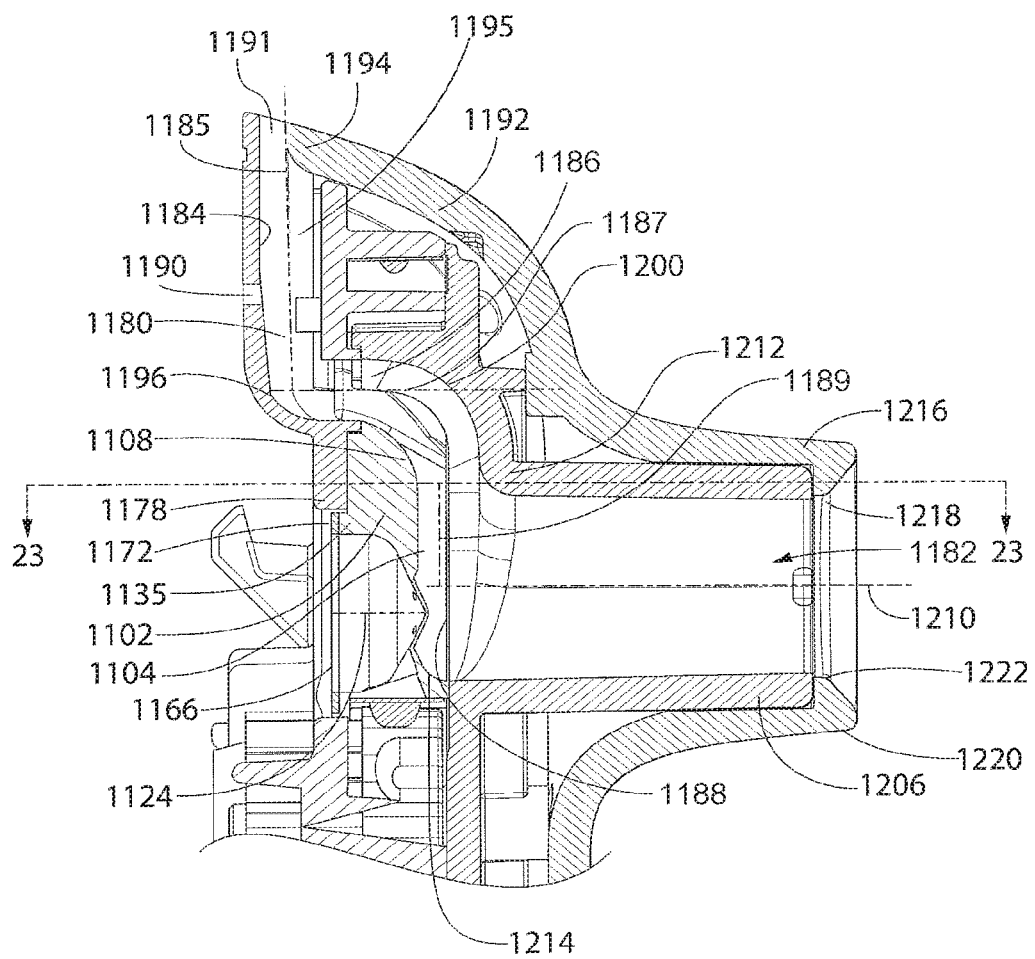
FIG. 18 is a sectional view of the front portion of the inhaler of FIG. 1 along a plane defined by line 18-18 of FIG. 17.

In some embodiments, as shown for example in FIG. 11, the inhaler 100 includes a dosing chamber housing 1102. Preferably, at least a portion of the dosing chamber housing 1102 defines the shape of the dosing chamber 1122. In one embodiment, the dosing chamber housing 1102 forms a boundary of the air flow conduit 1195 such that air flows through the inhaler 100 and picks up pharmaceutical that exits from the dosing chamber 1122, into the exit channel 1182, to deliver the pharmaceutical to a user. Turning now to FIGS. 12-13, one embodiment of a housing 1102 is shown. In one embodiment, the housing 1102 includes an upper surface 1104 which comprises a portion of the air flow conduit 1195 (the air flow conduit 1195 is best seen in FIG. 18).

In one embodiment, the housing includes a body 1103 below the upper surface 1104 which comprises the dosing chamber 1122 (best seen in FIG. 13). A border of a portion of the air flow conduit 1195 may include sidewalls 1106 which extend from the upper surface 1104 of the housing 1102. A transition at the junction between the upper surface 1104 (best seen in FIG. 12) and the sidewall 1106 may be in the form of a radius or a chamfer. In one embodiment, a channeling means (e.g., air flow conduit 1195) is configured for the promotion of laminar flow of air through the inhaler 100. In one embodiment, the upper surface 1104 and sidewall 1106 are smooth to promote laminar flow through the channeling means (e.g., air flow conduit 1195) as explained in greater detail below. In one embodiment, the upper surface 1104 and sidewalls 1106 define a housing volume 1107. In one embodiment, the upper surface 1104 is a first boundary of the housing volume 1107, the sidewalls 1106 are a second boundary of the housing volume 1107, and the housing volume 1107 is open on at least one side. In one embodiment, a portion of the chamber top 1110 extends away from the upper surface 1104 opposite the dosing chamber 1122. In one embodiment, the chamber top 1110 comprises an upper portion of the dosing chamber 1122 and a plane defined by at least a portion of the upper surface 1104 intersects the chamber top 1110 and/or the dosing chamber 1122. In one embodiment, the chamber top is co-planar with the upper face. In one embodiment, the chamber top 1110 is recessed with respect to the upper surface 1104. Upper surface 1104 may include a trough 1112 configured to surround the chamber top 1110. The trough 1112 may be recessed with respect to each of the chamber top 1110 and the upper surface 1104. In one embodiment, the housing 1102 is a monolithic element which includes the upper surface 1104 and the dosing chamber 1122. In one embodiment, the housing 1102 comprises a first element comprising the dosing chamber 1122 and a second element comprising the upper surface 1104 with the first element and second element coupled to each other.

In one embodiment, the dosing chamber housing 1102 includes an arm 1114 which extends generally away from the upper surface 1104 to at least partially secure the housing 1102 to the base plate 590 (FIG. 5A) via press fit, welding, fasteners (e.g., screws, dowels, anchors, heat stakes), adhesive, etc. The housing 1102 may include a lip 1116 which is configured to contact the backing tape 452 (best seen in FIG. 4A) of the blister strip 450 as the tape is peeled from the strip as previously described. The contact between the lip 1116 and the backing tape 452 may help peel the backing tape 452 from the blister strip 450. In one embodiment, the lip 1116 is a rounded edge to prevent severing the backing tape or may have a relatively small radius such that there is a relatively small contact surface area, which may reduce friction, between the backing tape 452 and the lip 1116. The arm 1114 may also counter any torque force applied to the housing 1102 as the backing tape 452 is peeled from the blister strip 450. In one embodiment, the arm 1114 includes a lower edge 1118 and a radius 1120. In one embodiment, the lower edge 1118 and radius 1120 are a portion of a track to guide the blister strip 450 as the blister strip engages the hub 440. In one embodiment, the radius 1120 is selected to generally follow the radius of the hub 440. This may allow different sized blisters to be used with the inhaler.

In some embodiments, the dosing chamber housing 1102 includes an internal passage in fluid communication with blister 130 and the exit channel 1182. The passage is configured to allow pharmaceutical from the blister 130 to be aerosolized and delivered to a user, for example. In some embodiments, the passage comprises a dosing chamber 1122 and a tunnel 1152. FIG. 13 is a sectional view of the housing 1102 along line 13-13 of FIG. 12. In one embodiment, dosing chamber 1122 is configured to receive the pharmaceutical or other substance from the blister 130 (or a container) and deliver the pharmaceutical through the exit channel 1182 and to the user, as described, for example, in more detail below.

In one embodiment, the dosing chamber 1122 includes a first portion 1128 having a lower sidewall 1126, a second portion 1130 having an intermediate sidewall 1138, and a third portion 1132 having an upper sidewall 1140. In one embodiment, the lower sidewall 1126 defines a cylindrical portion and the upper sidewall 1140 defines a conical portion. In one embodiment, the dosing chamber 1122 includes an axis of symmetry 1124 about which at least a portion of the lower sidewall 1126, intermediate sidewall 1138, and upper sidewall 1140 of dosing chamber 1122 are disposed (e.g., radially disposed). Dosing chamber 1122 may therefore include a circular cross-section in at least one plane. The lower sidewall 1126 may have a vertical portion that extends from an outer surface 1134 of the housing 1102. In one embodiment, the lower sidewall 1126 extends from the outer surface 1134 toward the upper surface 1104 of the housing 1102. The first portion 1128, second portion 1130 and third portion 1132 may be a monolithic element, or may comprise one or more separate elements that are coupled together to form the dosing chamber; for example, the lower sidewall 1126 or a portion thereof may be coupled an element comprising the intermediate sidewall 1138 and upper sidewall 1140 to form the dosing chamber.

Figure 16:
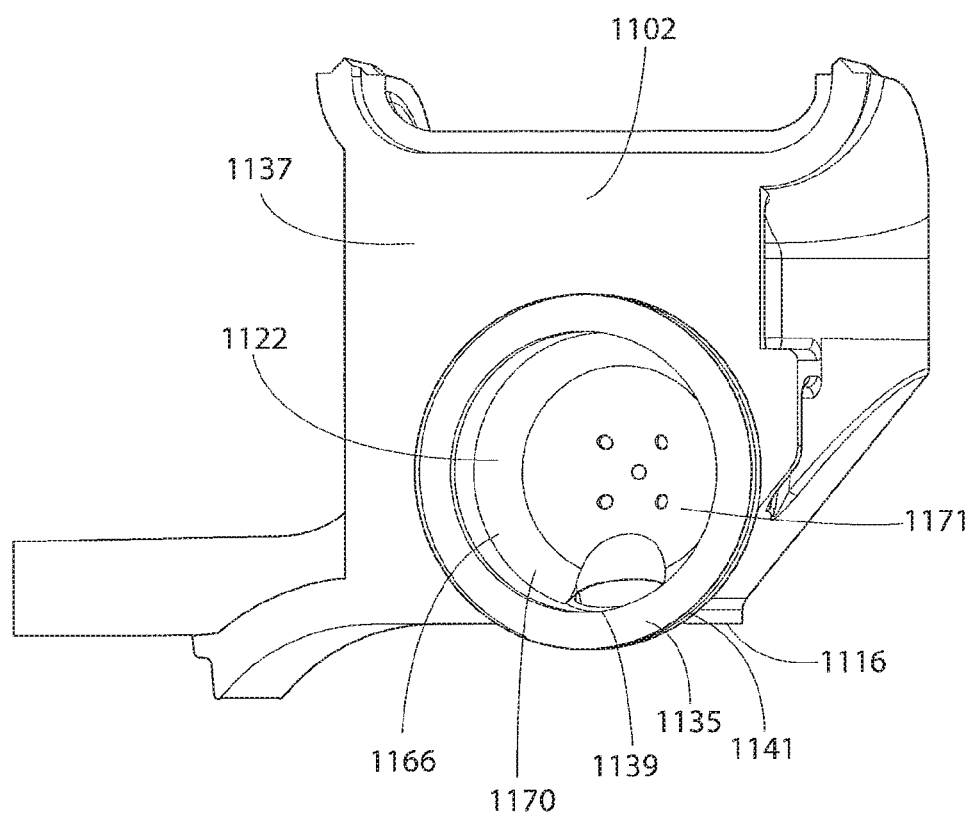
FIG. 16 is a rear perspective view of the housing of FIG. 12 coupled to the membrane of FIG. 14.

In one embodiment, the housing 1102 includes a crown 1135 which defines a lower portion of the lower sidewall 1126. The crown 1135, in one embodiment, is configured to protrude from a lower surface 1137 of the housing 1132 (best seen in FIGS. 13 and 16). The crown 1135 includes an inner face 1139 and an outer face 1141. Inner face 1139 and/or outer face 1141 are shaped to include inner and outer diameters, respectively. In one embodiment, the inner face 1139 is contiguous with a portion of the lower sidewall 1126. Although the lower sidewall 1126 is shown in FIG. 13 as a generally straight section, the lower sidewall could also be curved, angled inwardly/outwardly as the sidewall extends away from the outer surface 1134, stepped, or any other shape that provides sufficient synthetic jetting and dose delivery. The dosing chamber 1122 includes a height as measured along the axis of symmetry 1124 from the outer surface 1134 of the housing 1102 to an apex 1136 of the chamber, as explained in greater detail below. In one embodiment, the top of the chamber 1110 (best seen in FIG. 12) comprises the apex 1136 which includes an apex wall thickness that is less than a wall thickness of the remaining portions of the dosing chamber 1122.

In one embodiment, the height of the dosing chamber 1122 comprises the combined height of the first portion 1128, second portion 1130, and third portion 1132. In one embodiment, the lower sidewall 1126 defines a first portion height that is from 10%-75% of the chamber height. In one embodiment, the first portion height is from 20%-70% of the chamber height. In one embodiment, the first portion height is from 30%-65% of the chamber height. In one embodiment, the first portion height is from about 40%-60% of the chamber height. In one embodiment, the first portion height is from about 50%-55% of the chamber height. In one embodiment, a ratio of a height of the dosing chamber 1122 to a diameter of the first portion 1128 is from about 0.5 to about 0.65. In one embodiment, a ratio of a height of the dosing chamber 1122 to a diameter of the first portion 1128 is from about 0.55 to about 0.6. In one embodiment, a ratio of a length of the dosing chamber to a diameter of the first portion 1128 is from about 0.4 to about 0.75. In one embodiment, a ratio of the volume of the first portion 1128 to the combined volume of the second portion 1130 and the third portion 1132 is about 0.8 to about 1.3.

The exemplary dosing chamber 1122 illustrated in FIG. 13 includes the second portion 1130 having a perimeter defined by an intermediate sidewall 1138 adjacent the lower sidewall 1126. In one embodiment, the intermediate sidewall 1138 is configured to be concave relative to an interior of the chamber 1122 and the concave portion may be defined by an arc having a radius 1133, which can be seen when the dosing chamber 1122 is viewed in cross-section as in FIG. 13. In one embodiment, the intermediate sidewall 1138 is concave relative to the interior of the chamber 1122 and the intermediate sidewall has a radius 1133 with a centerpoint within the interior of the chamber. In one embodiment, the intermediate sidewall includes a continuous radius 1133 along the height of the intermediate sidewall 1138. In one embodiment, the intermediate sidewall 1138 includes portions each having different radii (not shown). In one embodiment, the intermediate sidewall 1138 includes a first radius convex to an interior of the chamber 1122 and a second radius (not shown) concave to an interior of the chamber. In one embodiment, the intermediate sidewall 1138 is a stepped portion that comprises the transition from the lower sidewall 1126 to the upper sidewall 1140. In one embodiment, the intermediate sidewall 1138 comprises a beveled or chamfered transition between the upper sidewall 1140 and the lower sidewall 1126. In one embodiment, the intermediate sidewall 1138 comprises a bevel between the upper sidewall 1140 and the lower sidewall 1126, the bevel disposed at a bevel angle relative to the lower sidewall 1126.

Third portion 1132, as illustrated in FIG. 13, is defined by upper sidewall 1140 radially disposed about axis 1124 to form a conical section. The exemplary intermediate sidewall 1138 illustrated in FIG. 13 is configured to transition to the upper sidewall 1140 extending away from the lower sidewall 1126. In one embodiment, the upper sidewall 1140 is at an angle relative to the chamber axis 1124. In one embodiment, the upper sidewall 1140 has a continuous slope as it extends between the intermediate sidewall 1138 and the apex 1136. In one embodiment, the upper sidewall 1140 has a first slope section at a first angle relative to the axis 1124 and a second section at a second angle (not shown) relative to the axis 1124 that is different from the first angle. In one embodiment, the upper sidewall 1140 includes a first section 1144 wherein the housing 1102 which forms the upper sidewall 1140 has a first thickness, and a second section 1146 having a second thickness, wherein the second thickness is less than the first thickness. In one embodiment, the trough 1112 in the upper surface 1104 of the housing 1102 comprises the demarcation between the first section 1144 and the second section 1146.

Still referring to FIG. 13, a portion of the upper sidewall 1140 extends beyond the upper surface 1104 of the housing 1102. In one embodiment, the apex 1136 is the portion of the upper sidewall 1140 which extends beyond the upper surface 1104. In other words, the chamber top 1110 (best seen in FIG. 12) comprises the apex which converges to a point 1136. Although the chamber top 1110 is shown having a preferred conical shape in FIG. 13, the chamber top could have alternative shapes as desired. In one embodiment, the portion of the upper sidewall 1140 comprising the apex 1136 has a uniform thickness along the length of the apex 1136.

One or more openings 1148 are configured to extend through the upper sidewall 1140 to provide fluid communication between the dosing chamber 1122 and the exit channel 1182. Preferably, at least the area of the apex surrounding the opening(s) satisfies the following parameters for synthetic jetting described in U.S. Pat. No. 7,318,434: 1) The aspect ratio of each opening, i.e., the length to cross-section or diameter of the passageway preferably is at least 0.5 and preferably is greater than or equal to about one. In some embodiments, this aspect ratio helps ensure that the mass of gas that moves back and forth in the passageway is created as discrete, well-formed slugs of air; and 2) The distance the gas moves back and forth through the passageway preferably is greater than about two times the cross-section or diameter of the passageway. This helps to ensure that dry-powder disaggregated by the vortex created has a chance to escape the vortex's presence before the gas moves back through the passageway.

In one embodiment, the portion of the upper sidewall 1140 comprising the apex 1136 has a tapered thickness. For example, the upper sidewall 1140 could have a first thickness for the portion adjacent the trough 1112 and a second thickness (different from the first thickness) for the portion at the tip of the apex 1136. In one embodiment, the first thickness is greater than the second thickness. In one embodiment, the first thickness is less than the second thickness. In one embodiment, the upper sidewall 1140 may be stepped or abruptly change between the first thickness and the second thickness. In one embodiment, the upper sidewall 1140 gradually transitions between the first thickness and the second thickness. In one embodiment, the apex 1136 has a radius of curvature 1151 at the peak of the apex which is smaller than a radius 1133 of the intermediate sidewall 1138.

One or more openings 1148 are configured to extend through the upper sidewall 1140 to provide fluid communication between the dosing chamber 1122 and the exit channel 1182. In one embodiment, the openings 1148 each have a centerpoint equidistantly spaced on a circle (not shown) having its center on the axis 1124 of the chamber 1122 and a radius of about 0.5 mm to about 1.0 mm. In one embodiment, the chamber 1122 includes a single opening 1148. In one embodiment, the dosing chamber 1122 includes four openings 1148. In one embodiment, the openings 1148 are asymmetrically positioned about the axis 1124. In one embodiment, one of the openings 1148 is positioned on the axis 1124. In one embodiment, the opening 1148 has a diameter of about 0.019 inches (0.48 mm)±0.012 inches (0.30 mm), preferably from about 0.015 (0.38 mm) inches to about 0.03 inches (0.76 mm). In one embodiment, each of the openings 1148 have an opening sidewall disposed about its own opening axis of symmetry 1150. In one embodiment, at least one of the openings 1148 has an opening axis of symmetry 1150 which is transverse to the axis 1124 of the dosing chamber 1122. In one embodiment, the opening axis 1150 of at least one of the openings 1148 is perpendicular to the upper sidewall 1140. In one embodiment, the dosing chamber 1122 includes more than one opening 1148, each having an axis 1150 which may all be parallel to each other, one not parallel to the others, each perpendicular to the surface of the upper sidewall 1140, and/or one parallel to the chamber axis 1124. In one embodiment, the diameter of the openings 1148 may be influenced by the number of openings in the apex 1136. For example, a chamber 1122 having two openings 1148 may have greater opening diameters than a chamber having four openings such that the dosing chamber has a consistent total opening surface area regardless of the number of openings. The openings 1148 are configured to have any desired shape (e.g., circular, elliptical, rectangular, etc.) provided that they allow an aerosolized pharmaceutical to pass therethrough. In one embodiment, the openings 1148 have a size selected to ensure that the pharmaceutical is of a size to permit it to pass to the lungs of a user.

Still referring to FIG. 13, one embodiment of a housing 1102 includes a tunnel 1152 configured to provide a passage for fluid communication between the dosing chamber 1122 and a blister 130 (best seen in FIG. 11) or another material source positioned outside the housing 1102. The tunnel 1152 is configured to include an upper tunnel wall 1154 and a lower tunnel wall 1156. In one embodiment, the cross-sectional shape of the tunnel 1152 is circular. In one embodiment, the cross-sectional shape of the tunnel 1152 square, elliptical, rectangular, any polygonal shape, etc. In one embodiment, the tunnel 1152 extends through the lower sidewall 1126, and is generally perpendicular to the lower sidewall 1126, such that the upper tunnel wall 1154 and the lower tunnel wall 1156 are generally of equal length.

In one embodiment, an axis 1158 of the tunnel 1152 is oblique to the chamber axis 1124. In one embodiment, the tunnel 1152 extends through the upper sidewall 1140 of the chamber 1122. In one embodiment, the tunnel axis 1158 is oblique to the chamber axis 1124, the upper tunnel wall 1154 intersects the upper sidewall 1140, and the lower tunnel wall 1156 intersects the intermediate sidewall 1138 or lower sidewall 1126 such that the length of the upper surface 1156 and lower tunnel wall 1156 are different from each other and an angle 1160 of the upper tunnel wall 1154 relative to the immediately adjacent interior chamber surface is different from an angle 1162 of the lower tunnel wall 1156 relative to the adjacent interior chamber surface. In one embodiment, the upper tunnel wall 1154 and lower tunnel wall 1156 are uniformly radially disposed about the tunnel axis 1158. In one embodiment, the upper tunnel wall 1154 and lower tunnel wall 1156 are generally parallel to each other. In one embodiment, the upper tunnel wall 1154 and lower tunnel wall 1156 converge toward the tunnel axis 1158. In one embodiment, one of the upper tunnel wall 1154 and the lower tunnel wall 1156 are generally straight and the other of the upper tunnel wall 1154 and lower tunnel wall 1156 are not straight (e.g., curved, stepped, bent). In one embodiment, the tunnel axis 1158 is straight. In one embodiment, the tunnel axis 1158 includes bends, curves, etc.

In one embodiment, a ratio of the length of the upper tunnel wall 1154 to an average diameter of the tunnel 1152 is about 4 to about 7.5. In one embodiment, a ratio of the length of the upper tunnel wall 1154 to a median length of the tunnel 1152 is about 1.5 to about 3. In one embodiment, a ratio of the length of the lower tunnel wall 1156 to a median length of the tunnel 1152 is about 1.25 to about 3. In one embodiment, a ratio of the diameter of the tunnel 1152 to the diameter of the chamber 1122 is about 0.2 to about 0.4. In one embodiment, an angle 1164 between the tunnel axis 1158 and chamber axis 1124 is about 100° to about 150°. In one embodiment, the angle 1164 is about 100° to about 140°. In one embodiment, the angle 1164 is about 100° to about 130°. In one embodiment, the angle 1164 is about 20°. In one embodiment, the lower tunnel wall 1156 is positioned at the intersection of the sidewall 1126 and the intermediate sidewall 1138. In one embodiment, the lower tunnel wall 1156 is positioned at the intersection of the intermediate sidewall 1138 and the upper sidewall 1140. In one embodiment, the length between the lower tunnel wall 1156 and the outer surface 1134 of the housing 1102 is greater than the distance between the entry point of the upper tunnel wall 1154 into the dosing chamber 1124 and the apex 1136. In one embodiment, the tunnel axis 1158 is oblique to a plane containing the blister face 1168 (best seen in FIG. 1H). In one embodiment, the upper tunnel wall 1154 defines an upper tunnel wall plane and the lower tunnel wall 1156 defines a lower tunnel wall plane, wherein extensions of each of the upper tunnel wall plane and the lower tunnel wall plane intersect outside of the dosing chamber 1122.

The dosing chamber housing 1102 is manufactured from a material which promotes the flow of the aerosolized pharmaceutical through the dosing chamber 1122 and the flow of air through at least a portion of the air flow conduit 1195 while reducing or eliminating deposits of the pharmaceutical on the surface of the air flow conduit. In one embodiment, the housing 1102 is formed of acrylonitrile butadiene styrene (ABS). Housing 1102 may include an anti-static additive or coating such as Permastat manufactured by RTP Company of Winona, Minnesota. In other embodiments, the housing 1102 is made from PVC, mylar, ABS, stainless steel, or any other material which will avoid reaction with the pharmaceutical in the blister strip. In one embodiment, the housing 1102 transfers vibration from the transducer 150 to the blister strip 131, as explained in greater detail below. The housing 1102 may be manufactured from a single material or different portions may be made from different materials. For example, the lower sidewall 1126, intermediate sidewall 1138, and upper sidewall 1140 of the dosing chamber 1122 may comprise a first material and the upper surface 1104 of the housing 1102 may comprise a second material.

According to preferred embodiments, a membrane is adhered to the dosing chamber and couples the chamber to the vibrating element. As used herein, a membrane is preferably a sheet of material disposed between the face of the transducer and the inside of the dosing chamber (e.g., as a partition), wherein the sheet of material is preferably pliable. The membrane preferably meets the following criteria: biocompatible; compliant material that effectively converts vibration to appropriate levels of acoustic activity; robustness to damage; reliable adhesion to the dosing chamber material; and having an appropriate coefficient of thermal expansion. Preferably, the membrane is capable of retaining tension and adhesion under expected environmental conditions throughout the inhaler's intended life, and remains smooth and flat while providing effective vibratory transfer to the dosing chamber acoustic resonance. Overall, the material and tension of the membrane should optimize energy transfer from the transducer to the dosing chamber, so that a fast onset of synthetic jetting and delivered dose uniformity can be achieved.

According to one embodiment, the inhaler comprises: a dosing chamber configured to receive medicament; a transducer confronting the dosing chamber, the transducer being configured to aerosolize the medicament when the transducer is activated; and a membrane between the dosing chamber and the transducer, the membrane being stretched across a dosing chamber opening and affixed to the dosing chamber; wherein the device produces a synthetic jet to deliver the aerosolized medicament to a user when the transducer is activated.

According to another embodiment, the medicament delivery device comprises a dosing chamber comprising an interior that is configured to contain dry powder medicament; a transducer confronting the dosing chamber, wherein the dosing chamber and the transducer are acoustically resonant such that the dosing chamber is configured to resonate in response to an activation of the transducer; and a membrane between the dosing chamber and the transducer, the membrane being stretched across a dosing chamber opening (and preferably affixed to the dosing chamber), the membrane being comprised of a material having a thickness. According to this embodiment, the membrane material and thickness affect the deaggregation and/or delivery of powder. For example, one or more of the speed of onset of synthetic jetting, maximum synthetic jetting, delivered dose per burst, total delivered dose, and aerodynamic particle size distribution may be affected by a change in the membrane material or thickness. Preferably, the membrane material and its thickness are selected such that the combined acoustic resonance of the transducer, dosing chamber and membrane is sufficient to cause aerosolization and delivery of the dry powder medicament having an MMAD within the preferred ranges described herein, e.g., about 6 μm or less, preferably with a fine particle fraction within ranges described herein, e.g., at least 30%. Maximum synthetic jetting is preferably achieved within the preferred ranges of time described herein, e.g., within about 500 ms or less from the start of a transducer activation.

According to one embodiment, the membrane has a tensile strength (MD or machine direction) of at least 30 MPa, more preferably at least 40 MPa, or at least 50 MPa, or at least 60 MPa, or at least 70 MPa, or at least 80 MPa, or at least 90 MPa, or at least 100 MPa, or at least 120 MPa, or at least 150 MPa, or at least 200 MPa; for example from about 30 MPa to about 200 MPa, or from about 40 MPa to about 200 MPa. According to one embodiment, the membrane has a tensile modulus of 7.0 GPa or less, or 6.0 GPa or less, or 5.0 GPa or less; for example, from about 1.0 GPa to about 7.0 GPa, or from about 1.0 GPa to about 6.0 GPa. According to one embodiment, the membrane has a tensile elongation at yield (MD or machine direction) of at least 50%, or at least 75%, or at least 100%; for example, from about 50% to about 300% elongation, or from about 75% to about 300% elongation at yield, or from about 100% to about 300% elongation at yield. According to one embodiment, the membrane has a coefficient of thermal expansion (CTE) of less than 120 ppm/° C., or less than 100 ppm/° C., or less than 90 ppm/° C., or less than 80 ppm/° C., or less than 70 ppm/° C.; for example, from about 10 ppm/° C. to about 100 ppm/° C., or from about 10 ppm/° C. to about 90 ppm/° C., or from about 10 ppm/° C. to about 80 ppm/° C., or from about 10 ppm/° C. to about 70 ppm/° C. According to one embodiment, the membrane has a Tg (glass transition temperature) of at least 60° C., or at least 70° C., or at least 80° C., or at least 90° C., or at least 100° C.; from example, from about 50° C. to about 250° C., or from about 60° C. to about 250° C., or from about 60° C. to about 200° C., or from about 60° C. to about 175° C.

According to one embodiment, the membrane has one or more of the following characteristics: a tensile strength (MD) of at least 30 MPa, a tensile modulus of 7.0 GPa or less, a tensile elongation (MD) of at least 50%, a CTE of less than 100 ppm/° C., and a Tg of at least 60° C. Non-limiting examples of such materials include polyethylene terephthalate (PET) (e.g., Mylar® 813), polyether ether ketone (PEEK) (e.g., APTIV® 2000-050), polycarbonate (e.g., LEXAN® SD8B14), polysulfone (e.g., Udel®), polyetherimide (e.g., ULTEM®), polyvinylidene fluoride (e.g., KYNAR®), and polyvinyl chloride.

According to another embodiment, the membrane has one or more of the following characteristics: a tensile strength (MD) of at least 40 MPa, a tensile modulus of 6.0 GPa or less, a tensile elongation (MD) of at least 75%, a CTE of less than 100 ppm/° C., and a Tg of at least 70° C. Preferably, the membrane is a material that is heat sealable to the dosing chamber. In one embodiment, the membrane is manufactured from one of polyethylene terephthalate (PET) (e.g., Mylar® 813), polyether ether ketone (PEEK) (e.g., APTIV® 2000-050), polycarbonate (e.g., LEXAN® SD8B14), polysulfone (e.g., Udel®), polyetherimide (e.g., ULTEM®), polyvinylidene fluoride (e.g., KYNAR®), polyvinyl chloride, or similar material with one or more of the properties described herein (e.g., tensile strength, tensile modulus, tensile elongation, CTE, Tg, etc.).

According to one embodiment, the membrane is under a tensile force of about 0.15 N/mm to about 1.0 N/mm, or 0.2 N/mm to about 1.0 N/mm, or from about 0.2 N/mm to about 0.8 N/mm, or from about 0.2 N/mm to about 6 N/mm (as measured when assembled with the dosing chamber). According to one embodiment, the membrane has a thickness of about 30 um to about 150 um, or about 40 um to about 100 um, or about 40 um to about 70 um, or about 40 um to about 60 um, or about 50 um to about 80 um. According to one embodiment, the membrane material is selected from at least one of PET, polycarbonate and PEEK. According to another embodiment, the membrane material is selected from at least one of PET and polycarbonate. According to one embodiment, the membrane has a membrane thickness which is about 0.38% to about 0.43% of a chamber height. Embodiments of the membrane are described in more detail below with reference to the Figures.

In one embodiment, the membrane 1166 is coupled to the housing and covers the opening to the dosing chamber 1122 such that the membrane is vibrated when the transducer 150 is activated. Turning now to FIGS. 14-15, a membrane 1166 (or film) is shown. The membrane 1166 is configured to be coupled to the outer surface 1134 of the housing 1102 such that the membrane 1166 covers the open end 1170 (best seen in FIG. 16) of the dosing chamber 1122. The membrane 1166 is configured to be coupled to the housing 1102 via adhesive, welding, anchors, etc. In one embodiment, the membrane 1166 is shaped similarly to the open end 1170 of the dosing chamber 1122 such that the membrane completely covers the open end. In one embodiment, the membrane 1166 has a uniform thickness as shown in FIG. 15. In one embodiment, some portions of the membrane 1166 are thicker or thinner than other portions. In one embodiment, for example, an outer region 1165 of the membrane 1166 is thicker than an inner region 1167. In one embodiment, the outer region 1165 is thinner than the inner region 1167. In one embodiment, the membrane 1166 tapers from the thicker of the outer region 1165 and inner region 1167 to the thinner of the outer region 1165 and the inner region 1167. In one embodiment, the transition between the outer region 1165 and the inner region 1167 is stepped when one region is thicker than another.

In one embodiment, the membrane 1166 is manufactured from a material that allows it to be stretched across the dosing chamber opening to promote efficient energy coupling between the transducer and membrane when the transducer vibrates. In one embodiment, the membrane 1166 is manufactured from one of polyethylene terephthalate (PET) (e.g., Mylar® 813), polyether ether ketone (PEEK) (e.g., APTIV® 2000-050), polycarbonate (e.g., LEXAN® SD8B14), polysulfone (e.g., Udel®), polyetherimide (e.g., ULTEM®), polyvinylidene fluoride (e.g., KYNAR®), polyvinyl chloride, or similar material provided that the membrane can be stretched across at least a portion of the open end 1170. In one embodiment, the membrane 1166 is under a tensile load when it is initially stretched across the open end 1170. In one embodiment, the tension is about 0.17 to about 1.09 N/mm. In one embodiment, the tension is about 0.17 N/mm to about 1.09 N/mm when the inhaler 100 is not in use. The tension value may be selected based, at least in part, by the material or thickness of the membrane 1166. For example, tension may be selected based on the membrane material and the resultant resonant frequency of a membrane having the selected material and tension such that the resonant frequency of the membrane approximates the resonant frequency of the transducer 150, as explained in greater detail below. In one embodiment, the membrane 1166 is opaque. In one embodiment, the membrane 1166 is translucent or semi-translucent. In one embodiment, the membrane 1166 comprises more than one layer of the same or different materials.

The membrane 1166 is preferably configured to be coupled to the crown 1135. The peel strength between the membrane 1166 and the crown 1135 may be selected to ensure that the membrane 1166 does not disengage from the crown 1135 after a selected number of uses when the membrane is vibrated. The peel strength may also be selected to reduce the likelihood of air entering or escaping the dosing chamber 1122 between the membrane 1166 and the crown 1135. The peel strength in one embodiment is configured to be about 75 g to about 250 g. In one embodiment, the portion of the membrane coupled to the crown is treated (e.g., chemical etching, physical scoring) prior to coupling to improve the bond between the elements. In one embodiment, the outer region 1165 of the membrane 1166 is thicker than the inner region 1167 and the outer region 1165 is treated (e.g., chemical etching, physical scoring) prior to coupling the membrane 1166 to the crown 1135. In one embodiment, the membrane 1166 comprises a sheet which is secured to the crown 1135 and trimmed in place such that the membrane has the same outer diameter as the crown 1135. In one embodiment, the membrane 1166 is wrapped around the edges and secured to the sides of the crown 1135. In one embodiment, the membrane 1166 includes a membrane effective area 1171. In the embodiment illustrated in FIG. 16, the membrane effective area 1171 is the portion of the membrane 1166 inside of the inner face 1139 of the crown 1135 above the open end 1170 of the dosing chamber 1122 such that the membrane effective area can move (or vibrate) without contacting the crown 1135. In one embodiment, the membrane thickness is about 0.1% to about 1%, or about 0.1% to about 0.8%, or about 0.1% to about 0.6%, or about 0.2% to about 1%, or about 0.2% to about 0.8%, or about 0.2% to about 0.6%, or about 0.38% to about 0.43% of the chamber height.

According to one embodiment, the membrane material is a PET material having a thickness from about 10 μm to about 40 μm; or a polycarbonate material having a thickness from about 20 μm to about 60 μm, wherein the material is heat sealed to the dosing chamber with an adhesive (e.g., Loctite® 4310). For example, it was found that a PET material (Mylar® 813) having a nominal thickness of about 23±10 μm or a polycarbonate material (LEXAN® Sabic SD8B14) having a nominal thickness of about 50±15 μm enabled optimal synthetic jetting (e.g., maximum synthetic jetting of at least 0.5 V in response to an activation of the transducer) and dose delivery, e.g., as demonstrated in Example 9.

Figure 17:
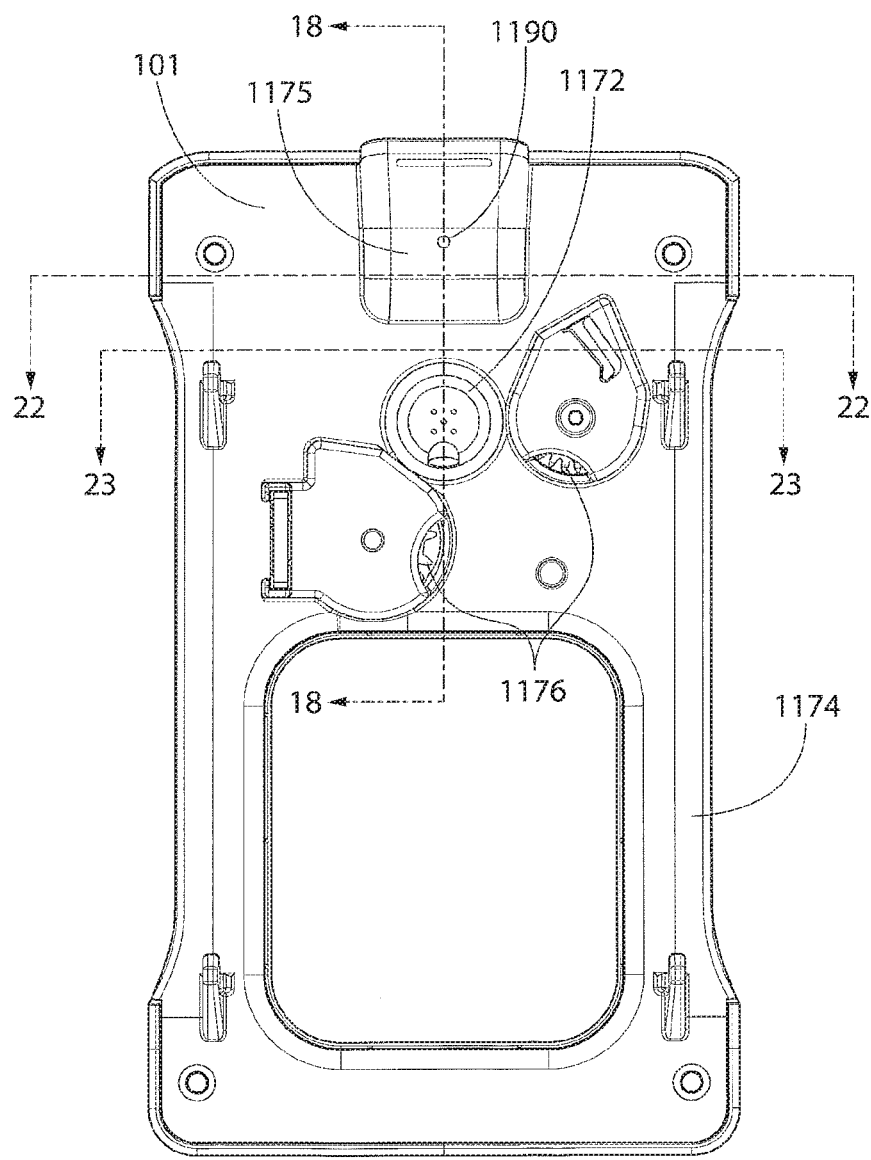
FIG. 17 is an isolated rear view of the front portion of the inhaler of FIG. 1.

The front portion 101 of the inhaler 100 includes a rear cover that in some embodiments includes accessways that expose the dosing chamber and gears of the blister advance mechanism for interaction with the transducer 150 and corresponding gears of the rear portion 102. Referring now to FIG. 17, an isolated, rear view of the front portion 101 of the inhaler 100 is shown. According to preferred embodiments, the front portion 101 is the replaceable component (also referred to as a removable cartridge) of the inhaler. The front portion 101 is configured to include a rear cover 1174 having a passageway 1172 aligned with the dosing chamber 1122. The passageway 1172 allows the membrane 1166 and the transducer 150 to be adjacent, or in contact with, one another when the inhaler 100 is assembled, as explained in greater detail below. In one embodiment, the crown 1135 of the housing 1102 extends partially into the passageway 1172 (best seen in FIG. 18). The rear cover 1174 is configured to include accessways 1176 for the sector gear 441 and the spooling gear 461 of the blister strip advance mechanism. In one embodiment, when assembled, the crown 1135 is recessed from a rear surface 1178 of the rear cover 1174. In one embodiment, the membrane 1166 is recessed about 0.5 to about 1.5 mm from the rear surface 1178.

According to particular embodiments, particularly those embodiments which employ a blister strip, the relative positioning of the inhaler's components (e.g., the blister relative to the vibratory element, dosing chamber, air inlet and outlet), and the shape and positioning of the air flow conduit, differ from those of prior dry powder delivery devices. For example, in several devices, the drug container (capsule or blister) was placed in front of the vibratory element, and in some cases in direct contact with the vibrating element, so that the vibratory energy was transferred directly from the vibratory element to the drug container with no structures positioned between them. See, e.g., U.S. Pat. Nos. 6,026,809 and 6,142,146. Unlike the prior art devices, according to embodiments of the present invention, the drug container (e.g., blister) is not directly in front of the vibratory element; instead, the inhaler comprises a dosing chamber positioned between the vibratory element and the container. For example, the inhaler may comprise a blister disposed about a blister axis; a dosing chamber disposed about a chamber axis; and a transducer confronting the dosing chamber, the transducer being configured to aerosolize the medicament when the transducer is activated; wherein the chamber axis is transverse to the blister axis when the blister is in a dosing position. Preferably, the relative position of these components provides a chimney-style air flow conduit outlet to a subject with an air intake at about 90° relative to the outlet. This is contrary to a cross-flow type of air flow conduit in which the outlet is on roughly the same axis as the blister axis, or is co-axial or at a slight angle to the blister axis.

According to an embodiment, a dry powder medicament delivery device comprises a blister disposed about a blister axis; a dosing chamber configured to receive dry powder medicament from the blister, the dosing chamber disposed about a chamber axis; a transducer confronting the dosing chamber, wherein the dosing chamber and the transducer are acoustically resonant such that the dosing chamber is configured to resonate in response to an activation of the transducer; an exit channel in fluid communication with the dosing chamber, the exit channel disposed about an exit channel axis; and a tunnel disposed about a tunnel median axis and in fluid communication with the dosing chamber and the blister such that dry powder medicament from the blister can travel through the tunnel and into the dosing chamber when the transducer is activated; wherein the exit channel axis and the chamber axis are substantially parallel, the chamber axis and the exit channel axis are transverse to the blister axis, and the tunnel median axis is oblique to the blister axis and transverse to the chamber axis and the exit channel axis.

According to preferred embodiments, the relative positioning of the inhaler components helps to achieve the following objectives: delivery of acceptable aerosol performance over a wide range of tidal breathing patterns; flow resistance that is comfortable for patients and repeatable; provision of access to a breath sensor; minimal accumulation of drug formulation on air flow conduit surfaces; and minimal regions of air flow stagnation regions that could result in drug formulation deposition.

According to one embodiment, a medicament delivery device (or inhaler) of the present invention comprises: a blister disposed about a blister axis; a dosing chamber configured to receive medicament from the blister, the dosing chamber disposed about a chamber axis; and a transducer confronting the dosing chamber, the transducer being configured to aerosolize the medicament when the transducer is activated; wherein the chamber axis is transverse to the blister axis when the blister is in a dosing position. According to a preferred embodiment, blisters are arranged along a blister strip and the blister strip is not in direct physical contact with the transducer, i.e., the blister strip does not touch the transducer face. Despite this lack of physical contact, powder may be aerosolized from the blister; it is believed that aerosolization occurs because mechanical vibration and acoustic resonance are effectively transferred from the transducer to the dosing chamber to the blister. This arrangement is contrary to many prior art devices, in which the blister strip is in physical contact with a vibrating element.

According to one embodiment, the chamber includes a sidewall disposed about the chamber axis such that the chamber axis is an axis of symmetry. According to one embodiment, a blister includes a blister sidewall disposed about the blister axis such that the blister axis is an axis of symmetry. According to one embodiment, the blister includes a rim surrounding a blister opening, wherein the blister rim is spaced from the transducer, e.g., about 2 mm to about 5 mm from the transducer, before the transducer is activated.

According to one embodiment, the device further comprises an exit channel disposed about an exit channel axis, wherein the aerosolized medicament from the dosing chamber is transferred through the exit channel and to the user. Preferably, the exit channel axis and the dosing chamber axis are parallel. Preferably, the transducer is disposed about a transducer axis of symmetry, wherein the dosing chamber axis and the transducer axis of symmetry are co-axial.

According to one embodiment, the device further comprises a tunnel disposed about a tunnel median axis and in fluid communication with the dosing chamber and the blister such that medicament from the blister travels through the tunnel and into the dosing chamber when the transducer is activated; wherein the tunnel median axis is oblique to the blister axis. Preferably, the tunnel median axis is transverse to the chamber axis.

According to one embodiment, the tunnel includes an upper wall and a lower wall, the tunnel configured to include at least one of (a) a top wall length to bottom wall length ratio of about 4 to about 7.5, (b) a top wall length to a median length of about 1.5 to about 3, and (c) a median length to bottom wall length of about 1.25 to about 3. Preferably, a ratio of a tunnel entrance diameter to a dosing chamber diameter is from about 0.2 to about 0.4.

The inhaler of the present invention comprises an air flow conduit (used interchangeably with the term "flow channel"), which preferably extends from an air inlet (an opening through which air is drawn into the air flow conduit when a user inhales through the device) to an outlet (an opening through which air entrained with dry powder medicament exits the inhaler's mouthpiece). An embodiment of the air flow conduit 1195, air inlet 1191, and outlet as part of the mouthpiece 1216 is illustrated in FIG. 18. The size and shape of the air flow conduit are designed to achieve the desired flow resistance (e.g., suitable for patients with COPD), accommodate the position of the aerosol engine within the inhaler, and provide a flow path from the dosing chamber to the outlet that does not obstruct the flow of dry powder. The flow resistance provided by the air flow conduit is preferably low enough to be comfortable for patients that have difficulty inhaling (e.g., COPD patients, cystic fibrosis patients, etc.) but high enough to be detectable by the flow sensor. As discussed herein, the inhaler is not a passive device because it comprises a flow sensor which can detect inhalation through the device at low flow rates, and send a signal to an aerosol engine that aerosolizes dry powder in response to the detected inhalation. Thus, a user does not need to generate a high inspiratory flow (i.e., to inhale forcefully) or to use slow, deep inhalation through the device in order to trigger dose delivery and deaggregate the powder (e.g., by generating turbulence), but inhales via tidal inhalation, i.e. at a normal inhalation without applying extra effort including inhalation that is slower, deeper, faster or stronger than normal breathing at rest. This is contrary to conventional DPI's, which often require increased inspiratory flow rates as resistance decreases, or which require slow, deep inhalation, in order to trigger dose delivery and effectively deaggregate the drug to produce particulates of optimal sizes (see, e.g., U.S. Pat. No. 6,116,237; Roberto W Dal Negro, Multidisciplinary Respiratory Medicine, 2015, 10:13; and Tiddens, H. A., et al., Journal of Aerosol Medicine, 19:4, 2006, pp. 456-465).

According to an exemplary embodiment, the air flow conduit provides a flow resistance from about 0.040 $cmH_2O^{0.5}$/LPM to about 0.1 $cmH_2O^{0.5}$/LPM, or from about 0.040 $cmH_2O^{0.5}$/LPM to about 0.090 $cmH_2O^{0.5}$/LPM, or from about 0.050 $cmH_2O^{0.5}$/LPM to about 0.1 $cmH_2O^{0.5}$/LPM, or from about 0.050 $cmH_2O^{0.5}$/LPM to about 0.090 $cmH_2O^{0.5}$/LPM, or from about 0.040 $cmH_2O^{0.5}$/LPM to about 0.085 cmH$_2$O$^{0.5}$/LPM, or from about 0.050 cmH$_2$O$^{0.5}$/LPM to about 0.085 cmH$_2$O$^{0.5}$/LPM, or from about 0.060 cmH$_2$O$^{0.5}$/LPM to about 0.085 cmH$_2$O$^{0.5}$/LPM at a flow rate of about 30 liters per minute (LPM).

Figure 37:
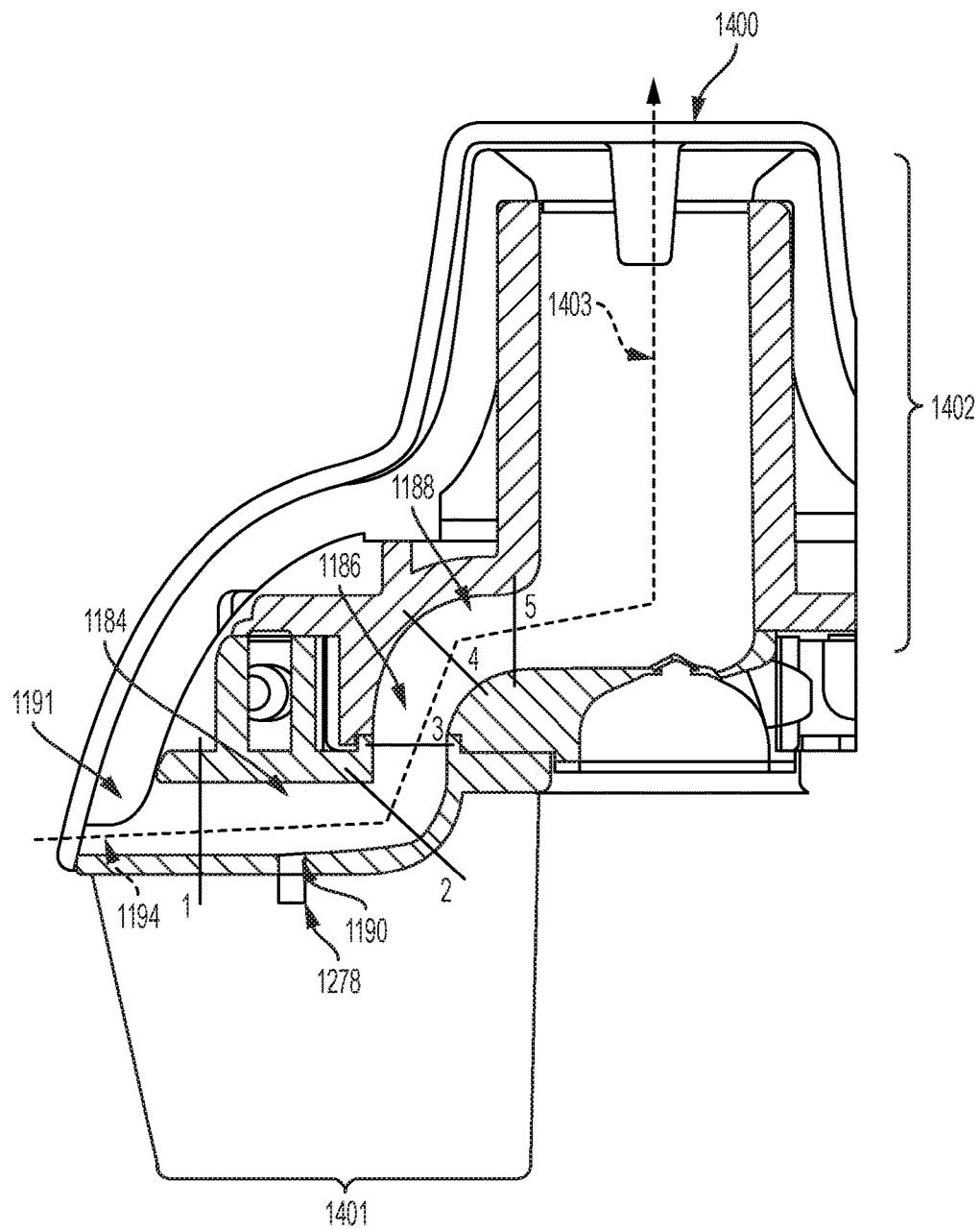
FIG. 37 illustrates an embodiment of the air flow conduit.

According to an embodiment, the air flow conduit has a constricted section 1400 with a cross-sectional area that is significantly less than the cross-sectional area(s) of the remainder of the air flow conduit, and which provides flow resistance. Embodiments of the constricted section 1400 are illustrated in FIG. 18 and FIG. 37, in which the general direction of air flow is illustrated by arrow 1403, wherein the air flows in a direction from upstream (e.g., inlet) to downstream (e.g., outlet). For example, the constricted section 1400 may be formed by at least one ledge 1194 or at least one protrusion that extends into the air flow conduit and creates a narrow cross-sectional area (e.g., there may be one ledge as shown in FIG. 37, or alternatively more than one ledge extending into the air flow conduit to create the constricted section 1400). Preferably, the constricted section 1400 is located in the upstream area 1401 of the air flow conduit, i.e., upstream from the area of the air flow conduit into which dry powder medicament is expelled from the opening(s) of the dosing chamber. Preferably, the constricted section 1400 is also located upstream from the flow sensor or from an aperture 1190 that provides fluid communication between the air flow conduit and the flow sensor. For example, the constricted section 1400 may be disposed at the air inlet 1191 (see e.g. FIG. 37), or near the air inlet 1191 (e.g., downstream from the air inlet and upstream from the flow sensor). Preferably, the constricted section is not located in the downstream area 1402 of the air flow conduit, i.e., in the area of the air flow conduit where the dry powder medicament is expelled (e.g., at the dosing chamber or in the exit channel), as a pressure drop over the dosing chamber, which might be caused by a reduced cross-sectional area, is not necessary to draw powder from the dosing chamber into the flow channel.

The cross-sectional area of the air flow conduit, with the exception of the constricted area, may be constant or may vary across the length of the air flow conduit; for example, from about 40 mm$^2$ to about 120 mm$^2$, or from about 40 mm$^2$ to about 100 mm$^2$, or from about 50 mm$^2$ to about 100 mm$^2$. FIG. 37 provides an example of five cross-sections 1-5 having the following cross-sectional areas: Cross-section 1=0.0840 in$^2$ (54.2204 mm$^2$); Cross-section 2=0.0858 in$^2$ (55.3790 mm$^2$); Cross-section 3=0.0854 in$^2$ (55.0889 mm$^2$); Cross-section 4=0.1054 in$^2$ (67.9824 mm$^2$); Cross-section 5=0.0974 in$^2$ (62.8359 mm$^2$). The shape of the cross-section may vary along the length of the air flow conduit; for example, the cross-section may be circular, elliptical, rectangular, etc. According to one embodiment, the portion of the exit channel disposed between the dosing chamber and the outlet has an average cross-sectional area that is larger than the average cross-sectional area of the air flow conduit disposed between the air inlet and the dosing chamber (excluding the constricted area); for example, the exit channel may have an average cross-sectional area of at least 75 mm$^2$, or from about 75 mm$^2$ to about 100 mm$^2$, while the average cross-sectional area of the air flow conduit disposed between the air inlet and the dosing chamber (excluding the constricted area) may be at least 50 mm$^2$, or from about 50 mm$^2$ to about 70 mm$^2$.

The constricted area preferably provides the smallest cross-sectional area of the air flow conduit. The remainder of the air flow conduit, excluding the constricted area, preferably has a minimum cross-sectional area that is larger than the average cross-sectional area of the constricted area (including the uppermost part of the constricted area down to the lowermost part of the constricted area). According to an embodiment, the smallest cross-sectional area of the air flow conduit, excluding the constricted area is at least about 1.75× (i.e., 1.75 times) at least about 2× (i.e., 2 times), or at least about 2.5×, or at least about 3, or at least about 3.5×, or at least about 4×, or at least about 4.5×, or at least about 5× greater than the smallest cross-sectional area of the constricted area. For example, the smallest cross-sectional area of the constricted area may be from about 18 mm$^2$ to about 30 mm$^2$, or from about 20 mm$^2$ to about 25 mm$^2$, and the smallest cross-sectional area of the air flow conduit excluding the constricted area may be from about 40 mm$^2$ to about 100 mm$^2$, or from about 50 mm$^2$ to about 90 mm$^2$. The cross-sectional area of the air flow conduit may vary along its length. According to an embodiment, the cross-sectional area of the air flow conduit, with the exception of the constricted area, has a cross-sectional area of at least about 40 mm$^2$, or at least about 45 mm$^2$, or at least about 50 mm$^2$; for example, a cross-sectional area that ranges from about 40 mm$^2$ to about 150 mm$^2$, or from about 40 mm$^2$ to about 120 mm$^2$, or from about 40 mm$^2$ to about 100 mm$^2$, or from about 50 mm$^2$ to about 150 mm$^2$, or from about 50 mm$^2$ to about 120 mm$^2$, or from about 50 mm$^2$ to about 100 mm$^2$ along its length.

As described in more detail below, according to an embodiment, the upstream area 1401 of the air flow conduit (i.e., upstream from the area of the air flow conduit into which dry powder medicament is expelled from the opening(s) of the dosing chamber) comprises at least a portion of the upper flow path 1180, for example, including a first leg 1184 of the upper flow path that has a first leg axis 1185 disposed above the dosing chamber. The upper flow path 1180 of the upstream area 1401 preferably comprises the air inlet, constricted area, and either the flow sensor or an aperture in fluid communication with the flow sensor. Optionally, the upper flow path 1180 further comprises a second leg 1186 and at least a portion of a third leg 1188 (i.e., a portion of the third leg 1188 disposed above the dosing chamber may be disposed in the upper flow path, whereas a lower portion of the third leg may extend into the downstream area of the air flow conduit), as described in more detail herein. It may be preferable for the air flow conduit to include a second leg and third leg, depending on the positioning of the dosing chamber within the inhaler, e.g., whether the air flow needs to be directed around the top of the dosing chamber via the second leg and third leg. The downstream area 1402 of the air flow conduit (i.e., the area of the air flow conduit into which the dry powder medicament is expelled from the dosing chamber) is preferably disposed within the exit channel 1182.

According to one embodiment, the inhaler of the present invention comprises: a dosing chamber configured to receive medicament from a blister, the dosing chamber disposed about a dosing chamber axis; a transducer confronting the dosing chamber, the transducer being configured to aerosolize the medicament when the transducer is activated; an exit channel disposed about an exit channel axis and fluidly connected to the dosing chamber such that the aerosolized pharmaceutical is delivered from the dosing chamber to a user through the exit channel in response to an activation of the transducer; and an upper flow path in fluid communication with the exit channel, the upper flow path including a first leg disposed about a first leg axis transverse to the exit channel axis. Preferably, the exit channel is configured to minimize accumulation of the aerosolized pharmaceutical on an exit channel surface.

According to another embodiment, a medicament delivery device comprises a dosing chamber comprising an interior configured to contain dry powder medicament, the dosing chamber disposed about a dosing chamber axis; a transducer confronting the dosing chamber, wherein the dosing chamber and the transducer are preferably acoustically resonant such that the dosing chamber is configured to resonate in response to an activation of the transducer; and an air flow conduit extending from an air inlet to an outlet. The air flow conduit preferably comprises (i) an upstream area disposed upstream from the area of the air flow conduit into which the dry powder medicament is expelled from the dosing chamber, and (ii) a downstream area disposed downstream from the area of the air flow conduit into which the dry powder medicament is expelled from the dosing chamber, the downstream area comprising the outlet and an exit channel disposed about an exit channel axis. The upstream area preferably comprises the air inlet and a first leg of an upper flow path in fluid communication with the exit channel, the first leg disposed about a first leg axis transverse to both the exit channel axis and the dosing chamber axis. As described herein, the air flow conduit preferably provides a flow resistance from about 0.040 cmH2O0.5/LPM to about 0.1 cmH2O0.5/LPM at a flow rate of about 30 liters per minute (LPM).

According to one embodiment, the ratio of the first leg length to the exit channel length is about 0.6 to about 0.9. According to one embodiment, the upper flow path includes a second leg fluidly connected to the first leg. Preferably, the second leg is disposed about a second leg axis, the second leg axis transverse to the first leg axis, and an elbow connects the first leg to the second leg. According to one embodiment, the upper flow path includes a third leg fluidly connected to the second leg. Preferably, the third leg is disposed about a third leg axis, the third leg axis transverse to the second leg axis and parallel to the first leg axis.

According to one embodiment, an air flow conduit comprising the first leg, second leg, third leg, and exit channel provide a path for air to move through the delivery device to the user (e.g., from the air inlet to the outlet/mouthpiece). In one embodiment, the upper flow path includes the first leg, second leg, and third leg. In one embodiment, air flows through the upper flow path upon inhalation. In one embodiment, the air flowing through the upper flow path combines with aerosolized pharmaceutical in the exit channel and the combined air and pharmaceutical is delivered to the user. According to one embodiment, each of the first leg, second leg, and third leg have different lengths.

According to one embodiment, the upper flow path and exit channel are configured to have a combined flow resistance from about 0.040 $cmH_2O^{0.5}$/LPM to about 0.1 $cmH_2O^{0.5}$/LPM, or from about 0.040 $cmH_2O^{0.5}$/LPM to about 0.090 $cmH_2O^{0.5}$/LPM, or from about 0.050 $cmH_2O^{0.5}$/LPM to about 0.1 $cmH_2O^{0.5}$/LPM, or from about 0.050 $cmH_2O^{0.5}$/LPM to about 0.090 $cmH_2O^{0.5}$/LPM, or from about 0.040 $cmH_2O^{0.5}$/LPM to about 0.085 $cmH_2O^{0.5}$/LPM, or from about 0.050 $cmH_2O^{0.5}$/LPM to about 0.085 $cmH_2O^{0.5}$/LPM, or from about 0.060 $cmH_2O^{0.5}$/LPM to about 0.085 $cmH_2O^{0.5}$/LPM at a flow rate of about 30 liters per minute (LPM).

According to one embodiment, a curvature connects the exit channel to the first leg. Preferably, the curvature is positioned above the dosing chamber. The curvature is preferably an S-shaped curvature. According to one embodiment, a plane defined by the dosing chamber axis is between a plane defined by the first leg axis and a plane defined by the third leg axis. According to one embodiment, the blister is disposed about a blister axis, wherein the first leg is positioned above the blister and the first leg axis is offset from the blister axis. Preferably, the blister axis and the first leg axis are parallel.

According to one embodiment, the transducer moves along an axis of motion when the transducer is activated and the axis of motion is parallel to the exit channel axis. According to one embodiment, the first leg comprises an air inlet through which air enters the device upon inhalation by a user. According to one embodiment, the exit channel axis is coaxial with the apex of the dosing chamber and the third leg axis is substantially perpendicular to the exit channel axis. According to one embodiment, the exit channel axis is parallel to the second leg axis, the first leg axis is parallel to the third leg axis, and the third leg axis is substantially perpendicular to the exit channel axis. Embodiments of the relative positioning of the inhaler's components, and embodiments of the air flow conduit, are described in more detail below with reference to the Figures.

The inhaler 100 includes, in some embodiments, the air flow conduit 1195 which is configured to provide a path for air to flow through the inhaler. In one embodiment, the air flow conduit 1195 is in fluid communication with the dosing chamber 1122 such that the aerosolized pharmaceutical is picked up by the air flowing through the air flow conduit and delivered to the user. FIG. 18 is a sectional view along line 18-18 (best seen in FIG. 17) of the front portion 101 of the inhaler 100 In one embodiment, the air flow conduit 1195 includes the upper flow path 1180 which includes a first leg 1184, a second leg 1186, and a third leg 1188. The first leg 1184, second leg 1186, and third leg 1188 may have a first leg axis 1185, a second leg axis 1187, and a third leg axis 1189, respectively. In one embodiment, the air flow conduit 1195 is configured (e.g., design, materials, dimensions) to avoid flow stagnation regions that could result in drug formulation deposition during use of the inhaler 100. For example, the air flow conduit design may include a smooth bore and avoid materials or physical features which could snare pharmaceutical as it exits the inhaler. The air flow conduit 1195 may also be manufactured from a material having anti-static properties to reduce the possibility of drug formulation deposition. In one embodiment, the rear cover 1174 of the front portion 101 comprises a portion of the first leg 1184. In one embodiment, a first leg cover 1175 comprises a rear surface of the first leg 1184 and the first leg cover 1175 sits proud of the rear cover 1174 of the first portion 101.

Figure 19:
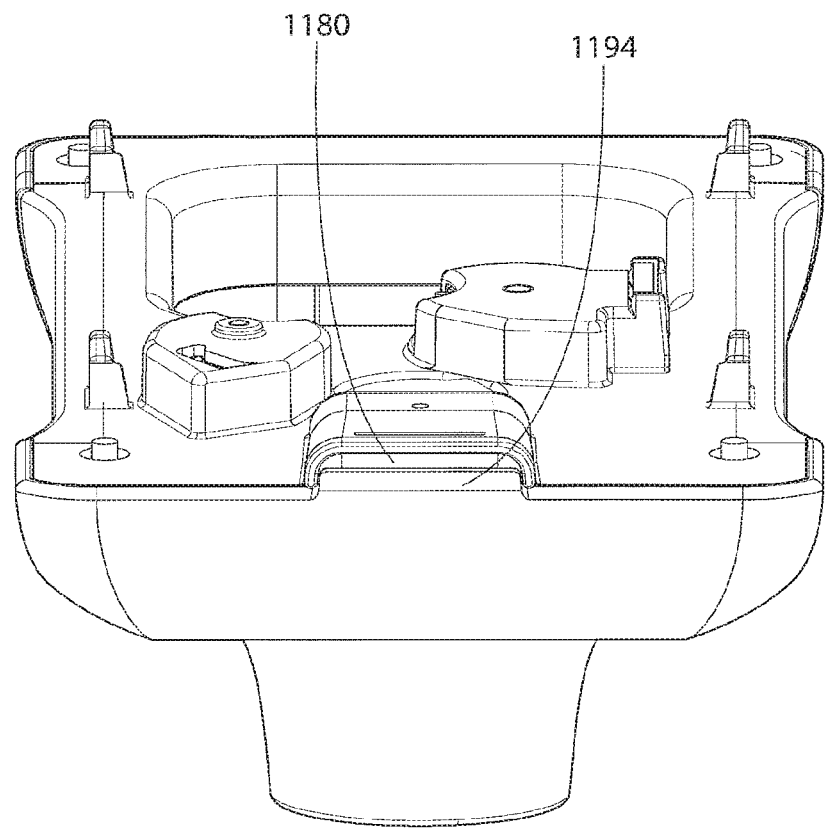
FIG. 19 is a top perspective view of the front portion of FIG. 17.

In some embodiments, the inhaler 100 includes a flow sensor 1278 to detect when a user is inhaling through the device. The sensor 1278, in some embodiments, provides a signal to the controller to advance the blister strip and/or activate the transducer to aerosolize the pharmaceutical from the blister 130. In one embodiment, the sensor 1278 is configured to detect airflow through the inhaler 100 and the sensor is configured to detect airflow from either or both of an inhalation or exhalation event. In one embodiment, the sensor is configured to discern between an inhalation and exhalation. The first leg 1184 includes, in one example, an aperture 1190 to provide fluid communication between the air flow conduit 1195 (or the upper flow path 1180) and a flow sensor 1278 (flow sensor is best seen in FIG. 31). In one embodiment, the aperture 1190 is positioned such that air flowing through in the upper flow path 1180 passes the location of the aperture 1190 before passing the location where the pharmaceutical is introduced into the air flow conduit 1195 to avoid the pharmaceutical from interfering with the operation of the flow sensor. As described above, one embodiment of the inhaler 100 includes a cover 1192 of the front portion 101 having a ledge 1194 (best seen in FIG. 19) which reduces the cross-sectional area of the first leg 1184 to increase the flow resistance across the air flow conduit 1195 and thus allow a flow sensor 1278 to detect a pressure change.

Figure 20:
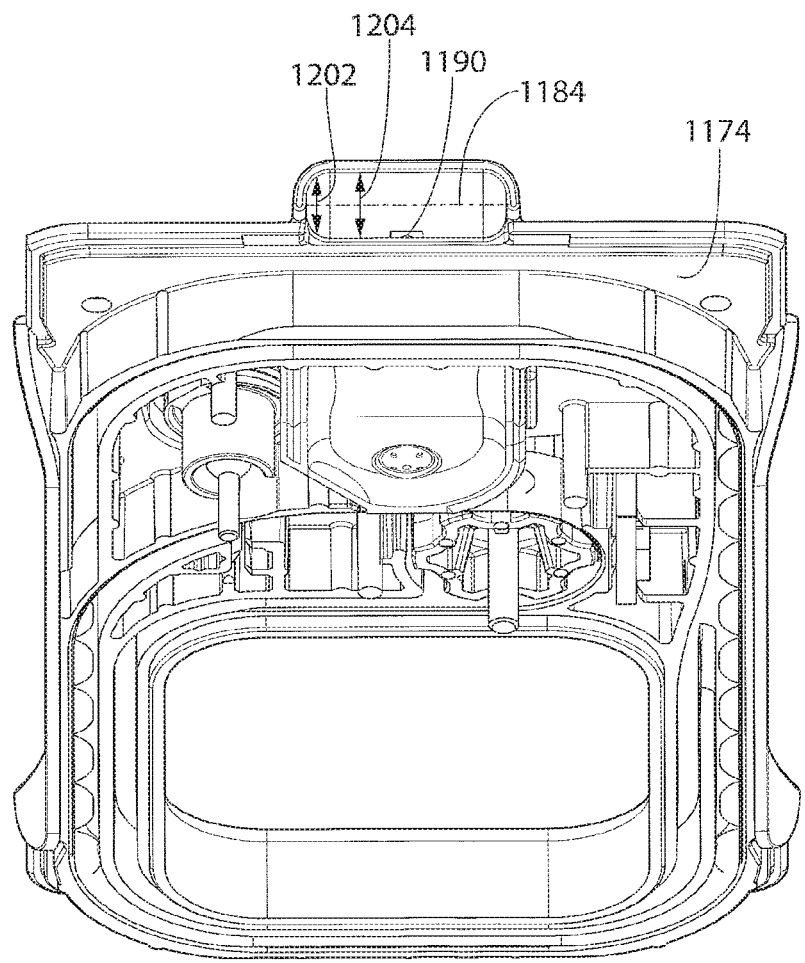
FIG. 20 is a top perspective view of the front portion of FIG. 19 with a cover removed.

In one embodiment, the flow resistance of the inhaler is from about 0.040 $cmH_2O^{0.5}$/LPM to about 0.1 $cmH_2O^{0.5}$/LPM, or from about 0.040 $cmH_2O^{0.5}$/LPM to about 0.090 $cmH_2O^{0.5}$/LPM, or from about 0.050 $cmH_2O^{0.5}$/LPM to about 0.1 $cmH_2O^{0.5}$/LPM, or from about 0.050 $cmH_2O^{0.5}$/LPM to about 0.090 $cmH_2O^{0.5}$/LPM, or from about 0.040 $cmH_2O^{0.5}$/LPM to about 0.085 $cmH_2O^{0.5}$/LPM, or from about 0.050 $cmH_2O^{0.5}$/LPM to about 0.085 $cmH_2O^{0.5}$/LPM, or from about 0.060 $cmH_2O^{0.5}$/LPM to about 0.085 $cmH_2O^{0.5}$/LPM at a flow rate of about 30 liters per minute (LPM). Flow resistance may be determined by known methods, such as the method described in Example 2. In one embodiment, the first leg 1184 has a width 1202 and a depth 1204 best seen in FIG. 20 which shows a top, front perspective view of the rear cover 1174. The first leg 1184 may have any cross-sectional shape desired (e.g., circle, rectangle, ellipse) to provide an air inlet through which air enters the device upon inhalation by a user. In one embodiment, the first leg 1184 has a length from an upper flow path inlet 1191 to the second leg axis 1187 of about 13 mm to about 18 mm. In one embodiment, the first leg 1184 is oblique or perpendicular to the exit channel 1182 and fluidly connected to the exit channel.

Figure 21:
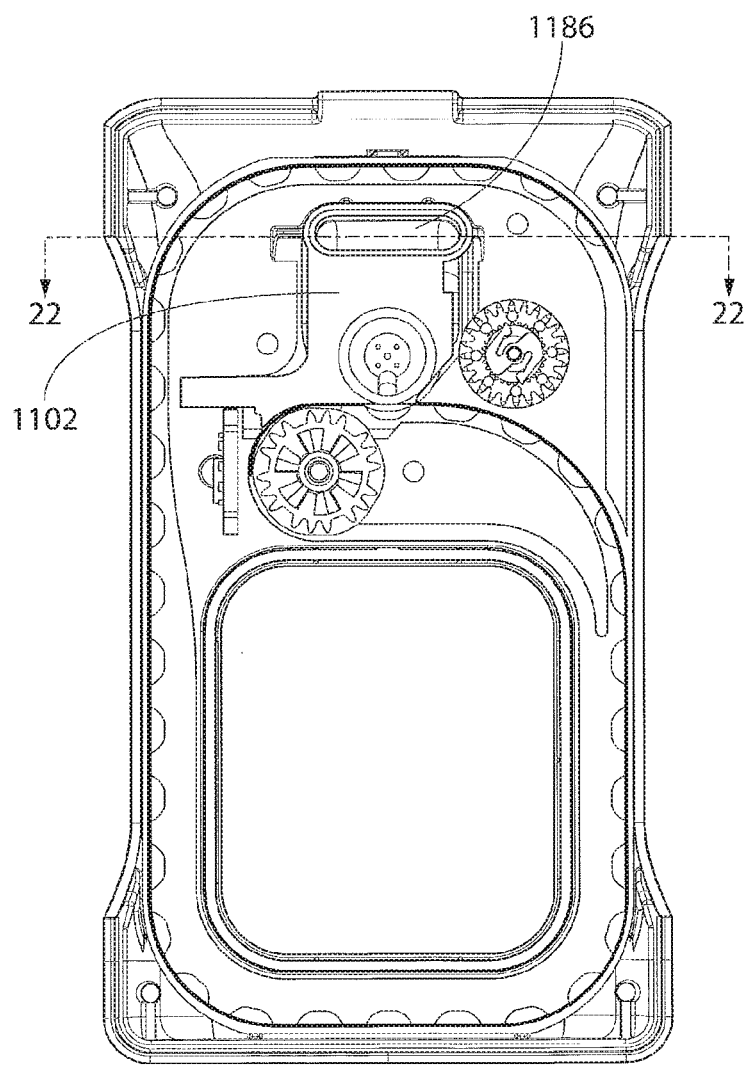
FIG. 21 is a rear view of the front portion of FIG. 17 with a cover removed.
Figure 22:
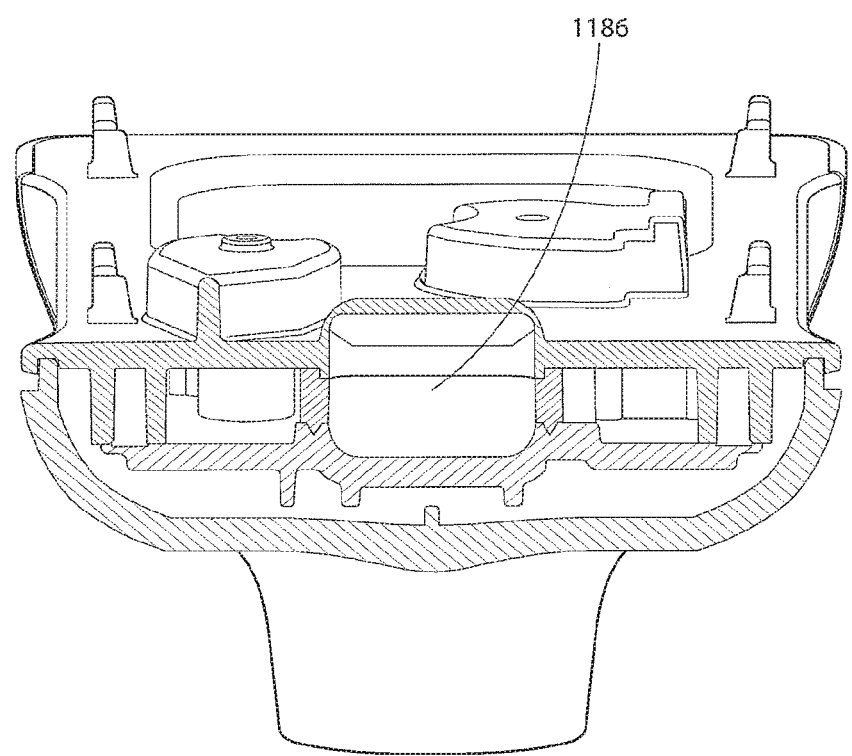
FIG. 22 is a top perspective view of the front portion along a plane defined by line 22-22 of FIG. 17.

The upper flow path 1180 includes the second leg 1186 that in some embodiments is configured to redirect air flow from a distal portion of the first leg 1184 to a proximal portion of the third leg 1188 such that the air flow conduit 1195 has sufficient length to allow a user to observe the indicator 554 during use of the inhaler 100 by a user. Referring again to FIG. 18, the transition between the first leg 1184 and the second leg 1186 is configured to include a first leg elbow 1196 to reduce or minimize flow resistance and promote laminar flow as the air moves between the first leg and second leg. In one embodiment, elbow 1196 comprises a radius, a portion of an ellipse, or an otherwise smooth transition between the first leg 1184 and second leg 1186. In one embodiment, the rear cover 1174 comprises a first portion of the second leg 1186. In one embodiment, the housing 1102 includes an elbow 1108 (best seen in FIGS. 12 and 18) which, in combination with an intermediate member 1206 of the front portion 101, comprises a second portion of the second leg 1186. In one embodiment, the elbow 1108 comprises a radius, a portion of an ellipse, or other shape that comprises the transition between the second leg and the third leg. In one embodiment, the second leg 1186 is oblique or perpendicular to the first leg 1184. In one embodiment, the second leg 1186 is perpendicular to the first leg 1184. In one embodiment, the second leg 1186 has a cross-sectional shape (best seen in FIG. 21) similar to that of the first leg 1184. In one embodiment, each leg of the upper flow path 1180 has the same or similar cross-sectional area at each cross-section even if one or more legs (or portions) of the upper flow path have a different shape. In one embodiment, each leg of the upper flow path 1180 has the same average cross-sectional area. In one embodiment, each leg of the upper flow path 1180 has a uniform cross-section. In one embodiment, each leg of the upper flow path 1180 has a uniform cross-section and the upper flow path has a substantially uniform cross section along its length. A consistent cross-sectional area throughout the upper flow path may promote a laminar air flow through the upper flow path. Alternatively, the cross-sectional area of the upper flow path may vary along its length but laminar air flow is still promoted as long as a minimum cross-sectional area is met, for example, at least about 40 $mm^2$, at least about 50 $mm^2$ or at least about 60 $mm^2$. In one embodiment, the average cross-sectional area of the second leg 1186 is different than the average cross sectional area of the first leg 1184. FIG. 22 shows a cross-sectional view of the first portion 101 along line 22-22 of FIG. 17 to illustrate a top-down view of the second leg 1186. In one embodiment, the second leg 1186 has a length of about 7 mm to about 12 mm as measured between the first leg axis 1185 and the third leg axis 1189. In one embodiment, the length of the second leg 1186 is about 50% to about 60% of the length of the first leg 1184.

Figure 23:
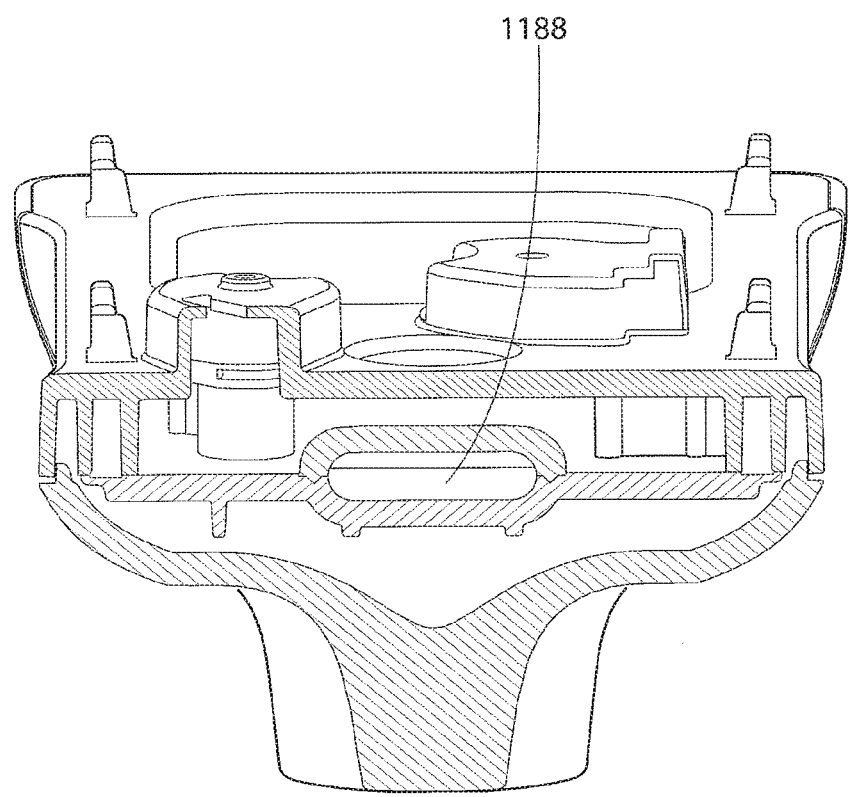
FIG. 23 is a top perspective view of the front portion along a plane defined by line 23-23 of FIG. 17.

The third leg 1188 of the upper flow path 1180 that is illustrated in FIG. 18 connects the second leg 1186 to the exit channel 1182 to deliver air and the pharmaceutical to the user. In one embodiment, the elbow 1108 of the housing 1102 comprises transition between the second leg 1186 and the third leg 1188. In one embodiment, the second leg 1186 and the third leg 1188 are combined into a single curvature connecting the first leg 1184 to the exit channel 1182. The single curvature may be an S-shaped curvature which connects the first leg 1184 and the exit channel 1182 which are transverse to each other. An upper elbow 1200 of the intermediate member 1206 is configured to form the other part of the transition between the second leg 1186 and the third leg 1188. In one embodiment, the radius of elbow 1108 is equal to the radius of upper elbow 1200. In one embodiment, the radius of elbow 1108 is equal to the radius of first leg elbow 1196. In one embodiment, each of the radii of first leg elbow 1196, the elbow 1108, and the upper elbow 1200 are equal. In one embodiment, the third leg 1188 has a length, as measured from a second leg axis 1187 to an exit channel axis 1210, of about 10 mm to about 15 mm. In one embodiment, a ratio of the length of the third leg 1188 to the length of the second leg 1186 is about 1.0 to about 1.5. In one embodiment, a ratio of the length of the third leg 1188 to the length of the first leg 1184 is about 0.5 to about 1.0. In one embodiment, the third leg 1188 has a cross-sectional shape (best seen in FIG. 23 which shows a cross-section of the first portion 101 along line 23-23 of FIG. 17) similar to that of either the first leg 1184 or the second leg 1186. In one embodiment, the third leg 1188 is parallel to the first leg 1184. In one embodiment, the third leg 1188 is oblique, or perpendicular, to the second leg 1186. In one embodiment, the third leg 1188 is oblique, or perpendicular, to the exit channel 1182.

The exit channel 1182 of the air flow conduit 1195 that is illustrated in FIG. 18 aligns with the dosing chamber 1122 and provides a passage for air flowing through the air flow conduit 1195 and the aerosolized pharmaceutical from the dosing chamber to mix and be delivered to the user through the mouthpiece. In one embodiment, the transition between the third leg 1188 and the exit channel 1182 includes an exit channel upper elbow 1212 and an exit channel lower elbow 1214. The intermediate member 1206 comprises the exit channel upper elbow 1212. The upper surface 1104 of the housing 1102 comprises the exit channel lower elbow 1214. In one embodiment, the transition between the third leg 1188 and the exit channel 1182 includes a convex elbow as the transition from the relatively wider third leg to the relatively narrower exit channel. In one embodiment, the exit channel 1182 has a length of about 20 mm to about 25 mm. In one embodiment, the exit channel 1182 comprises about 30% to about 35% of the length of the air flow conduit 1195. In one embodiment, the exit channel 1182 has a circular cross section (best seen in FIG. 24) with a diameter of about 8 mm to about 13 mm. In one embodiment, the length of the exit channel 1182 and the length of the second leg 1186 are such that is allows a user to visually observe an indicator 554 (best seen in FIG. 5B) during use of the inhaler 100 (e.g., while a mouthpiece 1216 is within the user's mouth). The indicator 554 may be an LED indicator and may provide a signal to the user regarding inhalation. For example, the indicator 554 may flash, change color, change flash pattern, change intensity, display text, etc. to indicate to a user to keep inhaling, stop inhaling, inhale harder, etc. In one embodiment, the exit channel 1182 is fluidly connected to the dosing chamber 1122 via the openings 1148 such that the aerosolized pharmaceutical is delivered from the dosing chamber through the exit channel 1182 when the transducer 150 is activated.

In some embodiments, the exit channel and dosing chamber are aligned to promote a laminar flow of the aerosolized pharmaceutical out of the dosing chamber and through the exit channel. In the exit channel 1182 of the air flow conduit 1195 of FIG. 18, the exit channel preferably has a width that inhibits or prevents the aerosolized pharmaceutical from contacting the surface of the exit channel and a length which allows the synthetic jet created in the dosing chamber to carry the pharmaceutical out of the exit channel even when there is only minimal air flow through the air flow conduit. In one embodiment, the exit channel axis 1210 and the dosing chamber axis 1124 are co-axial or parallel. In one embodiment, the exit channel axis 1210 and one of the openings 1148 of the dosing chamber 1122 are co-axial. Aligning the exit channel axis 1210 and the dosing chamber axis 1124 may help reduce or eliminate depositing of the pharmaceutical material during use of the inhaler 100. In one embodiment, the exit channel axis 1210 and the dosing chamber axis 1124 are offset from each other in at least one plane. In one embodiment, the exit channel axis 1210 and the dosing chamber axis 1124 are parallel and offset from each other. In one embodiment, the exit channel axis 1210 and the dosing chamber axis 1124 are transverse to each other. In one embodiment, the exit channel axis 1210 and the first leg axis 1185 are perpendicular to each other. In one embodiment, the exit channel axis 1210 and the second leg axis 1187 are parallel such that the length of the exit channel is configured to effectively deliver the aerosolized pharmaceutical (as explained below) while the inhaler has an overall length which is long enough to allow a user to visually observe the indicator 554 while using the inhaler 100. In one embodiment, the dosing chamber 1122 includes more than one opening 1148.

Figure 24:
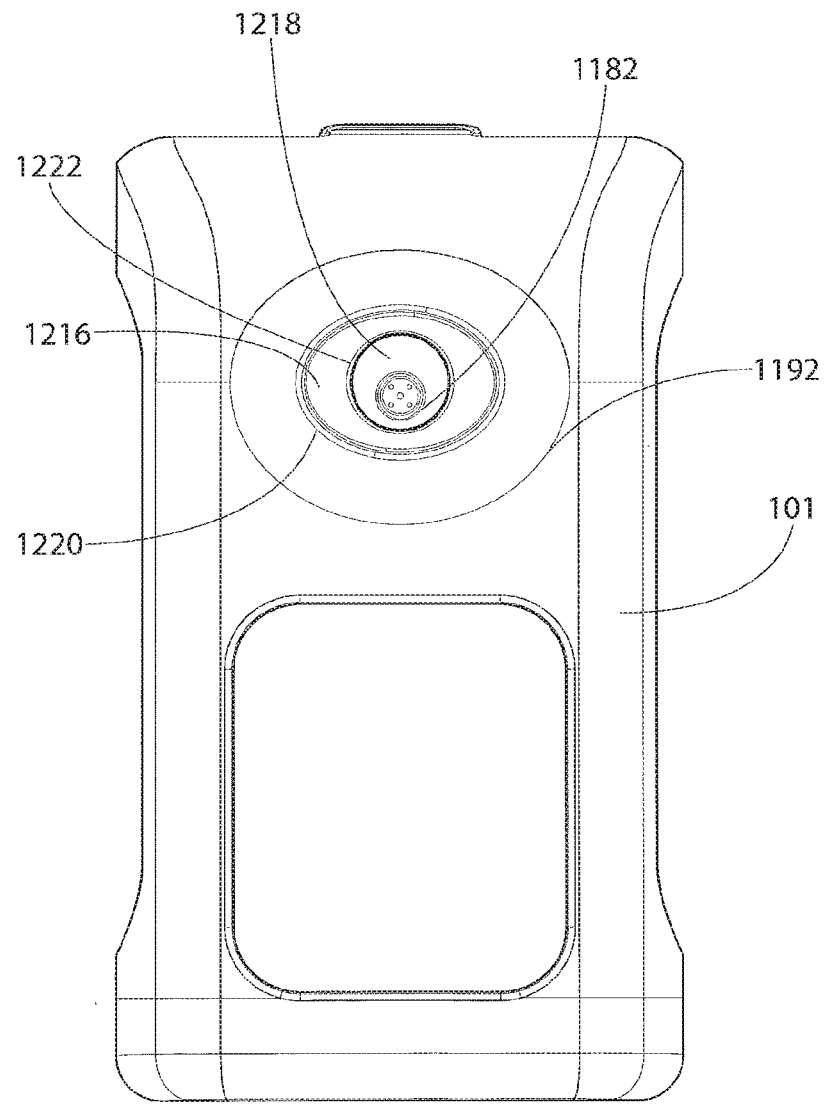
FIG. 24 is an isolated front view of the front portion of the inhaler of FIG. 1.

In one embodiment, cover 1192 includes a mouthpiece 1216. Mouthpiece 1216 may be integral with the cover 1192 of the first portion 101 of the inhaler 100 as best seen in FIG. 24. The mouthpiece 1216 is configured to have an internal opening 1218 similar in shape to the cross-sectional shape of the exit channel 1182 such that the mouthpiece 1216 does not block air flow from the exit channel 1182. In one embodiment, the mouthpiece 1216 includes an elliptical outer shape 1220 (or square, circle, triangle, or any other desired shape) such that the mouthpiece fits comfortably in a user's mouth during use of the inhaler 100. In one embodiment, the internal opening 1218 comprises a rim 1222 (best seen in FIG. 18) which is recessed in relation to the elliptical outer shape 1220. In some embodiments, the mouthpiece 1216 is adapted for nasal applications such that a user can breathe through their nose to use the inhaler. In one embodiment, the mouthpiece may be configured (e.g., have a size or shape) such that the mouthpiece covers a user's nose or is inserted into or abuts a user's nostrils. In one embodiment, the user may then breathe through their nose to use the inhaler in the manner described herein. In one embodiment, the mouthpiece 1216 may cover a user's mouth and nose such that a user may breathe through one or both of their nose and mouth to use the inhaler; or a mask may be fitted onto the mouthpiece so that a user may breathe through one or both of their nose and mouth.

The medicament delivery device of the present invention comprises a mounting system for the vibrating element (e.g., transducer). Several challenges were faced during the development of a suitable mounting system that would couple the vibrating element to the inhaler housing and apply sufficient pressure to the vibrating element so that its mechanical and acoustic energy would transfer to the blister, but without applying so much pressure that the vibratory energy would be dampened. A piezoelectric transducer, for example, should be mounted to the inhaler in a manner that does not interfere with vibratory output, that is compatible with high volume manufacturing methods, and that can be retained in the inhaler when the removable cartridge is not attached. The mounting system of the present invention is designed for minimal contact with the transducer housing to prevent attenuation of vibration. According to a preferred embodiment, a spiral wave spring provides force with a low profile and reasonably low spring rate to save space and allow reasonable robustness, e.g., a coil spring would typically require a greater length in order to provide the same amount of force. The transducer mounting system enables the transducer to be held in place when a cartridge is not attached while maintaining a sufficient pre-load force throughout the use life of the inhaler.

According to one embodiment, the inhaler comprises: a housing; a dosing chamber configured to receive a medicament; a transducer confronting the chamber, the transducer being configured to aerosolize the pharmaceutical when the transducer is activated; a holder configured to secure the transducer to the housing; and a biasing element between the holder and the housing.

According to another embodiment, the medicament delivery device comprises a housing; a dosing chamber configured to contain dry powder medicament; a transducer confronting the dosing chamber, wherein the dosing chamber and the transducer are preferably acoustically resonant such that the dosing chamber is configured to resonate in response to an activation of the transducer; and a transducer mounting assembly. The transducer mounting assembly preferably comprises (i) a holder configured to secure the transducer to the housing and (ii) a biasing element disposed between the holder and the housing. The biasing element presses the transducer against the dosing chamber with sufficient force to cause vibratory energy to be transferred from the transducer to the dosing chamber upon an activation of the transducer so that the dry powder medicament can be aerosolized and delivered from the dosing chamber via synthetic jetting (e.g., the dosing chamber resonates with acoustic energy, as evidenced by synthetic jetting, and mechanical vibrations). The holder provides additional surface area for the biasing element to interact with the transducer; for example, if the biasing element is a spring, the spring may not have enough surface area where it touches the transducer to sufficiently press the transducer against the dosing chamber. Preferably, less than half the outer surface area of the transducer is in contact with the holder.

According to a preferred embodiment, the subassembly helps to ensure that the face of the transducer maintains intimate contact with the back of the dosing chamber (e.g., the outer surface 1134 of the dosing chamber housing 1102), while not being configured to rigidly fix the transducer into place within the device. That way, if the face of the transducer becomes slightly misaligned with the back of the dosing chamber, there is enough freedom of motion for the transducer to be pressed back into position by the biasing element so that the face of the transducer and the back of the dosing chamber (e.g., including the membrane) remain substantially co-planar. As described herein, the back of the dosing chamber housing 1102 may include a crown 1135 which defines a lower portion of the lower sidewall 1126. The crown 1135, in one embodiment, is configured to protrude from a lower surface 1137 of the housing 1132 (best seen in FIGS. 13 and 16). According to an embodiment, the subassembly presses the face of the transducer against the back of the dosing chamber so at least an outer portion of the face of the transducer is pressed against the crown 1135 of the dosing chamber housing and an inner portion of the face of the transducer may be pressed against a membrane 1166 that is coupled to the crown 1135. The subassembly preferably constrains the concentricity of the transducer and the dosing chamber, i.e., the face of the transducer and an outer surface of the dosing chamber are substantially concentric so that the dosing chamber axis is substantially co-axial with the transducer axis of symmetry, e.g., the face of the transducer and the back of the dosing chamber (e.g., crown 1135) are substantially concentric. The transducer mounting assembly is preferably disposed about a mounting assembly axis of symmetry, which is also substantially co-axial with the dosing chamber axis 1124 and the transducer axis of symmetry.

Figure 25:
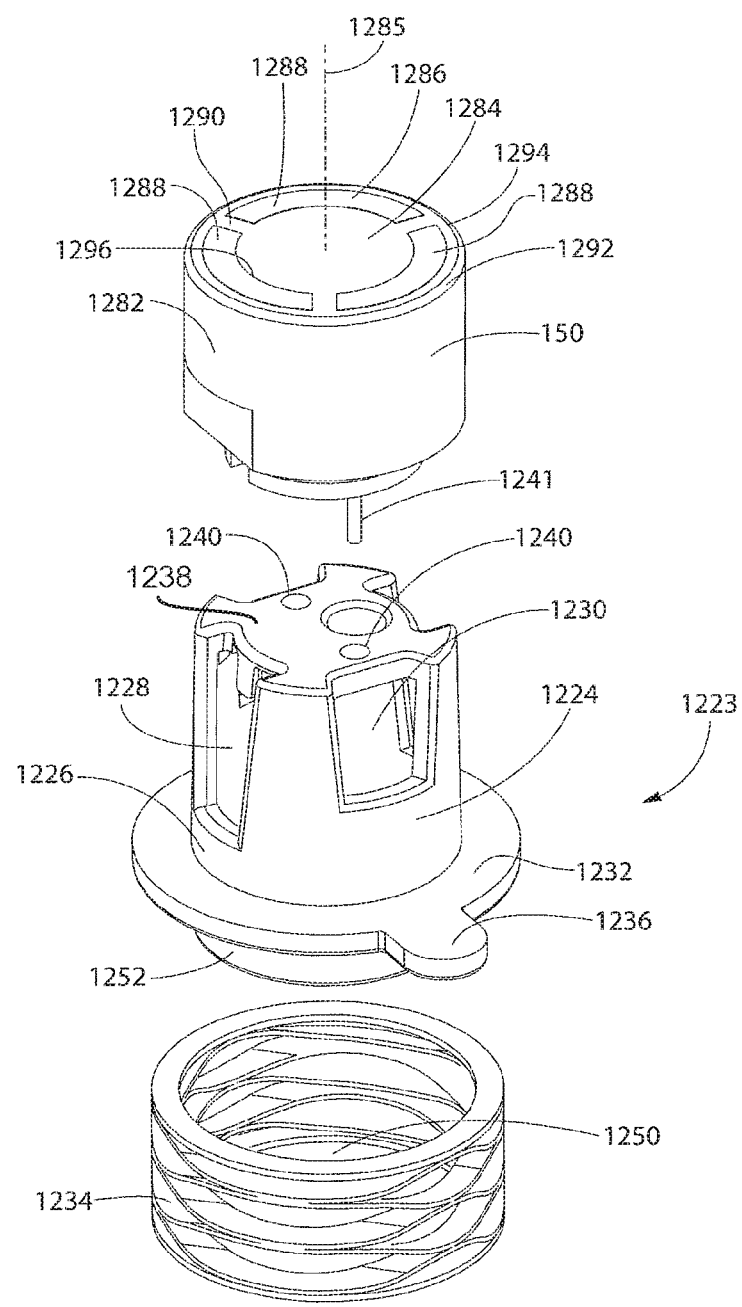
FIG. 25 is an exploded view of a transducer and holder in accordance with one embodiment of the present invention.

It is well-known that an object's acoustic resonance will change if that object is attached to another object because the overall mass of the structure is changed. Preferably, less than half the outer surface area of the transducer is in contact with the holder, more preferably less than a third of the outer surface area of the transducer is in contact with the holder. For example, a transducer may be shaped like a cylinder, as shown in FIG. 25, with its outer surface area including a front surface (i.e., transducer face 1284), a cylindrical body surface 1282 and a rear surface opposite the front surface. According to a preferred embodiment, only the rear surface of the transducer, or a portion thereof, comes into physical contact with the holder. Alternatively, a small portion of the cylindrical body surface may also come into contact with the holder while still maintaining that less than half the outer surface area of the transducer is in contact with the holder. By minimizing the amount of transducer surface area that is in contact with the holder, any dampening effect on the transducer's vibratory output is also minimized. Preferably, the mass of the holder and biasing element are also sufficiently low that they do not dampen the output of vibratory energy from the transducer. Preferably, the transducer mounting assembly, including the holder and biasing element, are caused to vibrate when the transducer is activated, e.g., parallel with the transducer axis of motion 1298.

Preferably, the transducer mounting assembly presses the transducer against the dosing chamber with sufficient force, and minimal dampening effect on the output of vibratory energy to cause aerosolization and delivery of the dry powder medicament having an MMAD within the preferred ranges described herein, e.g., about 6 μm or less, preferably with a fine particle fraction within the preferred ranges described herein, e.g., at least 30%. Maximum synthetic jetting is preferably achieved within ranges of time described herein, e.g., within about 500 ms or less from the start of a transducer activation.

Preferably, the biasing element is configured to provide a spring constant from about 1.0 lb/in (0.18 kg/cm) to about 4.0 lb/in (0.71 kg/cm). According to one embodiment, a ratio of a height of the holder to a height of the dosing chamber is from about 2 to about 3.5.

According to one embodiment, the holder comprises a proximal end, a distal end, and a sidewall extending from the proximal end to the distal end, the sidewall defining a receptacle configured to receive the transducer. According to one embodiment, the inhaler further comprises a mount configured to couple the transducer to the holder. According to one embodiment, the housing includes an arm configured to secure the holder to the housing. Preferably, the holder includes a sidewall opening, and the housing includes an arm having a first portion extending away from the housing and a second portion extending away from the first portion, the second portion generally parallel to the housing, wherein the second portion is positioned within the sidewall opening. According to one embodiment, the inhaler further comprises a ridge extending away from the housing, the ridge defining a receiving area configured to receive at least a portion of the holder.

According to one embodiment, the inhaler further comprises a lip extending from the sidewall, wherein the lip is contiguous to the ridge when the holder is secured to the housing. Preferably, the lip has a lip thickness and the holder has a holder height, wherein a ratio of the lip thickness to the holder height is from about 0.07 to about 0.12.

According to one embodiment, the biasing element is positioned within the receiving area when the holder is secured to the housing. Preferably, the biasing element comprises at least one of a coil spring, leaf spring, spiral wave spring, and a bellows spring. According to one embodiment, a ratio of a height of the holder to a height of the dosing chamber is from about 2 to about 3.5, or from about 1 to about 2. According to one embodiment, the lip has a lip thickness and the holder has a holder height, and a ratio of the lip thickness to the holder height is from about 0.07 to about 0.12.

Referring now to FIGS. 25-27, the inhaler 100 includes a transducer mounting system 1223 to secure the transducer 150 within the inhaler 100 while allowing slight movement of the transducer to enhance the energy coupling of the inhaler, as explained in greater detail below. In one embodiment, the transducer mounting system 1223 includes a transducer 150, a transducer holder 1224, and a biasing element 1234. A mounting system 1223 is preferably configured to secure the transducer 150 to the back portion 102 (or housing) of the inhaler 100 even when the front portion 101 (e.g., removable cartridge) and back portion 102 (e.g., base) are disengaged from each other. The transducer mounting system 1223 is configured to reduce, minimize, or eliminate interference with the vibratory output of the transducer 150. In one embodiment, the holder 1224 includes a body 1226 having a sidewall, with securement openings 1228 and wiring openings 1230 extending through the sidewall. In one embodiment, the securement opening 1228 and the wiring opening 1230 have the same size, shape, orientation, etc. and the openings 1228, 1230 are equidistantly spaced about the holder 1224. In one embodiment, the securement opening 1228 is larger than the wiring opening 1230. In one embodiment, a flange 1232 extends away from the body 1226 and provides an engagement surface for a biasing element 1234 (e.g., leaf spring, spiral wave spring, piston, resilient material) to maintain the position of the transducer 150 during use of the inhaler 100. In one embodiment, the flange 1232 extends completely around the body

1226. In one embodiment, the flange 1232 comprises one or more sections which extend around a portion of the body 1226. The flange 1232 may have the same shape (e.g., circle, rectangle, polygon, random) as the body 1226 but may be larger than the body 1226 such that the flange 1232 extends around the body 1226.

In one embodiment, a finger 1236 extends from the flange 1232 to align the holder 1224 on the back portion 102. For example, the finger 1236 may contact a protrusion or other element of the housing to prevent rotation of the holder 1224 about a central axis of the holder which could cause the wires (not shown) to interfere with (e.g., by wrapping around) the holder 1224 or other element of the transducer mounting system 1223. The holder 1224 includes a top 1238 having one or more through holes 1240 to allow leads 1241 of the transducer 150 to pass through the top 1238 and allow the transducer to sit on the top 1238 (best seen in FIG. 27). The body 1224 comprises a hollow portion to receive a printed circuit board (PCB) 1242 which may provide an activation signal to the transducer 150. In one embodiment, a nub 1244 extends from the bottom surface of the top 1238 of the holder and fits into a cutout 1246 on the PCB to maintain alignment of the PCB on the holder 1224. The body 1226 is configured to include an inner surface 1246 defining the cavity which receives the PCB 1242. In one embodiment, a retainer 1248 extends radially inward from the inner surface 1246 to secure the PCB between the retainer and the bottom surface of the top 1238 of the holder. In one embodiment, the retainer 1248 is a depressible wedge configured to be compressed as the PCB 1242 passes the retainer 1248 and return to its uncompressed state after the PCB passes and prevents the PCB from travelling in the reverse direction.

During manufacture, the transducer 150 may be positioned such that the leads 1241 extend through the through holes 1240 and the PCB 1242 positioned within the cavity of the holder 1224 and secured by the retainer 1248. In one embodiment, the lead 1241 is soldered to the PCB 1242 through the wiring opening 1230 either before or after the holder 1224 is secured to the back portion 102 of the inhaler 100. In one embodiment, the leads 1241 are soldered to the PCB 1242 prior to attaching the holder 1224 to the back portion 102 and thus, the wiring openings 1230 may be omitted. In one embodiment, the inner surface 1246 of the holder 1224 comprises a recess 1249 to receive a protrusion (not shown) from the back portion 102 of the inhaler 100 to further secure the holder 1224 in place. The biasing element 1234 includes a cavity 1250 which receives the lower portion 1252 of the body 1226 of the holder 1224 which is below the flange 1232. In one embodiment, the biasing element 1234 has a spring constant of about 1.0 lb/in (0.18 kg/cm) to about 4.0 lb/in (0.71 kg/cm). In one embodiment, the biasing element 1234 has a free height of about 0.1 inches (2.5 mm) to about 0.8 inches (20.3 mm), or about 0.1 inches (2.5 mm) to about 0.6 inches (15.2 mm), or about 0.1 inches (2.5 mm) to about 0.4 inches (10.2 mm), or about 0.2 inches (5.2 mm) to about 0.3 inches (7.6 mm). In one embodiment, the biasing element 1234 has a working height of about 0.075 inches (1.9 mm) to about 0.3 inches (7.6 mm), or about 0.1 inches (2.5 mm) to about 0.2 inches (5.1 mm). In one embodiment, the spring force may be about 0.25 (0.11 kg) to about 0.75 pounds (0.34 kg) at the working height of about 0.075 inches to about 0.3 inches (7.6 mm), or about 0.1 inches (2.5 mm) to about 0.2 inches (5.1 mm), preferably with a spring force of about 0.75 lb/in (0.13 kg/cm) to about 5.0 lb/in (0.89 kg/cm), more preferably about 1.0 lb/in (0.18 kg/cm) to about 4.0 lb/in (0.71 kg/cm). Preferably, the biasing element becomes compressed from its free height to its working height when the base and cartridge are attached together, at which time the transducer face is pressed against the membrane.

Figure 28:
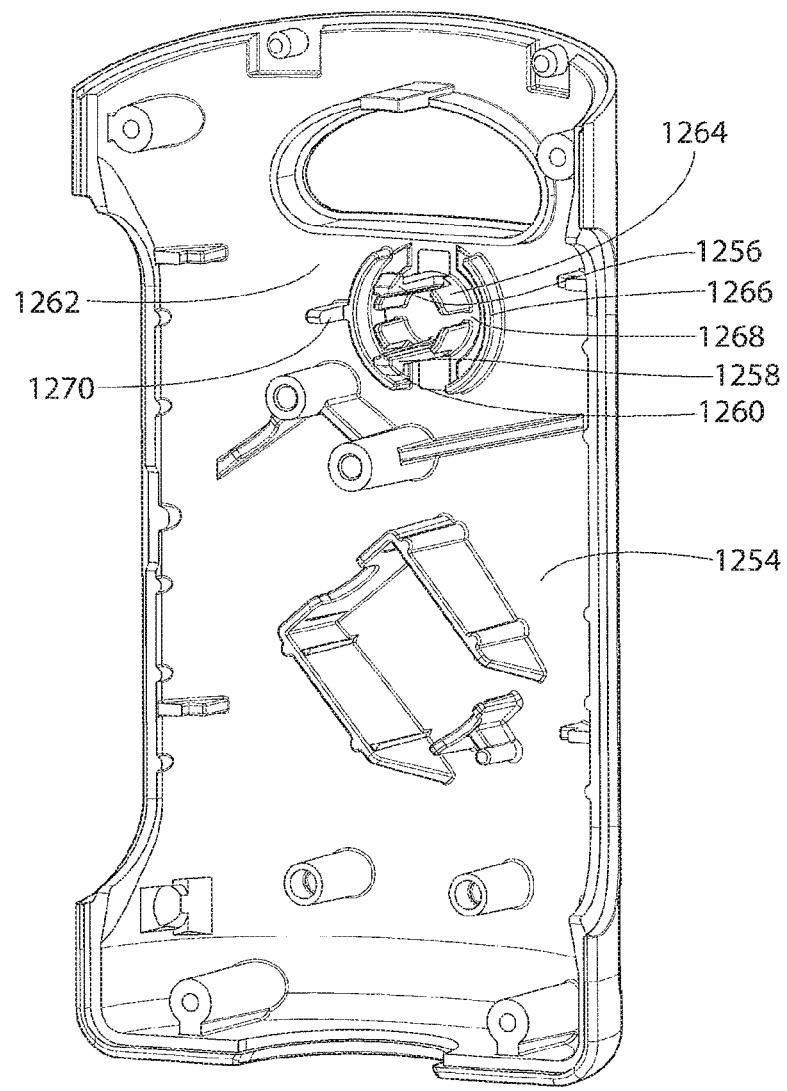
FIG. 28 is an isolated perspective view of a rear cover of the inhaler of FIG. 1.
Figure 29:
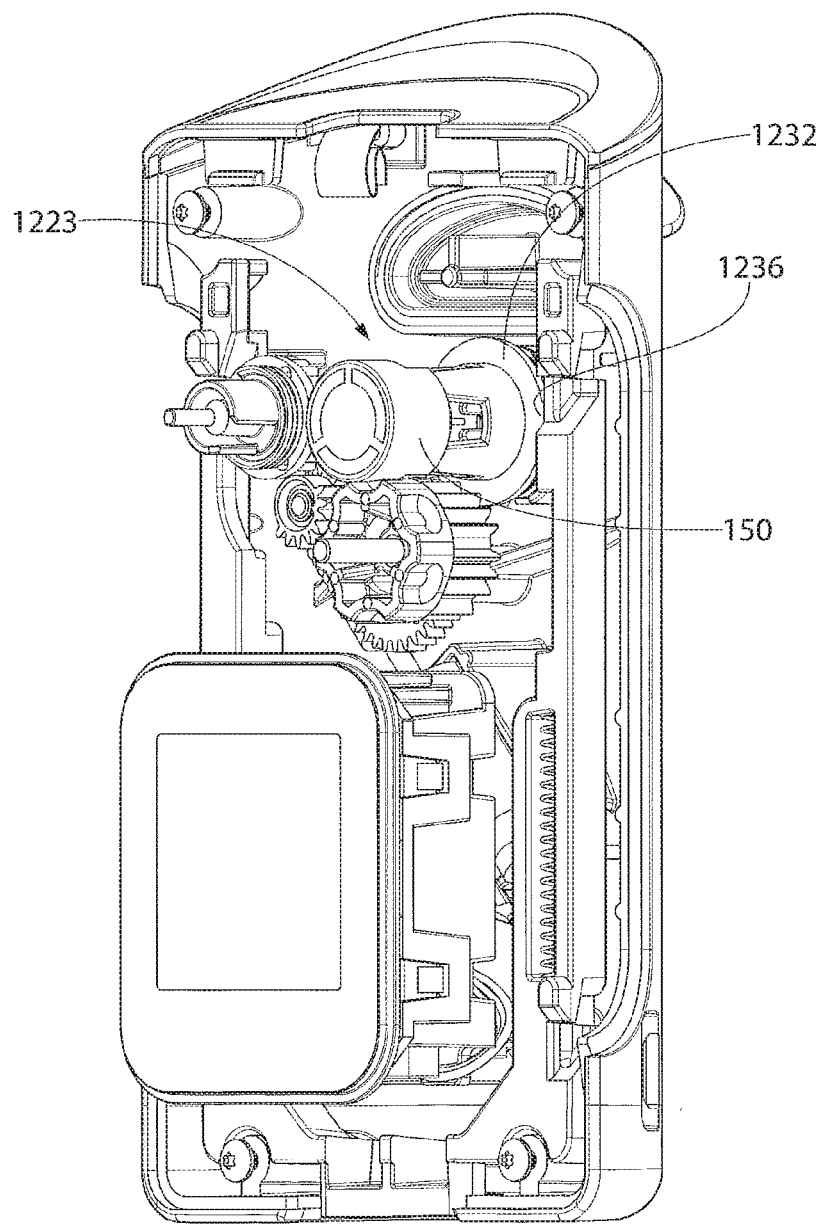
FIG. 29 is a side perspective view of a partially assembled rear portion of the inhaler of FIG. 1 including the rear cover of FIG. 28 and the transducer and holder of FIG. 25.

The back portion 102 of the inhaler 100 includes a shell 1254 (or cover) to secure the internal components within the inhaler and provide engagement features for securing the internal components in position. Turning now to FIG. 28, one embodiment of the shell 1254 of the back portion 102 is shown. The shell 1254 may be configured to include an arm 1256 which engages the securement opening 1228 of the holder 1224 to secure the holder to the shell 1254 or housing. In one embodiment, the arm 1256 includes a wedge shaped head 1258 with an intermediate sidewall 1260 that is generally transverse to the arm 1256. The arm 1256 is configured to be flexible such that as the wedge shape of the head 1258 causes the arm to deflect inwardly and the arm enters the internal cavity of the holder 1224. In one embodiment, the arm 1256 is configured to return to its undeflected state when the head 1258 is aligned with the securement opening 1228. In one embodiment, the intermediate sidewall 1260 is configured to engage the border of the securement opening 1228 to prevent removal of the holder 1224. In one embodiment, the distance between the intermediate sidewall 1260 and the shell 1254 is greater than the distance between the securement opening 1228 and the bottom of the body 1226 such that the holder 1224 does not contact a shell base 1262 when the two are coupled together and allows some vertical movement of the holder when the transducer 150 vibrates. In one embodiment, the shell 1254 includes protrusions 1264 adjacent the arm 1256 which at least partially enter the cavity of the holder 1224 when the holder is coupled to the shell 1254. In one embodiment, the protrusions 1264 and the arm 1256 form a shape similar to, but slightly smaller than, the shape defined by the inner surface 1246 of the holder 1224 to maintain the alignment of the holder on the shell. In one embodiment, a ridge 1266 extends upwardly away from the shell base 1262. In one embodiment, a receiving area 1268 for the biasing element 1234 and/or the holder 1224 comprises the space between the ridge 1266 and the arm 1256/protrusions 1264. In one embodiment, the shell 1254 includes a post 1270 extending from the ridge 1266. The post 1270 may be configured to be in contact with the flange 1232 if the holder 1224 moves too far toward the post. In one embodiment, the post 1270 is in continuous contact with the flange 1232 to provide a frictional resistance to motion (e.g., vertical) of the holder 1224. In one embodiment, the biasing element 1234 is configured to be positioned in the receiving area 1268 such that a lower portion of the biasing element 1234 is in contact with the shell base 1262. In one embodiment, the holder 1224 is configured to be positioned about the arm 1256 and protrusions 1264 as previously described such that the head 1258 is within the securement opening 1228 and the flange 1232 is in contact with the biasing element 1234 (best seen in FIG. 29). In one embodiment, the securement opening 1228 is slightly wider than the head 1258 to allow the holder to rotate slightly such that the transducer remains flush to the membrane 1166 when the transducer vibrates. In one embodiment, the biasing element 1234 is uncompressed or retains its unstressed length when the holder 1224 is coupled to the arm 1256. In one embodiment, the biasing element 1234 is compressed when the head 1258 is within the securement opening 1228. The head 1258 may be positioned toward a lower region of the securement opening 1228 to allow the holder 1224 to move vertically relative to the head 1258 when the transducer 150 is activated. Additional protrusions (not shown) may extend from the shell base 1262 to receive the finger 1236 and prevent rotational (or other) motion of the holder 1224. In one embodiment, the arm 1256 is arranged such that the holder 1224 is within a ring created by arms 1256 and the head 1258 engages the flange 1232 when the holder 1224 is coupled to the base 1262. In one embodiment, a ratio of the height of the holder 1224 to a height of the dosing chamber is about 2 to about 3.5. In one embodiment, a ratio of the thickness of the flange to a height of the holder 1224 is about 0.07 to about 0.12.

Figure 30:
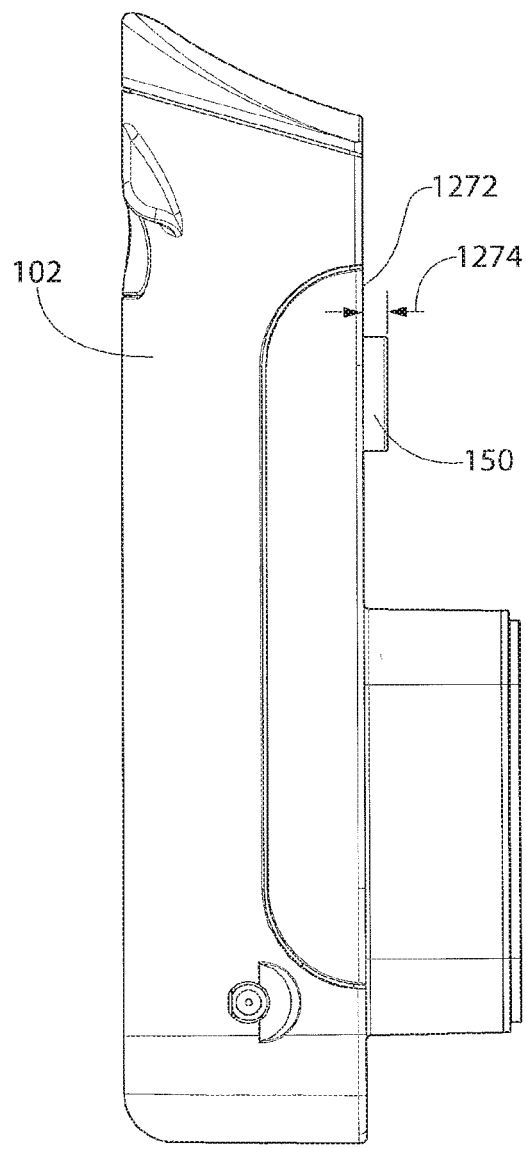
FIG. 30 is a side view of the rear portion of the inhaler of FIG. 1.

Turning now to FIG. 30, in one embodiment the transducer 150 extends beyond a surface 1272 of the back portion 102 of the inhaler 100. The distance 1274 which the transducer 150 extends may be about 0.1 mm to about 5.0 mm, or about 0.5 mm to about 4.0 mm, or about 1.0 mm to about 4.0 mm, or about 1.0 mm to about 3.0 mm. In one embodiment, the distance 1274 is equal to or within a percentage of the distance from the membrane 1166 to the rear surface 1178 of the front portion 101 (best seen in FIG. 18). In one embodiment, the transducer 150 is flush with, or recessed with respect to, the surface 1272 of the back portion 102 when assembled. In one embodiment, the transducer 150 sits proud of the back portion 102 such that a portion of the transducer 150 is within the passageway 1172 of the front portion 101 (best seen in FIG. 18).

Figure 31:
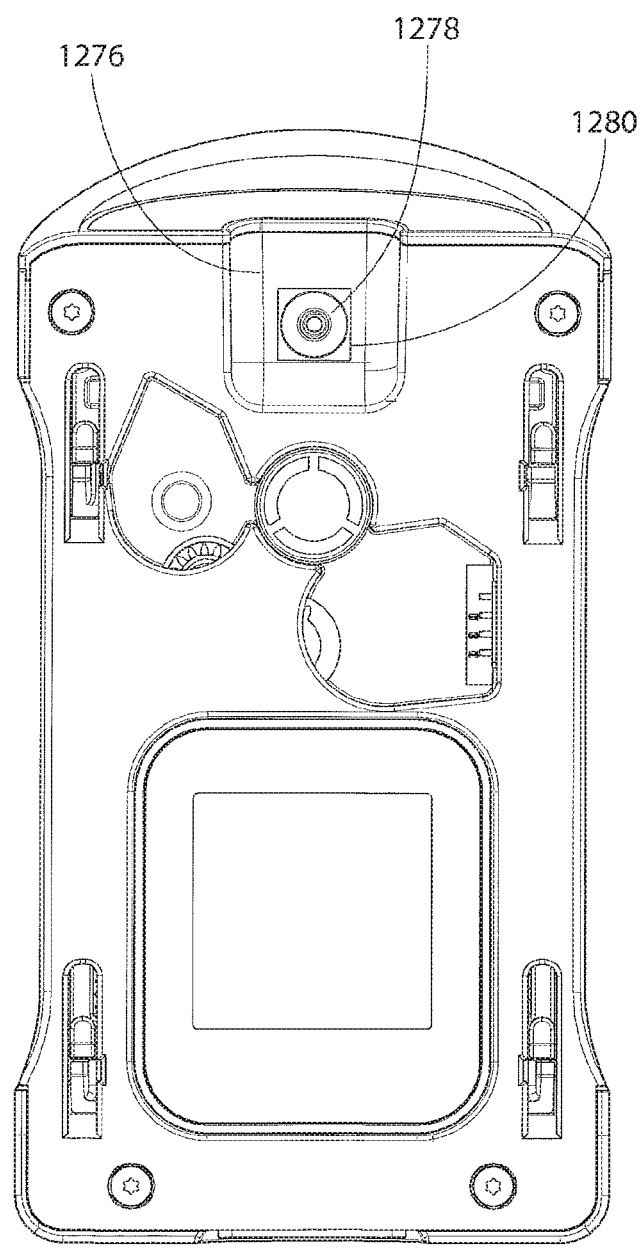
FIG. 31 is a front view of the rear portion of FIG. 30.

In one embodiment, the front portion 101 includes the first leg cover 1175 which sits proud of the rear cover 1174 to assist in aligning the front portion 101 and the back portion 102 of the inhaler. Turning now to FIG. 31, in one embodiment the back portion 102 includes a cutout 1276 or recess to receive the first leg cover. In one embodiment, the first leg cover 1175 within the cutout 1276 assists in positioning the front and rear portions relative to each other such that the transducer 1172 confronts the membrane 1166 when the inhaler 100 is assembled. In one embodiment, the cutout 1276 includes a sensor 1278 (e.g., in the form of a pressure sensor, air stream velocity sensor or temperature sensor, preferably a MEMS pressure sensor or NEMS pressure sensor) to detect when a user is inhaling and/or exhaling through the air flow conduit 1195. In one embodiment, the sensor 1278 is configured be aligned with the aperture 1190 of the first leg 1184 to allow the sensor 1278 to sample the air within the first leg. In one embodiment, a gasket 1280 may surround the sensor 1278 to effectively seal the first leg 1184 and reduce or eliminate pressure drop due to the aperture 1190.

As discussed herein, the inhaler of the present invention preferably employs synthetic jetting to aerosolize the drug powder. There exist the needs to 1) shorten the onset time for establishing the synthetic jet and delivering the drug in response to a patient's breath actuation (dose trigger); 2) conserve energy; 3) more effectively deagglomerate the drug formulation to ensure a consistent particle size distribution of the delivered dose; and 4) ensure consistent dosing and particle size distribution throughout the life of the device. During development of the present invention, extensive studies were conducted to couple the energy of the vibratory element (transducer) to the dosing chamber so that these objectives could be achieved. By providing an air column that extends between the transducer and the membrane, wherein at least a portion of the air column is defined by a separation means (e.g., spacer 1286), it was discovered that the air column increases power draw by allowing for higher displacement of the transducer face and membrane without contact between the two. It was also discovered that, in preferred embodiments, the air column shortens the onset time for establishing the synthetic jet and delivering the drug in response to a patient's breath actuation. This was found to be a particular advantage for those patients that perform short inhalations through the device during tidal breathing. An exemplary spacer that may be used in one embodiment is described in WO 2016/007356, which is incorporated by reference herein.

A spacer is not required for the aerosol engine to achieve sufficient synthetic jetting, dose delivery and aerodynamic particle size distribution, but it is an optional feature that may increase the overall robustness of the aerosol engine. For example, the inhaler's aerosol engine may still achieve maximum synthetic jetting within less than 1000 ms, less than 500 ms, or less than 100 ms without a spacer if the acoustic resonance of the system as a whole allows for sufficient energy transfer from the transducer to the dosing chamber. According to certain embodiments, the spacer shortens the amount of time to maximum synthetic jetting and/or increases the maximum synthetic jetting; for example, the amount of time to maximum synthetic jetting may be reduced by at least 10 ms, or at least 20 ms, or at least 30 ms, or at least 40 ms, or at least 50 ms when a spacer is employed.

According to an embodiment, the inhaler of the present invention comprises a dosing chamber configured to receive medicament; a transducer confronting the dosing chamber, the transducer being configured to aerosolize the medicament when the transducer is activated; a membrane disposed between the dosing chamber and the transducer, the membrane being affixed to the dosing chamber; and an air column extending between the transducer and the membrane, wherein at least a portion of the air column is defined by a separation means (e.g., a spacer), wherein the inhaler produces synthetic jetting to deliver the aerosolized medicament to a user when the transducer is activated.

According to another embodiment, the inhaler comprises a dosing chamber comprising an interior that is configured to contain dry powder medicament, and a transducer confronting the dosing chamber, wherein the dosing chamber and the transducer are acoustically resonant such that the dosing chamber is configured to resonate in response to an activation of the transducer, the transducer having a transducer face that deflects when the transducer is activated; a membrane disposed between the dosing chamber and the transducer; and a spacer disposed between the membrane and the transducer, the spacer being in contact with the transducer face and the membrane and defining an air column between the transducer face and the membrane. As described in more detail herein, a first portion of the transducer face deflects more than a second portion of the transducer face when the transducer is activated and the spacer is positioned on the second portion of the transducer face, wherein the first portion is the center of the transducer face and the second portion is an outer perimeter of the transducer face. According to certain embodiments, it has been found that the device achieves a maximum synthetic jetting that is greater than the same device with a spacer positioned on the first portion of the transducer face instead of the second portion, as measured from the start of transducer activation. According to certain embodiments, it has been found that the device achieves a maximum synthetic jetting that is greater than the same device without a spacer, as measured from the start of transducer activation. Preferably, the combined acoustic resonance of the transducer, the dosing chamber, the membrane and the air column is sufficient to cause aerosolization and delivery of the dry powder medicament having an MMAD within the preferred ranges described herein, e.g., about 6 µm or less, preferably with a fine particle fraction within the preferred ranges described herein, e.g., at least 30%. Maximum synthetic jetting is preferably achieved within ranges of time described herein, e.g., within about 500 ms or less from the start of a transducer activation.

Figure 36A:
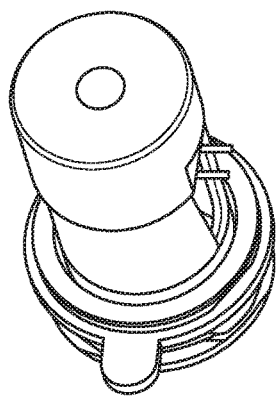
FIGS. 36A, 36B, and 36C each illustrate an embodiment of a spacer disposed on the face of a transducer.
Figure 36B:
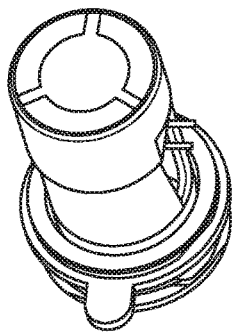
Figure 36C:
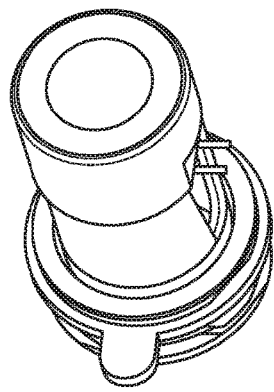

FIGS. 36A, 36B, and 36C each illustrate an embodiment of a transducer with a spacer disposed in the center of a transducer face (A), and transducers with a spacer disposed on an outer perimeter of a transducer face for a segmented spacer (B) and unsegmented spacer (C). In one example, devices according to embodiments B and C achieved greater maximum synthetic jetting than embodiment A, and greater maximum synthetic jetting than a device without a spacer.

The spacer may at least partially define the air column extending between the face of the transducer and the membrane. According to a preferred embodiment, a spacer is disposed on the face of the transducer (e.g., dielectric ink printed on the transducer). According to an alternative embodiment, the spacer is disposed on the membrane, or on a portion of the dosing chamber. The spacer preferably at least partially defines an air column that extends between the face of the transducer and the membrane. For example, the spacer may comprise material that is separate from the transducer and coupled to the face of the transducer, or material that is not separate from the transducer, i.e., it may be an integral portion of the transducer face that is raised.

According to particular embodiments, the transducer comprises a rigid case formed of, for example aluminum, that is closed at one end by a wall, wherein the outer surface of the wall is the face of the transducer 1284. The rigid case is preferably cylindrical. A piezoelectric element (e.g., a ceramic material, such as barium titanate or lead zirconate titanate) is preferably located within the cylinder in contact with the inner surface of the wall. According to an embodiment, the face of the transducer includes a first portion and a second portion. The first portion is that portion of the transducer face that has an inner surface coupled to the piezoelectric element and the second portion is that portion of the transducer face that does not have an inner surface coupled to the piezoelectric element. Typically, the face of the transducer is displaced (deflects) when the transducer is activated, wherein the first portion of the transducer face deflects more than the second portion of the transducer face when the transducer is activated. For example, the first portion is located in the center of the transducer face and the second portion is an outer perimeter of the transducer face. According to one embodiment, from 0% to 25% of the surface area of the spacer is positioned over the first portion, and from 75% to 100% of the surface area of the spacer is positioned over the second portion; or from 0% to 10% of the surface area of the spacer is positioned over the first portion, and from 90% to 100% of the surface area of the spacer is positioned over the second portion. According to a preferred embodiment, the spacer is positioned entirely on the second portion, and not on the first portion. It is believed that if too much of the spacer material is positioned over the first portion of the transducer face, it has a dampening effect on the piezoelectric element.

According to particular embodiments, the spacer is continuous, which means that there are no gaps along a perimeter of the spacer, e.g., as shown in FIG. 36C. For example, the spacer may be a continuous ring, oval, square or rectangle. Preferably, the spacer is discontinuous, which means that there are one or more gaps, or clefts, along the perimeter of the spacer. For example, the spacer may be a discontinuous ring, oval, square or rectangle with one or more clefts, e.g., as shown in FIG. 36B. According to a preferred embodiment, the spacer is a discontinuous ring that is disposed on the face of the transducer.

The air column is preferably optimized to efficiently couple mechanical vibration from the transducer into acoustic resonance of the dosing chamber, e.g., so that the transfer of energy from the transducer to the dosing chamber and possibly a blister can be maximized; and to enable faster onset of ultrasonic energy transfer into the dosing chamber so that drug delivery occurs more rapidly in response to a short burst duration of the transducer.

According to one embodiment of an inhaler comprising a spacer, dry powder medicament is ejected from the one or more openings in the dosing chamber in response to an activation of the transducer in less time (as measured from the start of the activation) than the same inhaler without a spacer. According to one embodiment, the inhaler achieves maximum synthetic jetting faster when the inhaler has a spacer between the face of the transducer and the dosing chamber membrane than when the same inhaler does not have a spacer between the face of the transducer and the dosing chamber membrane. For example, the inhaler may achieve maximum synthetic jetting within less than 200 ms of transducer activation (preferably within 175 ms or less, or 150 ms or less, or 125 ms or less, or 100 ms or less, or within 50-175 ms, or 50-150 ms, or 50-125 ms, or 50-100 ms, or 100-175 ms, or 100-150 ms) when the inhaler has a spacer between the face of the transducer and the dosing chamber membrane. In contrast, according to certain embodiments, it was found that when a spacer was not used in the same inhaler, maximum synthetic jetting was not achieved until the transducer had been activated for 200 ms or more. In accordance with these embodiments, the use of a spacer causes drug to be ejected from the dosing chamber via synthetic jetting sooner, thereby enabling the medicament to be entrained in a user's inhaled air earlier in the inhalation. This is particularly beneficial for those users that have inhalations of short duration and a limited amount of chase air to carry medicament into the lungs. According to one embodiment, an inhaler with a spacer achieves maximum synthetic jetting within at least 10% less time (from the start of transducer activation), or at least 20% less time, or at least 30% less time, or at least 40% less time, or at least 50% less time than the same inhaler without a spacer.

According to another embodiment, an inhaler with a spacer achieves a maximum synthetic jetting in response to activation of the transducer that is greater than the maximum synthetic jetting achieved by the same inhaler without a spacer. For example, it has been found according to certain embodiments that an inhaler comprising a spacer achieves maximum synthetic jetting of at least 0.5 V in response to an activation of the transducer (e.g., at least 0.5 V, or at least 0.6 V, or at least 0.7 V, or at least 0.8 V, or at least 0.9 V, or at least 1.0 V, or at least 1.1 V, or at least 1.2 V, or at least 1.3 V, or at least 1.4 V, or at least 1.5 V, or at least 1.6 V, or at least 1.7 V; for example, between 0.5 V and 1.7 V, or 0.5 V and 1.6 V, or 0.5 V and 1.5 V, or 0.5 V and 1.4 V, or 0.5 V and 1.3 V, or 0.5 V and 1.2 V, or 0.5 V and 1.0 V, or between 0.6 V and 1.7 V, or 0.6 V and 1.6 V, or 0.6 V and 1.5 V, or 0.6 V and 1.4 V, or 0.6 V and 1.3 V, or 0.6 V and 1.2 V, or 0.6 V and 1.0 V), whereas the same inhaler without a spacer achieves maximum synthetic jetting that is less than 0.5 V. According to one embodiment, a ratio of maximum synthetic jetting achieved by an inhaler without a spacer to maximum synthetic jetting achieved by the same inhaler with a spacer is about 0.9:1 or less, or about 0.8:1 or less, or about 0.7:1 or less, or about 0.6:1 or less, or from about 0.01:1 to about 0.9:1, or about 0.01:1 to about 0.8:1, or about 0.01:1 to about 0.7:1, or about 0.01:1 to about 0.6:1, or about 0.1:1 to about 0.9:1, or about 0.1:1 to about 0.8:1, or about 0.1:1 to about 0.7:1, or about 0.1:1 to about 0.6:1.

Embodiments of the spacer are described in more detail below with reference to the Figures Preferably, the spacer is in contact with both the face of the transducer and the membrane. As described below, the spacer height (e.g., measured between the face of the transducer and the membrane) is preferably about 10 μm to about 100 μm. Synthetic jetting may be measured in accordance with known methods, such as the method described in Example 1.

In some embodiments, the inhaler 100 includes a spacer 1286 between the transducer 150 and the membrane 1166 to enhance the transfer of acoustic vibration and physical vibration between the transducer 150 and the membrane 1166. In some embodiments, the presence of air between the transducer 150 and membrane 1166 enhances the vibrational energy transfer between the two, thus, in some embodiments, the inhaler 100 does not include a spacer but a gap is provided between the transducer and membrane. Turning to FIG. 25, in one embodiment the transducer 150 comprises a piezoelectric transducer. Piezoelectric transducers are well-known and readily available to those skilled in the art. According to one embodiment, the piezoelectric transducer resonates at approximately 37 to approximately 43 kHz, or approximately 38 to approximately 41 kHz. In one embodiment, the transducer 150 includes a cylindrical body 1282 and a transducer face 1284 having an axis of symmetry 1285. In one embodiment, a spacer 1286 is positioned on the transducer face 1284. In one embodiment, the spacer 1286 and the transducer face 1284 are a monolithic element. In one embodiment, the spacer 1286 is a dielectric ink (e.g., Acheson ML25240 UV Cure Dielectric Ink, electrically non-conductive ink) and is screen printed onto the transducer face 1284.

The spacer 1286 may be configured to be an interface between the transducer 150 and the membrane 1166. In some embodiments, the spacer 1286 is coupled to the membrane 1166. In some embodiments, the spacer 126 is coupled to the transducer 150. In embodiments where the spacer is bonded to either the transducer or the membrane, an appropriate bond strength is selected to ensure continuity of the bond during operation.

In some embodiments, the spacer is configured to effect transfer of physical vibration from the transducer 150 through the membrane 1166 and to the dosing chamber housing 1102. In one embodiment, the spacer 1286 is hard or rigid such that the spacer does not deform when it is in contact with one or both of the transducer 150 and the dosing chamber housing 1102. The spacer 1286 may be a metallic or plastic element and secured to the transducer face 1284 or body 1282 via adhesive, welding, fasteners, or the like. In some embodiments, the spacer 1286 is configured to deform when the spacer contacts the membrane 1166 and return to its undeformed state when the spacer is no longer in contact with the membrane.

In some embodiments, the spacer 1286 is configured to separate the membrane 1166 from the transducer face 1284 while simultaneously maintaining contact between the transducer face 1284 and the membrane 1166. In some embodiments, the spacer 1286 includes an internal opening such that the transducer face confronts the membrane effective area 1171 to allow an unobstructed transfer of vibration from the transducer to the membrane. The spacer 1286 may comprise a discontinuous ring with sections 1288 separated by a cleft 1290. In one embodiment, the cleft 1290 extends completely through the spacer 1286 such that the sections 1288 are separate elements from each other. In one embodiment, the cleft 1290 does not extend completely through the spacer but is a portion of the spacer having a reduced thickness. In one embodiment, the spacer sections 1288 and the clefts 1290 are arranged in a generally circular pattern and a ratio of the arc length of the spacer sections 1288 to the arc length of the clefts 1290 is about 18 to about 20. In one embodiment, the spacer 1286 is any desired shape (e.g., circular, triangular, rectangular, or randomized shapes). The transducer and spacer may be visible when the front portion 101 and back portion 102 of the inhaler 100 are separated from each other and the spacer 1286 may be shaped as a logo or other indicia. The transducer face 1284 may have a transducer face surface area and the spacer may include a spacer face surface area which is equivalent to about 45% to about 55% of the transducer face surface area. The spacer 1286 may include a spacer height as measured extending upwardly away from the transducer face 1284. The spacer height may be about 10 μm to about 100 μm, or about 20 μm to about 100 μm, or about 30 μm to about 100 μm, or about 20 μm to about 90 μm, or about 30 μm to about 90 μm, or about 40 μm to about 100 μm, or about 40 μm to about 90 μm, or about 50 μm to about 100 μm, or about 50 μm to about 90 μm, or about 50 μm to about 80 μm, or about 50 μm to about 70 μm, or about 50 μm to about 60 μm, or about 25 μm to about 80 μm. In one embodiment, the spacer 1286 has an inner diameter of about 7 mm to 8 mm, and an outer diameter of about 10 mm to about 11 mm. The transducer face surface area may be about 0.1 in$^2$ (65 mm$^2$) to about 0.3 in$^2$ (194 mm$^2$). The transducer face 1284 may deflect when the transducer is vibrated. In one embodiment, some portions of the transducer face 1284 may deflect more than others. For example, a first portion or center of the transducer face 1284 may deflect more than a second portion or outer diameter. In one embodiment, the spacer 1286 may be positioned on the second portion of the transducer face 1284 to avoid or eliminate a reduction in deflection distance caused by the spacer on the transducer face 1284. The spacer 1286 may deflect with the transducer face 1284 when the spacer 1286 is coupled to the transducer face and the transducer 150 is activated. In one embodiment, the spacer 1286 is adjacent an outer diameter 1292 of the transducer face 1284. In one embodiment, the spacer 1286 is separated from the outer perimeter 1292 by an offset 1294. In one embodiment the spacer 1286 includes a spacer inner perimeter 1296. In one embodiment, the transducer face 1284 includes a transducer effective area 1297 (best seen in FIG. 27) which includes the portion of the transducer face which is not covered by the spacer 1286 or the area of the transducer face which is inside of the spacer inner diameter 1296.

Figure 32:
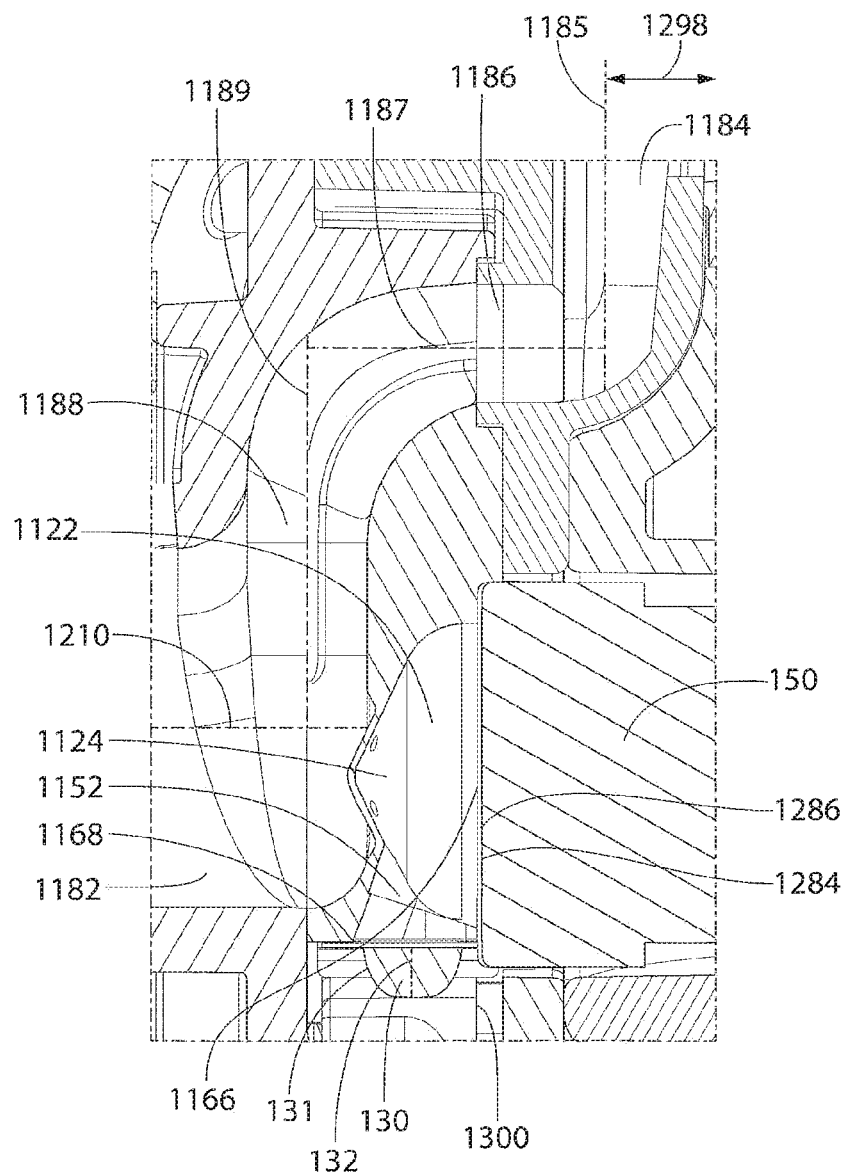
FIG. 32 is a close up view of a portion of FIG. 11.

FIG. 11 shows a sectional view of the inhaler 100 including the relative position of the dosing chamber 1122 and the transducer 150. FIG. 32 shows a close up sectional view of the inhaler 100. The transducer face 1286 is configured to confront the dosing chamber 1122 (or membrane 1166) when the front portion 101 and rear portion 102 are coupled to each other. In some embodiments, the outer diameter 1292 of the transducer 150 is equal to, slightly larger, or slightly smaller than, the size of the crown outer face 1141 of the housing 1102. In some embodiments, the crown inner face 1139 is equal to, slightly larger, or slightly smaller than, the spacer inner diameter 1296. In other words, the membrane effective area 1171 may be equal to, slightly larger, or slightly smaller than, the transducer face effective area 1297. In one embodiment, the transducer face effective area 1297 is about 0.05 in$^2$ (32 mm$^2$) to about 0.09 in$^2$ (58 mm$^2$).

Preferably, the spacer 1286 contacts the membrane 1166 when the inhaler 100 is assembled and separates the transducer face 1284 from the membrane 1166 during operation of the inhaler 100. In one embodiment, an air column is within the inner diameter 1296 of the spacer 1284 between the transducer face 1284 and the membrane 1166.

In one embodiment, when in use, the transducer 150 is deflected (or vibrated) along an axis 1298 when the front portion 101 and back portion 102 are coupled to each other and the transducer 150 is activated. In one embodiment, the transducer 150 is deflected from about 0.03 in (0.76 mm) to about 0.08 in (2.03 mm) when the front portion 101 and back portion 102 are coupled to each other. In one embodiment, the biasing element 1234 pushes back against the deflection of the transducer 150 such that energy from the biasing element is transferred through the transducer 150 to the membrane 1166.

In some embodiments, physical vibration is transferred from the transducer 150 through the housing 1102 and ultimately to a blister 120. In some embodiments, the physical vibration of the blister 130 at least partially assists in aerosolizing the pharmaceutical therein. In one embodiment, the blister strip 131 is in contact with the dosing chamber housing 1102 and the blister 130 is aligned with the tunnel 1152 when the inhaler 100 is assembled and the blister strip has been advanced to a dosing position as explained above. In one embodiment, the spring finger 172 (best seen in FIG. 1I) biases the blister strip 131 into contact with the housing 1102. Thus, a continuous physical link is configured to be established between the transducer holder 1224, transducer 150, optional spacer 1284, membrane 1166, dosing chamber housing 1102, tunnel 1152, and blister strip 131 when the inhaler 100 is assembled. The acoustic resonance of this continuous physical link enables vibratory energy from the transducer to aerosolize and expel dry powder medicament to a user, in some embodiments from a blister to a user, preferably by way of mechanical vibration and acoustic waves (synthetic jetting).

In one embodiment, a blister strip edge 1300 is separated from the transducer face 1284 by about 0.1 mm to about 5.0 mm, or about 0.1 mm to about 4.0 mm, or about 0.1 mm to about 3.0 mm, or about 0.1 mm to about 2.0 mm, or about 0.5 mm to about 5.0 mm, or about 0.5 mm to about 4.0 mm, or about 0.5 mm to about 3.0 mm, or about 0.5 mm to about 2.0 mm, or about 0.5 mm to about 1.5 mm when the transducer 150 is at rest. In one embodiment, the blister 130 is positioned between a plane define by the first leg axis 1185 and a plane defined by the third leg axis 1189. In one embodiment, the blister strip face 1168 is parallel to one, or both, of the second leg axis 1187 and the exit channel axis 1210. In one embodiment, the blister strip face 1168 is parallel to one or more of the transducer face axis of symmetry 1285, the dosing chamber axis of symmetry 1124, and the exit channel axis 1210. In one embodiment, the tunnel axis 1158 is oblique to the blister strip face 1168. In one embodiment, the first leg 1184 is perpendicular to the dosing chamber axis of symmetry 1124. In one embodiment, the second leg 1186 is parallel to the dosing chamber axis of symmetry 1124. In one embodiment, the third leg 1188 is perpendicular to the dosing chamber axis of symmetry 1124. In one embodiment, the transducer face 1284 is parallel to one, or both, of the first leg axis 1185 and the third leg axis 1189. In one embodiment, the dosing chamber 1122 is positioned between a plane defined by the first leg axis 1185 and a plane defined by the third leg axis 1189. In one embodiment, the transducer face axis of symmetry 1285 is parallel to the dosing chamber axis of symmetry 1124. In one embodiment, the transducer face axis of symmetry 1285, the dosing chamber axis of symmetry 1124, and the exit channel axis 1210 are all generally parallel to each other. In one embodiment, the blister 130 includes a blister axis 132 perpendicular to the dosing chamber axis 1124. In one embodiment, the transducer axis of motion 1298 is parallel to the exit channel axis 1210. In one embodiment, the blister strip 131 is spaced from the dosing chamber 1122 and the transducer 150 when the blister is in the dosing position. In other words, the blister strip 131 may not be in contact with either of the dosing chamber 1122 and the transducer 150 when the blister 130 is in the dosing position. In another embodiment, a portion of the blister strip surrounding the pocket only comes into contact with the tunnel and has no contact with the dosing chamber or transducer when in dosing position. In one embodiment, the air flow conduit 1195 is positioned above the blister 130 when a user is inhaling the pharmaceutical from the inhaler 100. In one embodiment, the curvature defined by the second leg 1186 and the third leg 1188 is positioned above the dosing chamber 1122. In one embodiment, the biasing element 1234, transducer holder 1224, transducer 150, optional spacer 1286, membrane 1166, dosing chamber 1122, and exit channel 1182 are stacked and each has a central axis that is co-axial or parallel with the other central axes. In one embodiment, each of the biasing element 1234, transducer holder 1224, transducer 150, optional spacer 1286, membrane 1166, and dosing chamber 1122 have a central axis and all the central axes are co-axial. In one embodiment, the biasing element 1234, transducer holder 1224, transducer 150, spacer 1286, membrane 1166, dosing chamber 1122, and exit channel 1182 are stacked in proximal to distal order when the inhaler 100 is assembled.

In a preferred embodiment, the vibration of the transducer 150 is configured to transfer the vibratory energy through physical vibration of the housing 1102 as well as through acoustic vibration as previously described. The transfer of vibrational energy through the inhaler 100 may be made more efficient by matching resonant frequency across the various components of the system. Vibrating an element at its resonant frequency will amplify the vibration of the element. Some vibration is cancelled out when an element is vibrated at a frequency other than its resonant frequency. A system with elements that each have the same (or common) resonant frequency may achieve synthetic jetting faster when the system is driven at the common resonant frequency than a system with elements having mismatched resonant frequencies. In some embodiments, the inhaler 100 includes elements (e.g., transducer, dosing chamber, membrane and air column) which have a common resonant frequency to efficiently transfer vibrational energy throughout the system. The transducer 150 may be characterized by an acoustic resonant frequency (or resonant frequency). In one embodiment, the features (e.g., dimensions, materials, orientation) of each of the spacer 1286, the membrane 1166, and the dosing chamber 1122 are adjusted such that the resonant frequency of each component, as well as the resonant frequency of the system comprised of these components, is matched or is closely related to the resonant frequency of the transducer 150. For example, without being limited by any particular theory, changing the material used for any of the components may affect the resonant frequency of each component and/or the overall system. However, this does not mean that a common resonant frequency for the system cannot be achieved simply because the materials comprising the elements are substituted. Instead, other elements or features of the system can be changed to recoordinate the resonant frequency of the system. For example, changing the height or width or wall thickness of the dosing chamber also affects the resonant frequency of the dosing chamber 1122 and the system. Thus, the material used to manufacture the housing 1102 containing the dosing chamber 1122 could be changed, and the dimensions of the dosing chamber also changed to maintain the resonant frequency of the dosing chamber and the system. Any element of the system may be changed and one or more of the remaining elements of the system may also be changed to maintain a common resonant frequency of each element and across the system. Individual elements, segments of the system, and/or the system as a whole, may be configured to have more than one resonant frequency or harmonic which may be a multiple of the first resonant frequency.

In one embodiment, the desired resonant frequency is selected by choosing a transducer 150, determining its resonant frequency, and then configuring a system which has a similar resonant frequency. In one embodiment, a dosing chamber is configured to fit within a desired inhaler, or a dosing chamber is manufactured from a certain material that will avoid negative interactions with a pharmaceutical is chosen and the rest of the components and system are configured to match the resonant frequency of the dosing chamber. In one embodiment, the resonant frequency of the system is determined when there is no pharmaceutical within the dosing chamber. In one embodiment, the resonant frequency of the system is determined when the aerosolized pharmaceutical is within the dosing chamber. In one embodiment, a system having the same or a similar acoustic resonance reduces the onset time to establish synthetic jetting and reduce the battery power needed to deliver a pharmaceutical to a user through the inhaler.

Acoustic impedance is generally the relationship between the acoustic pressure applied to a system and the resulting particle velocity in the direction of that pressure at its point of application. Acoustic impedance is generally defined as $Z_0 = \rho_0 \cdot c_0$ where $Z_0$ is acoustic impedance in units of Rayls (Pa·s/m); $\rho_0$ is density of the medium (kg/m3); and $c_0$ is the speed of sound through the medium (m/s). A system that has identical or a small variation in acoustic impedance across the elements of the system creates a more efficient energy transfer (or energy coupling) during operation of the system. The onset time for synthetic jetting is reduced in a system with greater acoustic impedance matching compared to a system with less acoustic impedance matching. The acoustic impedance may be thought of as the "stiffness" of each element. When the acoustic impedance is matched or is within a narrow range, the elements of the system (e.g., the air column, membrane, and the air within the chamber) can move in relative unison as the transducer vibrates, thus each vibration of the transducer may transfer more vibration energy to the air within the dosing chamber.

In one embodiment, the transducer 150 is characterized by a transducer acoustic impedance. In one embodiment, the air column within the spacer 1286 between the transducer face 1284 and the membrane 1166 is characterized by an air column acoustic impedance. In one embodiment, the air column acoustic impedance is less than the transducer acoustic impedance. In one embodiment, the membrane 1166 is characterized by a membrane acoustic impedance that is less than the transducer acoustic impedance. In one embodiment, the membrane acoustic impedance is greater than the air column acoustic impedance. In one embodiment, the air within the dosing chamber 1122 has an acoustic impedance that is less than one or more of the transducer 150, the air column, and the membrane 1166. In one embodiment, the transducer acoustic impedance is substantially equivalent to at least one of the chamber acoustic impedance, the membrane acoustic impedance, and the air column acoustic impedance. In one embodiment, the transducer acoustic impedance is the maximum acoustic impedance of the inhaler. The dosing chamber acoustic impedance may be measured with or without the aerosolized pharmaceutical in the dosing chamber.

In accordance with particular embodiments of the present invention, the applicants discovered that dry powder tends to get "stuck" in low pressure nodes of the dosing chamber (those areas with little or no oscillating pressure), which causes the synthetic jetting and resulting delivered dose to decrease substantially. Applicants further discovered that the drive scheme could be changed in a way that addresses this problem; specifically, the resonant frequency of the transducer is periodically interrupted of "switched off" to a non-resonant frequency (or "hop frequency"), according to particular embodiments. Switching off the resonant frequency interrupts the levitation of the particles so that they do not remain stuck in the low pressure nodes. According to preferred embodiments, the inclusion of a hop frequency significantly improves the gravimetric clearance of powder out of a dose. For example, a drive scheme without a hop frequency may result in a gravimetric clearance of less than 50%, or less than 40% of powder from a dose (e.g., a dose contained in a blister), whereas a drive scheme including a hop frequency may result in a gravimetric clearance of greater than 60%, preferably greater than 70%, or greater than 80% or greater than 90% or greater than 95% of powder from a dose (e.g., a dose contained in a blister).

According to one embodiment, a method of driving a piezoelectric transducer in a medicament delivery device comprises: activating the transducer by providing an electric signal to the transducer for a period of time, wherein the electric signal provides a first frequency which causes the transducer to oscillate at its resonant frequency, and a second frequency that is different from the first frequency and does not cause the transducer to oscillate at its resonant frequency, wherein the electric signal alternates between the first frequency and the second frequency during said period of time. According to an additional embodiment, a medicament delivery device comprises a dosing chamber comprising an interior that is configured to contain dry powder medicament; a transducer confronting the dosing chamber, wherein the dosing chamber and the transducer are acoustically resonant such that the dosing chamber is configured to resonate in response to an activation of the transducer; and a controller configured to send an electric signal to the transducer that alternates between a first frequency and a second frequency during a transducer activation, wherein the first frequency causes the transducer to oscillate at its resonant frequency, and the second frequency is different from the first frequency and does not cause the transducer to oscillate at its resonant frequency (e.g., the device contains a program code capable of generating said electric signal).

Preferably, the signal alternates between the first frequency and the second frequency multiple times during a transducer activation. The second frequency may be referred to as a "hop frequency." The use of a hop frequency preferably causes aerosolization and delivery of the dry powder medicament having an MMAD within the preferred ranges described herein, e.g., about 6 μm or less, preferably with a fine particle fraction within the preferred ranges described herein, e.g., at least 30%. Maximum synthetic jetting is preferably achieved within ranges of time described herein, e.g., within about 500 ms or less from the start of a transducer activation. According to an embodiment, maximum synthetic jetting and/or speed of onset of synthetic jetting is greater for a device that employs a hop frequency than a device that does not employ a hop frequency. Delivered dose per burst, total delivered dose, and aerodynamic particle size distribution may also be improved when a hop frequency is used.

Preferably, the first frequency is substantially equivalent to the resonant frequency of the piezoelectric transducer; and the second frequency is not substantially equivalent to the resonant frequency of the piezoelectric transducer. A frequency that is substantially equivalent to the resonant frequency of the piezoelectric transducer refers to a frequency that is equal to the resonant frequency of the piezoelectric transducer, or sufficiently close to the resonant frequency of the piezoelectric transducer that it causes the transducer to produce oscillations that are sufficient to generate synthetic jetting.

According to one example, the transducer's resonant frequency is between 37-42 kHz; during a dosing breath, the transducer is activated by an electric signal having a first frequency that is also between 37-42 kHz, and the first frequency is subsequently "interrupted" by a second frequency that is outside the range of 37-42 kHz, i.e., less than 37 kHz or greater than 42 kHz. During a dosing breath, the first frequency is provided for the majority of the transducer's "on-time" while the second frequency briefly interrupts the first frequency intermittently so that dry powder particles do not remain stuck in low pressure nodes inside the dosing chamber. A brief interruption by the second frequency ("hop frequency") is still considered part of the on-time.

According to one embodiment, the method comprises activating the transducer for from about 50 ms to about 1000 ms upon each dosing breath; for example from about 50 ms to about 900 ms, or about 50 ms to about 800 ms, about 50 ms to about 700 ms, or about 50 ms to about 600 ms, or about 50 ms to about 500 ms, or about 50 ms to about 400 ms, or about 50 ms to about 300 ms, or about 50 ms to about 200 ms, or about 50 ms to about 100 ms, or about 100 ms to about 900 ms, or about 100 ms to about 800 ms, or about 100 ms to about 700 ms, or about 100 ms to about 600 ms, or about 100 ms to about 500 ms, or about 100 ms to about 400 ms, or about 100 ms to about 300 ms, or about 100 ms to about 200 ms upon each dosing breath. As described herein, an inhalation cycle preferably includes multiple dosing breaths.

According to one embodiment, the method comprises providing the first frequency for at least about 70%, or at least about 75%, or at least about 80%, or at least about 85%, or at least about 90% or of the period of time that the transducer is activated, and providing the second frequency for at most about 30%, or at most about 25%, or at most about 20%, or at most about 15%, or at most about 10% of the period of time that the transducer is activated. For example, the method may comprise providing the first frequency for about 90% of the period of time that the transducer is activated, and providing the second frequency for about 10% of the period of time that the transducer is activated.

According to one embodiment, the method comprises activating the transducer for about 500 ms, wherein during that time the signal provides the first frequency for about 90 ms and the second frequency for about 10 ms, e.g., the signal alternates five times between the first frequency for about 90 ms and the second frequency for about 10 ms. According to another embodiment, the method comprises activating the transducer for about 100 ms, wherein during that time the signal alternates between providing the first frequency for about 90 ms and providing the second frequency for about 10 ms.

According to one embodiment, the first frequency is from about 37 kHz to about 42 kHz, and the second frequency is either 36 kHz or less, or 43 kHz or more. For example, the second frequency may be from 0 kHz to about 30 kHz, or from about 45 kHz to about 75 kHz, or from about 50 kHz to about 60 kHz.

According to an embodiment, a method of treating a respiratory disease or disorder (e.g., COPD, asthma, cystic fibrosis, idiopathic pulmonary fibrosis, etc.) comprises using an embodiment of the inhaler described herein (e.g., by making consecutive inhalations through the inhaler) to administer a therapeutically effective amount of one or more medicaments.

The inhaler of the present invention is suitable for the delivery of many classes of medicaments by inhalation, and may be used for the treatment of various diseases and disorders. According to preferred embodiments, the inhaler is used for the treatment of respiratory disorders (e.g., COPD, asthma, cystic fibrosis, idiopathic pulmonary fibrosis, etc.). The inhaler may also be used to treat non-respiratory disorders.

According to particular embodiments, the methods described herein include methods for treating a respiratory disease or disorder amenable to treatment by respiratory delivery of a dry powder composition as described herein. For example, the compositions, methods and systems described herein can be used to treat inflammatory or obstructive pulmonary diseases or conditions. In certain embodiments, the compositions, methods and systems described herein can be used to treat patients suffering from a disease or disorder selected from asthma, chronic obstructive pulmonary disease (COPD), exacerbation of airways hyper reactivity consequent to other drug therapy, allergic rhinitis, sinusitis, pulmonary vasoconstriction, inflammation, allergies, impeded respiration, respiratory distress syndrome, pulmonary hypertension, pulmonary vasoconstriction, and any other respiratory disease, condition, trait, genotype or phenotype that can respond to the administration of, for example, a LAMA, LABA, corticosteroid, or other active agent as described herein, whether alone or in combination with other therapies. In certain embodiments, the compositions, systems and methods described herein can be used to treat pulmonary inflammation and obstruction associated with cystic fibrosis. As used herein, the terms "COPD" and "chronic obstructive pulmonary disease" encompass chronic obstructive lung disease (COLD), chronic obstructive airway disease (COAD), chronic airflow limitation (CAL) and chronic obstructive respiratory disease (CORD) and include chronic bronchitis, bronchiectasis, and emphysema. As used herein, the term "asthma" refers to asthma of whatever type or genesis, including intrinsic (non-allergic) asthma and extrinsic (allergic) asthma, mild asthma, moderate asthma, severe asthma, bronchitic asthma, exercise-induced asthma, occupational asthma and asthma induced following bacterial infection. Asthma is also to be understood as embracing wheezy-infant syndrome.

According to a preferred embodiment, the inhaler delivers one or more medicaments for the treatment of COPD; in particular, for the long-term, maintenance bronchodilator treatment of airflow obstruction in patients with chronic obstructive pulmonary disease (COPD), including chronic bronchitis and/or emphysema.

A range of classes of medicaments have been developed to treat respiratory disorders and each class has differing targets and effects.

Bronchodilators are employed to dilate the bronchi and bronchioles, decreasing resistance in the airways, thereby increasing the airflow to the lungs. Bronchodilators may be short-acting or long-acting. Typically, short-acting bronchodilators provide a rapid relief from acute bronchoconstriction, whereas long-acting bronchodilators help control and prevent longer-term symptoms.

Different classes of bronchodilators target different receptors in the airways. Two commonly used classes are anticholinergics and β2-agonists.

Anticholinergics (or "antimuscarinics") block the neurotransmitter acetylcholine by selectively blocking its receptor in nerve cells. On topical application, anticholinergics act predominantly on the M3 muscarinic receptors located in the airways to produce smooth muscle relaxation, thus producing a bronchodilatory effect. Non-limiting examples of long-acting muscarinic antagonists (LAMA's) include tiotropium and pharmaceutically acceptable salts thereof (e.g., tiotropium bromide), oxitropium and pharmaceutically acceptable salts thereof (e.g., oxitropium bromide), aclidinium and pharmaceutically acceptable salts thereof (e.g., aclidinium bromide), ipratropium and pharmaceutically acceptable salts thereof (e.g., ipratropium bromide) glycopyrronium and pharmaceutically acceptable salts thereof (e.g., glycopyrronium bromide, also referred to as glycopyrrolate), oxybutynin and pharmaceutically acceptable salts thereof (e.g., oxybutynin hydrochloride or oxybutynin hydrobromide), tolterodine and pharmaceutically acceptable salts thereof (e.g., tolterodine tartrate), trospium and pharmaceutically acceptable salts thereof (e.g., trospium chloride), solifenacin and pharmaceutically acceptable salts thereof (e.g., solifenacin succinate), fesoterodine and pharmaceutically acceptable salts thereof (e.g., fesoterodine fumarate), darifenacin and pharmaceutically acceptable salts thereof (e.g., darifenacin hydrobromide) and umeclidinium and pharmaceutically acceptable salts thereof (e.g., umeclidinium bromide).

β2-Adrenergic agonists (or "β2-agonists") act upon the β2-adrenoceptors and induce smooth muscle relaxation, resulting in dilation of the bronchial passages. Non-limiting examples of long-acting β2-adrenergic agonists (LABA's) include formoterol and pharmaceutically acceptable salts thereof (e.g., formoterol fumarate), salmeterol and pharmaceutically acceptable salts thereof (e.g., salmeterol xinafoate), indacaterol and pharmaceutically acceptable salts thereof (e.g., indacaterol maleate), bambuterol and pharmaceutically acceptable salts thereof (e.g., bambuterol hydrochloride), clenbuterol and pharmaceutically acceptable salts thereof (e.g., clenbuterol hydrochloride), olodaterol and pharmaceutically acceptable salts thereof (e.g., olodaterol hydrochloride), carmoterol and pharmaceutically acceptable salts thereof (e.g., carmoterol hydrochloride), tulobuterol and pharmaceutically acceptable salts thereof (e.g., tulobuterol hydrochloride) and vilanterol and pharmaceutically acceptable salts thereof (e.g., vilanterol triphenylacetate). Non-limiting examples of short-acting β2-agonists (SABA's) include albuterol and pharmaceutically acceptable salts thereof (e.g., albuterol sulfate) and levalbuterol and pharmaceutically acceptable salts thereof (e.g., levalbuterol tartrate). According to one embodiment, the formulation comprises albuterol (sulfate).

Another class of medicaments employed in the treatment of respiratory disorders are inhaled corticosteroids (ICS's). ICS's are steroid hormones used in the long-term control of respiratory disorders. They function by reducing the airway inflammation. Non-limiting examples of inhaled corticosteroids include budesonide and pharmaceutically acceptable salts thereof, beclomethasone and pharmaceutically acceptable salts thereof (e.g., beclomethasone dipropionate), fluticasone and pharmaceutically acceptable salts thereof (e.g., fluticasone propionate), mometasone and pharmaceutically acceptable salts thereof (e.g., mometasone furoate), ciclesonide and pharmaceutically acceptable salts thereof, and dexamethasone and pharmaceutically acceptable salts thereof (e.g., dexamethasone sodium).

According to an embodiment, the medicament delivery device delivers one or more medicaments selected from the group comprising or consisting of tiotropium and pharmaceutically acceptable salts thereof (e.g., tiotropium bromide), oxitropium and pharmaceutically acceptable salts thereof (e.g., oxitropium bromide), aclidinium and pharmaceutically acceptable salts thereof (e.g., aclidinium bromide), ipratropium and pharmaceutically acceptable salts thereof (e.g., ipratropium bromide) glycopyrronium and pharmaceutically acceptable salts thereof (e.g., glycopyrronium bromide, also referred to as glycopyrrolate), oxybutynin and pharmaceutically acceptable salts thereof (e.g., oxybutynin hydrochloride or oxybutynin hydrobromide), tolterodine and pharmaceutically acceptable salts thereof (e.g., tolterodine tartrate), trospium and pharmaceutically acceptable salts thereof (e.g., trospium chloride), solifenacin and pharmaceutically acceptable salts thereof (e.g., solifenacin succinate), fesoterodine and pharmaceutically acceptable salts thereof (e.g., fesoterodine fumarate), darifenacin and pharmaceutically acceptable salts thereof (e.g., darifenacin hydrobromide), umeclidinium and pharmaceutically acceptable salts thereof (e.g., umeclidinium bromide), formoterol and pharmaceutically acceptable salts thereof (e.g., formoterol fumarate), salmeterol and pharmaceutically acceptable salts thereof (e.g., salmeterol xinafoate), indacaterol and pharmaceutically acceptable salts thereof (e.g., indacaterol maleate), bambuterol and pharmaceutically acceptable salts thereof (e.g., bambuterol hydrochloride), clenbuterol and pharmaceutically acceptable salts thereof (e.g., clenbuterol hydrochloride), olodaterol and pharmaceutically acceptable salts thereof (e.g., olodaterol hydrochloride), carmoterol and pharmaceutically acceptable salts thereof (e.g., carmoterol hydrochloride), tulobuterol and pharmaceutically acceptable salts thereof (e.g., tulobuterol hydrochloride), vilanterol and pharmaceutically acceptable salts thereof (e.g., vilanterol triphenylacetate), albuterol and pharmaceutically acceptable salts thereof (e.g., albuterol sulfate), levalbuterol and pharmaceutically acceptable salts thereof (e.g., levalbuterol tartrate), beclomethasone and pharmaceutically acceptable salts thereof (e.g., beclomethasone dipropionate), fluticasone and pharmaceutically acceptable salts thereof (e.g., fluticasone propionate), mometasone and pharmaceutically acceptable salts thereof (e.g., mometasone furoate), ciclesonide and pharmaceutically acceptable salts thereof and dexamethasone and pharmaceutically acceptable salts thereof (e.g., dexamethasone sodium) and a combination thereof.

According to an embodiment, the medicament delivery device delivers a formulation comprising DNase (an enzyme that catalyzes cleavage of DNA), preferably DNase I or a variant thereof, most preferably human DNase I or a variant thereof. The DNase may be produced by known methods of recombinant DNA technology. The DNase may be administered for the treatment of a respiratory disease or disorder, such as cystic fibrosis (CF) or pneumonia. The medicament delivery device preferably administers an amount of DNase that is effective to reduce the viscoelasticity of pulmonary secretions (mucus) in diseases such as CF or pneumonia, thereby aiding in the clearing of respiratory airways. As used herein, the term "human DNase I" refers to a polypeptide having the amino acid sequence of native human DNase I (see, e.g., SEQ. ID NO. 1 of U.S. Pat. No. 6,348,343). A "variant" of native human DNase I is a polypeptide having an amino acid sequence different from that of native human DNase I, e.g., at least 80% sequence identity (homology), preferably at least 90% sequence identity, more preferably at least 95% sequence identity, and most preferably at least 98% sequence identity with native human DNase I. The human DNase I or variant thereof exhibits DNA hydrolytic activity.

According to an embodiment, the medicament delivery device delivers a formulation comprising one or more antibiotics. The antibiotic(s) may be administered for the treatment of a respiratory disease or disorder, such as cystic fibrosis. Non-limiting examples of the classes of antibiotics that may be delivered by the medicament delivery device include tetracycline (e.g., doxycycline, minocycline, oxytetracycline, tigecycline), fluoroquinolone (e.g., ciprofloxacin, gemifloxacin, levofloxacin, moxifloxacin, norfloxacin, ofloxacin, sitafloxacin), carbapenem (e.g., meropenem, imipenem), polymyxin (e.g., colistin, polymyxin B) and combinations thereof. For example, a drug formulation may comprise an antibiotic selected from the group comprising or consisting of doxycycline, minocycline, oxytetracycline, tigecycline, ciprofloxacin, gemifloxacin, levofloxacin, moxifloxacin, norfloxacin, ofloxacin, sitafloxacin, meropenem, imipenem, colistin, polymyxin B and a combination thereof. A drug formulation may further comprise one or more adjuvants (potentiators of antibiotic activity) in combination with one or more antibiotics. According to an embodiment, a drug formulation comprises two or more antibiotics in combination, from the same class or different classes of antibiotic. A drug formulation may comprise one or more prodrugs of any of the aforementioned medicaments.

According to one embodiment, the medicament delivery device delivers a formulation comprising colistimethate sodium (a form of colistin) for the treatment of cystic fibrosis, or a formulation comprising doxycycline monohydrate for the treatment of cystic fibrosis, or a formulation comprising both colistimethate sodium and doxycycline monohydrate. According to another embodiment, the medicament delivery device delivers a formulation comprising pirfenidone for the treatment of idiopathic pulmonary fibrosis (IPF) or a symptom thereof.

According to particular embodiments, the inhaler delivers a combination of at least two different medicaments (two, three, four, etc.) which belong to the same or different classes. According to one embodiment, the medicament delivery device delivers a "triple combination" of three different medicaments. The three medicaments may belong to three different medicament classes (e.g., LAMA, LABA, ICS); alternatively, two or three of the medicaments may belong to the same class.

According to a preferred embodiment, the inhaler delivers one or more medicaments selected from the group comprising or consisting of a long-acting muscarinic antagonist (LAMA), a long-acting β2-adrenergic agonist (LABA) and a combination thereof. Thus, the medicament delivery device may deliver a formulation comprising one or more LAMA's in combination with one or more LABA's. A particularly suitable combination comprises glycopyrronium bromide (i.e., glycopyrrolate) and formoterol fumarate. Another suitable combination comprises tiotropium bromide and formoterol fumarate. Such combinations may be used for the treatment of COPD; in particular, for the long-term, maintenance bronchodilator treatment of airflow obstruction in patients with chronic obstructive pulmonary disease (COPD), including chronic bronchitis and/or emphysema. According to one embodiment, a combination of glycopyrrolate and formoterol fumarate, or tiotropium bromide and formoterol fumarate, is administered twice daily via oral tidal inhalation. Preferably, the combination achieves clinically significant bronchodilation vs. placebo at peak through trough (e.g., >100 ml), and/or significantly better bronchodilation (FEV$_1$) at peak through trough than monotherapy LABA (e.g., formoterol fumarate) or LAMA (e.g., glycopyrrolate or tiotropium bromide), and/or an onset of bronchodilation compared to placebo at 5 minutes after the first dose.

According to additional embodiments, the inhaler delivers one or more medicaments selected from the group comprising or consisting of a long-acting muscarinic antagonist (LAMA), a long-acting β2-adrenergic agonist (LABA), an inhaled corticosteroid (ICS) and a combination thereof. Thus, the medicament delivery device may deliver a formulation comprising one or more LAMA's, one or more LABA's and one or more ICS's. That is, the device may deliver a double combination of a LAMA and a LABA, a LAMA and an ICS, or a LABA and an ICS; or a triple combination of a LAMA, a LABA and an ICS.

Generally, as discussed herein, powdered medicament particles suitable for delivery to the bronchial or alveolar region of the lung have an aerodynamic diameter of less than 10 μm, preferably less than 6 μm. Other sized particles may be used if delivery to other portions of the respiratory tract is desired, such as the nasal cavity, mouth or throat. The medicament may be delivered as pure drug, but may alternatively be delivered together with one or more carriers and/or one or more excipients which are suitable for inhalation.

According to preferred embodiments, a powder formulation (also referred to herein as a "drug composition," "composition," "drug formulation," "pharmaceutical composition," "medicament formulation" or "API formulation") comprises the medicament in combination with one or more carriers and/or one or more excipients. For example, a dose of medicament may be delivered in the form of a formulation comprising at least one medicament, at least one carrier (e.g., lactose) and optionally at least one excipient. According to particular embodiments, each blister on a blister strip contains a formulation dose in powder form, wherein each formulation dose comprises at least one medicament (e.g., a single medicament, or a combination of two medicaments, such as a LAMA and LABA), at least one carrier (e.g., lactose) and optionally at least one excipient (e.g., magnesium stearate). According to one example, each dose may comprise, consist essentially of, or consist of at least one medicament (e.g., a single medicament, or a combination of two medicaments, such as a LAMA and LABA) and a carrier (e.g., lactose) without any excipients.

Pharmaceutically acceptable carriers and excipients for dry powder formulations are known in the art. Lactose is a preferred carrier and magnesium stearate is a preferred excipient. Particles of a drug formulation may comprise surfactants, wall forming materials, or other components considered desirable by those of ordinary skill in the art. Particles of powdered medicament and/or powdered formulation may be produced by conventional techniques, for example by micronisation, milling, sieving or spray drying.

Additionally, medicament and/or formulation powders may be engineered with particular densities, size ranges, or characteristics.

The drug formulations of the present invention are preferably propellant-free (e.g., free of propellant commonly used in inhalers, such as hydrofluoroalkane (HFA) propellant).

Embodiments of the present invention may be further understood by reference to the Examples provided below.

EXAMPLES

Unless indicated otherwise, the medicament delivery device used in the examples below (e.g., "Tidal Inhaler") is an embodiment of the handheld device described herein, having a base and removable cartridge comprising a blister strip and powered by a rechargeable battery, similar to the device illustrated in FIGS. 5A-D. The piezoelectric transducer has a spacer of dielectric ink screen printed on its face (e.g., Acheson ML25240 UV Cure Dielectric Ink, electrically non-conductive ink) in the pattern of a discontinuous ring positioned at or near the perimeter of the transducer face, similar to FIG. 25. The nominal spacer thickness applied to the face of the piezo is about 53 µm±25 µm. The piezo is pressed against the dosing chamber membrane via a mounting system comprising a holder and spring, similar to FIGS. 25-27. The aluminum piezo is driven at a resonant frequency between 38-42 kHz with a hop frequency of about 54 kHz and voltage of 200-240 V p-p. The membrane is co-extruded polyethylene terephthalate (PET, DuPont Mylar® 813) with one side heat sealable amorphous PET, having a nominal thickness of about 23 µm±10 µm. The dosing chamber and air flow conduit of the device are similar to those illustrated in FIGS. 12, 13, 16 and 18. The dosing chamber has four openings in the apex with diameters of 0.019 inches (0.48 mm) 0.012 inches (0.30 mm). The flow resistance is between 0.050-0.09 cmH$_2$O$^{0.5}$/LPM at a flow rate of 30 LPM. For in vitro tests described below, unless indicated otherwise, a flow rate of 30 LPM was used.

All aerodynamic particle size distributions (APSD) were determined using a Next Generation Impactor (NGI). Samples were analyzed using single-point calibration on an HPLC system with UV detection at 220 nm.

Example 1: Synthetic Jetting Test Procedure

Reference: Service and Instruction Manual, Rudolph Pneumotachometers (PNT) and Heater Controllers ISO 9001/ISO 13485.

Materials and Equipment:
Linear Pneumotachometer 3500 Series 0-35 L/min by Hans Rudolph, Inc. (or equivalent)
Pneumotach Amplifier 1 Series 1110 by Hans Rudolph, Inc. (or equivalent)
Digital Storage Oscilloscope (or equivalent)
Inhaler Subassembly with Aerosol Engine comprising jetting fixture (or equivalent)
Breakout Board and Flat Flex Jumper Assembly 50363 (or equivalent)
Remote Start Switch (or equivalent)
BNC Coaxial Cable (or equivalent)
Ribbon Insertion Tool 50627 (or equivalent)
Connector Latch Tool P2767 (or equivalent)

Figure 35:
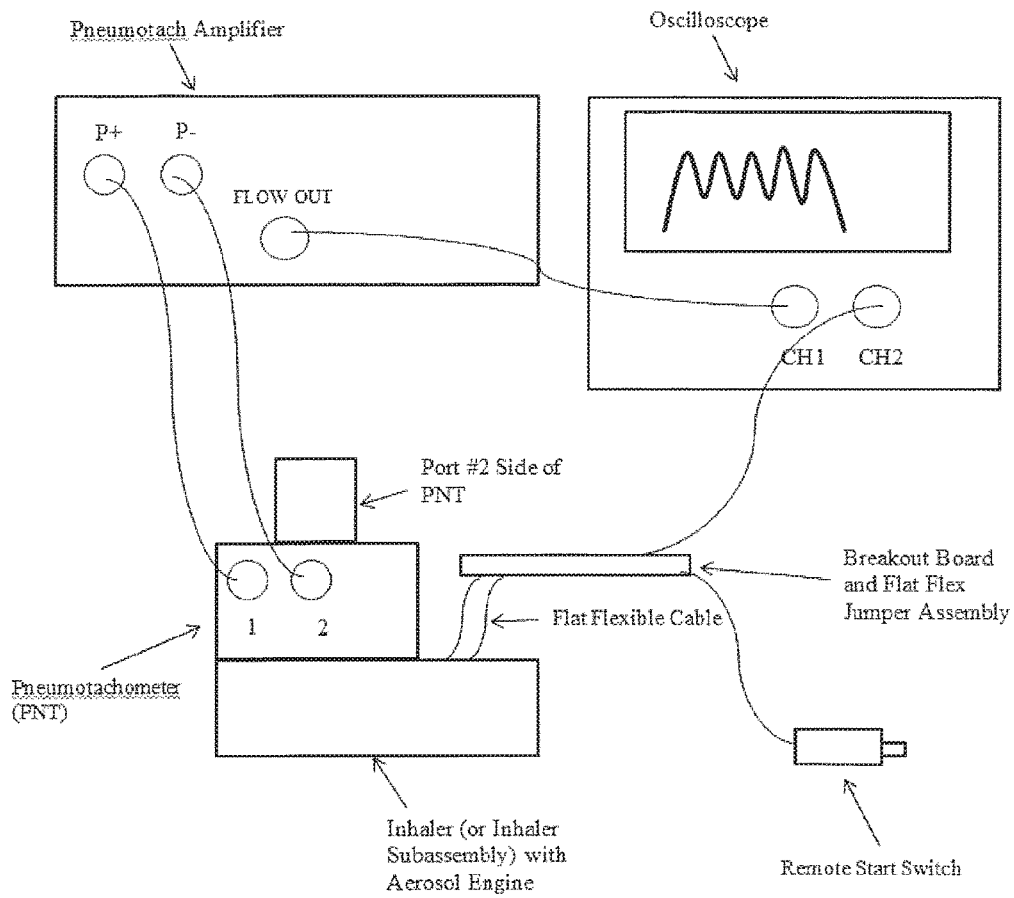
FIG. 35 is a schematic diagram of an inhaler property observation rig in accordance with one embodiment of the present invention.

An example of the Equipment Setup is illustrated in FIG. 35. A flat flex cable (FFC) provides control and feedback signals so that the jetting signal can be aligned with the piezoelectric transducer firing on the oscilloscope. The pneumotachometer is preferably installed so that the net jetting flow out of the mouthpiece port generates a positive signal on the oscilloscope. The PNT is positioned over the dosing chamber holes using the mask port, and captures the net flow exiting all the hole(s) of the dosing chamber. The net flow is the cumulative effect of the outward momentum of each of the individual jets occurring at the piezo drive frequency (e.g., approximately 37-42 kHz).

Equipment Setup Example:
1. Connect the Flat Flexible Cable (FFC) jumper locking lever to the inhaler. A ribbon insertion tool may be used to guide the FFC into the inhaler. The blue insulator on the end of the cable should be facing the inhaler. A locking lever may be used to lock the FFC in place. The aerosol engine/jetting fixture should be clamped securely in place.
2. Attach the pneumotachometer (PNT) to the inhaler. The Port #2 side of the PNT should be facing away from the device.
3. Attach the PNT tubing to connect the pneumotachometer to the pneumotach amplifier. The tubing with a white label should be attached to the PNT input labeled "1" and the "P+" input on the pneumotach amplifier. The tubing with a black label should be attached to the PNT input labeled "2" and the "P−" input on the amplifier.
4. Use a BNC coaxial cable to connect the amplifier "Flow Out" to "CH1" on the oscilloscope.
5. Run the oscilloscope in the following setting:
   a. Time Mode: Roll
6. Verify the baseline voltage is at zero. If not, use a screwdriver to adjust the "ZERO" setting on the pneumotach amplifier until a zero voltage reading is displayed.
7. Connect the coaxial cable attached to the breakout board TP1 and GND pins to "CH2" on the oscilloscope.
8. Adjust the oscilloscope settings as follows:
   a. CH1: 50 mV/div with a 150 mV offset
   b. CH2: 200 mV/div with a 600 mV offset
   c. Time Mode: Normal with 100 ms hold off
   d. TRIG: CH2 rising edge at a 850 mV level
   e. HORZ: 5 ms/div with a 10 ms left position delay
9. Press the "Quick Measure" button on the oscilloscope and select to measure the Source 1 Pk-Pk voltage.
10. Connect the remote start switch to the breakout board SW1 and GND pins.
11. Press the remote start switch to turn on the device. Verify the device has powered on by observing the light-up sequence display on the device overlay.
12. Press and hold the remote start switch for at least 5 seconds until the device triggers. When this happens a trace will appear on the oscilloscope.
13. Record the Pk-Pk (1) voltage as the peak PNT signal.
14. Repeat steps 11-13 as required.

Example 2: Test Procedure for Determining Flow Resistance of Air Flow Conduit References, each of which is incorporated by reference herein in their entirety:
1. United States Pharmacopia General Chapters <601> Aerosols, Nasal Sprays, Meter-Dose Inhalers, and Dry Powder Inhalers;
2. "Testing Inhalers" David Harris, Pharmaceutical Technology Europe, September 2007, pg 29-35;
3. A. R. Clarke and A. M. Hollingworth, J. Aerosol Med., 6 99-110 (1993).

Materials and Equipment:
1. Inhaler air flow conduit and mouthpiece adapter to the testing apparatus volume (or equivalent);
2. Air flow conduit adapter chamber with pressure port P1 part #1987A as part of Subassembly 50417A (or equivalent);
3. Differential Pressure Meter-Digitron Model #2020P or 2000P for 0-10" W.C. range and Model #2022P for >10" W.C. (or equivalent)
4. Flow Meter—Cole Parmer Model #32908-75 (or equivalent)
5. Flow Control Valve with a Cv≥1.0—Parker Hannifin type 8F-V12LN-SS (or equivalent)
6. Vacuum Pump—Gast Type 1023, 1423 or 2565 (or equivalent)
7. Tubing—Tygon B-44-4X 10 mm ID and Tygon 4 mm (5/32') ID (or equivalent)

Figure 39:
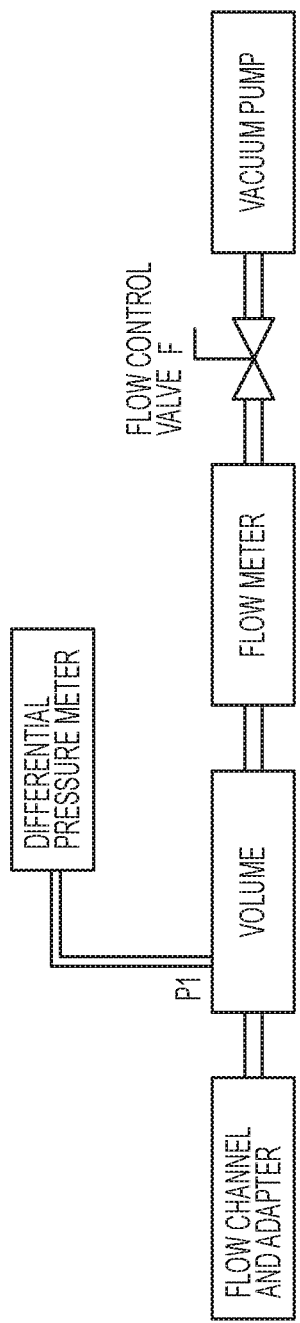
FIG. 39 is a schematic diagram of a system for measuring flow resistance in accordance with one embodiment of the present invention.

Procedure:
Set up the system with the diagram shown in FIG. 39.
1. Apply power to both the Flow Meter and Pressure Sensor and allow 10 minutes for warm-up. After warm-up, zero both the pressure sensor and flow meter.
2. Ensure tight air seals on all connections. When the thumb is placed over the opening at the air flow conduit adapter chamber, the Flow Meter should read zero.
3. To measure the inhaler flow resistance, insert an empty blister into the inhaler, and insert the inhaler into the air flow conduit adapter chamber. Turn on the vacuum pump and adjust Flow Control valve F until the flow meter reads the required tested flow rate. Record the pressure differential (PI) from the Differential Pressure Meter in inches W.C.; convert to cm W.C.
4. Calculate the inhaler flow resistance using the following equation:

$$\text{Flow Resistance} = \text{Square Root (Pressure in cm } W.C.)/\text{Flow Rate in L/min}$$
$$= \text{Square Root } (P1 \times 2.54^*)/\text{flow rate}$$
$$= \text{cm } H_2O^{1/2} \cdot (L/\text{min})^{-1}$$

*Conversion from inches to centimeters; 1 inch = 2.54 cm

Example 3: Glycopyrronium Bromide and Formoterol Fumarate Formulations

Glycopyrronium Bromide Formulation: Micronized glycopyrronium bromide (GB) is formulated as a dry powder for inhalation by blending the drug substances with inhalation-grade lactose (RESPITOSE® ML001, DFE Pharma). The range of strengths is from approximately 5 mcg low (0.25% weight by weight [w/w] GB) to approximately 30 mcg high (1.5% w/w GB).

Formoterol Fumarate (FF) Formulation: Micronized FF dihydrate is formulated as a dry powder for inhalation by blending the drug substances with inhalation-grade lactose (RESPITOSE® ML001, DFE Pharma). The range of strengths is from approximately 5 mcg low (0.26% w/w FF dihydrate), approximately 10 mcg medium (0.52% w/w FF dihydrate), and approximately 12 mcg high (0.62% w/w FF dihydrate).

Glycopyrronium Bromide-Formoterol Fumarate Combination: Micronized GB and FF dihydrate are formulated as a dry powder for inhalation by blending the drug substances with inhalation-grade lactose (RESPITOSE® ML001, DFE Pharma). Strengths are similar to those shown above for the monotherapy formulations.

Active blends are filled into aluminium-polymer laminate blister strips to meet the target dose range, as presented in Table 1. The target delivered dose refers to the amount of GB and FF dihydrate, in micrograms, that exits from the inhaler mouthpiece. The blister strips contain 32 filled blister pockets.

TABLE 1

| Description | Glycopyrronium Bromide | | Formoterol Fumarate Dihydrate | |
|---|---|---|---|---|
| | Loaded dose (mcg) | Targeted delivered dose (mcg) | Loaded dose (mcg) | Targeted delivered dose (mcg) |
| Low strength | 5 | 4 | 5 | 4 |
| Medium strength | 15 | 12 | 10 | 8 |
| High strength | 30 | 24 | 12 | 10 |
| Placebo | 0 | 0 | 0 | 0 |

Example 4: Piezo Drive Schemes

Formoterol Fumarate (FF) Formulation: Micronized FF dihydrate is formulated as a dry powder for inhalation by blending the drug substances with inhalation-grade lactose (RESPITOSE® ML001, DFE Pharma). The formulation used for the drive scheme study comprised approximately 12 mcg FF (0.62% w/w FF dihydrate) with remainder lactose. The target delivered dose was about 10 mcg.

Figure 44:
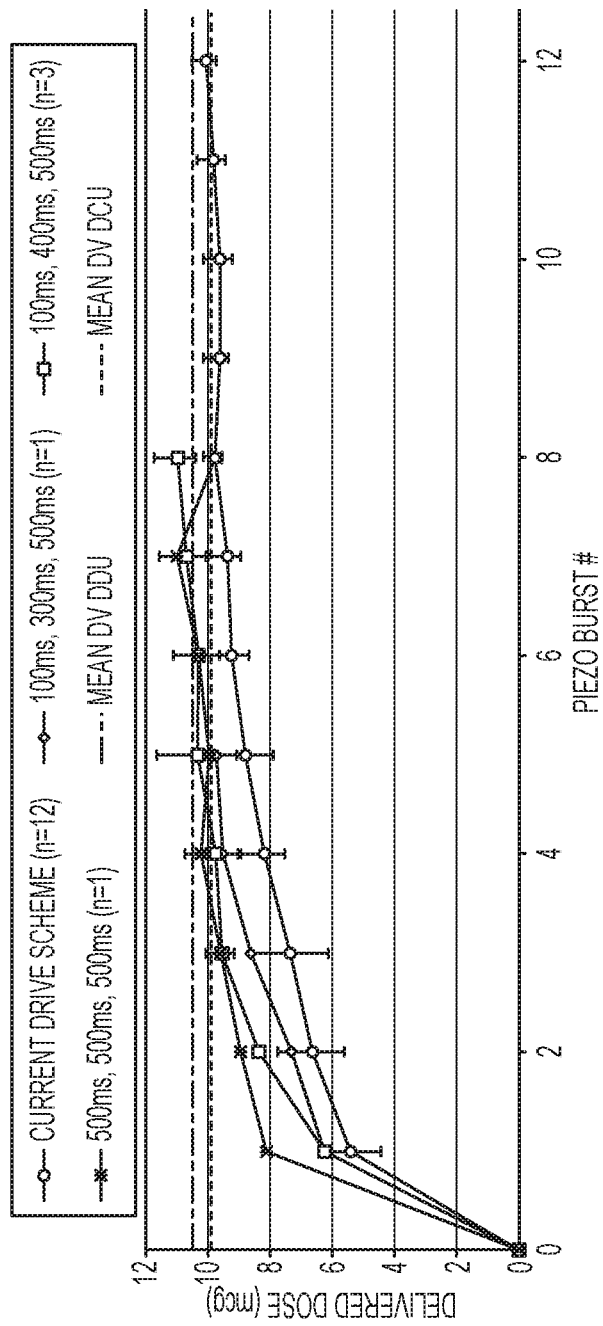
FIG. 44 provides a graph showing delivered dose (mcg) per piezo burst for different embodiments of the drive schemes of the inhaler.

The graph in FIG. 44 shows various piezo drive schemes of the inhaler. For the drive schemes that were 100/300/500 ms, 100/400/500 ms and 500/500/500 ms, the three numbers represent the number of milliseconds (ms) per burst for three bursts. The bursts after those first three bursts were each 500 ms (i.e., in those examples, bursts 4-8 were each 500 ms). The "current drive scheme" in the FIG. 44 graph refers to a drive scheme that includes 4 bursts of 100 ms followed by 4 bursts of 300 ms.

For every dosing scheme, the entire dose was delivered after 8 bursts and at least 4 mcg of drug were delivered on the first burst. In some instances, the entire dose was delivered after 4 bursts, 5 bursts, 6 bursts, or 7 bursts, as shown in FIG. 44. In the case of the 100/300/500 ms, 100/400/500 ms and 500/500/500 ms drive schemes, the entire dose, or nearly the entire dose, was delivered after 4 or 5 bursts. In the case of the 500/500/500 ms drive scheme, at least 8 mcg of drug were delivered on the first burst and the entire dose was delivered after 4 bursts.

Example 5: Drive Schemes for the Tidal Inhaler Using Glycopyrrolate and Formoterol Drive schemes were tested for the delivery of glycopyrrolate and formoterol. According to the "control" dosing scheme, the piezo is activated for 8 timed bursts (4 bursts for 100 ms followed by 4 bursts for 300 ms) to achieve powder delivery to the user. Combined with the two initial breaths required for breath confirmation and dose advancement, 10 breaths are needed to complete a single use session. In order to determine if the number of breaths could be reduced while maintaining acceptable aerosol performance, a base unit programmed with a modified drive scheme comprising a 500 ms piezo pulse length for 4 timed bursts (6 breaths total when combined with the two initial breaths for breath confirmation and dose advancement) was tested alongside a control base unit programmed with the first dosing software (10 breaths total).

Reporting Requirements for APSD by NGI:

1. Report Mass Deposition to ±0.001
2. For Tidal Inhaler/dose, calculate derived delivered dose (DDD), to three significant figures.
3. Aerosol Particle Size Distribution (use the DDD value per dose to calculate the FPF)
   a. FPD≤5.0 μm: to ±0.01 μg
   b. % FPF≤5.0 μm: to ±1%
   c. Report MMAD and GSD to ±0.1 μm
   d. Report entire NGI profile (throat to MOC, means and SD).

Cartridges containing two strengths of Glycopyrronium Bromide (GPB), 5 mcg and 30 mcg, were tested for Delivered Dose Uniformity (DDU, n=10) and Aerodynamic Particle Size Distribution (APSD) by Next Generation Impactor (NGI) (n=3) using each of the base units. As shown in Tables 2 and 3 below, the delivered dose and APSD results from the 5 mcg GPB cartridges with the control and 500 ms (for 4 bursts) drive scheme were similar, indicating that the 500 ms drive scheme can be used to deliver a complete dose and the APSD is not affected by the changed drive scheme.

The robustness of the device enables dose delivery within 75% to 125% or 80% to 120% of a mean delivered dose over a wide range of drive schemes, wherein the drive schemes vary by the number of bursts (e.g., 4-8 bursts) and the amount of activation time per burst (e.g., 100 ms-500 ms). The device also maintains a substantially consistent APSD across drive schemes, wherein the MMAD is consistently 6 μm (microns) or less, or 5 μm or less, or 4 μm or less, or 3.75 μm or less, or 3.5 μm or less, or 3.0 μm or less.

TABLE 2

DDU testing of 5 mcg GPB

| Drive Scheme: | Control | 500 ms (4 bursts) |
|---|---|---|
| Mean (Delivered Dose amount, μg) | 3.23 | 3.33 |
| % RSD (Delivered Dose) | 3.7 | 3.3 |
| Minimum Percentage of Overall Mean, % | 95 | 95 |
| Maximum Percentage of Overall Mean, % | 108 | 108 |

TABLE 3

NGI testing of 5 mcg GPB

| Drive Scheme: | Control | 500 ms (4 bursts) |
|---|---|---|
| Mean derived Delivered Dose (DDD), μg | 3.06 | 3.17 |
| Mean Fine Particle Dose (FPD) <5.0 μm, μg | 1.27 | 1.33 |
| Mean Fine Particle Fraction (FPF) <5.0 μm, % | 41 | 42 |
| Mean Mass Median Aerodynamic Diameter (MMAD), μm | 3.5 | 3.5 |
| Mean Geometric Standard Deviation (GSD) | 1.9 | 1.9 |

As shown in Tables 4 and 5 below, the delivered dose and APSD results from the 30 mcg GPB cartridges with the 500 ms (for 4 bursts) drive scheme showed an increase in aerosol performance when compared to the control. These data indicates that the 500 ms drive scheme can be used to deliver a complete dose with comparable APSD.

TABLE 4

DDU testing of 30 mcg GPB

| Drive Scheme: | Control | 500 ms (4 bursts) |
|---|---|---|
| Mean (Delivered Dose amount, Jlg) | 18.0 | 18.8 |
| % RSD (Delivered Dose) | 3.6 | 6.2 |
| Minimum Percentage of Overall Mean, % | 93 | 93 |
| Maximum Percentage of Overall Mean, % | 106 | 118 |

TABLE 5

NGI testing of 30 mcg GPB

| Drive Scheme: | Control | 500 ms (4 bursts) |
|---|---|---|
| Mean derived Delivered Dose (DDD), μg | 18.4 | 18.5 |
| Mean Fine Particle Dose (FPD) <5.0 μm, μg | 8.84 | 9.58 |
| Mean Fine Particle Fraction (FPF) <5.0 μm, % | 48 | 52 |
| Mean Mass Median Aerodynamic Diameter (MMAD), | 3.3 | 3.2 |
| Mean Geometric Standard Deviation (GSD) | 1.8 | 1.8 |

Cartridges containing two strengths of Formoterol Fumarate Dihydrate (FFD), 5 mcg and 12 mcg, were tested for Delivered Dose Uniformity (DDU, n=10) and Aerodynamic Particle Size Distribution (APSD) by Next Generation Impactor (NGI) (n=3) using each of the base units. As shown in Tables 6 and 7 below, the delivered dose uniformity data was similar from the 5 mcg FFD cartridges with the control and 500 ms drive schemes. The APSD data showed a slight increase in the derived delivered dose, FPD, and FPF with the 500 ms drive scheme when compared to the control data. There was no difference in MMAD between the two drive schemes.

TABLE 6

DDU testing of 5 mcg FFD

| Drive Scheme: | Control | 500 ms (4 bursts) |
|---|---|---|
| Mean (Delivered Dose amount, μg) | 4.53 | 4.60 |
| % RSD (Delivered Dose) | 3.5 | 4.6 |
| Minimum Percentage of Target Specification, % | 103 | 104 |
| Maximum Percentage of Target Specification, % | 119 | 124 |

TABLE 7

NGI testing of 5 mcg FFD

| Drive Scheme: | Control | 500 ms (4 bursts) |
|---|---|---|
| Mean derived Delivered Dose (DDD), μg | 4.20 | 4.34 |
| Mean Fine Particle Dose (FPD) <5.0 μm, μg | 1.91 | 2.01 |
| Mean Fine Particle Fraction (FPF) <5.0 μm, % | 45 | 46 |
| Mean Mass Median Aerodynamic Diameter (MMAD), | 2.9 | 2.9 |
| Mean Geometric Standard Deviation (GSD) | 2.2 | 2.2 |

As shown in Tables 8 and 9 below, the delivered dose uniformity and APSD were similar from the 12 mcg FFD cartridges with the control and 500 ms drive schemes.

TABLE 8

DDU testing of 12 mcg FFD

| Drive Scheme: | Control | 500 ms (4 bursts) |
|---|---|---|
| Mean (Delivered Dose amount, μg) | 10.5 | 10.5 |
| % RSD (Delivered Dose) | 4.1 | 5.7 |
| Minimum Percentage of Target Specification, % | 104 | 103 |
| Maximum Percentage of Target Specification, % | 126 | 127 |

TABLE 9

NGI testing of 12 mcg FFD

| Drive Scheme: | Control | 500 ms (4 bursts) |
|---|---|---|
| Mean derived Delivered Dose (DDD), μg | 9.34 | 9.70 |
| Mean Fine Particle Dose (FPD) <5.0 μm, μg | 4.69 | 5.16 |
| Mean Fine Particle Fraction (FPF) <5.0 μm, % | 50 | 53 |
| Mean Mass Median Aerodynamic Diameter (MMAD), | 2.7 | 2.6 |
| Mean Geometric Standard Deviation (GSD) | 2.1 | 2.1 |

Example 6: Flow Rate Analysis

Figure 45A:
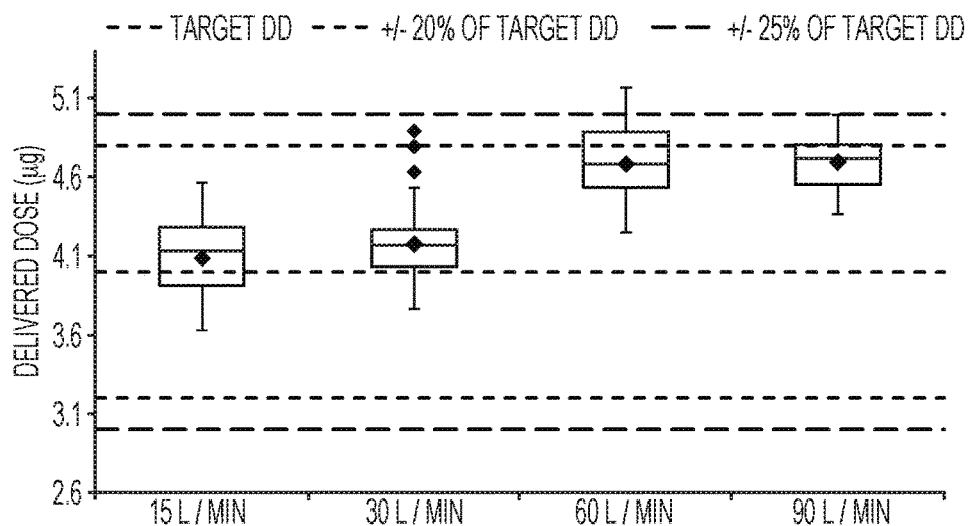
FIG. 45A provides a graph showing delivered dose of formoterol fumarate dihydrate at flow rates of 15 LPM, 30 LPM, 60 LPM and 90 LPM according to embodiments described in Example 6.
Figure 45B:
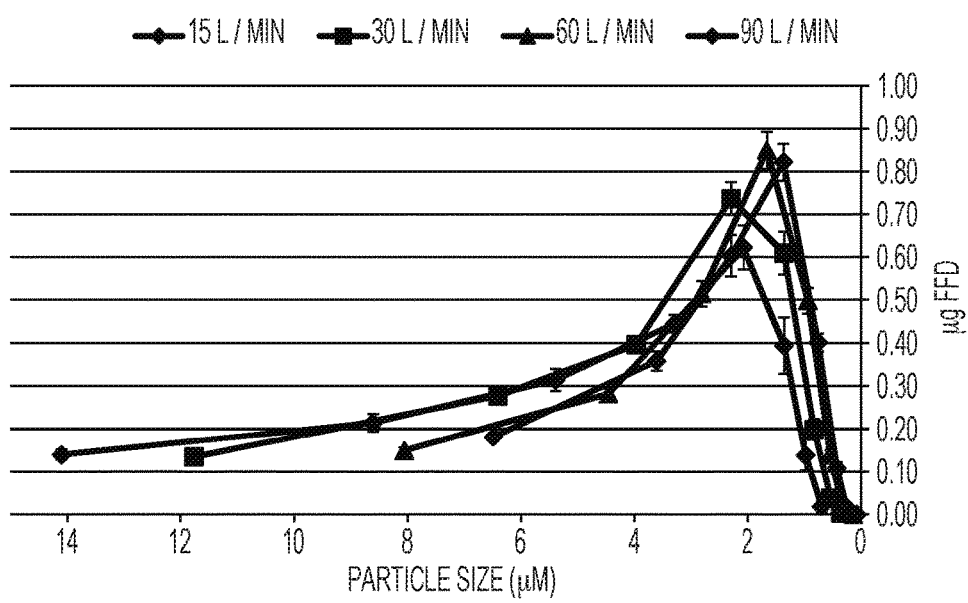
FIG. 45B provides a graph showing the particle size of formoterol fumarate dihydrate delivered at flow rates of 15 LPM, 30 LPM, 60 LPM and 90 LPM according to embodiments described in Example 6.
Figure 45C:
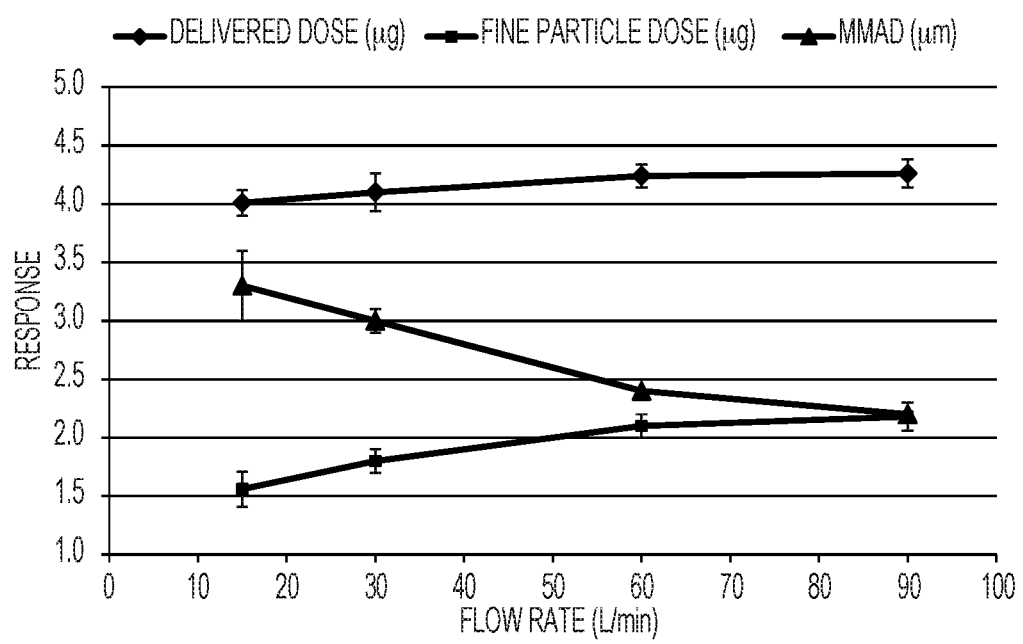
FIG. 45C provides a graph showing the delivered dose, fine particle dose and MMAD of formoterol fumarate dihydrate delivered at flow rates of 15 LPM, 30 LPM, 60 LPM and 90 LPM according to embodiments described in Example 6.

The aerosol performance of the Tidal Inhaler was tested at the following inspiration flow rates: 15 L/min (LPM), 30 L/min, 60 L/min and 90 L/min. Aerosol performance was measured by Delivered Dose Uniformity (DDU) and Aerodynamic Particle Size Distribution (APSD) using 5 microgram (mcg) cartridges of formoterol fumarate dihydrate (FF). Micronized FF dihydrate was formulated as a dry powder for inhalation by blending the drug substance (0.26% w/w FF dihydrate) with inhalation-grade lactose (RESPITOSE® ML001, DFE Pharma). The drive scheme comprised 8 total piezo activations (bursts): 4 bursts of 100 ms followed by 4 bursts of 300 ms. Results are shown in FIGS. 45A-C and Tables 10 and 11 below. An increase in delivered dose was observed at flow rates above 30 L/min; however, the device maintained a mean delivered dose uniformity of ±20% across the four flow rates, i.e., within 80% to 120% of the targeted delivered dose of 4 mcg. The MMAD was less than 4 microns and the FPF was greater than 30% across all four flow rates.

TABLE 10

| | Delivered Dose | | | |
|---|---|---|---|---|
| Flow Rate (L/min) | 15 | 30 | 60 | 90 |
| # of DDU doses | 45 | 45 | 45 | 45 |
| Delivered Dose (% RSD) | 4.09 (6.8%) | 4.18 (6.5%) | 4.68 (6.0%) | 4.70 (4.0%) |
| DD % Mean Range | 85-114 | 89-117 | 86-110 | 89-107 |
| Mean % of Target DD (4.00 μg) | 102 | 105 | 117 | 118 |

TABLE 11

| | Particle Size Distribution | | | |
|---|---|---|---|---|
| Flow Rate (L/min) | 15 | 30 | 60 | 90 |
| # of NGI's collected | 9 | 9 | 9 | 9 |
| Derived Delivered Dose, μg (% RSD) | 4.01 (2.7%) | 4.1 (3.9%) | 4.24 (2.4%) | 4.26 (2.8%) |
| Fine Particle Dose ≤5.0 μm, μg (% RSD) | 1.56 (9.6%) | 1.80 (5.6%) | 2.10 (4.8%) | 2.18 (5.5%) |
| % Fine Particle Fraction ≤5.0 μm | 39 | 44 | 49 | 51 |
| MMAD, μm | 3.3 | 3.0 | 2.4 | 2.2 |

Example 7: Target Delivered Dose for the Formoterol Fumarate Tidal Inhaler

The dose content uniformity (DCU) of Tidal Inhaler cartridges with 5 µg formoterol fumarate dehydrate (FFD) (0.26% (w/w)) was evaluated by collecting the first dose after three priming doses across 189 cartridges. As shown in Table 12 below, the mean delivered dose was 3.99 µg with a 4.0% RSD. The mean DCU was 100% of the Target Delivered Dose (4.00 µg), and the range is 86% to 110% of the Target Delivered Dose (n=189).

TABLE 12

Dose Content Uniformity

| | |
|---|---|
| Overall Mean (µg): | 3.99 |
| Overall SD: | 0.16 |
| Overall % RSD: | 4.0 |
| Count: | 189 |
| Target Delivered Dose (µg): | 4.00 |
| Mean % of Target Delivered Dose: | 100 |
| Min % of Target Delivered Dose: | 86 |
| Max % of Target Delivered Dose: | 110 |

The dose content uniformity (DCU) of Tidal Inhaler cartridges with 10 µg formoterol fumarate dihydrate (FFD) (0.52% (w/w)) was evaluated for 32 cartridges. As shown in Table 13 below, the mean delivered dose was 8.57 µg with a 4.0% RSD. The mean DCU was 100% of the Target Delivered Dose (8.60 µg), and the range was 91% to 108% of the Target Delivered Dose (n=32). From those 32 cartridges, 3 cartridges were tested through life for Delivered Dose Uniformity (DDU) and Aerodynamic Particle Size Distribution by Next Generation Impactor (NGI). As shown in Tables 14 and 15 below, all acceptance criteria specified by the study design were met. Acceptance Criteria included: No error conditions present during dosing (indicated by "Replace Drug" on the reusable base assembly LCD); and Individual delivered dose value within ±25% of the overall mean.

TABLE 13

DCU testing

| | |
|---|---|
| Overall Mean (µg): | 8.57 |
| Overall SD: | 0.34 |
| Overall % RSD: | 4.0 |
| Count: | 32 |
| Target Delivered Dose (p.tg): | 8.60 |
| Mean % of Target Delivered Dose: | 100 |
| Min % of Target Delivered Dose: | 91 |
| Max % of Target Delivered Dose: | 108 |

TABLE 14

DDU testing (3 cartridges)

| | |
|---|---|
| Overall Mean (pg): | 8.83 |
| Overall SD: | 0.60 |
| Overall % RSD: | 6.8 |
| Min % of Mean Delivered Dose: | 89 |
| Max % of Mean Delivered Dose: | 109 |

TABLE 15

NGI through Life (3 cartridges)

| | | % RSD |
|---|---|---|
| Mean Derived Delivered Dose (DDD) (µg): | 7.86 | 4.0 |
| Range for DDD (Minimum-Maximum, µg) | 7.29-8.19 | |
| Mean Fine Particle Dose (FPD) ≤5.0 µm (µg) | 4.24 | 5.7 |
| Range for FPD (Minimum-Maximum, µg) | 3.87-4.54 | |
| Mean Fine Particle Fraction ≤5.0 µm % of DDD | 54 | |
| Mean MMAD (µg) | 2.5 | |
| Mean GSD | 2.0 | |

The dose content uniformity (DCU) of Tidal Inhaler cartridges with 12 µg formoterol fumarate dehydrate (FFD) (0.62% (w/w)) was evaluated by collecting the first dose after three priming doses across 197 cartridges. As shown in Table 16 below, the mean delivered dose was 9.32 µg with a 4.5% RSD. The mean DCU was 100% of the Target Delivered Dose (9.30 µg), and the range is 87% to 110% of the Target Delivered Dose (n=197).

TABLE 16

Dose Content Uniformity

| | |
|---|---|
| Overall Mean (µg): | 9.32 |
| Overall SD: | 0.42 |
| Overall % RSD: | 4.5 |
| Count: | 197 |
| Target Delivered Dose (µg): | 9.30 |
| Mean % of Target Delivered Dose: | 100 |
| Min % of Target Delivered Dose: | 87 |
| Max % of Target Delivered Dose: | 110 |

Example 8: Delivered Dose for the Glycopyrronium Bromide Tidal Inhaler

Tidal Inhaler devices containing doses of 18 µg glycopyrronium bromide (0.94% w/w) were tested for Delivered Dose Uniformity (DDU) and Aerodynamic Particle Size Distribution by Next Generation Impactor (NGI). Results are shown in Table 17 below.

TABLE 17

Delivered Dose and APSD for 18 doses of 18 µg GPB delivered by Tidal Inhaler

| | |
|---|---|
| Overall Mean delivered dose (µg) | 12.3 |
| Min % delivered dose within Mean | 96 |
| Max % delivered dose within Mean | 104 |
| Mean Derived Delivered Dose (µg) | 11.6 |
| Mean Fine Particle Dose (FPD) ≤5.0 µm (µg) | 4.96 |
| Mean % Fine Particle Fraction (% FPF) | 43 |
| Mean MMAD (µm) | 3.0 |

Example 9: Comparison of Membrane Materials

Several membrane materials were tested for use with the inhaler, as shown in Table 18:

| Base | Film | Tensile Strength MD (MPa) | Tensile Modulus (GPa) | Tensile Elongation MD (%) | Water Absorption (%) | Tg (C.) |
|---|---|---|---|---|---|---|
| PET | Mylar ® 813 | 165 | 5.0 | 116 | 0.10 | 70 |
| PEEK | APTIV ® 2000-050 | 200 | 1.8 | 200 | 0.21 | 143 |
| PC | LEXAN ® SD8B14 (Polycarbonate) | 65 | 2.5 | 125 | 0.35 | 153 |
| PSU | Udel ®/Thermalux ® (Polysulfone) | 75 | 2.5 | 100 | 0.30 | 190 |
| PEI | ULTEM ® (Polyetherimide) | 116 | 2.5 | 50 | 0.25 | 217 |
| PVDF | KYNAR ® (Polyvinylidene Fluoride) | 38 | 2.2 | 300 | 0.04 | 160 |

The preferred specifications of the membrane material included:
1. Tensile strength=biaxially oriented;
2. Tensile Modulus<5 GPa (greater strain);
3. Elongation>100%;
4. CTE<100 ppm/C;
5. Tg>100 C (higher Tg reduces concerns about dimensional stability).

Several thicknesses of polycarbonate (PC) membrane were tested for synthetic jetting performance when assembled in the inhaler, according to the synthetic jetting test described in Example 1. Samples with 30, 50, 75, 100, and 150 μm thicknesses were tested with the polycarbonate (PC) membrane (LEXAN® Sabic SD8B14). The results are illustrated in FIG. 46A, which shows that peak jetting occurred at the 50 micron thickness.

Delivered Dose performance was also tested with dosing chambers assembled with 50 μm thick PC membranes and 23 μm thick Mylar® 813 membranes. Both membranes had similar results for dose delivery. Results are shown in FIG. 46B, in which C305, CM64 and CM65 each represents a different membrane sample. The polycarbonate membrane (LEXAN® SD8B14) at a thickness of about 50 microns, and PET membrane (Mylar® 813) at a thickness of about 23 microns, had optimal performance in terms of synthetic jetting and delivered dose.

Example 10: Phase Ib Formoterol Fumarate Clinical Study

The clinical study was a Single-Dose, Double-Blind, Randomized, Placebo and Active Controlled, Five Treatment Crossover, Dose-Ranging Study to Assess the Efficacy, Pharmacokinetics, and Safety of Inhaled Formoterol Fumarate Administered Using the Tidal Inhaler and FORADIL® AEROLIZER® in Patients with Chronic Obstructive Pulmonary Disease.

Each dose of dry powder drug formulation in the Tidal Inhaler was delivered over eight dosing breaths. Upon detection of each dosing breath, the piezoelectric transducer was activated to vibrate for 100 ms for the first four dosing breaths, and 300 ms for the subsequent four dosing breaths over the course of eight total dosing breaths (for a total of 1.6 seconds). Prior to the eight dosing breaths, the first two breaths constituted a verifying breath to activate the device followed by a dose advance breath to advance the blister into dosing position.

The subjects in the clinical study were instructed to place their mouth around the mouthpiece and inhale from the Tidal Inhaler as if taking a normal breath (i.e., not rapidly and deeply but via tidal inhalation), and then remove the mouthpiece from their mouth and exhale away from the Tidal Inhaler. The subjects were instructed to repeat inhaling normally and exhaling away from the Tidal Inhaler for 10-12 inhalations. An indicator light on the device blinked blue during each detected inhalation and blinked green when the dose was complete.

FORADIL® AEROLIZER® delivers a dry powder formulation of formoterol fumarate via oral inhalation. The inhalation powder is packaged in clear hard gelatin capsules; each capsule contains a dry powder blend of 12 μg of formoterol fumarate and 25 mg of lactose as a carrier. The amount of drug delivered to the lung depends on factors such as inspiratory flow rate and inspiratory time. Under standardized in vitro testing at a fixed flow rate of 60 L/min for 2 seconds, the AEROLIZER Inhaler delivers 10 mcg of formoterol fumarate from the mouthpiece. To use the delivery system, a FORADIL capsule is placed in the well of the AEROLIZER Inhaler, and the capsule is pierced by pressing and releasing the buttons on the side of the device. The formoterol fumarate formulation is dispersed into the air stream when the patient inhales rapidly and deeply through the mouthpiece.

The study was a 10 Sequence, 5 Treatment, 5 Period Crossover Study. Williams design was used to balance for period, treatment and first order carryover. As used herein, "FFTI" refers to Formoterol Fumarate in the Tidal Inhaler and "PTI" refers to Placebo in the Tidal Inhaler. Treatments included: Treatment A: FFTI (5 μs); Treatment B: FFTI (10 μg); Treatment C: FFTI (12 μg); Treatment D: open-label FORADIL® AEROLIZER® (12 μg) (1 capsule inhaled); Treatment E: PTI. During the treatment period visits, patients performed serial spirometry at specified time points up to 24 hours postdose.

The patient population was men or women with chronic obstructive pulmonary disease (COPD), 40 through 75 years of age. Randomization: 55 patients were planned to be randomized to provide 50 completed patients overall (including a pharmacokinetics subset of 15 patients). Five patients planned to be randomized to each of 10 treatment sequences. The treatment periods were single dose.

The primary objective of the study was to determine the dose of FFTI that provides comparable efficacy to FORADIL® AEROLIZER®. The secondary objectives of the study were to evaluate safety and pharmacokinetics following treatment with FFTI and FORADIL® AEROLIZER®.

Efficacy Measures included the following: Standardized baseline-adjusted forced expiratory volume in 1 second area under the curve over 12 hours ($FEV_1$ $AUC_{0-12}$); Standardized baseline-adjusted forced expiratory volume in 1 second area under the curve over 24 hours ($FEV_1$ $AUC_{0-24}$); Baseline-adjusted trough 12-hour forced expiratory volume in 1 second ($FEV_1$); Baseline-adjusted trough 24-hour $FEV_1$; Maximum change from predose $FEV_1$ over 6 hours postdose; Baseline-adjusted 12- and 24-hour forced expiratory flow between 25% and 75% ($FEF_{25-75}$) of the forced vital capacity (FVC); Maximum change from predose $FEF_{25-75}$ over 6 hours postdose; Baseline-adjusted 12- and 24-hour FVC; and Time to maximum response ($FEV_1$, FVC, and $FEF_{25-75}$).

Pharmacokinetic endpoints included the following: Area under the plasma concentration-time curve from time 0 to 0.5 hours after study drug administration ($AUC_{0-0.5}$); Area under the plasma concentration-time curve from time 0 to 12 hours after study drug administration ($AUC_{0-12}$); Area under the plasma concentration-time curve from time 0 to 24 hours after study drug administration ($AUC_{0-24}$); Maximum observed plasma drug concentration ($C_{max}$) Area under the plasma concentration-time curve from time 0 to the time of the last quantifiable drug concentration ($AUC_{0-t}$); Area under the plasma concentration-time curve from time 0 to infinity ($AUC_{0-\infty}$); Time to maximum observed plasma drug concentration ($t_{max}$); Percentage of AUC0-∞ due to extrapolation (% AUCextrap); and Apparent plasma terminal elimination rate constant ($\lambda z$) and associated apparent elimination half-life ($t_{1/2}$).

Figure 46A:
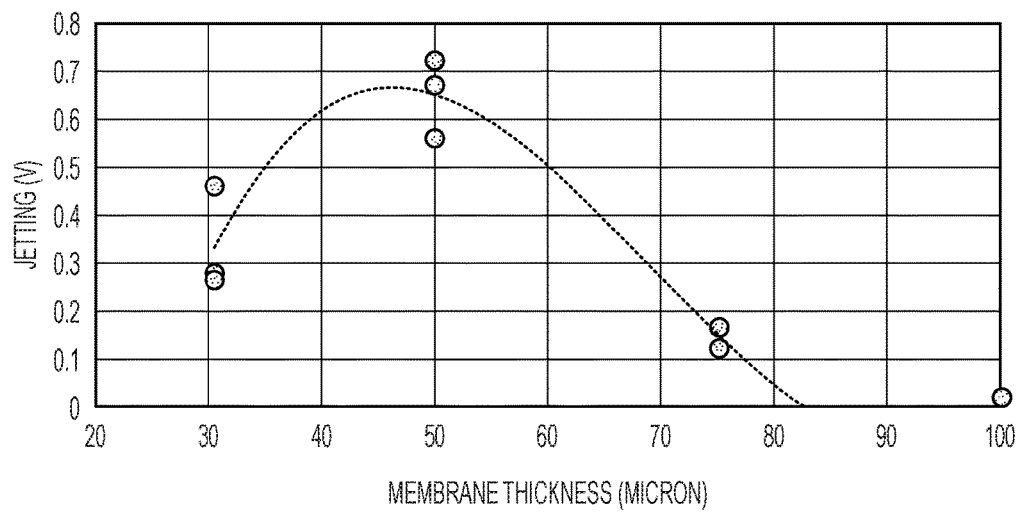
FIG. 46A provides a graph of synthetic jetting performance for different thicknesses of polycarbonate (PC) membrane according to embodiments described in Example 9.
Figure 46B:
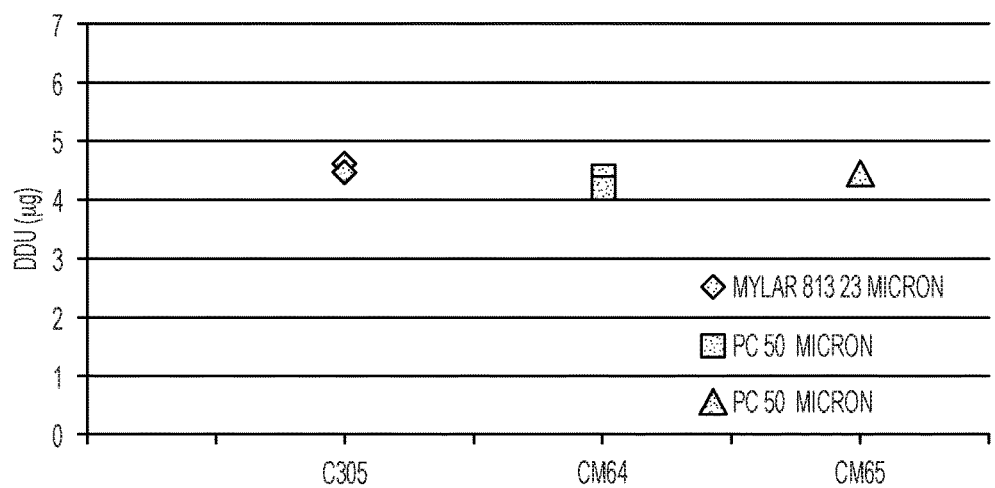
FIG. 46B provides a graph of delivered dose performance for dosing chambers assembled with 50 μm thick PC membranes and 23 μm thick Mylar® 813 membranes according to embodiments described in Example 9.

Clinical Study Results:

Table 19 below provides the $FEV_1$ endpoint results; and Table 20 provides the Non-$FEV_1$ endpoint results. FIG. 46 illustrates the mean change from baseline $FEV_1$ (mL) by treatment and timepoint out to 12 hours post-dose.

TABLE 19

| Endpoint Difference from placebo, 95% CI, p-value | FFTI 5 µg | FFTI 10 µg | FFTI 12 µg | Foradil Aerolizer 12 µg |
|---|---|---|---|---|
| $FEV_1$ $AUC_{0-12}$ (mL) | 133 (103-160) <0.001 | 175 (146, 203) <0.002 | 169 (140-197) <0.001 | 176 (148, 204) <0.001 |
| $FEV_1$ $AUC_{0-24}$ (mL) | 104 (76, 132) <0.001 | 133 (105, 161) <0.001 | 132 (104, 160) <0.001 | 135 (107, 163) <0.001 |
| Baseline-adjusted trough 12-hour $FEV_1$ (mL) | 82 (40-125) <0.001 | 125 (82, 167) <0.001 | 114 (71, 156) <0.001 | 131 (88, 173) <0.001 |
| Baseline-adjusted trough 24-hour $FEV_1$ (mL) | 53 (13-93) 0.009 | 45 (30, 110) <0.001 | 70 (6, 85) 0.025 | 48 (9, 88) 0.017 |
| $FEV_1$ max change over 6 hours (mL) | 160 (125, 195) <0.001 | 183 (148, 218) <0.001 | 188 (153, 223) <0.001 | 190 (155, 225) <0.001 |
| Time to max $FEV_1$(h): Median/median PTI p-value | 2.0/4.0 0.034 | 2.0/4.0 0.022 | 2.0/4.0 0.13 | 4.0/4.0 0.462 |

TABLE 20

| Endpoint Difference from placebo, 95% CI, p-value | FFTI 5 µg | FFTI 10 µg | FFTI 12 µg | Foradil Aerolizer 12 µg |
|---|---|---|---|---|
| Baseline-adjusted 12-hour $FEF_{25-75}$ (L/s) | 0.049 (0.017, 0.081) <0.001 | 0.080 (0.048, 0.112) <0.001 | 0.057 (0.025, 0.088) <0.001 | 0.066 (0.034, 0.098) <0.001 |
| Baseline-adjusted 24-hour $FEF_{25-75}$ (L/s) | 0.027 (0.004, 0.050) 0.019 | 0.041 (0.019, 0.064) <0.001 | 0.045 (0.023, 0.068) <0.001 | 0.031 (0.008, 0.053) 0.008 |
| $FEF_{25-75}$ max change over 6 hours (L/s) | 0.070 (0.039, 0.100) <0.001 | 0.125 (0.094, 0.0156) <0.001 | 0.091 (0.061, 0.122) <0.001 | 0.098 (0.067, 0.128) <0.001 |
| Baseline-adjusted 12-hour FVC (L) | 0.135 (0.059, 0.211) <0.001 | 0.184 (0.109, 0.260) <0.001 | 0.168 (0.092, 0.243) <0.001 | 0.181 (0.106, 0.257) <0.001 |
| Baseline-adjusted 24-hour FVC (L) | 0.056 (−0.020, 0.132) 0.150 | 0.024 (−0.052, 0.099) 0.533 | 0.078 (0.002, 0.154) 0.044 | 0.038 (−0.038, 0.114) 0.323 |
| Time to max FVC (h): Median/median PTI p-value | 2.0/4.0 0.084 | 2.1/4.0 0.044 | 2.0/4.0 0.044 | 3.0/4.0 0.406 |
| Time to max $FEF_{25.75}$ (h): Median/median PTI p-value | 2.1/7.0 0.012 | 3.9/7.0 0.027 | 2.2/7.0 0.011 | 4.0/7.0 0.022 |

Figure 47:
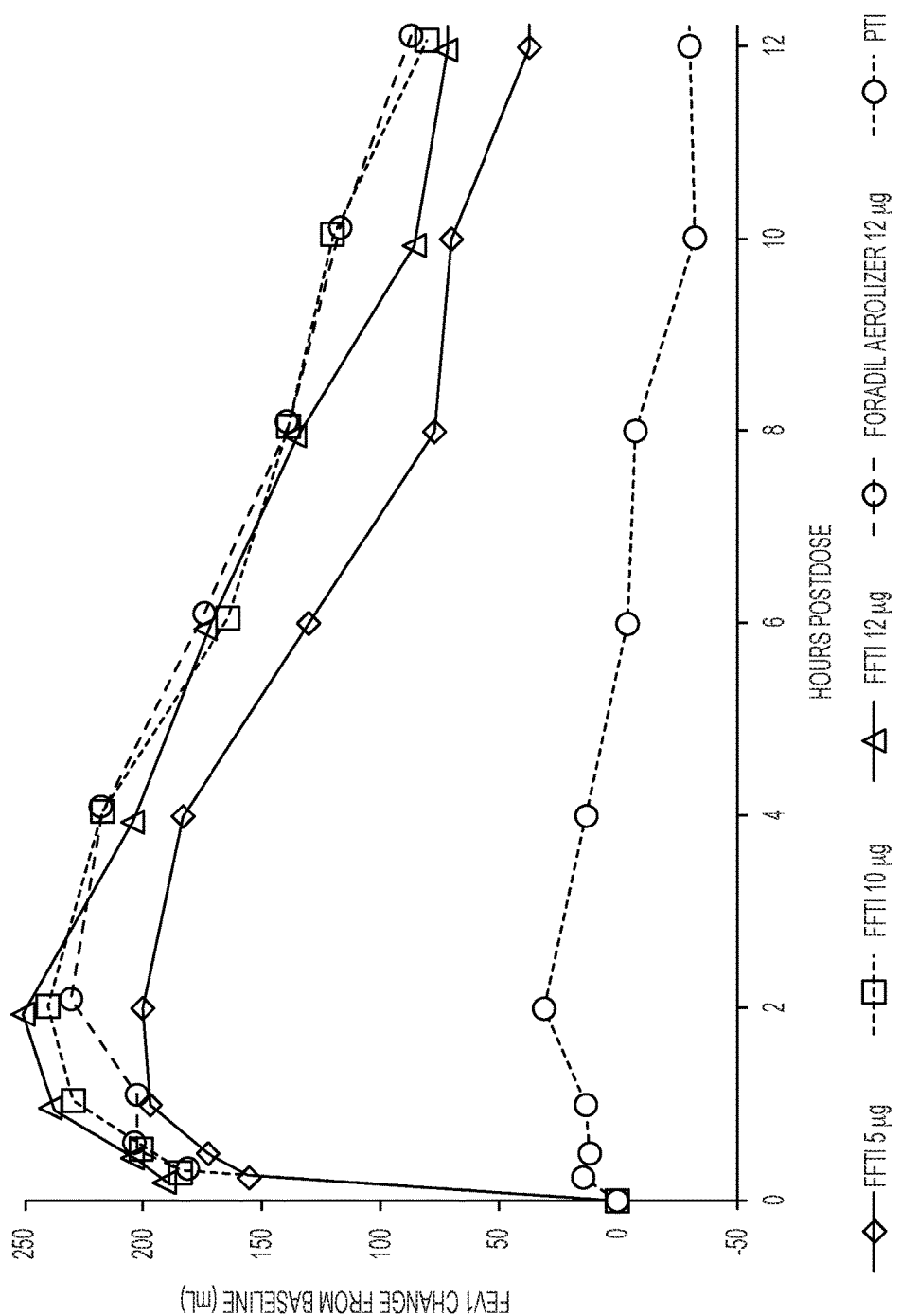
FIG. 47 provides a graph showing the mean change from baseline $FEV_1$ (mL) by treatment and time point out to 12 hours post-dose for the Phase 1b Formoterol Fumarate Clinical Study described in Example 10.
Figure 48:
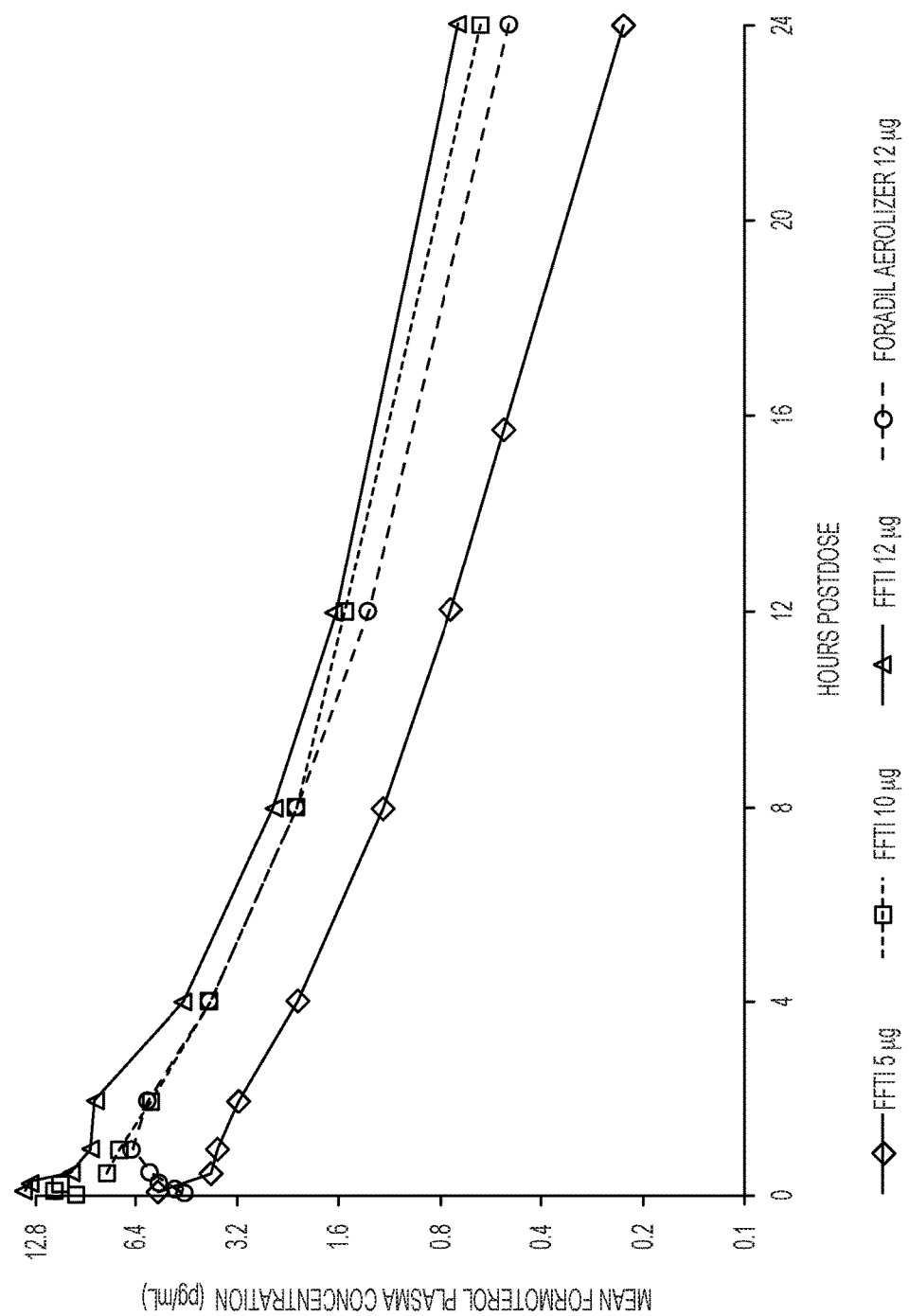
FIG. 48 provides a graph showing the arithmetic mean formoterol plasma concentration versus time profile by treatment over 24 hours for the Phase 1b Formoterol Fumarate Clinical Study described in Example 10.
Figure 49:
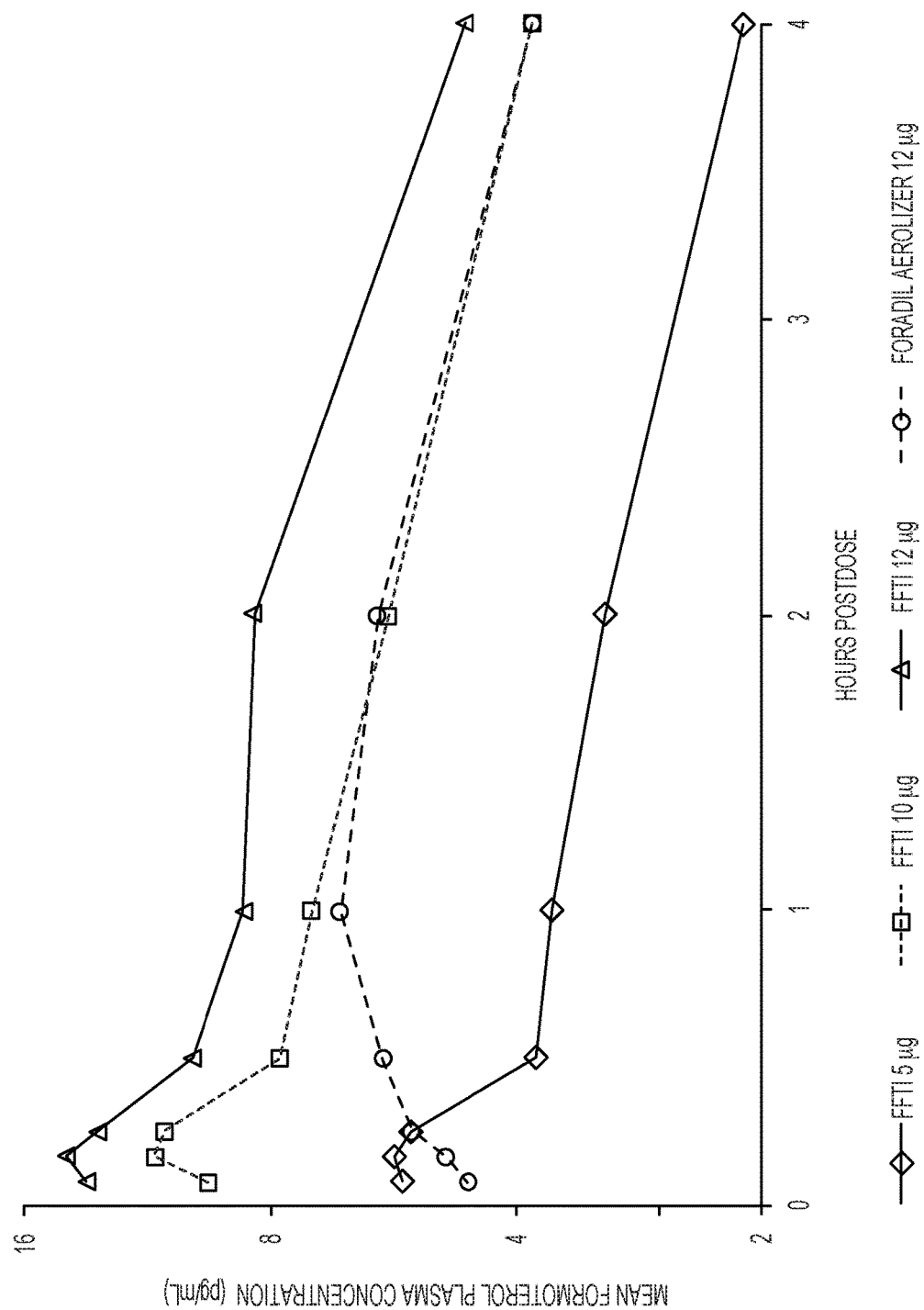
FIG. 49 provides a graph showing the arithmetic mean formoterol plasma concentration versus time profile by treatment over the first 4 hours for the Phase 1b Formoterol Fumarate Clinical Study described in Example 10.

Table 21 below illustrates the pharmacokinetic endpoint results. FIGS. 47 and 48 illustrate the arithmetic mean formoterol plasma concentration versus time profile by treatment over 24 hours (FIG. 47) and the first 4 hours (FIG. 48).

TABLE 21

| Endpoint Geometric Mean, GMR % compared to Foradil, 90% CI for GMR % | FFTI 5 µg | FFTI 10 µg | FFTI 12 µg | Foradil Aerolizer 12 µg |
|---|---|---|---|---|
| $AUC_{0-0.5}$ (h*pg/mL) | 2.227 104.86 (88.82, 123.79) | 4.211 198.30 (167.19, 235.20) | 5.482 258.15 (218.12, 305.53) | 2.124 |

TABLE 21-continued

| Endpoint Geometric Mean, GMR % compared to Foradil, 90% CI for GMR % | FFTI 5 μg | FFTI 10 μg | FFTI 12 μg | Foradil Aerolizer 12 μg |
|---|---|---|---|---|
| $AUC_{0-12}$ (h*pg/mL) | 22.832 59.50 (53.97, 65.59) | 43.465 113.27 (102.46, 125.21) | 53.894 140.44 (127.18, 155.09) | 38.374 |
| $AUC_{0-24}$ (h*pg/mL) | 28.332 59.43 (53.67, 65.81) | 54.895 115.15 (103.68, 127.88) | 67.026 140.59 (126.74, 155.96) | 47.674 |
| $C_{max}$ (pg/mL) | 6.012 85.67 (72.68, 100.98) | 10.996 156.68 (132.31, 185.53) | 15.821 225.43 (190.78, 266.37) | 7.018 |
| $t_{max}$ (h) | | | | |
| Mean | 0.15 | 0.27 | 0.28 | 0.97 |
| Median | 0.17 | 0.17 | 0.17 | 0.98 |
| Min, Max | 0.05, 0.25 | 0.08, 1.95 | 0.08, 1.92 | 0.08, 2.00 |
| $T_{1/2}$ (h) | | | | |
| Mean | 7.57 | 8.60 | 8.78 | 7.73 |
| Median | 6.87 | 9.02 | 8.42 | 8.12 |
| Min, Max | 2.45, 13.12 | 4.67, 14.04 | 3.97, 13.81 | 4.08, 10.30 |

Across lung function parameters, formoterol fumarate 10 and 12 μg administered using the Tidal Inhaler provided similar efficacy compared with FORADIL AEROLIZER 12 μg. For all three formoterol fumarate doses administered using the Tidal Inhaler, time to maximum $FEV_1$, time to maximum FVC, and time to maximum $FEF_{25-75}$ were numerically shorter (by approximately 1 to 2 hours) when compared with FORADIL AEROLIZER 12 μg. The time to maximum $FEV_1$ for formoterol fumarate 12 μg administered using the Tidal Inhaler was shorter, and the difference was statistically significant compared with FORADIL AEROLIZER 12 μg.

Following administration of formoterol fumarate using the Tidal Inhaler, the formoterol mean plasma concentration versus time profile for each dose was characterized by a rapid absorption phase followed by a biexponential elimination phase. The mean plasma formoterol concentrations increased with each increasing dose using the Tidal Inhaler. Median $t_{max}$ was 0.167 hours across the 5- to 12-μg dose range administered using the Tidal Inhaler and occurred earlier than the median $t_{max}$ using FORADIL AEROLIZER 12 μg (0.983 hours).

The mean t½ for formoterol was similar across the dose range using the Tidal Inhaler (range: 7.6 to 8.8 hours) and was comparable to formoterol t½ using FORADIL AEROLIZER (7.7 hours). Both CL/F and Vz/F for formoterol were generally comparable across all dose levels using the Tidal Inhaler and between the Tidal Inhaler and FORADIL AEROLIZER treatment groups.

At the 12-μg dose level, the geometric LS means for plasma formoterol exposure (ie, $AUC_{0-12}$, $AUC_{0-t}$, $AUC_{0-24}$, and $AUC_{0-inf}$ were approximately 1.4- to 1.5-fold higher for the Tidal Inhaler treatment group compared with the FORADIL AEROLIZER treatment group. However, the 10-μg dose administered using the Tidal Inhaler produced formoterol AUC exposures that were comparable to that of FORADIL AEROLIZER 12 μg, as the ratio of the geometric LS means was 1.1 to 1.2. The geometric LS means for formoterol $AUC_{0-0.5}$ were 2.0- and 2.6 fold higher for the Tidal Inhaler treatment group at 10 and 12 μg, respectively, compared with that of FORADIL AEROLIZER 12 μg, reflecting the delayed absorption of formoterol using FORADIL AEROLIZER. The geometric LS means for peak formoterol exposure (Cmax) were 1.6- and 2.3-fold higher for the Tidal Inhaler treatment group at 10 and 12 μg, respectively, compared with the FORADIL AEROLIZER 12 μg treatment group.

Clinical Study Conclusions:

All active treatments including the approved active comparator, FORADIL AEROLIZER, showed a separation from placebo in lung function efficacy responses, thus demonstrating an assay sensitivity of this study. The formoterol fumarate 10-μg dose administered using the Tidal Inhaler provided the most comparable efficacy to FORADIL AEROLIZER 12 μg as there was no statistically significant difference in any of the efficacy parameters between these two treatments. Formoterol fumarate 12 μg administered using the Tidal Inhaler also showed comparable efficacy responses with no statistical difference versus FORADIL AEROLIZER 12 μg, with the exception of time to maximum $FEV_1$, where formoterol fumarate 12 μg administered using the Tidal Inhaler was significantly faster.

The formoterol fumarate Tidal Inhaler at 10 μg produced formoterol AUC exposures (i.e., $AUC_{0-12}$, $AUC_{0-24}$, $AUC_{0-t}$, and $AUC_{0-inf}$) that were comparable to that of FORADIL AEROLIZER 12 μg, as the ratio of the geometric LS means was 1.1 to 1.2. The formoterol fumarate Tidal Inhaler at 10 and 12 μg exhibited a statistically significantly higher $C_{max}$ than FORADIL AEROLIZER 12 μg. The Tidal Inhaler resulted in faster appearance of formoterol in plasma than did FORADIL AEROLIZER, as demonstrated by $t_{max}$.

Single doses of formoterol fumarate 5, 10, and 12 μg using the Tidal Inhaler and formoterol fumarate 12 μg using FORADIL AEROLIZER were generally safe and well tolerated by COPD patients in this study, and the safety profile was consistent with previous studies of inhaled formoterol fumarate.

It will be appreciated by those skilled in the art that changes may be made to the exemplary embodiments shown and described above without departing from the broad inventive concepts thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and various features of the disclosed embodiments may be combined. Selected features of any illustrative embodiment may be incorporated into an additional embodiment unless clearly stated to the contrary. The words "right", "left", "lower" and "upper" designate directions in the drawings to which reference is made. The words "inwardly" and "outwardly" refer to directions toward and away from, respectively, the geometric center of the inhaler. Unless specifically set forth herein, the terms "a", "an" and "the" are not limited to one element but instead should be read as meaning "at least one". Elements shown in the Figures are not necessarily drawn to scale, but only to illustrate operation.

As used herein and in the claims, the terms "comprising" and "including" are inclusive or open-ended and do not exclude additional unrecited elements, compositional components, or method steps. Accordingly, the terms "comprising" and "including" encompass the more restrictive terms "consisting essentially of" and "consisting of." Unless specified otherwise, all values provided herein include up to and including the endpoints given, and the values of the constituents or components of the compositions are expressed in weight percent of each ingredient in the composition.

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the methods of the present invention do not rely on the particular order of steps set forth herein, the particular order of the steps should not be construed as limitation on the claims. Any claims directed to the methods of the present invention should not be limited to the performance of their steps in the order written, and one skilled in the art can readily appreciate that the steps may be varied and still remain within the spirit and scope of the present invention.

We claim:

1. A medicament delivery device comprising:
   a dosing chamber comprising an interior that is configured to contain dry powder medicament received from a medicament container,
   a transducer confronting the dosing chamber, wherein the dosing chamber and the transducer are acoustically resonant such that the dosing chamber is configured to resonate in response to an activation of the transducer, and
   a controller electrically coupled to the transducer and configured to send an electrical signal that activates the transducer when the medicament delivery device senses a subject's dosing breath,
   the medicament delivery device having a flow resistance in a range from about 0.040 cmH2O$^{0.5}$/LPM to about 0.1 cmH2O$^{0.5}$/LPM at 30 liters per minute (LPM) and capable of delivering a therapeutically effective dose of dry powder medicament in response to between 2-20 tidal inhalations, the dose having a mass median aerodynamic diameter (MMAD) of about 6 microns or less and a fine particle fraction of at least 30%.

2. The medicament delivery device of claim 1, wherein the controller is configured to activate the transducer for a total on-time of 5 seconds or less over the 2-20 tidal inhalations.

3. The medicament delivery device of claim 1, wherein the controller is configured to activate the transducer for between 50 ms and about 1000 ms during each dosing breath.

4. The medicament delivery device of claim 1, wherein the medicament delivery device is capable of delivering the dose of dry powder medicament at flow rates at least within a range of about 15 LPM to about 30 LPM.

5. The medicament delivery device of claim 1, wherein the medicament delivery device is capable of delivering the dose of dry powder medicament at flow rates at least within a range of about 15 LPM to about 90 LPM.

6. The medicament delivery device of claim 1, wherein the medicament delivery device is configured to administer at least 10% of the dry powder medicament dose in response to a first dosing breath.

7. The medicament delivery device of claim 1 comprising a base and a removable cartridge, and one or more doses of dry powder medicament are contained in the removable cartridge.

8. The medicament delivery device of claim 7, wherein the amount of each of the one or more doses of dry powder medicament is from about 1 mg to about 10 mg.

9. The medicament delivery device of claim 1 comprising one or more lights configured to illuminate when a dose has been administered.

10. A method of treating a respiratory disease or condition, or one or more symptoms thereof, the method comprising:
    inhaling a therapeutically effective dose of dry powder medicament through a medicament delivery device using between 2-20 tidal inhalations over the course of an inhalation cycle, the inhalation cycle comprising dosing breaths,
    wherein the medicament delivery device comprises a vibratory element that is activated upon each dosing breath and causes dry powder medicament to be aerosolized within a dosing chamber and expelled from one or more openings in the dosing chamber into an air flow conduit, the dosing chamber receiving the dry powder medicament from a medicament container, wherein pressure oscillations in the dosing chamber are sufficiently high at the one or more openings to aerosolize and expel the dry powder medicament via synthetic jetting,
    the medicament delivery device having a flow resistance in a range from about 0.040 cmH2O$^{0.5}$/LPM to about 0.1 cmH2O$^{0.5}$/LPM at 30 liters per minute (LPM) and capable of delivering the dose of dry powder medicament at flow rates at least within a range of about 15 LPM to about 30 LPM,
    wherein the dose of dry powder medicament administered by the medicament delivery device has a mass median aerodynamic diameter (MMAD) of about 6 microns or less and a fine particle fraction of at least 30%.

11. The method of claim 10 further comprising exhaling away from the medicament delivery device after each tidal inhalation.

12. The method of claim 10, wherein the medicament delivery device comprises a base and a removable cartridge, the method further comprising attaching the base and the removable cartridge together.

13. The method of claim 10, wherein the medicament delivery device administers at least 10% of the dry powder medicament dose in response to the first dosing breath in the inhalation cycle.

14. The method of claim 10, wherein the transducer has an on-time of about 5 seconds or less over the course of the inhalation cycle.

15. The method of claim 10, wherein the medicament delivery device achieves maximum synthetic jetting within about 1000 ms or less from the start of each transducer activation.

16. The method of claim 10, wherein the dose of dry powder medicament is administered within 2 minutes or less.

17. The method of claim 10, wherein the respiratory disease or condition is COPD.

18. The method of claim 10, wherein the respiratory disease or condition is COPD and the dry powder medicament comprises a LAMA and a LABA.

19. The method of claim 10, wherein the respiratory disease or condition is COPD and the dry powder medicament comprises glycopyrronium bromide and formoterol fumarate.

20. The method of claim 10, wherein the respiratory disease or condition is asthma.

21. The method of claim 10, wherein the respiratory disease or condition is cystic fibrosis and the dry powder medicament comprises one or more antibiotics.

22. The method of claim 10, wherein the respiratory disease or condition is cystic fibrosis and the dry powder medicament comprises DNase.

23. The method of claim 10, wherein the respiratory disease or condition is idiopathic pulmonary fibrosis and the dry powder medicament comprises pirfenidone.

24. A method of increasing $FEV_1$ in a subject, the method comprising:

inhaling a therapeutically effective dose of dry powder medicament through a medicament delivery device using between 2-20 tidal inhalations over the course of an inhalation cycle, the inhalation cycle comprising dosing breaths, wherein the medicament delivery device comprises a vibratory element that is activated upon each dosing breath and causes dry powder medicament to be aerosolized within a dosing chamber and expelled from one or more openings in the dosing chamber into an air flow conduit, the dosing chamber receiving the dry powder medicament from a medicament container, wherein pressure oscillations in the dosing chamber are sufficiently high at the one or more openings to aerosolize and expel the dry powder medicament via synthetic jetting, the medicament delivery device having a flow resistance in a range from about 0.040 $cmH2O^{0.5}$/LPM to about 0.1 $cmH2O^{0.5}$/LPM at 30 liters per minute (LPM) and capable of delivering the dose of dry powder medicament at flow rates at least within a range of about 15 LPM to about 30 LPM, wherein the dose of dry powder medicament delivered by the medicament delivery device has a mass median aerodynamic diameter (MMAD) of about 6 microns or less and a fine particle fraction of at least 30%.

25. The method of claim 24, wherein the medicament delivery device administers at least 10% of the dry powder medicament dose in response to the first dosing breath in the inhalation cycle.

26. The method of claim 24, wherein the transducer has an on-time of about 5 seconds or less over the course of the inhalation cycle.

27. The method of claim 24, wherein the medicament delivery device achieves maximum synthetic jetting within about 1000 ms or less from the start of each transducer activation.

28. The method of claim 24, wherein the dry powder medicament comprises formoterol fumarate.

29. The method of claim 24, wherein the medicament delivery device is capable of delivering the dose of dry powder medicament at flow rates at least within a range of about 15 LPM to about 20 LPM.

30. A medicament delivery device comprising:

a dosing chamber comprising an interior that is configured to contain dry powder medicament, a transducer confronting the dosing chamber, wherein the dosing chamber and the transducer are acoustically resonant such that the dosing chamber is configured to resonate in response to an activation of the transducer, a controller electrically coupled to the transducer and configured to send an electrical signal that activates the transducer when the medicament delivery device senses a subject's dosing breath, and an air flow conduit extending from an air inlet to an outlet, the air flow conduit comprising (i) an upstream area disposed upstream from an area of the air flow conduit into which the dry powder medicament is expelled from the dosing chamber, and (ii) a downstream area disposed downstream from the area of the air flow conduit into which the dry powder medicament is expelled from the dosing chamber, the downstream area comprising the outlet and an exit channel disposed about an exit channel axis, wherein the upstream area comprises the air inlet and a first leg of an upper flow path in fluid communication with the exit channel, the first leg disposed about a first leg axis transverse to both the exit channel axis and a dosing chamber axis, wherein the dosing chamber's interior shape is at least partially defined by a lower sidewall that transitions to a shoulder, the shoulder transitions to an apex extending away from the lower sidewall, and the apex converges to a point, wherein one or more openings in the dosing chamber are disposed in the apex, and wherein an internal height of the dosing chamber is configured so that pressure oscillation at the one or more openings is sufficiently high to cause the dry powder medicament to become aerosolized and delivered from the one or more openings, the medicament delivery device having a flow resistance in a range from about 0.040 $cmH2O^{0.5}$/LPM to about 0.1 $cmH2O^{0.5}$/LPM at 30 liters per minute (LPM) and capable of delivering a therapeutically effective dose of dry powder medicament in response to between 2-20 tidal inhalations, the dose having a mass median aerodynamic diameter (MMAD) of about 6 microns or less and a fine particle fraction of at least 30%.

* * * * *